United States Patent
Kawaguchi et al.

(10) Patent No.: US 7,531,537 B2
(45) Date of Patent: *May 12, 2009

(54) BENZOFURAN DERIVATIVE

(75) Inventors: Takayuki Kawaguchi, Tokyo-to (JP); Hidenori Akatsuka, Toda (JP); Toru Iijima, Toda (JP); Yasunori Tsuboi, Ashiya (JP); Takashi Mitsui, Nishitokyo (JP); Jun Murakami, Saitama (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 576 days.

This patent is subject to a terminal disclaimer.

(21) Appl. No.: 10/508,512

(22) PCT Filed: Mar. 27, 2003

(86) PCT No.: PCT/JP03/03807

§ 371 (c)(1),
(2), (4) Date: Sep. 21, 2004

(87) PCT Pub. No.: WO03/082847

PCT Pub. Date: Oct. 9, 2003

(65) Prior Publication Data

US 2005/0282808 A1    Dec. 22, 2005

(30) Foreign Application Priority Data

Mar. 28, 2002 (JP) ............................. 2002-091686
Dec. 26, 2002 (JP) ............................. 2002-376158

(51) Int. Cl.
*A61K 31/5377* (2006.01)
*A61K 31/443* (2006.01)
*C07D 413/14* (2006.01)
*C07D 405/12* (2006.01)

(52) U.S. Cl. .................. 514/237.2; 514/337; 544/124; 546/284.1

(58) Field of Classification Search ............... 546/284.1; 514/337, 237.2; 544/124
See application file for complete search history.

(56) References Cited

FOREIGN PATENT DOCUMENTS

| EP | 0 937 711 A1 | 8/1999 |
|---|---|---|
| EP | 1 310 488 A1 | 5/2003 |
| WO | WO-99/42439 | 8/1999 |
| WO | WO-00/39118 A | 7/2000 |
| WO | WO-02/12189 A1 | 2/2002 |

OTHER PUBLICATIONS

Viti et al., J. Heterocyclic Chemistry, vol. 27, No. 5, pp. 1369-1375, (Jul.-Aug. 1990).
Nagahara et al., J. Med. Chem., vol. 37, pp. 1200-1207, (1994).
Sogorinsho, vol. 41, No. 11 (1992) pp. 2913-2918.
Freedman, J. Clin. Pharmacol., vol. 32 (1992) pp. 196-209.
Oates, The New England Journal of Medicine, vol. 324, No. 26 (1991) pp. 1865-1875.
Sixma et al., Erratum, vol. 68, No. 6 (1992) pp. 507-513.
Matsuo, O. ed., "t-PA and Pro-UK", Gakusaikikaku, 1986, pp. 5-40.
Kaiser et al., Biomed. Biochem. Acta., vol. 44, No. 7/8 (1985) pp. 1201-1210.
Tidwell et al., Thrombosis Research, vol. 19 (1980) pp. 339-349.
Harwalkar et al., Indian Journal of Heterocyclic Chemistry, vol. 3 (1994) pp. 247-252.
Viti et al., Journal of Heterocyclic Chemistry, (1990), 27 (5), 1369-75.

*Primary Examiner*—Patricia L Morris
(74) *Attorney, Agent, or Firm*—Birch, Stewart, Kolasch & Birch, LLP.

(57) ABSTRACT

The present invention provides a benzofuran derivative of the formula [1]:

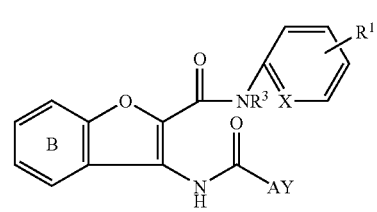

[1]

wherein x is a group of the formula: —N═ or —CH═; Y is an optionally substituted amino group, an optionally substituted cycloalkyl group or an optionally substituted saturated heterocyclic group; A is a single bond, a carbon chain optionally having a double bond within or at the end(s) of the chain, or an oxygen atom; $R^1$ is a hydrogen atom or a halogen atom; Ring B is an optionally substituted benzene ring; and $R^3$ is a hydrogen atom, or a pharmaceutically acceptable salt thereof, which is useful as a medicament, especially as an activated blood coagulation factor X inhibitor.

17 Claims, No Drawings

BENZOFURAN DERIVATIVE

TECHNICAL FIELD

The present invention relates to a benzofuran derivative useful as a medicament, particularly as an inhibitor of activated blood coagulation factor X, or pharmaceutically acceptable salt thereof.

BACKGROUND ART

In late years, as the westernization of living habit and the aging of populations, thromboembolic diseases such as myocardial infarction, cerebral infarction and peripheral arterial thrombosis increase year by year, and social importance of treatment thereof has risen more and more.

Among therapies of thromboembolic diseases, anticoagulant therapy, as well as fibrinolytic therapy and antiplatelet therapy, takes part in medical therapy for treatment and prevention of thrombosis (Sogorinsho 41: 2141-2145, 1989). In particular, the safety sustainable to chronic administration and the reliable and appropriate expression of anticoagulant activity are essential in the prevention of thrombosis. A coumarin derivative, especially warfarin potassium, has often been used all over the world as only anticoagulant available orally. However, owing to the characteristics arisen from the mechanism of action, it requires long time until the drug efficacy manifests and has very long half-life in blood, although the concentration range for expression of drug efficacy is relatively narrow, and also shows significant differences in the effective dose among individuals. For these reasons, the anticoagulant ability can hardly be controlled (Journal of Clinical Pharmacology, 1992, vol. 32, pp. 196-209; NEW ENGLAND JOURNAL OF MEDICINE, 1991, vol. 324, no. 26, pp. 1865-1875). In addition, there may be adverse drug reactions such as risk of bleeding, nausea, vomiting, diarrhea, depilation, etc., and therefore the clinical application thereof is very difficult and the development of anticoagulants that are useful and easy to handle has been demanded.

In addition, enhancement of blood clotting ability is one of significant causative factors of unstable angina, cerebral infarction, cerebral embolism, myocardial infarction, pulmonary infarction, pulmonary embolism, Buerger's disease, deep vein thrombosis, disseminated intravascular coagulation, thrombogenesis after artificial heart valve displacement, reocclusion after blood circulation reconstruction and thrombogenesis during extracorporeal circulation, etc. Therefore, a distinguished anticoagulant that shows good dose response and lower risk of hemorrhage with few side-effects, and can exert sufficient effects upon oral administration has been desired (Thrombosis Research, 1992, vol. 68, pp. 507-512). Thrombin participates not only in the conversion of fibrinogen to fibrin, which is the final stage of the coagulation cascade, but also deeply in the activation and aggregation of blood platelets (Matsuo, O., "t-PA and Pro-UK", Gakusaikikaku, 1986, pp. 5-40), and an inhibitor thereof has long been the center of the research in anticoagulants as a target of development of new drugs. However, a thrombin inhibitor shows low bioavailability upon oral administration and also has drawbacks in regard to safety such as bleeding tendency as one of side effects (Biomedica Biochimica Acta, 1985, Vol. 44, p. 1201-1210), and there have been no thrombin inhibitors marketed so far, which can be orally administered.

The activated blood coagulation factor X is a key enzyme located in the position of the common pathway of both extrinsic and intrinsic coagulation cascade reactions. The factor Xa is located upstream from thrombin in the coagulation cascade. Therefore, the inhibition of the factor Xa is possibly more effective and specific in the inhibition of coagulation system compared to the inhibition of thrombin (Thrombosis Research, 1980, Vol. 19, pp. 339-349).

Thus, among inhibitors of activated blood coagulation factor X, a substance, which inhibits blood coagulation factor Xa and shows distinguished enzyme selectivity and high bioavailability, is expected to undergo control of its anticoagulant activity for a long period of time and can express superior therapeutic effect upon oral administration compared to the existing anticoagulants. Accordingly, the development of a novel inhibitor of activated blood coagulation factor X (FXa inhibitor) that can be administered orally has been earnestly demanded.

Examples of known compounds having inhibitory effect on activated blood coagulation factor X include thiobenzamide compounds that are useful in prevention or treatment of thrombosis (WO99/42439).

The following benzofuran compounds have also been known (Indian Journal of Hetero Cyclic Chemistry, 1994, Vol. 3, pp. 3247-3252), but said literature does not mention about the inhibitory effect of the compounds on activated blood coagulation factor X.

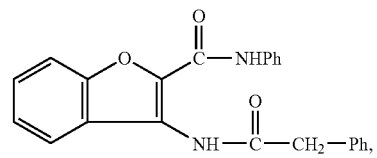

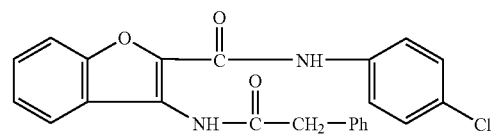

Condensed bicyclic amide compounds of the formula:

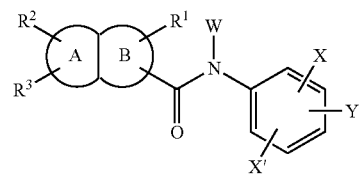

which has an activity of suppressing the growth of activated lymphocytes and are useful as a drug for preventing or treating autoimmune diseases are also known (WO02/12189). The WO02/12189 does not mention about the inhibitory effect on activated blood coagulation factor X either. In the pamphlet, compounds having a condensed ring of pyridine and furan to which ring an amide and a carbamoyl groups are di-substituted are disclosed; however, said compounds all have a benzene ring on the nitrogen atom of the carbamoyl group, said benzene ring being substituted by X and Y simultaneously.

DISCLOSURE OF INVENTION

The present invention provides a novel benzofuran derivative having excellent inhibitory effect on activated blood coagulation factor X, or a pharmaceutically acceptable salts thereof.

The present inventors have intensively studied and have found that a benzofuran derivative of the formula below has excellent inhibitory effect on activated blood coagulation factor X and have accomplished the present invention.

That is, the present invention is as follows:

(i) A benzofuran derivative of the formula [1]:

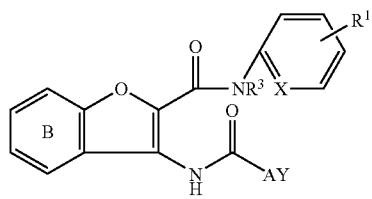

[1]

wherein x is a group of the formula: —N= or the formula: —CH=;

Y is an optionally substituted amino group, an optionally substituted cycloalkyl group or an optionally substituted saturated heterocyclic group;

A is a single bond, a carbon chain optionally having a double bond within or at the end(s) of the chain, or an oxygen atom;

R$^1$ is a hydrogen atom, a halogen atom, a lower alkyl group, a lower alkoxy group, a cyano group or an amino group optionally substituted by a lower alkyl group;

Ring B of the formula:

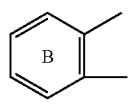

is an optionally substituted benzene ring; and

R$^3$ is a hydrogen atom or a lower alkyl group, or a pharmaceutically acceptable salt thereof.

(ii) The compound according to (i), wherein Ring B is a benzene ring optionally substituted by a group(s) selected independently from a halogen atom, an optionally substituted lower alkyl group, a hydroxy group, an optionally substituted lower alkoxy group, an oxy group substituted by an optionally substituted saturated heterocyclic group, a substituted carbonyl group, an optionally substituted amino group, a nitro group, a cyano group, a 4,5-dihydroxazolyl group or a group of the formula:

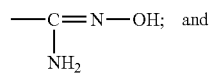

the "optionally substituted cycloalkyl group" for Y is a cycloalkyl group optionally substituted by a group selected from an optionally substituted amino group, an optionally substituted group of a formula selected from the formulas:

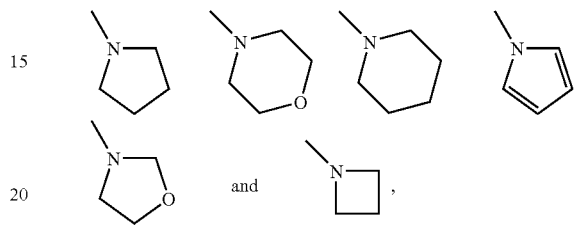

and an optionally substituted lower alkyl group.

(iii) The compound according to (ii), wherein the "optionally substituted saturated heterocyclic group" for Y is a saturated heterocyclic group optionally substituted by a group selected from the followings:
(1) a lower alkyl group,
(2) a lower alkyl group substituted by a pyridyl group,
(3) a piperidyl group substituted by a lower alkyl group,
(4) a piperidyl group,
(5) a piperidyl group substituted by a lower alkoxycarbonyl group,
(6) an unsaturated heterocyclic group selected from a pyridyl group, a pyrimidinyl group, a 4,5-dihydroxazolyl group and a thiazolyl group,
(7) a lower alkanoyl group,
(8) a lower alkanoyl group substituted by a di-lower alkylamino group,
(9) a carbonyl group substituted by a pyridyl group,
(10) a lower alkylsulfonyl group,
(11) a lower alkoxycarbonyl group,
(12) a lower alkyl group substituted by a di-lower alkylamino group, and
(13) an oxo group;

the "optionally substituted amino group" for Y is an amino group optionally substituted by a group selected from the followings:
(1) a piperidyl group substituted by a lower alkyl group,
(2) a lower alkyl group, and
(3) a lower alkoxycarbonyl group;

the "optionally substituted amino group" as a substituent on the cycloalkyl group for Y is an amino group optionally substituted by a group selected from the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group, (7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,
(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxyl group, and
(23) a hydroxy-lower alkanoyl group;

the "optionally substituted group of a formula selected from the formulas:

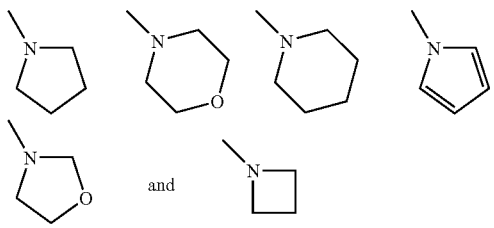

as a substituent on the cycloalkyl group for Y is a group selected from the groups of the formulas:

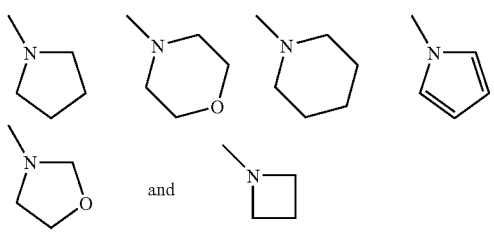

that is optionally substituted by an oxo group;

the "optionally substituted lower alkyl group" as a substituent on the cycloalkyl group for Y is a lower alkyl group optionally substituted by a group selected from the followings:
(1) an oxopyrrolidinyl group,
(2) an oxomorpholinyl group, and
(3) an amino group optionally substituted by a group selected from (a) a lower alkyl group, (b) a lower alkoxycarbonyl group, and (c) a lower alkanoyl group;

the "optionally substituted lower alkyl group" as a substituent for Ring B is a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group;

the "optionally substituted lower alkoxy group" as a substituent for Ring B is a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group,
(7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(14) a group of the formula: —O—NH—C(=NH)NH$_2$;

the "oxy group substituted by an optionally substituted saturated heterocyclic group" as a substituent for Ring B is an oxy group substituted by a heterocyclic group optionally substituted by an aryl group;

the "substituted carbonyl group" as a substituent for Ring B is a carbonyl group substituted by a group selected from the followings:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group, (7) a pyrrolidinyl group substituted by a hydroxy-lower alkyl group, and
(8) a lower alkyl-piperazinyl group;

the "optionally substituted amino group" as a substituent for Ring B is an amino group optionally substituted by a group selected from the followings:
(1) a lower alkyl group,
(2) a lower alkoxy-lower alkyl group,
(3) a hydroxy-lower alkyl group,
(4) a lower alkanoyl group,
(5) a lower alkoxy-lower alkanoyl group,
(6) a hydroxy-lower alkanoyl group,
(7) a lower alkanoyl group substituted by a lower alkanoyloxy group,
(8) a lower alkanoyl group substituted by an amino group optionally substituted by a group selected from (a) a lower alkyl group and (b) a lower alkanoyl group,
(9) a lower alkoxycarbonyl group,
(10) a lower alkoxycarbonyl group substituted by an aryl group,
(11) a carbamoyl group substituted by a lower alkyl group,
(12) a lower alkylsulfonyl group, and
(13) a lower alkylsulfonyl group substituted by a morpholinyl group.

(iv) The compound according to (iii), wherein B is an unsubstituted benzene ring; and Y is a saturated heterocyclic group optionally substituted by a group selected from the followings:
(1) a lower alkyl group,
(2) a lower alkyl group substituted by a pyridyl group
(3) a piperidyl group substituted by a lower alkyl group,
(4) a piperidyl group,
(5) a piperidyl group substituted by a lower alkoxycarbonyl group,
(6) an unsaturated heterocyclic group selected from a pyridyl group, a pyrimidinyl group, a 4,5-dihydroxazolyl group and a thiazolyl group,
(7) a lower alkanoyl group,
(8) a lower alkanoyl group substituted by a di-lower alkylamino group,
(9) a carbonyl group substituted by a pyridyl group,
(10) a lower alkylsulfonyl group,
(11) a lower alkoxycarbonyl group,
(12) a lower alkyl group substituted by a di-lower alkylamino group, and
(13) an oxo group.

(v) The compound according to (iii), wherein B is an unsubstituted benzene ring; and Y is an amino group optionally substituted by a group selected from the followings:
(1) a piperidyl group substituted by a lower alkyl group,
(2) a lower alkyl group, and
(3) a lower alkoxycarbonyl group.

(vi) The compound according to (iii), wherein B is an unsubstituted benzene ring; and Y is a cycloalkyl group optionally substituted by the followings:

A) an amino group optionally substituted by the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group,
(7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,
(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxy group, and
(23) a hydroxy-lower alkanoyl group;

B) a group of a formula selected from the formulas:

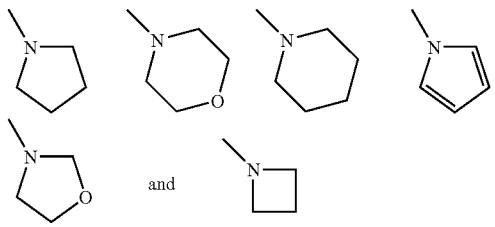

that is optionally substituted by an oxo group; or

C) a lower alkyl group optionally substituted by a group selected from the followings:
(1) an oxopyrrolidinyl group,
(2) an oxomorpholinyl group, and
(3) an amino group optionally substituted by (a) a lower alkyl group, (b) a lower alkoxycarbonyl group, and (c) a lower alkanoyl group.

(vii) The compound according to (iii), wherein Ring B is a benzene ring substituted by a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group, (7) a carbonyl group substituted by a hydroxyl group-substituted piperidyl group, and
(8) a hydroxyl group; and Y is a saturated heterocyclic group optionally substituted by a group selected from the followings:
(1) a lower alkyl group,
(2) a lower alkyl group substituted by a pyridyl group
(3) a piperidyl group substituted by a lower alkyl group,
(4) a piperidyl group,
(5) a piperidyl group substituted by a lower alkoxycarbonyl group,
(6) an unsaturated heterocyclic group selected from a pyridyl group, a pyrimidinyl group, a 4,5-dihydroxaolyl group and a thiazolyl group,
(7) a lower alkanoyl group,
(8) a lower alkanoyl group substituted by a di-lower alkylamino group,
(9) a carbonyl group substituted by a pyridyl group,
(10) a lower alkylsulfonyl group,
(11) a lower alkoxycarbonyl group,
(12) a lower alkyl group substituted by a di-lower alkylamino group, and
(13) an oxo group.

(viii) The compound according to (iii), wherein Ring B is a benzene ring substituted by a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group; and Y is an amino group optionally substituted by a group selected from the followings:
(1) a piperidyl group substituted by a lower alkyl group,
(2) a lower alkyl group, and
(3) a lower alkoxycarbonyl group.

(ix) The compound according to (iii), wherein Ring B is a benzene ring substituted by a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group; and Y is a cycloalkyl group optionally substituted by the followings:

A) an amino group optionally substituted by the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group,
(7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,
(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxy group, and
(23) a hydroxy-lower alkanoyl group;

B) a group of a formula selected from the formulas:

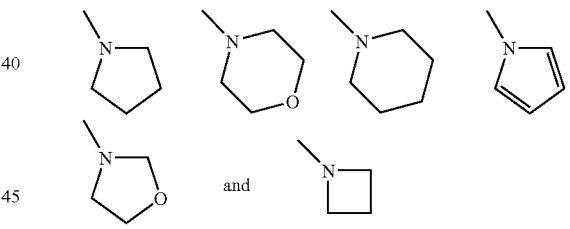

that is optionally substituted by an oxo group; or

C) a lower alkyl group optionally substituted by a group selected from the followings:
(1) an oxopyrrolidinyl group,
(2) an oxomorpholinyl group, and
(3) an amino group optionally substituted by (a) a lower alkyl group, (b) a lower alkoxycarbonyl group, and (c) a lower alkanoyl group.

(x) The compound according to (iii), wherein Ring B is a benzene ring substituted by a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group, (7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(14) a group of the formula: —O—NH—C(=NH)NH$_2$; and Y is a saturated heterocyclic group optionally substituted by a group selected from the followings:
(1) a lower alkyl group,
(2) a lower alkyl group substituted by a pyridyl group
(3) a piperidyl group substituted by a lower alkyl group,
(4) a piperidyl group,
(5) a piperidyl group substituted by a lower alkoxycarbonyl group,
(6) an unsaturated heterocyclic group selected from a pyridyl group, a pyrimidinyl group, a 4,5-dihydroxaolyl group and a thiazolyl group,
(7) a lower alkanoyl group,
(8) a lower alkanoyl group substituted by a di-lower alkylamino group,
(9) a carbonyl group substituted by a pyridyl group,
(10) a lower alkylsulfonyl group,
(11) a lower alkoxycarbonyl group,
(12) a lower alkyl group substituted by a di-lower alkylamino group, and
(13) an oxo group.

(xi) The compound according to (iii), wherein Ring B is a benzene ring substituted by a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group,
(7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(14) a group of the formula: —O—NH—C(=NH)NH$_2$; and Y is an amino group optionally substituted by a group selected from the followings:
(1) a piperidyl group substituted by a lower alkyl group,
(2) a lower alkyl group, and
(3) a lower alkoxycarbonyl group.

(xii) The compound according to (iii), wherein Ring B is a benzene ring substituted by a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group,
(7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(14) a group of the formula: —O—NH—C(=NH)NH$_2$; and Y is a cycloalkyl group optionally substituted by the followings:
A) an amino group optionally substituted by the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group,
(7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,

(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxy group, and
(23) a hydroxy-lower alkanoyl group;

B) a group of a formula selected from the formulas:

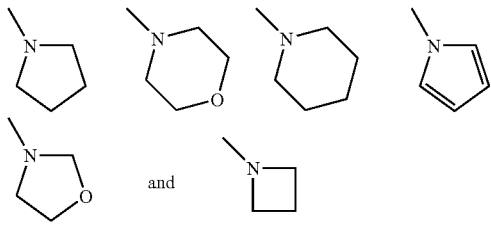

that is optionally substituted by an oxo group; or

C) a lower alkyl group optionally substituted by a group selected from the followings:
(1) an oxopyrrolidinyl group,
(2) an oxomorpholinyl group, and
(3) an amino group optionally substituted by (a) a lower alkyl group, (b) a lower alkoxycarbonyl group, and (c) a lower alkanoyl group.

(xiii) The compound according to (iii), wherein Ring B is a benzene ring substituted by a carbonyl group substituted by a group selected from the followings:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group; and Y is a saturated heterocyclic group optionally substituted by a group selected from the followings:
(1) a lower alkyl group,
(2) a lower alkyl group substituted by a pyridyl group
(3) a piperidyl group substituted by a lower alkyl group,
(4) a piperidyl group,
(5) a piperidyl group substituted by a lower alkoxycarbonyl group,
(6) an unsaturated heterocyclic group selected from a pyridyl group, a pyrimidinyl group, a 4,5-dihydroxaolyl group and a thiazolyl group,
(7) a lower alkanoyl group,
(8) a lower alkanoyl group substituted by a di-lower alkylamino group,
(9) a carbonyl group substituted by a pyridyl group,
(10) a lower alkylsulfonyl group,
(11) a lower alkoxycarbonyl group,
(12) a lower alkyl group substituted by a di-lower alkylamino group, and
(13) an oxo group.

(xiv) The compound according to (iii), wherein Ring B is a benzene ring substituted by a carbonyl group substituted by a group selected from the followings:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group; and Y is an amino group optionally substituted by a group selected from the followings:
(1) a piperidyl group substituted by a lower alkyl group,
(2) a lower alkyl group, and
(3) a lower alkoxycarbonyl group.

(xv) The compound according to (iii), wherein Ring B is a benzene ring substituted by a carbonyl group substituted by a group selected from the followings:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group; and Y is a cycloalkyl group optionally substituted by the followings:

A) an amino group optionally substituted by the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group,
(7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,
(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxy group, and
(23) a hydroxy-lower alkanoyl group;

B) a group of a formula selected from the formulas:

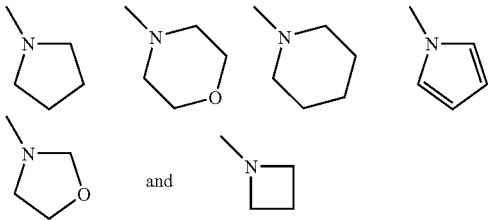

that is optionally substituted by an oxo group; or

C) a lower alkyl group optionally substituted by a group selected from the followings:
(1) an oxopyrrolidinyl group,
(2) an oxomorpholinyl group, and
(3) an amino group optionally substituted by (a) a lower alkyl group, (b) a lower alkoxycarbonyl group, and (c) a lower alkanoyl group.

(xvi) The compound according to (i), (ii), (iii), (iv), (vii), (x) or (xiii), wherein the saturated heterocyclic ring is a saturated 4- to 7-membered heterocyclic group containing 1 to 4 hetero atoms selected independently from the group consisting of nitrogen atom, oxygen atom and sulfur atom.

(xvii) The compound according to (i), (ii), (iii), (iv), (vii), (x) or (xiii), wherein the saturated heterocyclic group is imidazolidinyl, piperazolidinyl, piperidyl, piperazinyl, morpholinyl, thiomorpholinyl, homopiperazinyl, homopiperidyl, pyrrolidinyl, oxazolidinyl or 1,3-dioxanyl.

(xviii) The compound according to (iii), wherein the group of the formula:

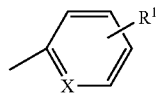

is the group of the formula:

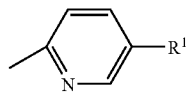

and the group of the formula:

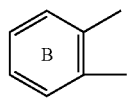

is a group of the formula:

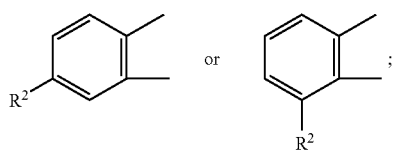

$R^1$ is a halogen atom or a lower alkyl group;
$R^2$ is a group selected from the followings:
A) a hydrogen atom,
B) a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group;
C) a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group, (7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by a group selected from (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group, and
(14) a group of the formula: —O—NH—C(=NH)NH$_2$; or D) a carbonyl group substituted by a group selected from the followings:
(1) a lower alkoxy group,
(2) a hydroxyl group,
(3) an amino group optionally substituted by a group selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group;
A is a single bond; and
R$^3$ is a hydrogen atom.

(xix) The compound according to (xviii), wherein Y is a group selected from the followings:
(1) a piperidyl group substituted by a lower alkyl group,
(2) a cycloalkyl group substituted by an amino group optionally substituted by a group selected from (a) a lower alkyl group, (b) a lower alkoxycarbonyl group, and (c) a lower alkanoyl group,
(3) a cycloalkyl group substituted by a group of a formula selected from the formulas:

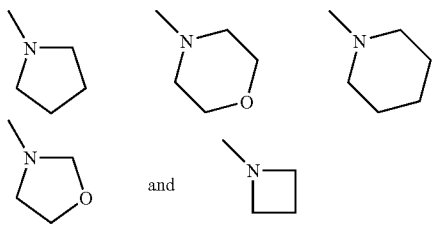

that is optionally substituted by an oxo group,
(4) a cycloalkyl group substituted by an amino group substituted by a lower alkyl group substituted by an amino group optionally substituted by a group selected from (a) a lower alkanoyl group and (b) a lower alkoxycarbonyl group, and
(5) a cycloalkyl group substituted by a lower alkyl group substituted by an amino group optionally substituted by a lower alkyl group; and R$^2$ is a group selected from the followings:
(1) a hydrogen atom,
(2) a cyano group,
(3) an amino group optionally substituted by a lower alkyl group,
(4) a hydroxyl group,
(5) a lower alkoxy group,
(6) a lower alkoxy group substituted by a lower alkoxy group,
(7) a lower alkoxy group substituted by a hydroxyl group,
(8) a lower alkoxy group substituted by an amino group optionally substituted by a lower alkyl group,
(9) a lower alkoxycarbonyl group,
(10) a carboxyl group,
(11) an aminocarbonyl group optionally substituted by a group selected from (a) lower alkyl group, and (b) a hydroxy-lower alkyl group,
(12) a morpholinylcarbonyl group, a pyrrolidinylcarbonyl group, a piperidylcarbonyl group or a thiomorpholinylcarbonyl group,
(13) a piperidylcarbonyl group substituted by a hydroxy-lower alkyl group or a pyrrolidinylcarbonyl group substituted by a hydroxy-lower alkyl group,
(14) a lower alkyl group,
(15) a lower alkyl group substituted by a lower alkoxycarbonyl group,
(16) a carboxy-lower alkyl group,
(17) a lower alkyl group substituted by a carbamoyl group optionally substituted by a group selected from (a) lower alkyl group and (b) a hydroxy-lower alkyl group,
(18) a lower alkyl group substituted by a morpholinylcarbonyl group,
(19) a lower alkyl group substituted by a piperidylcarbonyl group substituted by a hydroxy-lower alkyl group, or a lower alkyl group substituted by a pyrrolidinylcarbonyl group substituted by a hydroxy-lower alkyl group, or
(20) a hydroxy-lower alkyl group.

(xx) The compound according to (xviii), wherein Y is a cycloalkyl group substituted by a group of a formula selected from the formulas:

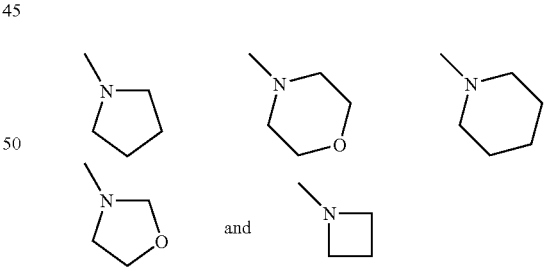

that is optionally substituted by an oxo group, or a cycloalkyl group substituted by an amino group optionally substituted by a group selected from (a) a lower alkyl group and (b) a lower alkanoyl group; and R$^2$ is a group selected from the followings:
(1) a hydrogen atom,
(2) an amino group-substituted carbonyl group optionally substituted by a group selected from (a) a lower alkyl group and (b) a lower alkoxy-lower alkyl group,
(3) a lower alkoxycarbonyl group, (4) a morpholinylcarbonyl group, a pyrrolidinylcarbonyl group, a piperidylcarbonyl group or a thiomorpholinylcarbonyl group,
(5) a lower alkyl group substituted by a lower alkyl group-substituted carbamoyl group,
(6) a carboxy-lower alkyl group,
(7) a lower alkyl group substituted by a morpholinylcarbonyl group, and
(8) a hydroxy-lower alkyl group.

(xxi) The compound according to (xviii), wherein Y is a cycloalkyl group substituted by an oxopyrrolidinyl group, a cycloalkyl group substituted by an oxomorpholinyl group or a cycloalkyl group substituted by an amino group optionally substituted by a group selected from (a) a lower alkyl group and (b) a lower alkanoyl group; and $R^2$ is a group selected from the followings:
(1) a hydrogen atom,
(2) a hydroxy-lower alkyl group,
(3) a carboxy-lower alkyl group,
(4) a lower alkoxy group substituted by a lower alkoxy group, or
(5) a carbonyl group substituted by a group selected from (a) an amino group optionally substituted by a lower alkyl group and (b) a morpholinyl group.

(xxii) The compound according to (xviii), wherein Y is a group selected from the followings:
(1) a cycloalkyl group substituted by an amino group substituted by a lower alkyl group having 1 to 3 carbon atoms,
(2) a cycloalkyl group substituted by an amino group substituted by a lower alkanoyl group having 1 to 2 carbon atoms,
(3) a cycloalkyl group substituted by a pyrrolidin-1-yl group optionally substituted by an oxo group,
(4) a cycloalkyl group substituted by a piperidin-1-yl group optionally substituted by an oxo group,
(5) a cycloalkyl group substituted by a morpholin-4-yl group optionally substituted by an oxo group,
(6) a cycloalkyl group substituted by a lower alkyl group substituted by an amino group substituted by a lower alkyl group having 1 to 3 carbon atoms, or
(7) a cycloalkyl group substituted by a lower alkyl group substituted by an amino group substituted by a lower alkanoyl group having 1 to 2 carbon atoms.

(xxiii) A compound selected from
trans-5-Dimethylaminocarbonyl-3-[4-(N-formyl-N-methylamino)cyclohexylcarbonylamino]-N-(5-chloropyridin-2-yl)benzofuran-2-carboxamide;
trans-3-[4-(N-acetyl-N-methylamino)cyclohexylcarbonylamino]-5-(2-hydroxyethyl)-N-(5-chloropyridin-2-yl) benzofuran-2-carboxamide;
trans-5-(morpholine-4-ylcarbonyl)-3-[4-(2-oxo-pyrrolidin-1-yl)cyclohexylcarbonylamino]-N-(5-chloropyridin-2-yl)benzofuran-2-carboxamide; and
trans-3-(4-dimethylaminocyclohexylcarbonylamino)-N-(5-chloropyridin-2-yl)benzofuran-2-carboxamide, or a pharmaceutically acceptable salt thereof.

(xxiv) A benzofuran derivative having a partial structure of the formula [1-1]:

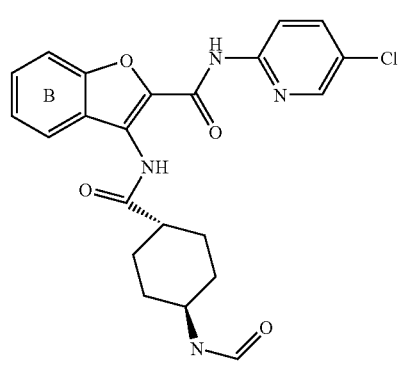

[1-1]

wherein the symbols are the same as defined above, or a pharmaceutically acceptable salt thereof.

(xxv) A benzofuran derivative of the formula [2]:

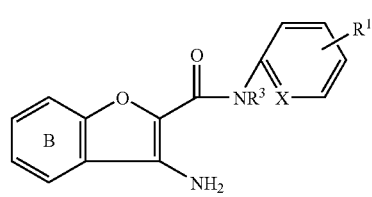

[2]

wherein the symbols are the same as defined above, or a salt thereof.

(xxvi) A pharmaceutical composition, which comprises as an active ingredient a compound according to any one of (i) to (xxiv) above or a pharmaceutically acceptable salt thereof.

(xxvii) A method for treatment of thrombosis, which comprises administering an effective amount of a compound according to any one of (i) to (xxiv) above or a pharmaceutically acceptable salt thereof, to a patient in need thereof (xxviii) Use of a compound according to any one of (i) to (xxiv) above or a pharmaceutically acceptable salt thereof in treatment of patients suffering from thrombosis.

(xxix) A medicament for treatment of thrombosis substantially free of phospholipidosis, which comprises as an active ingredient a factor Xa (FXa) inhibitor showing a distribution volume of 0.1-3.0 L/kg and an FXa inhibitory effect with the $IC_{50}$ value of 100 nM or below.

(xxx) A medicament for treatment of thrombosis substantially free of hepatotoxicity, which comprises as an active ingredient an FXa inhibitor showing a distribution volume of 0.1-3.0 L/kg or below and an FXa inhibitory effect with the $IC_{50}$ value of 100 nM or below.

(xxxi) A medicament for oral administration for treatment of thrombosis substantially free of phospholipidosis, which comprises as an active ingredient a factor Xa (FXa) inhibitor showing a distribution volume of 0.1-3.0 L/kg and an FXa inhibitory effect with the $IC_{50}$ value of 100 nM or below.

(xxxii) A medicament for oral administration for treatment of thrombosis substantially free of hepatotoxicity, which comprises as an active ingredient an FXa inhibitor showing a distribution volume of 0.1-3.0 L/kg or below and an FXa inhibitory effect with the $IC_{50}$ value of 100 nM or below.

(xxxiii) A medicament for treatment of thrombosis substantially free of phospholipidosis, which comprises as an active ingredient an FXa inhibitor having a partial structure of the formula:

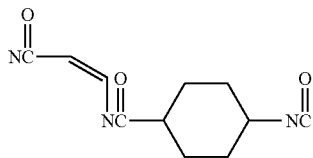

and showing a distribution volume of 0.1-3.0 L/kg and an FXa inhibitory effect with the $IC_{50}$ value of 100 nM or below.

(xxxiv) A medicament for treatment of thrombosis substantially free of hepatotoxicity, which comprises as an active ingredient an FXa inhibitor having a partial structure of the formula:

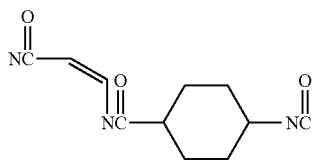

and showing a distribution volume of 0.1-3.0 L/kg and an FXa inhibitory effect with the $IC_{50}$ value of 100 nM or below.

(xxxv) A medicament for oral administration for treatment of thrombosis, which causes substantially no phospholipidosis and comprises as an active ingredient an FXa inhibitor having a partial structure of the formula:

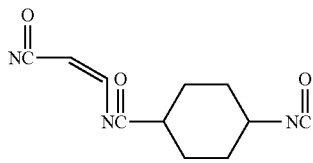

and showing a distribution volume of 0.1-3.0 L/kg and an FXa inhibitory effect with the $IC_{50}$ value of 100 nM or below.

(xxxvi) A medicament for oral administration for treatment of thrombosis substantially free of hepatotoxicity, which comprises as an active ingredient an FXa inhibitor having a partial structure of the formula:

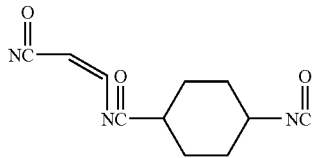

and showing a distribution volume of 0.1-3.0 L/kg and an FXa inhibitory effect with the $IC_{50}$ value of 100 nM or below.

BEST MODE FOR CARRYING OUT THE INVENTION

The compound [1] of the present invention will be hereinafter described in detail.

The term "lower" used in the definition of the formulas herein described means unless otherwise noted a straight- or branched-carbon chain having 1 to 6 carbon atoms.

Thus, examples of "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, etc. Among them, alkyl groups having 1 to 4 carbon atoms are preferred, and methyl, ethyl, propyl, isopropyl, butyl, isobutyl, sec-butyl and tert-butyl are especially preferred.

The term "lower alkoxy group" means a substituent wherein an oxygen atom is bound to the above-mentioned alkyl group. Among them, alkoxy groups having 1 to 4 carbon atoms are preferred, and methoxy, ethoxy, propoxy, isopropoxy, butoxy, isobutoxy, sec-butoxy and tert-butoxy groups are especially preferred.

Examples of "carbon chain optionally having a double bond within or at the end(s) of the chain" include "lower alkylene group", "lower alkenylene group" and "lower alkenylidene group".

Examples of "lower alkylene group" include a straight- or branched-chain alkylene group having 1 to 6 carbon atoms, specifically, methylene, ethylene, trimethylene, tetramethylene, pentamethylene, hexamethylene, etc. Among them, an alkylene group having 1 to 5 carbon atoms is preferred.

Examples of "lower alkenylene group" include a straight- or branched-chain alkenylene group having 2 to 6 carbon atoms, specifically, vinylene, propenylene, butenylene, pentenylene, etc. Among them, an alkenylene group having 2 to 5 carbon atoms is preferred.

Examples of "lower alkenylidene group" include alkenylidenes having 2 to 6 carbon atoms, specifically, vinylidene, propenylidene, butenylidene, pentenylidene, etc.

Examples of "lower alkanoyl group" include alkanoyl groups formed by removing a "OH" group from the carboxyl group of a lower carboxylic acid, specifically, formyl, acetyl, propionyl, butyryl, etc.

The "saturated heterocyclic group" means a saturated heterocyclic group containing 1 to 4 hetero atoms selected independently from the group consisting of nitrogen atom, oxygen atom and sulfur atom, preferably a 4- to 7-membered heterocyclic group containing 1 to 4 hetero atoms selected independently from the group consisting of nitrogen atom, oxygen atom and sulfur atom. A condensed heterocyclic ring is included. Specific examples include imidazolidinyl, pyrazolidinyl, piperidyl, piperazinyl, morpholinyl, thiomorpholinyl, homopiperazinyl, homopiperidyl, pyrrolidinyl, oxazolidinyl, 1,3-dioxanyl, etc. Above all, piperidyl, piperazinyl, homopiperazinyl and pyrrolidinyl are preferred.

The "unsaturated heterocyclic group" means an unsaturated heterocyclic group containing 1 to 4 hetero atoms selected independently from the group consisting of nitrogen atom, oxygen atom and sulfur atom, preferably a 4- to 7-membered heterocyclic group containing 1 to 4 hetero atoms selected independently from the group consisting of nitrogen atom, oxygen atom and sulfur atom. A condensed heterocyclic ring is included. Specific examples include pyridyl, pyrimidinyl, pyrazinyl, furyl, thienyl, pyrrolyl, imidazolyl, pyrazolyl, oxazolyl, isoxazolyl, 4,5-dihydro-oxazolyl, thiazolyl, isothiazolyl, etc. Above all, pyridyl, pyrimidinyl, pyrazinyl, thienyl, oxazolyl, 4,5-dihydro-oxazolyl and thiazolyl are preferred.

Examples of "halogen atom" include fluorine, chlorine, bromine or iodine atom. Above all, fluorine, chlorine or bromine atom is preferred.

The term "cycloalkyl group" means a cyclic lower alkyl group, preferably a cyclohexyl group.

The term "aryl group" means a phenyl or a naphthyl group, preferably phenyl group.

The symbol "Y", when A and Y are bound via a double bond, refers to the corresponding bivalent group.

The pharmaceutically acceptable salt of the compound [1] includes a salt with an inorganic acid such as hydrochloric acid, hydrobromic acid, hydroiodic acid, sulfuric acid, nitric acid, phosphoric acid, etc.; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; salt with an acidic amino acid such as aspartic acid, glutamic acid, etc.; salt with a metal such as sodium, potassium, magnesium, calcium, aluminium, etc.; salt with an organic base such as methylamine, ethylamine, ethanolamine, etc.; or a salt with a basic amino acid such as lysine, ornithine, etc.

The compound [1] of the present invention can be in the form of quaternary ammonium salt and such a quaternary ammonium salt falls within the scope of the present compound [1].

Further, the compound [1] of the present invention includes a intramolecular salt. hydrate, solvate or crystalline polymorphism, etc.

Besides, when the compound [1] has a double bond(s), it may exist in the form of a geometrical isomer (cis, trans), when the compound [1] has an unsaturated bond such as carbonyl, it may exist in the from of a tautomerism, when the compound [1] has an asymmetric carbon atom(s), it can exist as an optical isomer, and the present invention encompass these isomers and a mixture thereof.

Additionally, the compound [1] of the present invention encompasses a prodrug of a compound as mentioned above. Examples of a prodrug include those prepared by protecting a functional group such as an amino or carboxy group of a compound above with a conventional protecting group.

The compound of the present invention may be prepared by the following processes.

[Process A]

Among the compound [1] of the present invention, a compound wherein A is a single bond or a carbon chain optionally having a double bond within or at the end(s) of the chain, i.e., a compound of the formula [1-A]:

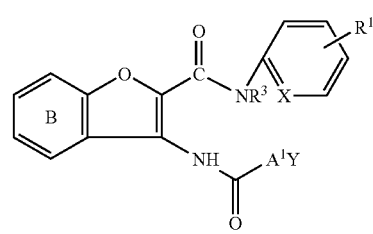

[1-A]

wherein $A^1$ is a single bond or a carbon chain optionally having a double bond within or at the end(s) of the chain, and the other symbols are the same as defined above, can be prepared by reacting an amino compound of the formula [2]:

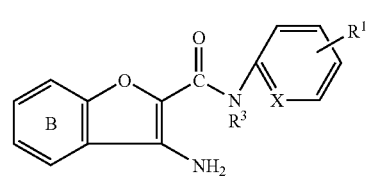

[2]

wherein the symbols are the same as defined above, with a carboxylic acid compound of the formula [3-A]:

YA$^1$-COOH                                    [3-A]

wherein the symbols are the same as defined above, or a reactive derivative thereof at its carboxyl group.

[Process B]

Among the compound [1] of the present invention, a compound wherein A is an oxygen atom, or A is a single bond, and Y is an optionally substituted amino group, i.e., a compound of the formula [1-B]:

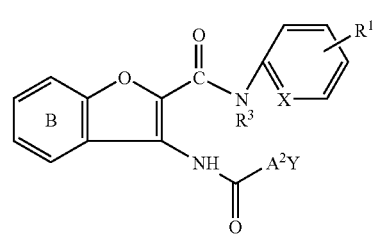

[1-B]

wherein $A^2$ is an oxygen atom and the other symbols are the same as defined above, or wherein $A^2$ is a single bond and the other symbols are the same as defined above, can be prepared by reacting the compound [2] above with a compound of the formula [3-B1]:

YA$^2$-H                                      [3-B1]

wherein the symbols are the same as defined above, and a compound of the formula [3-B2]:

L$^1$-CO-L$^2$                                [3-B2]

wherein $L^1$ and $L^2$ are the same or different and each a leaving group.

The compound [1] can also be prepared, if necessary, through the mutual conversion, wherein the residue Y and/or the substituent for Ring B ($R^2$) of resulting compound [1-A] or [1-B] is adequately converted into a compound [1] through the mutual conversion by alkylation, reductive alkylation, amidation, sulfonyl-amidation, amidino-etherification, arylation, reduction, dealkylation, hydrolysis, quaternary amination, formylation, pyrrolylation, protection of amino or carboxyl group and deprotection, etc.

[Manufacturing Process for Starting Materials: Preparation of Compound [2]]

The compound [2] can be prepared by a process comprising:

converting the aldehyde group of a compound of the formula [10]:

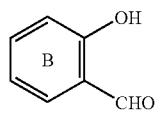
[10]

wherein the symbols are the same as defined above, into cyano group to give a compound of the formula [9]:

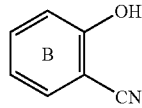
[9]

wherein the symbols are the same as defined above, reacting the compound [9] with a compound of the formula [8]:

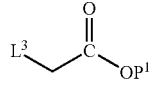
[8]

wherein $L^3$ is a leaving group and $P^1$ is a protecting group for carboxyl group, to give a compound of the formula [7]:

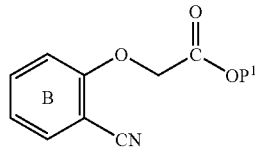
[7]

wherein the symbols are the same as defined above, deprotecting the protecting group $P^1$ of the compound [7] to give a compound of the formula [6]:

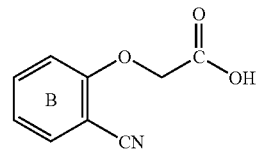
[6]

wherein the symbols are the same as defined above, reacting the compound [6], if necessary, after converting into a reactive derivative at the carboxyl group thereof, with a compound [5]:

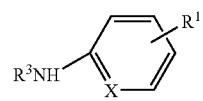
[5]

wherein the symbols are the same as defined above, to give a compound of the formula [4]:

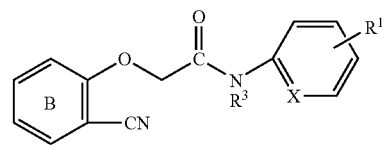
[4]

and subjecting the compound [4] to cyclization.

Further, the compound [4] can also be prepared by reacting a compound of the formula [9] with a compound of the formula [12]:

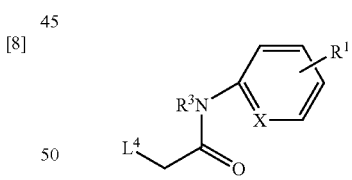
[12]

wherein $L^4$ is a leaving group and the other symbols are the same as defined above.

The compound [4] can also be prepared by reacting a compound of the formula [13]:

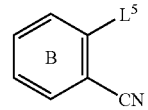
[13]

wherein L⁵ is a leaving group and the other symbols are the same as defined above with a compound of the formula [14]:

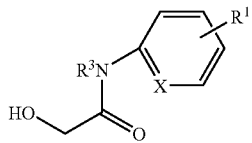

wherein the symbols are the same as defined above.

Further, the compound of the formula [10] can be prepared by formylating a compound of the formula [11]:

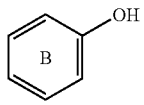

wherein the symbols are the same as defined above.

The Processes [A] and [B] above can be carried out in the following manner.

[Process A]

The reaction where a compound [1-A] is prepared using a compound [2] and a compound [3-A] can be carried out in a conventional manner for amidation. That is, the reaction can be carried out by reacting a compound [2] with a compound [3-A], a reactive derivative thereof, or a salt thereof in the presence or absence of a condensing agent, and if necessary, in the presence of an acid scavenger, in an appropriate solvent.

The condensing agent includes conventional agents such as N,N-dicyclohexylcarbodiimide (DCC), 1-ethyl-3-(3-dimethylaminopropyl)carbodiimide (EDC) or a hydrochloride thereof, carbonyldiimidazole (CDI), diphenylphosphorylazide (DPPA), diethyl cyanophosphonate (DEPC), etc. Above all, DCC, EDC or a hydrochloride thereof is preferred.

Examples of the reactive derivative of the compound [3-A] include those conventionally used such as an acid halide, a mixed anhydride, a reactive ester, etc. Examples of an activator that can be used for converting the compound [3-A] into the reactive derivative thereof include thionyl chloride, thionyl bromide, oxalyl chloride, N-hydroxylamines such as 1-hydroxysuccinimide, 1-hydroxybenzotriazole, etc., and phenols such as p-nitrophenol, etc. Above all, thionyl chloride, oxalyl chloride, 1-hydroxysuccinimide and 1-hydroxybenzotriazole are preferred. The acid chloride method is especially preferable.

Examples of the salt of a compound [3-A] or a reactive derivative of the compound [3-A] include a salt with an inorganic acid such as hydrochloric acid, hydrobromic acid, sulfuric acid, etc. An acid scavenger is also usable depending on the method to be employed, which includes inorganic or organic bases.

The present reaction may be facilitated when it is carried out in the presence of a base or by using such a base as a solvent. Examples of inorganic bases include inorganic bases such as alkali metal carbonates (sodium carbonate, potassium carbonate, cesium carbonate, etc.), alkali earth metal carbonates (calcium carbonate, etc.), alkali metal hydrogen carbonates (sodium hydrogen carbonate, potassium hydrogen carbonate, etc.), alkali metal hydroxides (sodium hydroxide, potassium hydroxide, lithium hydroxide, etc.). Examples of organic bases include tri-lower alkylamines (triethylamine, tributylamine, diisopropylethylamine, etc.), tertiary-amines (1,4-diazabicyclo[2.2.2]octane, 1,5-diazabicyclo[4.3.0]non-5-ene, 1,8-diazabicyclo[5.4.0]undec-7-ene, etc.), amines (N,N-dimethylaniline, N,N-diethylaniline, 4-dimethylaminopyridine, etc.), pyridine, lutidine, collidine, etc. Above all, triethylamine, diisopropylethylamine, 4-dimethylaminopyridine, or pyridine is preferred for carrying out the reaction. The present reaction can be carried out in the presence or absence of a solvent, preferably in the presence of a solvent.

Examples of the solvent include any inert solvent which does not disturb the reaction, such as halogenated hydrocarbons (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), esters (ethyl acetate, etc.), amides (N,N-dimethylformamide, N,N-dimethylacetamide, 1,3-dimethyl-2-imidazolidinone, etc.), nitriles (acetonitrile, etc.), dimethylsulfoxide, pyridine, 2,6-luthidine, etc., a mixed solvent comprising two or more of these solvents, if necessary, and also a mixture of any one(s) of these solvents and water. It is preferred to select any appropriate solvent depending on the method used. Above all, dichloromethane, chloroform, toluene, xylene, tetrahydrofuran, dioxane, N,N-dimethylformamide, N,N-dimethylacetamide, 1,3-dimethyl-2-imidazolidinone, pyridine, and the like are preferred, and dichloromethane, chloroform, N,N-dimethylformamide and pyridine are especially preferred. The present reaction can be carried out in a wide range of temperature from a temperature of under cooling to under heating. For example, the reaction can be preferably carried out at a temperature of −10° C. to the boiling point of the reaction mixture, especially from under ice-cooling to 60° C.

[Process B]

The process wherein the compound [1-B] is prepared by reacting a compound [2] with compounds of the formulas [3-B1] and [3-B2], respectively, can be carried out in accordance with a conventional method for carbonylation in the presence of an appropriate acid scavenger in an appropriate solvent.

Examples of a leaving group for a compound of the formula [3-B2] include a halogen atom. Examples of a compound [3-B2] include phosgene, triphosgene, CDI, etc., and triphosgene is preferred.

Examples of acid scavenger used in the reaction include both the inorganic and organic bases. Examples of inorganic bases include alkali metal carbonates (sodium carbonate, potassium carbonate, cesium carbonate, etc.) and alkali metal hydrogen carbonates (sodium hydrogen carbonate, potassium hydrogen carbonate, etc.). Examples of organic bases include tri-lower alkylamines (triethylamine, tributylamine, diisopropylethylamine, etc.), tertiary-amines (1,4-diazabicyclo[2.2.2]octane, 1,5-diazabicyclo[4.3.0]non-5-ene, 1,8-diazabicyclo[5.4.0]-undec-7-ene, etc.), amines (N,N-dimethylaniline, N,N-diethylaniline, 4-dimethylaminopyridine, etc.), pyridine, lutidine, collidine, etc. Above all, triethylamine, diisopropylethylamine, 4-dimethylaminopyridine and pyridine are preferred.

Examples of the solvent include any inert solvent which does not disturb the reaction, such as halogenated hydrocarbons (chloroform, dichloromethane, dichloroethane, etc.), ethers (diethyl ether, diisopropyl ether, tetrahydrofuran, dioxane, 1,2-dimethoxyethane, etc.), esters (ethyl acetate, etc.), amides (N,N-dimethylformamide, N,N-dimethylacetamide, 1,3-dimethyl-2-imidazolidinone, etc.), nitriles (acetonitrile, etc.), pyridine, 2,6-luthidine, etc., and a mixed solvent comprising two or more of these solvents, if necessary. It is preferred to select any appropriate solvent depending on the method used. Above all, dichloromethane, tetrahydrofuran, N,N-dimethylformamide, N,N-dimethylacetamide, 1,3-dimethyl-2-imidazolidinone, pyridine, and the like are preferred, and dichloromethane and N,N-dimethylformamide are especially preferred. The present reaction can be carried out in a wide range of temperature from −78° C. to the boiling point of the reaction mixture. For example, the reaction can be preferably carried out at a temperature of −10° C. to the boiling point of the reaction mixture, especially at a temperature of under ice-cooling to room temperature.

Furthermore, after carrying out the Processes [A] and [B], the objective compound [1] can also be obtained, if necessary, through a mutual conversion by conducting the following reaction(s), on condition that the resulting compounds of the formula [1-A] and/or [1-B] has one or more moieties available to a further reaction(s) in the substituent(s) for group Y and/or Ring B (mainly referring to, for example, a protecting group for amine, alcoholic or phenolic OH, ester, carboxylic acid, nitro, halogen, etc.)

The reactions for alkylation, reductive alkylation, amidation, sulfonyl-amidation, amidino-etherification, arylation, reduction, dealkylation, hydrolysis, quaternary amination, pyrrolylation, protection and deprotection of amino or carboxyl group, which are conducted when needed, can be carried out as follows.

The alkylation can be carried out in a conventional manner, when needed. For example, this reaction can be carried out by reacting a compound [1] with an alkyl halide such as alkyl chloride, alkyl bromide, alkyl iodide, etc. in the presence or absence of a base in an appropriate solvent.

Examples of the bases usable include inorganic and organic bases. The inorganic bases include alkali metal carbonates (sodium carbonate, potassium carbonate, cesium carbonate, etc.), alkali metal hydrogen carbonates (sodium hydrogen carbonate, potassium hydrogen carbonate, etc.), alkali metal hydroxides (sodium hydroxide, potassium hydroxide, lithium hydroxide, etc.). Examples of organic bases include tri-lower alkylamines (triethylamine, tributylamine, diisopropylethylamine, etc.), tertiary-amines (1,4-diazabicyclo[2.2.2]octane, 1,5-diazabicyclo[4.3.0]-non-5-ene, 1,8-diazabicyclo[5.4.0]undec-7-ene, etc.), pyridine, lutidine, collidine, etc. Above all, alkali metal carbonates such as sodium carbonate, potassium carbonate and cesium carbonate, triethylamine, diisopropylethylamine, pyridine, etc. are preferred.

An alkali metal iodide such as lithium iodide, sodium iodide, potassium iodide, etc. can also be added, which may facilitate the reaction.

Any inert solvents which do not disturb the reaction can be used without limitation, and examples thereof include ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitrites (acetonitrile, etc.), alcohols (methanol, ethanol, propanol, etc.), dimethylsulfoxide, pyridine, 2,6-luthidine, etc., and a mixed solvent comprising two or more of these solvents, if necessary. It is preferred to select any appropriate solvent depending on the method used. Above all, tetrahydrofuran, N,N-dimethylformamide, N,N-dimethylacetamide, 1,3-dimethyl-2-imidazolidinone, acetonitrile, ethanol, dimethylsulfoxide, etc., are preferred and N,N-dimethylformamide, acetonitrile, ethanol, and a mixed solvent thereof are more preferred.

The present reaction can be carried out in a wide range of temperature from a temperature of under cooling to under heating, preferably at −10° C. to the boiling point of the reaction mixture.

The reductive alkylation can be carried out in a conventional manner, when needed. For example, this reaction can be carried out by reacting a compound [1] with a corresponding carbonyl compound in the presence of an appropriate metal hydride reducing agent, or under the condition for catalytic reduction in the presence of an appropriate metal catalyst, in an appropriate solvent.

In the reaction, any conventional metal hydride reducing agents can be used without limitation; however, reducing agents which do not affect the amide bonds etc., such as sodium borohydride, sodium triacetoxy borohydride, sodium cyano borohydride, etc. are preferred.

Besides, organic acids such as acetic acid, etc. or mineral acids such as hydrochloric acid, etc. can also be added to the present reaction, which may facilitate the reaction.

Furthermore, when the compound [1] used is an amine in the form of a salt with a mineral acid such as hydrochloric acid, etc., an appropriate neutralizing agent such as an organic base (e.g., triethylamine) or an alkali metal acetate (e.g., sodium acetate) may be added to the reaction, which may facilitate the reaction.

Any inert solvents which do not disturb the reaction can be used without limitation, and examples thereof include halogenated hydrocarbons (chloroform, dichloromethane, dichloroethane, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitrites (acetonitrile, etc.), aromatic hydrocarbons (benzene, toluene, xylene, etc.), alcohols (methanol, ethanol, propanol, etc.), water, and a mixed solvent comprising two or more of these solvents, if necessary. It is preferred to select any appropriate solvent depending on the method used. Above all, dichloromethane, dichloroethane, tetrahydrofuran, 1,2-dimethoxyethane, methanol, ethanol, propanol, etc. are preferred, and dichloromethane, dichloroethane and tetrahydrofuran are especially preferred.

The reaction can be carried out in a wide range of temperature from a temperature of under cooling to under heating. For example, the reaction can be preferably carried out at a temperature of −10° C. to the boiling point of the reaction mixture, especially from under ice-cooling to the boiling point of the mixture.

The present reaction can similarly be carried out according to the catalytic hydrogenation in the presence of a metal catalyst. Examples of the metal catalyst include palladium-carbon, platinum-carbon, platinum oxide, Raney Nickel, etc.

Besides, organic acids such as acetic acid, etc. or mineral acids such as hydrochloric acid, etc. can also be added to the present reaction, which may facilitate the reaction.

Furthermore, when the compound [1] used is an amine in the form of a salt with a mineral acid such as hydrochloric acid, etc., an appropriate neutralizing agent such as an organic base (e.g., triethylamine) or an alkali metal acetate (e.g., sodium acetate) may be added to the reaction, which may facilitate the reaction.

Any inert solvents which do not disturb the reaction can be used without limitation, and examples thereof include ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), aromatic hydrocarbons (benzene, toluene, xylene, etc.), alcohols (methanol, ethanol, propanol, etc.), water, and a mixed solvent comprising two or more of these solvents, if necessary. It is preferred to select any appropriate solvent depending on the method used. Above all, tetrahydrofuran, N,N-dimethylformamide, methanol, ethanol, etc. are preferred, and tetrahydrofuran, methanol, ethanol, etc. are especially preferred.

The reaction can be carried out in a wide range of temperature from a temperature of under cooling to under heating. For example, the reaction can be preferably carried out at a temperature of −10° C. to the boiling point of the reaction mixture, especially from under ice-cooling to room temperature.

The amidation can be carried out in a manner similar to the above-mentioned reaction between a compound [2] and a compound [3-A], when needed.

The sulfonylamidation can be carried out in a conventional manner, when needed. For example, this reaction can be carried out by reacting a compound [1] with an optionally substituted alkylsulfonic acid halide in the presence or absence of a base in an appropriate solvent. For the reaction, similar acid scavenger, solvent and reaction temperature to those used in the amidation reaction between a compound [2] and a compound [3-A] above can be employed.

The amidino-etherification can be carried out in a conventional manner, when needed. For example, the reaction can be carried out by reacting a compound [1] with 2-bromoethyl isocyanate or 2-chloroethyl isocyanate in the presence or absence of an appropriate acid scavenger in an appropriate solvent.

Examples of the bases usable include inorganic and organic bases. The inorganic bases include alkali metal carbonates (sodium carbonate, potassium carbonate, cesium carbonate, etc.), alkali metal hydrogen carbonates (sodium hydrogen carbonate, potassium hydrogen carbonate, etc.), etc. Examples of organic bases include tri-lower alkylamines (triethylamine, tributylamine, diisopropylethylamine, etc.), tert-amines (1,4-diazabicyclo[2.2.2]octane, 1,5-diazabicyclo[4.3.0]-non-5-ene, 1,8-diazabicyclo[5.4.0]undec-7-ene, etc.), amines (N,N-dimethylaniline, N,N-diethylaniline, 4-dimethylaminopyridine, etc.), pyridine, lutidine, collidine, etc. Above all, triethylamine and diisopropylethylamine are preferred.

The present reaction can be carried out in the presence or absence of a solvent, preferably in the presence of a solvent.

Any inert solvents which do not disturb the reaction can be used without limitation, and examples thereof include halogenated hydrocarbons (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), dimethylsulfoxide, pyridine, 2,6-luthidine, etc., and a mixed solvent comprising two or more of these solvents, if necessary. Above all, dichloromethane, tetrahydrofuran, N,N-dimethylformamide, etc. are preferred and tetrahydrofuran is more preferred.

The reaction can be carried out in a wide range of temperature from a temperature of under cooling to under heating. For example, the reaction can be preferably carried out at a temperature of −10° C. to the boiling point of the reaction mixture, especially from under ice-cooling to room temperature.

The arylation can be carried out in a conventional manner, when needed. For example, the reaction can be carried out by reacting a compound [1] with a halogenated aryl compound in the presence or absence of an appropriate base in an appropriate solvent.

Examples of the bases usable include inorganic and organic bases. The inorganic bases include alkali metal carbonates (sodium carbonate, potassium carbonate, cesium carbonate, etc.), alkali metal hydrogen carbonates (sodium hydrogen carbonate, potassium hydrogen carbonate, etc.), etc. Examples of organic bases include tri-lower alkylamines (triethylamine, tributylamine, diisopropylethylamine, etc.), tert-amines (1,4-diazabicyclo[2.2.2]octane, 1,5-diazabicyclo[4.3.0]-non-5-ene, 1,8-diazabicyclo[5.4.0]undec-7-ene, etc.), amines (N,N-dimethylaniline, N,N-diethylaniline, 4-dimethylaminopyridine, etc.), pyridine, lutidine, collidine, etc. Above all, triethylamine, diisopropylethylamine, potassium carbonate, etc. are preferred.

The present reaction can be carried out in the presence or absence of a solvent, preferably in the presence of a solvent.

Any inert solvents which do not disturb the reaction can be used without limitation, and examples thereof include aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitrites (acetonitrile, etc.), alcohols (methanol, ethanol, propanol, 2-butanol, etc.), dimethylsulfoxide, pyridine, 2,6-luthidine, etc., and a mixed solvent comprising two or more of these solvents, if necessary. Above all, xylene, tetrahydrofuran, N,N-dimethylacetamide, 1,3-dimethyl-2-imidazolidinone, ethanol, 2-butanol, etc. are preferred and tetrahydrofuran, N,N-dimethylacetamide and 2-butanol are more preferred.

The reaction can be carried out in a wide range of temperature from a temperature of under cooling to under heating. For example, the reaction can be preferably carried out at a temperature of −10° C. to the boiling point of the reaction mixture, especially from room temperature to the boiling point of the reaction mixture.

The reduction can be carried out in a conventional manner, when needed. For example, the reaction can be carried out by reacting a compound [1] with an appropriate reducing agent, or with hydrogen in the presence of a metal catalyst in an appropriate solvent.

In the reaction, any conventional reducing agents can be used without limitation; however, metal hydride reducing agents such as lithium aluminium hydride, lithium borohydride, sodium borohydride, etc., metals such as zinc, iron, stannum, etc., and metal salts such as tin chloride, etc. are preferred, and metals such as stannum, etc. and metal salts such as tin chloride, etc. are more preferred. In the catalytic hydrogenation, any conventional metal catalysts can be used without limitation; however, palladium-carbon, Raney Nickel, Raney Cobalt, platinum oxide, etc. are preferred and metals such as Raney Nickel, etc. are more preferred. Furthermore, depending on the method used, the reaction can sometimes be facilitated when it is carried out under an acidic condition in the co-existence of a mineral acid such as hydrochloric acid, etc.

In the reaction where a metal hydride reducing agent is used, any inert solvents which do not disturb the reaction can be used without limitation, and examples thereof include ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), aromatic hydrocarbons (benzene, toluene, xylene, etc.), alcohols (methanol, ethanol, propanol, etc.), water, etc., and a mixed solvent comprising two or more of these solvents, if necessary. It is preferred to select any appropriate solvent depending on the method used.

In the reaction where a metal such as zinc, iron, stannum, etc., or a metal salt such as tin chloride, etc. is used, any inert solvents which do not disturb the reaction can be used without limitation, and examples thereof include water, alcohols (methanol, ethanol, propanol etc.), esters (ethyl acetate, etc.), ethers (diethyl ether, diisopropyl ether, tetrahydrofuran, 1,2-dimethoxyethane, etc.), amides (N,N-dimethylformamide, N,N-dimethylacetamide, 1,3-dimethyl-2-imidazolidinone, etc.), nitrites (acetonitrile, etc.), aromatic hydrocarbons (benzene, toluene, xylene, etc.), and a mixed solvent comprising two or more of these solvents, if necessary. It is preferred to select any appropriate solvent depending on the method used. Above all, ethyl acetate, water, or a mixed solvent comprising water and an alcohol, an ether, an amide, a nitrile etc. is preferred.

In the reaction where hydrogenation is carried out in the presence of a metal catalyst, any inert solvents which do not disturb the reaction can be used without limitation, and examples thereof include alcohols, ethers, aliphatic hydrocarbons, aromatic hydrocarbons, amides, esters (ethyl acetate, etc.), organic acids (formic acid, acetic acid, propionic acid, trifluoroacetic acid, etc.), and a mixed solvent comprising two or more of these solvents, if necessary. It is preferred to select any appropriate solvent depending on the method used.

The present reaction can be carried out in a wide range of temperature from a temperature of under cooling to under heating. For example, the reaction can be preferably carried out at a temperature of −10° C. to the boiling point of the reaction mixture.

The hydrogen pressure used in the catalytic hydrogenation reaction is generally about 1-100 atm.

The reaction time for the present reaction varies depending on the kind of the reducing agent or the activity of the catalyst used; however, it is generally between about 10 minutes and 24 hours.

The dealkylation can be carried out in a conventional manner, when needed. For example, this reaction can be carried out by reacting a compound [1] with an appropriate dealkylating agent in an appropriate solvent or without solvent.

Any conventional dealkylating agents can be used without limitation, and preferred examples thereof include boron tribromide, boron trichloride, iodotrimethylsilane, aluminium (III) chloride, pyridinium chloride, etc., and boron tribromide, iodotrimethylsilane, etc. are preferred.

Any inert solvents which do not disturb the reaction can be used without limitation, and examples thereof include halogenated hydrocarbons (chloroform, dichloromethane, dichloroethane, etc.), amides (N,N-dimethylformamide, N,N-dimethylacetamide, 1,3-dimethyl-2-imidazolidinone, etc.), nitrites (acetonitrile, etc.), and a mixed solvent comprising two or more of these solvents, if necessary. It is preferred to select any appropriate solvent depending on the method used.

The reaction can be carried out in a wide, range of temperature from a temperature of under cooling to under heating, preferably from −78° C. to the boiling point of the reaction mixture.

The hydrolysis can be carried out in a conventional manner, when needed.

The quaternary amination can be carried out in a conventional manner, when needed. This reaction can be conducted in a similar manner to the above-mentioned alkylation.

The pyrrolylation can be carried out by, for example, reacting a compound having an amino group with tetrahydro-2,5-dimethoxyfuran in the presence of an acid in an appropriate solvent.

Examples of the acids include an organic acid such as formic acid, acetic acid, propionic acid, trifluoroacetic acid, etc., and a mineral acid such as hydrochloric acid, etc, which acids can also be used as a solvent.

Any inert solvents, in addition to the above-mentioned organic acids and mineral acids, which do not disturb the reaction can be used without limitation, and examples thereof include halogenated hydrocarbons (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), etc., and organic acids are preferred.

The reaction can be carried out in a wide range of temperature from a temperature of under cooling to under heating, preferably from −78° C. to the boiling point of the reaction mixture.

The protection of an amino or a carboxy group, or deprotection of the protected group can be carried out, when needed, according to any of known methods.

[Manufacturing Process for Starting Materials: Preparation of Compound [2]]

(1) The reaction for converting the aldehyde group of the compound [10] into a cyano group to give the compound [9] can be carried out by reacting the compound [10] with a hydroxylamine or hydrochloride thereof in the presence or absence of sodium formate in an appropriate solvent. A dehydrating agent may be added. The solvent available includes an organic lower fatty acid such as formic acid; however, it is preferred to select an appropriate solvent depending on the method used.

The present reaction can be carried out in a wide range of temperature from a temperature of under cooling to under heating. For example, the reaction can be preferably carried out at a temperature of under ice-cooling to the boiling point of the reaction mixture, especially at the boiling point of the reaction mixture.

(2) The next reaction between the resulting compound [9] and the compound [8] to give the compound [7] can be carried out in a conventional manner for O-alkylation of a phenol compound. The present reaction can be carried out by reacting the compound [9] with the compound [8] in an appropriate solvent in the presence of a base or by using such a base as the solvent.

The leaving group in the compound [8] can be preferably, for example, a halogen atom. Examples of a preferred protecting group for the carboxyl group of the compound [8] include a lower alkyl group and a phenyl-lower alkyl group.

Examples of the base usable include both the inorganic and organic bases such as alkali metal carbonates (sodium carbonate, potassium carbonate, etc.), alkali metal hydrogen carbonates (sodium hydrogen carbonate, potassium hydrogen carbonate, etc.), alkali metal hydroxides (sodium hydroxide, potassium hydroxide, lithium hydroxide, etc.), alkali metal hydrides (sodium hydride, etc.), alkali metal alkoxides (sodium methoxide, potassium t-butoxide, etc.), tri-lower alkylamines (triethylamine, tributylamine, diisopropylethylamine, etc.), tertiary-amines (1,4-diazabicyclo[2.2.2]octane, 1,5-diazabicyclo[4.3.0]non-5-ene, 1,8-diazabicyclo[5.4.0]undec-7-ene, etc.), amines (N,N-dimethylaniline, N,N-diethylaniline, 4-dimethylaminopyridine, etc.), pyridine, lutidine, collidine, etc. Above all, alkali metal carbonate, diisopropylethylamine, pyridine, etc. are preferred.

Examples of the solvent include any inert solvent which does not disturb the reaction, such as ketones (e.g., acetone, methylethyl ketone, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), alcohols (methanol, ethanol, propanol, 2-butanol, etc.), dimethylsulfoxide, pyridine, 2,6-luthidine, etc., and a mixed solvent comprising two or more of these solvents, if necessary. Above all, ketones such as acetone, methylethyl ketone, etc., and amides such as N,N-dimethylformamide, N,N-dimethylacetamide, 1,3-dimethyl-2-imidazolidinone, etc. are preferred.

The present reaction can be carried out in a wide range of temperature from a temperature of under cooling to under heating. For example, the reaction can be preferably carried out at a temperature of under ice-cooling to the boiling point of the reaction mixture.

An alkali metal iodide such as lithium iodide, sodium iodide, potassium iodide, etc. can also be added, which may facilitate the reaction.

(3) The reaction for removing a protecting group from the compound [7] to give the compound [6] can be carried out by a method generally used for the deprotection of carboxyl group.

(4) The reaction for condensing the compound [5] with the compound [6] to give the compound [4] can be carried out in a manner similar to that for reacting the compound [2] with the compound [3-A].

(5) The reaction for cyclizing the compound [4] to give the compound [2] can be carried out by treating the compound [4] with a base in an appropriate solvent.

Examples of the base usable include both the inorganic and organic bases such as alkali metal carbonates (sodium carbonate, potassium carbonate, etc.), alkali metal hydroxides (sodium hydroxide, potassium hydroxide, lithium hydroxide, etc.), alkali metal hydrides (sodium hydride, etc.), alkali metal alkoxides (sodium methoxide, potassium t-butoxide, etc.), tri-lower alkylamines (triethylamine, tributylamine, diisopropylethylamine, etc.), tert-amines (1,4-diazabicyclo[2.2.2]octane, 1,5-diazabicyclo[4.3.0]-non-5-ene, 1,8-diazabicyclo[5.4.0]undec-7-ene, etc.), amines (N,N-dimethylaniline, N,N-diethylaniline, 4-dimethylaminopyridine, etc.), pyridine, lutidine, collidine, etc. Above all, alkali metal carbonate, alkali metal alkoxides, diisopropylethylamine, pyridine, etc. are preferred.

The present reaction can be carried out in the presence or absence of a solvent, preferably in the presence of a solvent. Examples of the solvent include any inert solvent which does not disturb the reaction, such as aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), alcohols (methanol, ethanol, propanol, 2-butanol, etc.), dimethylsulfoxide, pyridine, 2,6-luthidine, etc., and a mixed solvent comprising two or more of these solvents, if necessary. Above all, xylene, tetrahydrofuran, N,N-dimethylformamide, N,N-dimethylacetamide, 1,3-dimethyl-2-imidazolidinone, methanol, pyridine, etc. are preferred, and N,N-dimethylacetamide and 1,3-dimethyl-2-imidazolidinone are especially preferred.

The present reaction can be carried out in a wide range of temperature from a temperature of under cooling to under heating, preferably at a temperature of under ice-cooling to the boiling point of the reaction mixture.

(6) The reaction between the compound [9] and the compound [12] to give the compound [4] can be carried out in the presence of a base in an appropriate solvent, if necessary. The leaving group in the compound [12] can be preferably, for example, a halogen atom.

Examples of the base usable in the present reaction include the inorganic and organic bases. The inorganic bases include alkali metal carbonates (sodium carbonate, potassium carbonate, etc.), alkali metal hydrogen carbonates (sodium hydrogen carbonate, potassium hydrogen carbonate, etc.), alkali metal hydroxides (sodium hydroxide, potassium hydroxide, lithium hydroxide, etc.), alkali metal hydrides (sodium hydride, etc.). A mixture of cesium carbonate and sodium iodide can also be used. The organic bases include alkali metal alkoxides (sodium methoxide, potassium t-butoxide, etc.), tri-lower alkylamines (triethylamine, tributylamine, diisopropylethylamine, etc.), tert-amines (1,4-diazabicyclo[2.2.2]octane, 1,5-diazabicyclo[4.3.0]non-5-ene, 1,8-diazabicyclo[5.4.0]-undec-7-ene, etc.), amines (N,N-dimethylaniline, N,N-diethylaniline, 4-dimethylaminopyridine, etc.), pyridine, lutidine and collidine, etc. Above all, alkali metal carbonates, diisopropylethylamine, pyridine, etc. are preferred. In the present reaction, the bases above can also be used as a solvent.

Examples of the solvent usable in the present reaction include any inert solvent which does not disturb the reaction, such as ketones (e.g., acetone, methylethyl ketone, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), alcohols (methanol, ethanol, propanol, 2-butanol, etc.), dimethylsulfoxide, pyridine, 2,6-luthidine, etc. A mixed solvent comprising two or more of these solvents can also be used. Above all, ketones and amides are preferred.

The present reaction can generally be carried out at a temperature of under ice-cooling to the reflux temperature of the solvent.

The reaction time for the present reaction is generally between 30 minutes and 24 hours; however, longer or shorter reaction time can be selected appropriately, if necessary. Further, an alkali metal iodide such as lithium iodide, sodium iodide, potassium iodide, etc. can also be added, which may facilitate the reaction.

The reaction between the compound [13] and the compound [14] can be carried out in the presence of a base in an appropriate solvent, if necessary. The leaving group in the compound [13] can be preferably, for example, a halogen atom or a nitro group.

Examples of the base usable in the present reaction include alkali metal carbonates (sodium carbonate, potassium carbonate, cesium carbonate, etc.), alkali metal hydrides (sodium hydride, etc.) and alkali metal alkoxides (sodium methoxide, potassium t-butoxide, etc.). Above all, sodium hydride is preferred.

Examples of the solvent usable in the present reaction include amides (N,N-dimethylformamide, N,N-dimethylacetamide, 1,3-dimethyl-2-imidazolidinone, etc.) and ethers (diethyl ether, diisopropyl ether, tetrahydrofuran, dioxane, 1,2-dimethoxyethane, etc.), and N,N-dimethylformamide, N,N-dimethylacetamide, 1,3-dimethyl-2-imidazolidinone, etc. are preferred.

The reaction for formylation of the compound [11] to give the compound [10] can be carried out in a conventional manner, if necessary. For example, the reaction can be carried out by reacting a formylating agent in accordance with the method for Duff reaction, Gatterman-Koch reaction, Vilsmeier reaction, etc. in an appropriate solvent.

Any conventional formylating agent can be used without limitation, and hexamethylenetetramine, etc. are preferred.

Examples of the solvent include any inert solvent which does not disturb the reaction, such as organic acids (acetic acid, propionic acid, trifluoroacetic acid, methanesulfonic acid, etc.), halogenated hydrocarbons (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), ketones (acetone, methylethyl ketone, etc.), esters (ethyl acetate, etc.), amides (N,N-dimethylformamide, N,N-dimethylacetamide, 1,3-dimethyl-2-imidazolidinone, etc.), nitrites (acetonitrile, etc.), water, and a mixed solvent comprising two or more of these solvents, if necessary. It is preferred to select any appropriate solvent depending on the method used.

The present reaction can be carried out in a wide range of temperature from a temperature of under cooling to under heating, preferably at −78° C. to the boiling point of the reaction mixture.

The resulting compounds of the present invention thus produced can be isolated and purified by a procedure well known in the field of organic chemistry such as recrystallization, column chromatography, etc.

The present compound [1] or a pharmaceutically acceptable salt thereof has an excellent inhibitory effect on activated blood coagulation factor X, and hence is useful in the prevention and treatment of various disorders caused by thrombi and emboli in a mammal (e.g., human, monkey, rabbit, dog, cat, pig, horse, bull, mouse, rat, guinea pig, etc.), which disorders include, for example, stable angina pectoris, unstable angina pectoris, cerebral thrombosis, cerebral infarction, cerebral embolism, transient ischemic attack (TIA), ischemic cerebrovascular disease such as cerebrovascular spasm after subarachnoid hemorrhage, ischemic heart disease caused by coronary artery thrombogenesis, congestive chronic heart failure, myocardial infarction, acute myocardial infarction, pulmonary infarction, pulmonary embolism, pulmonary vascular disorders, economy-class syndrome, kidney disease (diabetic renal disease, chronic glomerulonephritis, IgA nephropathy, etc.), thrombogenesis with atherosclerosis, peripheral arterial occlusion, peripheral venous occlusion, Buerger's disease, deep vein thrombosis, disseminated intravascular coagulation (DIC), thrombogenesis after implantation of a synthetic vascular prosthesis or replacement of artificial heart valve or joint, intermittent claudication, thrombogenesis and reocclusion after blood circulation reconstruction such as percutaneous transluminal coronary angioplasty (PTCA) or percutaneous transluminal coronary artery recanalization (PTCR), systemic inflammatory response syndrome (SIRS), multiple organ failure (MODS), thrombogenesis in extracorporeal circulation, blood coagulation in case of blood drawing, diabetic circulatory disturbance, graft rejection, organ protection and improvement of function in case of transplantation, etc.

The present compound is characterized in that it shows excellent inhibitory effect on activated blood coagulation factor X, decreased toxicity, and causes few side effects (bleeding, etc.) that are seen in the existing anticoagulants.

When a FXa inhibitor has a small distribution volume (internal medicine/blood concentration), it would be substantially free of side effects such as phospholipidosis, hepatotoxicity, etc. Accordingly, FXa inhibitors, especially those having the distribution volume of 0.1-3.0 L/kg and the FXa inhibitory effect with the $IC_{50}$ value of 100 nM or below are substantially free of side effects such as phospholipidosis, hepatotoxicity, etc., and useful as a medicament for treating thrombosis. For example, trans-5-dimethylaminocarbonyl-3-[4-(N-formyl-N-methylamino)-cyclohexylcarbonylamino]-N-(5-chloropyridin-2-yl)-benzofuran-2-carboxamide has the distribution volume of 0.8 L/kg and the FXa inhibitory effect with the $IC_{50}$ value of less than 100 nM, and can be an excellent medicine being substantially free of side effects such as phospholipidosis, hepatotoxicity, etc.

FXa inhibitors having small distribution volume have preferably the following partial structure:

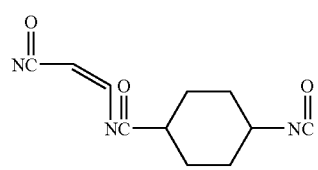

and more preferably the following partial structure:

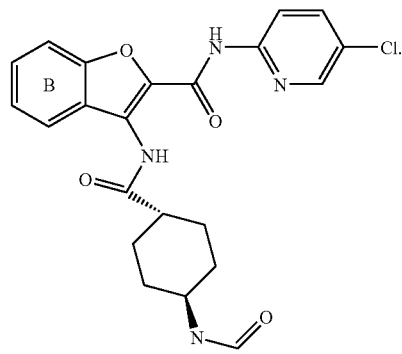

The present compound (1) or a pharmaceutically acceptable salt thereof can be formulated into a pharmaceutical composition comprising a therapeutically effective amount of the compound (1) and a pharmaceutically acceptable carrier therefor. The pharmaceutically acceptable carriers include diluents, binders (e.g., syrup, gum arabic, gelatine, sorbit, tragacanth, polyvinylpyrrolidone), excipients (e.g., lactose, sucrose, corn starch, potassium phosphate, sorbit, glycine), lubricants (e.g., magnesium stearate, talc, polyethylene glycol, silica), disintegrants (e.g., potato starch) and wetting agents (e.g., sodium lauryl sulfate), etc.

The compound [1] of the present invention or a pharmaceutically acceptable salt thereof can be administered orally or parenterally, and be used as an appropriate pharmaceutical preparation. Examples of an appropriate preparation for oral administration include solid preparations (tablets, granules, capsules, powders, etc.), solutions, suspensions and emulsions. Examples of an appropriate preparation for parenteral administration include suppository, injections or preparation for continuous infusion prepared using distilled water for injection, physiological saline or aqueous glucose solution, etc., or inhalant.

The dose of the compound [1] or a pharmaceutically acceptable salt thereof of the present invention may vary

39 depending on the administration routes, and the age, weight and condition of the patient, or the kind or severity of the disease, it is usually in the range of about 0.1 to 50 mg/kg/day, preferably about 0.1 to 30 mg/kg/day.

EXAMPLES

The present invention will be illustrated in detail by Examples and Reference Examples, but should not be construed to be limited thereto.

Example 1

Trans-5-methoxycarbonyl-3-[4-(2-oxopyrrolidin-1-yl)cyclohexylcarbonylamino]-N-(5-chloropyridin-2-yl)-benzofuran-2-carboxamide Trans-4-(2-oxopyrrolidin-1-yl)cyclohexanecarboxylic acid (634 mg) obtained in Reference Example 113 is dissolved in thionyl chloride (10 ml), and the mixture stirred at room temperature for 4 hours. The reaction solution is concentrated under reduced pressure, and the residue is dissolved in chloroform (5 ml). The mixture is added dropwise into a suspension of 3-amino-5-methoxycarbonyl-N-(5-chloropyridin-2-yl)benzofuran-2-carboxamide (691 mg) obtained in Reference Example 72 in pyridine (15 ml) under ice-cooling. After the addition, the reaction solution is warmed to room temperature, and then stirred for 17 hours. To the reaction solution is poured a saturated aqueous sodium hydrogen carbonate solution, and the mixture is extracted with chloroform. The organic layer is washed with a saturated brine, dried over sodium sulfate, and the solvent is evaporated under reduced pressure. The resulting residue is purified by NH-silica gel column chromatography (eluent: chloroform) to give the title compound (785 mg).

APCI-MS M/Z: 539/541 [M+H]$^+$

40

Example 2

Trans-3-[4-(N-acetyl-N-methylamino)cyclohexylcarbonylamino]-5-methoxycarbonylmethyl-N-(5-chloropyridin-2-yl)benzofuran-2-carboxamide

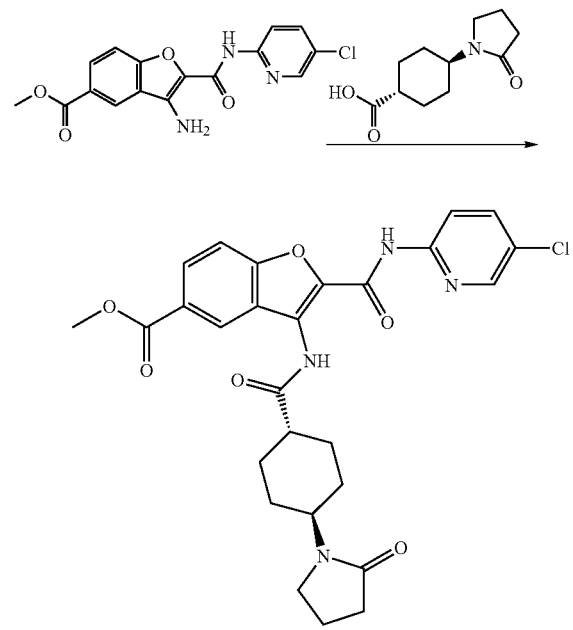

Trans-4-(N-acetyl-N-methylamino)cyclohexanecarboxylic acid (1.80 g) obtained in Reference Example 114 is dissolved in thionyl chloride (20 ml), and the mixture is stirred at room temperature for 12 hours. The reaction solution is concentrated under reduced pressure, and the residue is dissolved in chloroform (70 ml), and thereto is added 3-amino-5-methoxycarbonylmethyl-N-(5-chloropyridin-2-yl)benzofuran-2-carboxamide (2.20 g) obtained in Reference Example 73 under ice-cooling. To the mixture is further added pyridine (4.95 ml), and the reaction solution is warmed to room temperature, and stirred for 3 hours. To the reaction solution is poured a saturated aqueous sodium hydrogen carbonate solution, and the mixture is extracted with chloroform. The organic layer is washed successively with water and a saturated brine, dried over sodium sulfate, and the solvent is evaporated under reduced pressure. The resulting residue is purified by NH-silica gel column chromatography (eluent: n-hexane/ethyl acetate=1/1, then ethyl acetate only) to give the title compound (2.97 g).

APCI-MS M/Z: 541/543 [M+H]$^+$

Example 3

3-[2-(1-Isopropylpiperidin-4-yl)acetylamino]-N-(5-chloropyridin-2-yl)benzofuran-2-carboxamide dihydrochloride -continued

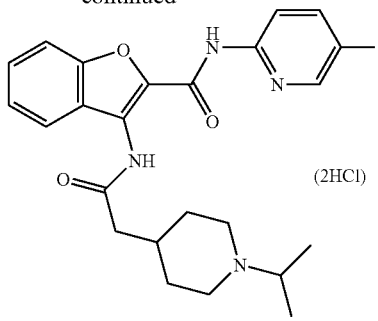
(2HCl)

(1-Isopropylpiperidin-4-yl)acetic acid hydrochloride (432 mg) obtained in Reference Example 129 is dissolved in thionyl chloride (5 ml), and the mixture is stirred at room temperature for 3 hours. The thionyl chloride is evaporated under reduced pressure, and the resulting residue is dissolved in dichloromethane (10 ml), and cooled with ice. To this solution are added 3-amino-N-(5-chloropyridin-2-yl)benzofuran-2-carboxamide (374 mg) obtained in Reference Example 74 and pyridine (420 µl), and the reaction solution is warmed to room temperature, and stirred for 3 hours. To the reaction solution was added water and a saturated aqueous sodium hydrogen carbonate solution, and the mixture is extracted with ethyl acetate. The organic layer is washed with water and a saturated brine, dried over sodium sulfate, and the solvent was evaporated under reduced pressure. The resulting residue is purified by silica gel column chromatography (eluent: chloroform, then chloroform/methanol=10/1, further 6/1) to give 3-[2-(1-isopropylpiperidin-4-yl)acetylamino]-N-(5-chloropyridin-2-yl)benzofuran-2-carboxamide (489 mg), which is further dissolved in dichloromethane (10 ml), and thereto is added 4N hydrogen chloride in dioxane (5 ml), and the mixture is stirred at room temperature for 30 minutes. The reaction solution is concentrated under reduced pressure, and the resulting residue is suspended in methanol-chloroform. The precipitates are collected by filtration to give the title compound (423 mg).

APCI-MS M/Z: 455/457 [M+H]+

Examples 4-75

The corresponding amino compounds and carboxylic acid compounds are treated in a similar manner to Example 1, Example 2 or Example 3 to give the following compounds in a free form, which are further treated with hydrogen chloride to give hydrochlorides thereof.

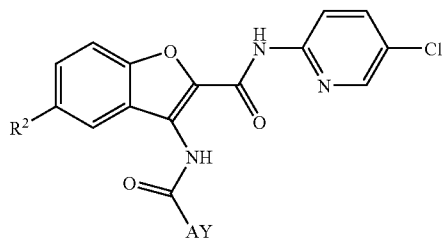

| Ex. No. | —R² | —AY | Physicochemical properties |
|---|---|---|---|
| 4 |  | 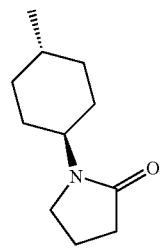 | APCI-MS M/Z: 511/513 [M + H]+ |
| 5 | 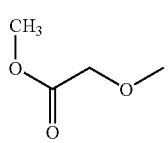 | 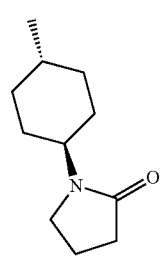 | APCI-MS M/Z: 369/571 [M + H]+ |

-continued
| | | | |
|---|---|---|---|
| 6 |  | 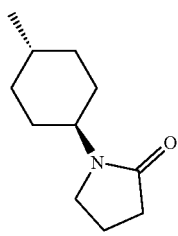 | APCI-MS M/Z: 506/508 [M + H]+ |
| 7 |  | 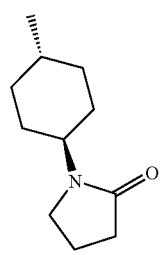 | APCI-MS M/Z: 497/499 [M + H]+ |
| 8 | 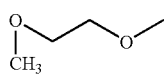 | 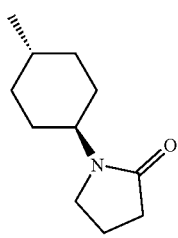 | APCI-MS M/Z: 555/557 [M + H]+ |
| 9 | 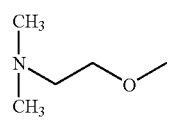 | 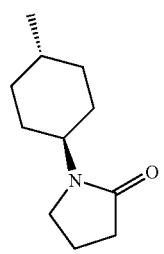 | APCI-MS M/Z: 568/570 [M + H]+ Hydrochloride |
| 10 | 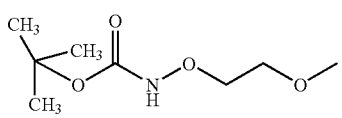 | 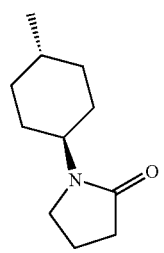 | APCI-MS M/Z: 673/675 [M + NH4]+ |
| 11 | 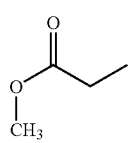 | 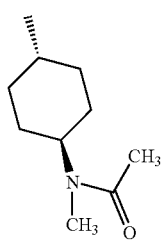 | APCI-MS M/Z: 541/543 [M + H]+ |

-continued
| | | | |
|---|---|---|---|
| 12 |  | 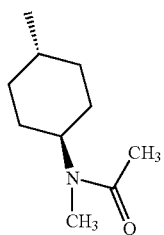 | APCI-MS M/Z: 499/501 [M + H]+ |
| 13 | 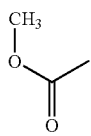 | 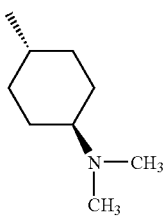 | APCI-MS M/Z: 499/501 [M + H]+ Dihydrochloride |
| 14 | 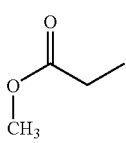 | 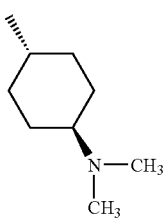 | APCI-MS M/Z: 513/515 [M + H]+ Hydrochloride |
| 15 |  | 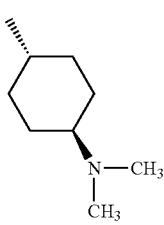 | APCI-MS M/Z: 475/477 [M + H]+ |
| 16 |  | 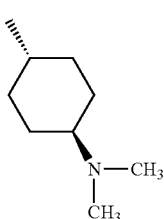 | APCI-MS M/Z: 519/521 [M + H]+ |
| 17 |  | 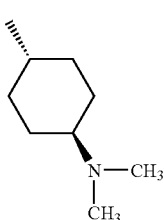 | APCI-MS M/Z: 455/457 [M + H]+ Dihydrochloride |
| 18 |  | 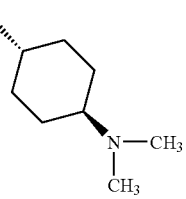 | APCI-MS M/Z: 486/488 [M + H]+ Hydrochloride |

-continued
| | | | |
|---|---|---|---|
| 19 |  | 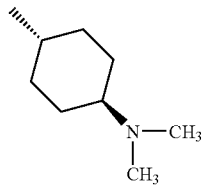 | APCI-MS M/Z: 471/473 [M + H]+ Hydrochloride |
| 20 | 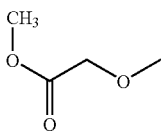 | 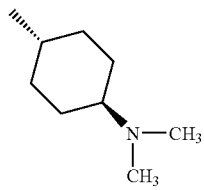 | APCI-MS M/Z: 529/531 [M + H]+ |
| 21 | 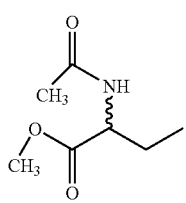 | 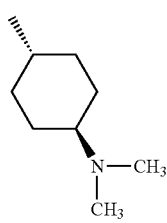 | APCI-MS M/Z: 584/586 [M + H]+ |
| 22 | 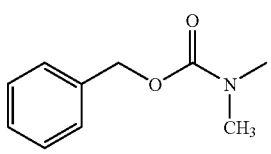 | 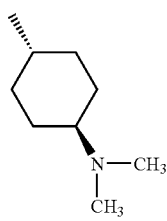 | APCI-MS M/Z: 604/606 [M + H]+ Hydrochloride |
| Ex. No. | Structure | Physicochemical Properties |
|---|---|---|
| 23 | 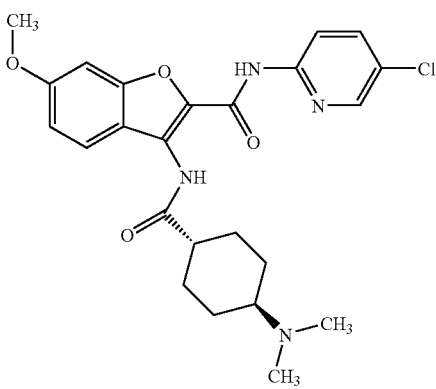 | APCI-MS M/Z: 471/473 [M + H]+ Hydrochloride |

-continued
| | | |
|---|---|---|
| 24 | 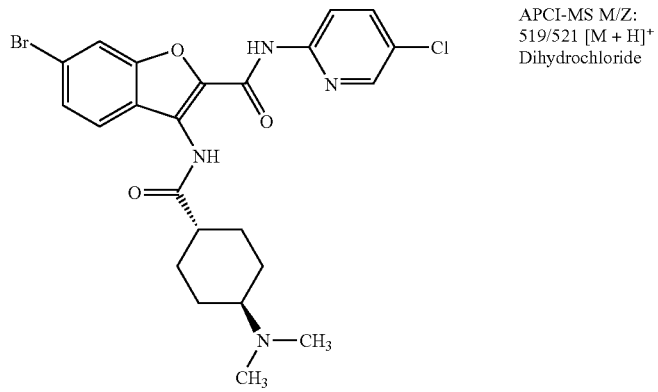 | APCI-MS M/Z: 519/521 [M + H]$^+$ Dihydrochloride |
| 25 | 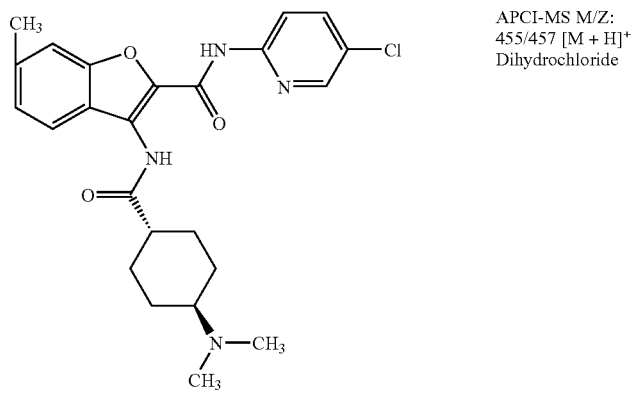 | APCI-MS M/Z: 455/457 [M + H]$^+$ Dihydrochloride |
| 26 | 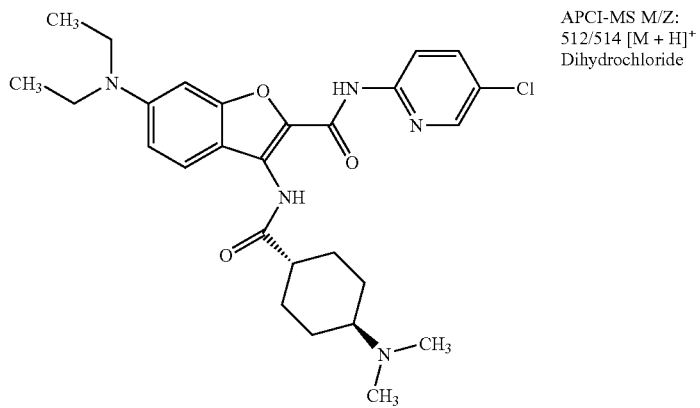 | APCI-MS M/Z: 512/514 [M + H]$^+$ Dihydrochloride |
| 27 | 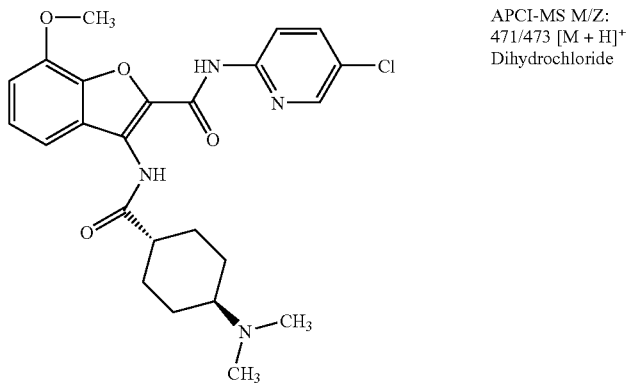 | APCI-MS M/Z: 471/473 [M + H]$^+$ Dihydrochloride |

-continued
| 28 | 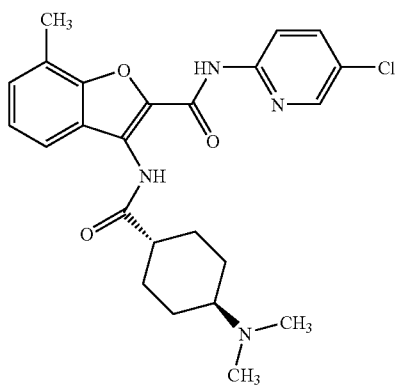 | APCI-MS M/Z: 455/457 [M + H]+ Dihydrochloride |
| --- | --- | --- |
| 29 | 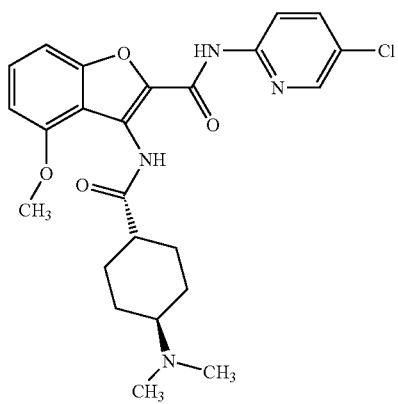 | APCI-MS M/Z: 471/473 [M + H]+ Hydrochloride |
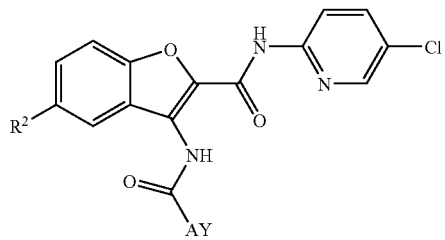
| Ex. No. | —R² | —AY | Physicochemical Properties |
| --- | --- | --- | --- |
| 30 |  | 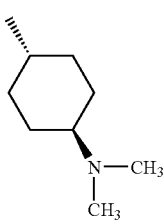 | APCI-MS M/Z: 466/468 [M + H]+ Hydrochloride |
| 31 | 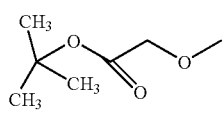 | 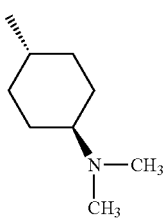 | APCI-MS M/Z: 571/573 [M + H]+ |

-continued
| | | | |
|---|---|---|---|
| 32 | 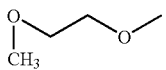 | 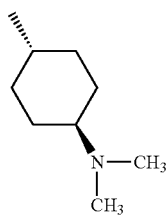 | APCI-MS M/Z: 515/517 [M + H]+ Dihydrochloride |
| 33 | 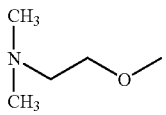 | 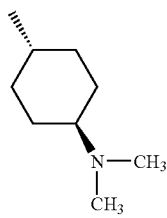 | APCI-MS M/Z: 528/530 [M + H]+ Trihydrochloride |
| 34 | 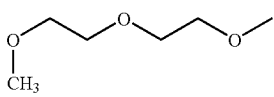 | 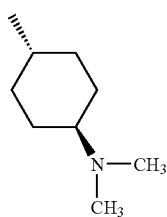 | APCI-MS M/Z: 559/561 [M + H]+ Dihydrochloride |
| 35 | 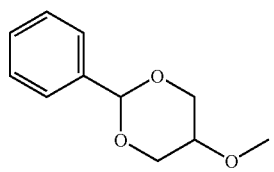 | 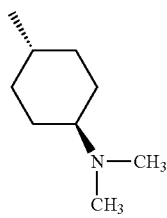 | APCI-MS M/Z: 619/621 [M + H]+ |
| 36 | 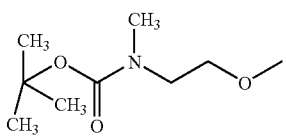 | 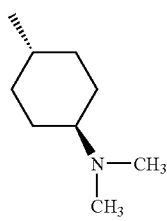 | APCI-MS M/Z: 614/616 [M + H]+ |
| Ex. No. | Structure | Physicochemical Properties |
|---|---|---|
| 37 | 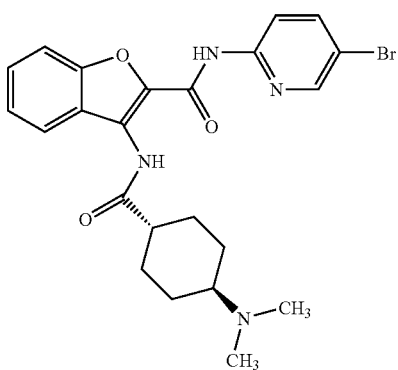 | APCI-MS M/Z: 485/487 [M + H]+ |

| | | |
|---|---|---|
| 38 | 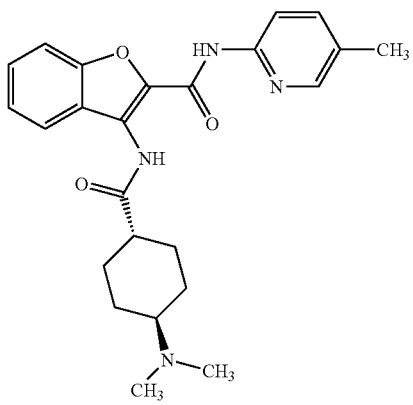 | APCI-MS M/Z:<br>421 [M + H]+<br>Hydrochloride |
| 39 | 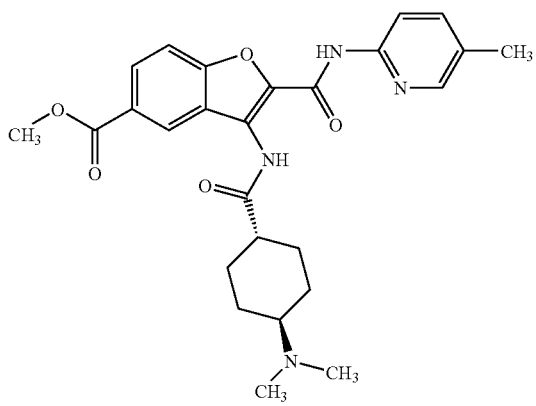 | APCI-MS M/Z:<br>479 [M + H]+<br>Dihydrochloride |
| 40 | 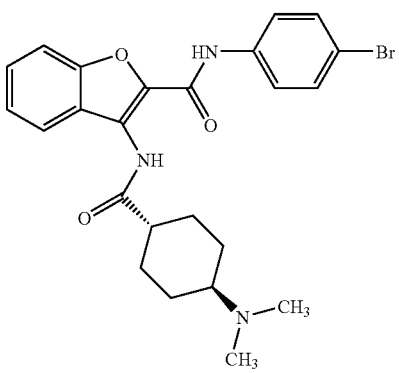 | APCI-MS M/Z:<br>484/486 [M + H]+ |
| 41 | 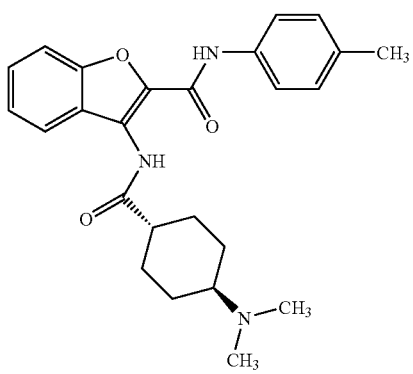 | APCI-MS M/Z:<br>420 [M + H]+ |

-continued
| 42 | 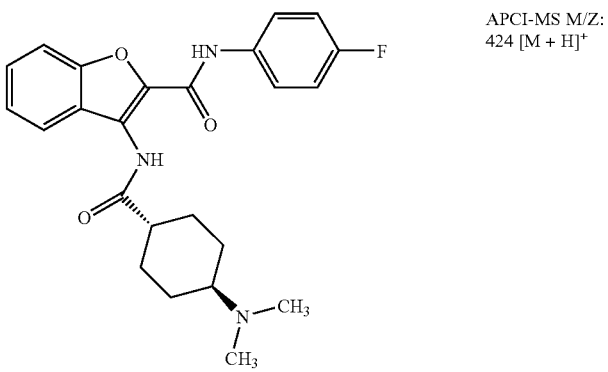 | APCI-MS M/Z: 424 [M + H]+ |
| --- | --- | --- |
| 43 | 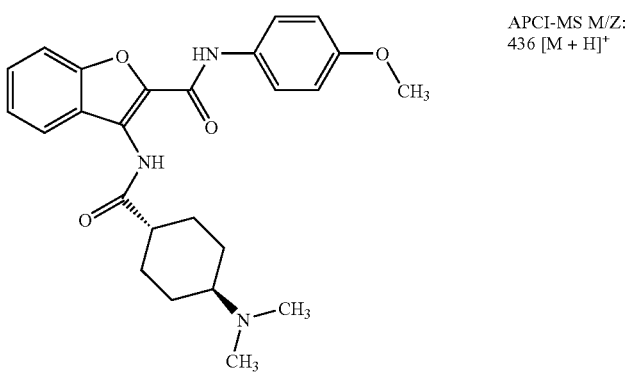 | APCI-MS M/Z: 436 [M + H]+ |
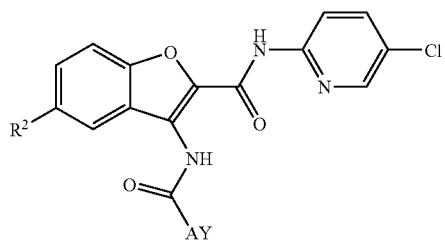
| Ex. No. | —R² | —AY | Physicochemical Properties |
| --- | --- | --- | --- |
| 44 | 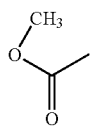 | 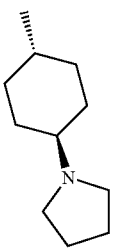 | APCI-MS M/Z: 525/527 [M + H]+ Dihydrochloride |
| 45 | 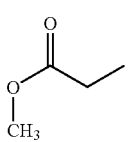 |  | APCI-MS M/Z: 539/541 [M + H]+ Dihydrochloride |

-continued
| | | | |
|---|---|---|---|
| 46 | 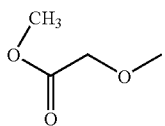 | 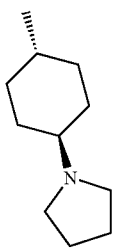 | APCI-MS M/Z: 555/557 [M + H]+ |
| 47 | 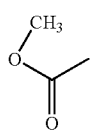 | 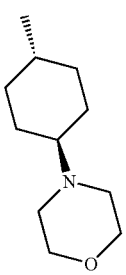 | APCI-MS M/Z: 541/543 [M + H]+ Dihydrochloride |
| 48 | 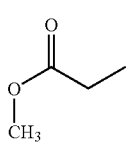 | 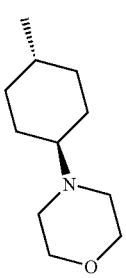 | APCI-MS M/Z: 555/557 [M + H]+ Hydrochloride |
| 49 | —H | 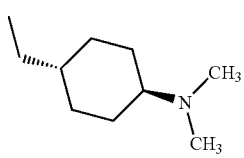 | APCI-MS M/Z: 455/456 [M + H]+ Dihydrochloride |
| 50 |  Cl | 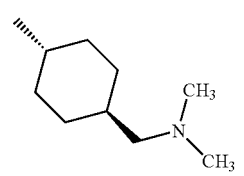 | APCI-MS M/Z: 489/491 [M + H]+ Hydrochloride |
| 51 |  Br | 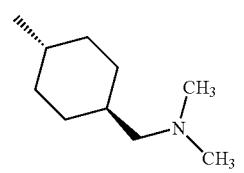 | APCI-MS M/Z: 533/535 [M + H]+ Hydrochloride |
| 52 | 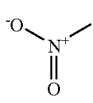 | 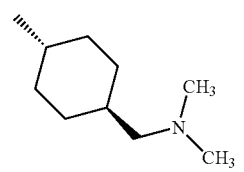 | APCI-MS M/Z: 500/502 [M + H]+ Hydrochloride |

-continued
| | | |
|---|---|---|
| 53 | 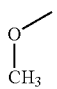 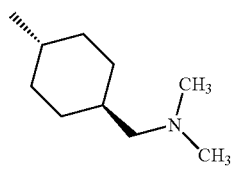 | APCI-MS M/Z: 485/487 [M + H]+ Hydrochloride |
| Ex. No. | Structure | Physicochemical Properties |
|---|---|---|
| 54 | 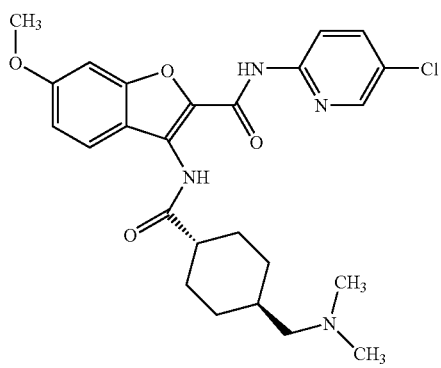 | APCI-MS M/Z: 485/487 [M + H]+ Dihydrochloride |
| 55 | 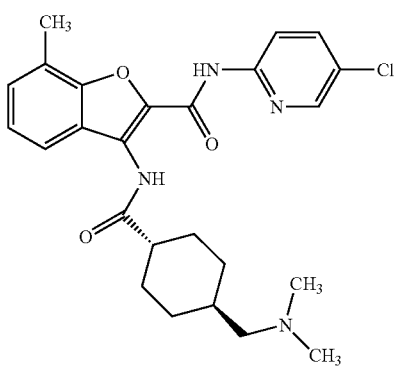 | APCI-MS M/Z: 469/471 [M + H]+ Hydrochloride |
| Ex. No. | —R² | —AY | Physicochemical Properties |
|---|---|---|---|
| 56 |  Cl | 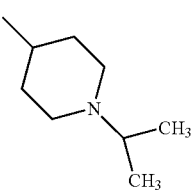 | APCI-MS M/Z: 475/477 [M + H]+ Dihydrochloride |

-continued
| | | | |
|---|---|---|---|
| 57 |  Br | ![piperidine-isopropyl] | APCI-MS M/Z:<br>519/521 [M + H]+<br>Dihydrochloride |
| 58 |  -O-N+=O | ![piperidine-isopropyl] | APCI-MS M/Z:<br>486/488 [M + H]+<br>Dihydrochloride |
| 59 |  O-CH3 | ![piperidine-isopropyl] | APCI-MS M/Z:<br>471/473 [M + H]+<br>Dihydrochloride |
| Ex. No. | Structure | Physicochemical Properties |
|---|---|---|
| 60 | 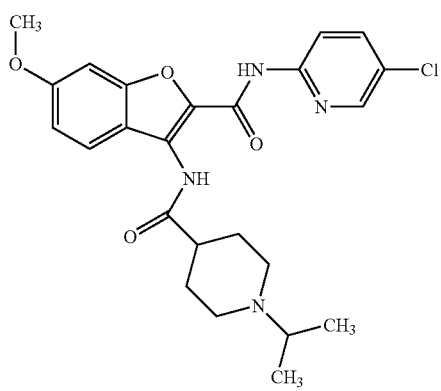 | APCI-MS M/Z:<br>471/473 [M + H]+<br><br>Dihydrochloride |
| 61 | 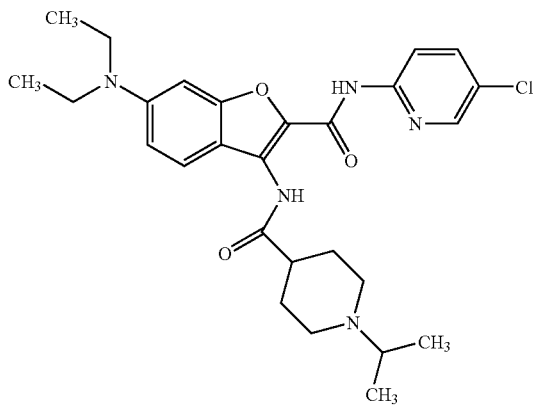 | APCI-MS M/Z:<br>512/514 [M + H]+<br>Trihydrochloride |

-continued
| | | |
|---|---|---|
| 62 | 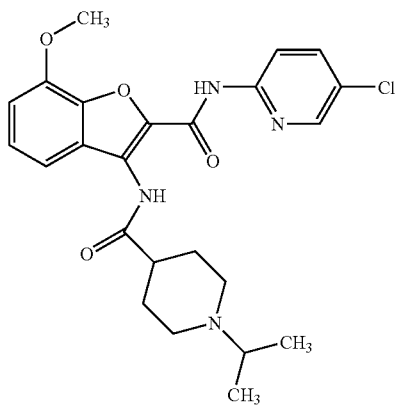 | APCI-MS M/Z: 471/473 [M + H]+ Dihydrochloride |
| 63 | 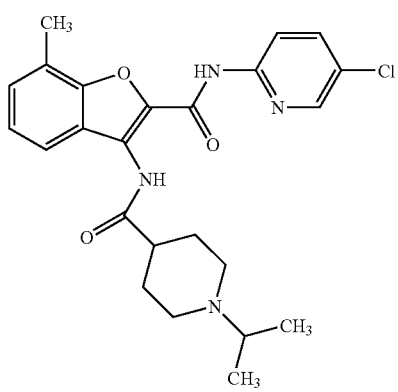 | APCI-MS M/Z: 455/457 [M + H]+ Dihydrochloride |
| 64 | 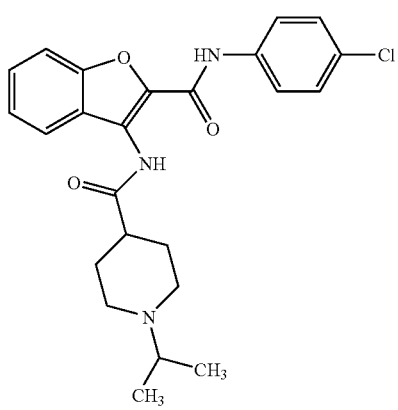 | APCI-MS M/Z: 440 [M + H]+ |
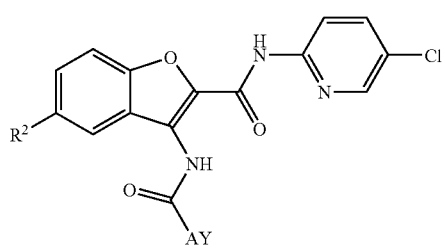
| Ex. No. | —$R^2$ | —AY | Physicochemical Properties |
|---|---|---|---|

-continued
| | | | |
|---|---|---|---|
| 65 |  | 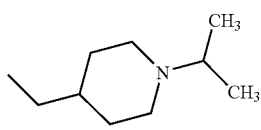 | APCI-MS M/Z: 533/535 [M + H]⁺ Dihydrochloride |
| 66 |  | 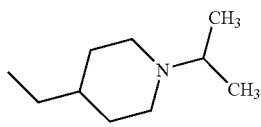 | APCI-MS M/Z: 485/487 [M + H]⁺ Dihydrochloride |
| Ex. No. | Structure | Physicochemical Properties |
|---|---|---|
| 67 | 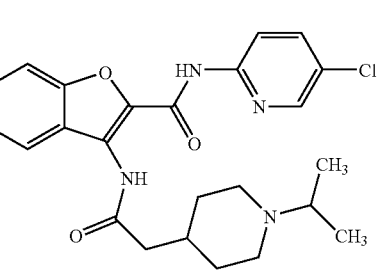 | APCI-MS M/Z: 485/487 [M + H]⁺ Dihydrochloride |
| 68 | 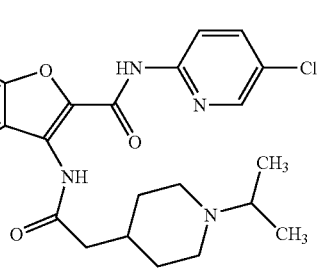 | APCI-MS M/Z: 469/471 [M + H]⁺ Dihydrochloride |
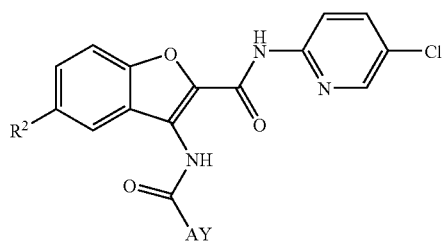
| Ex. No. | —R² | —AY | Physicochemical Properties |
|---|---|---|---|
| 69 | —H | 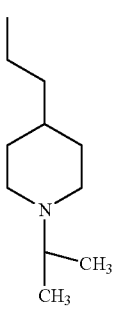 | APCI-MS M/Z: 469/471 [M + H]⁺ Dihydrochloride |

-continued
| | | | |
|---|---|---|---|
| 70 | —H | 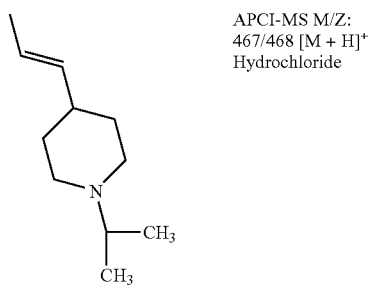 | APCI-MS M/Z: 467/468 [M + H]+ Hydrochloride |
| 71 | —H | 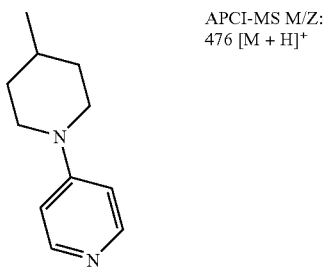 | APCI-MS M/Z: 476 [M + H]+ |
| 72 | —H | 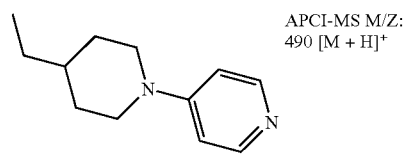 | APCI-MS M/Z: 490 [M + H]+ |
| 73 | —H | 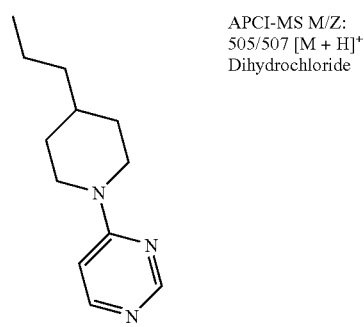 | APCI-MS M/Z: 505/507 [M + H]+ Dihydrochloride |
| 74 | —H | 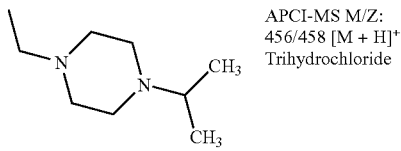 | APCI-MS M/Z: 456/458 [M + H]+ Trihydrochloride |
| 75 | —H | 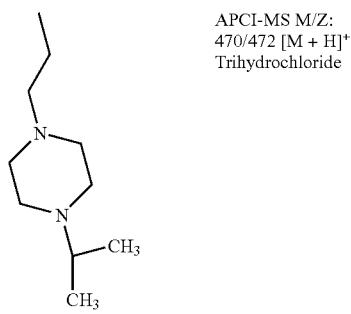 | APCI-MS M/Z: 470/472 [M + H]+ Trihydrochloride |

Example 76

3-[(1-Isopropylpiperidin-4-yl)carbonylamino]-N-(5-chloropyridin-2-yl)benzofuran-2-carboxamide

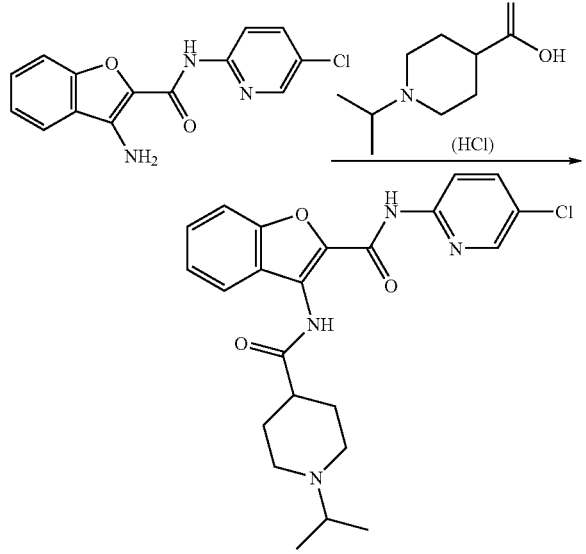

3-Amino-N-(5-chloropyridin-2-yl)benzofuran-2-carboxamide (201 mg) obtained in Reference Example 74 is dissolved in N,N-dimethylformamide (6 ml), and thereto are successively added (1-isopropylpiperidin-4-yl)carboxylic acid hydrochloride (199 mg) obtained in Reference Example 130, 4-dimethylaminopyridine (137 mg) and 1-ethyl-3-(3-dimethylaminopropyl)carbodiimide hydrochloride (203 mg), and the mixture is stirred at 60° C. for 4 hours. The reaction solution is diluted with ethyl acetate, and water and a saturated aqueous sodium hydrogen carbonate solution are poured thereto, and the mixture is extracted with ethyl acetate. The organic layer is washed with water and a saturated brine, dried over sodium sulfate, and charged onto NH-silica gel pad. The solvent is evaporated under reduced pressure, and the resulting residue is purified recycled HPLC and suspended in diethyl ether/n-hexane. The precipitates are collected by filtration to give the title compound (174 mg).

APCI-MS M/Z: 441 [M+H]$^+$

Example 77

Trans-5-carboxy-3-[4-(2-oxopyrrolidin-1-yl)-cyclohexylcarbonylamino]-N-(5-chloropyridin-2-yl)benzofuran-2-carboxamide

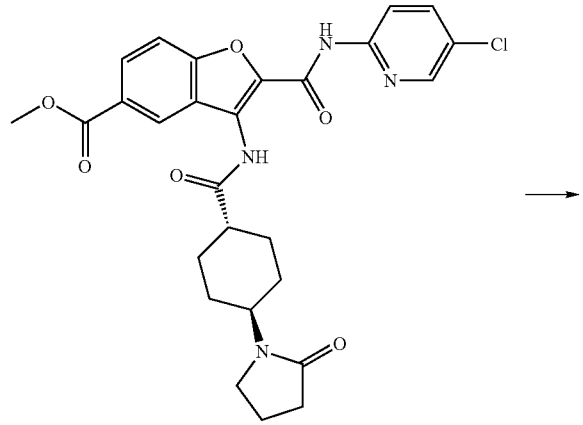

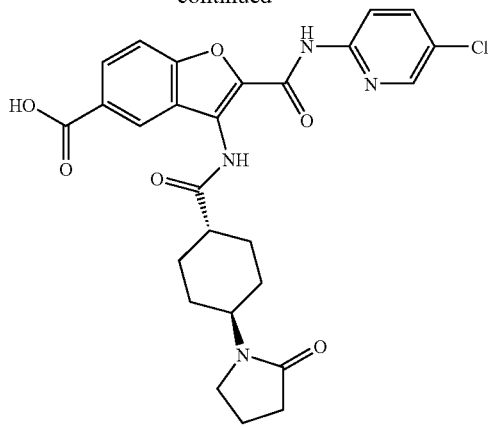

Trans-5-methoxycarbonyl-3-[4-(2-oxopyrrolidin-1-yl)-cyclohexylcarbonylamino]-N-(5-chloropyridin-2-yl)benzofuran-2-carboxamide (710 mg) obtained in Example 1 is suspended in tetrahydrofuran-methanol (1:1, 10 ml), and thereto is added 4N aqueous sodium hydroxide solution (2 ml) under ice-cooling. The mixture is warmed to room temperature, and stirred for 18 hours. The reaction solution is concentrated under reduced pressure, and thereto is poured ice-water, and the mixture is neutralized with 10% hydrochloric acid. The precipitates are collected by filtration, washed with water, and dried to give the title compound (655 mg).

ESI-MS M/Z: 523/525 [M−H]$^−$

Examples 78-86

The corresponding carboxylic acid esters are treated in a similar manner to Example 77 to give the following compounds in a free form, which are further treated with hydrogen chloride to give hydrochlorides thereof.

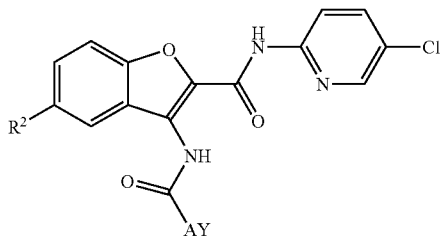

| Ex. No. | —R$^2$ | —AY | Physicochemical Properties |
|---|---|---|---|
| 78 | HO-C(=O)- | trans-cyclohexyl-N(CH$_3$)$_2$ | APCI-MS M/Z: 483/485 [M − H]$^−$ |

| Ex. No. | Structure | Physicochemical Properties |
|---|---|---|

-continued

| | | | Physicochemical Properties |
|---|---|---|---|
| 79 | 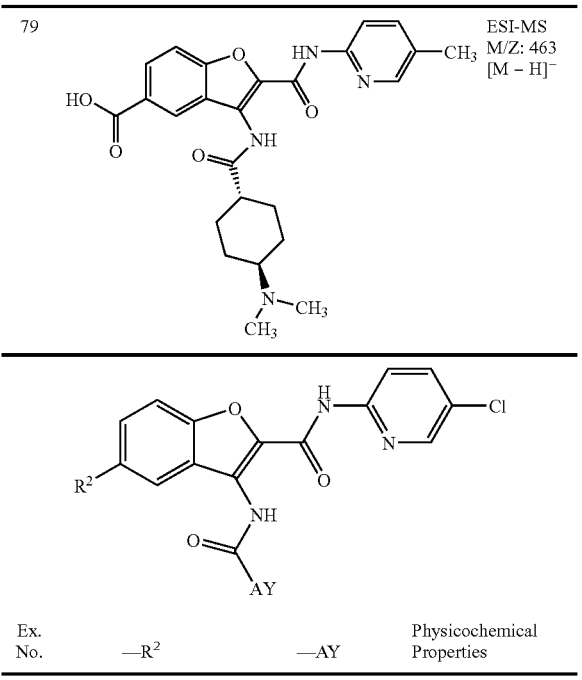 | | ESI-MS M/Z: 463 [M − H]⁻ |

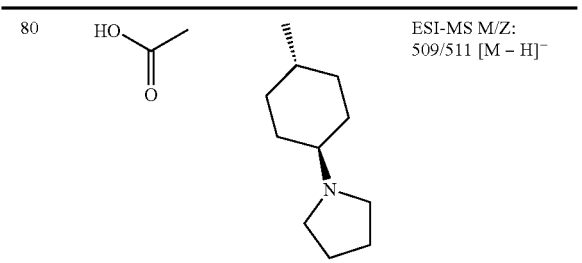

| Ex. No. | —R² | —AY | Physicochemical Properties |
|---|---|---|---|
| 80 |  | | ESI-MS M/Z: 509/511 [M − H]⁻ |
| 81 | 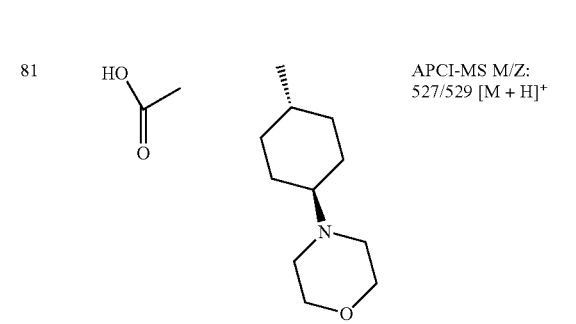 | | APCI-MS M/Z: 527/529 [M + H]⁺ |
| 82 | | | ESI-MS M/Z: 537/539 [M − H]⁻ |

-continued

| Ex. No. | —R² | —AY | Physicochemical Properties |
|---|---|---|---|
| 83 | | | ESI-MS M/Z: 525/527 [M − H]⁻ |
| 84 | | | ESI-MS M/Z: 497/499 [M − H]⁻ |
| 85 | | | ESI-MS M/Z: 523/525 [M − H]⁻ |
| 86 | | | ESI-MS M/Z: 541/543 [M + H]⁺ |

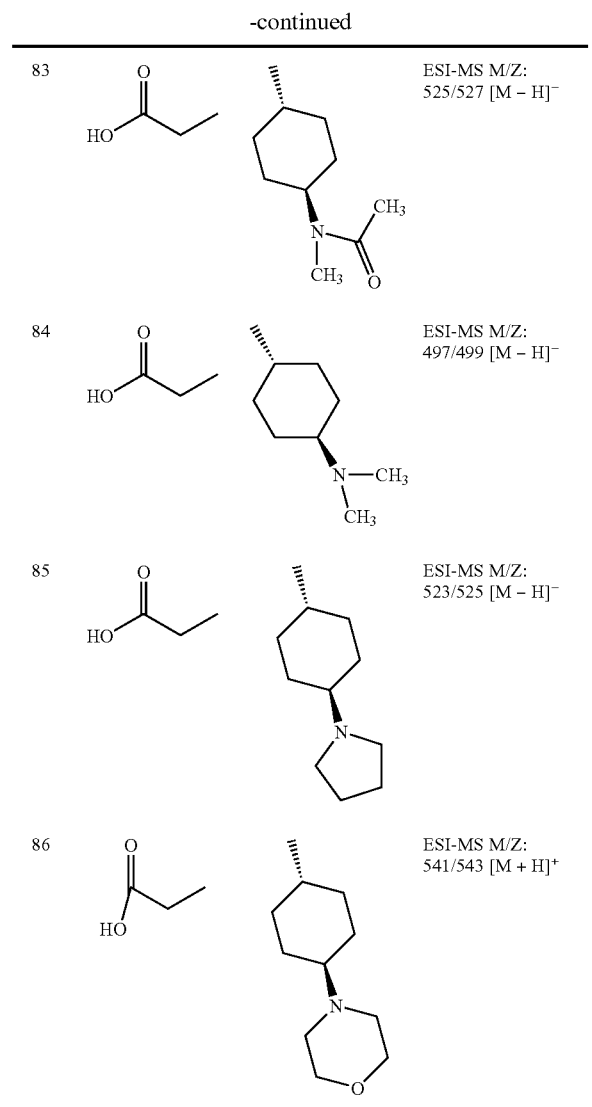

Example 87
Trans-5-(morpholin-4-ylcarbonyl)-3-[4-(2-oxopyrrolidin-1-yl)cyclohexylcarbonylamino]-N-(5-chloropyridin-2-yl)benzofuran-2-carboxamide

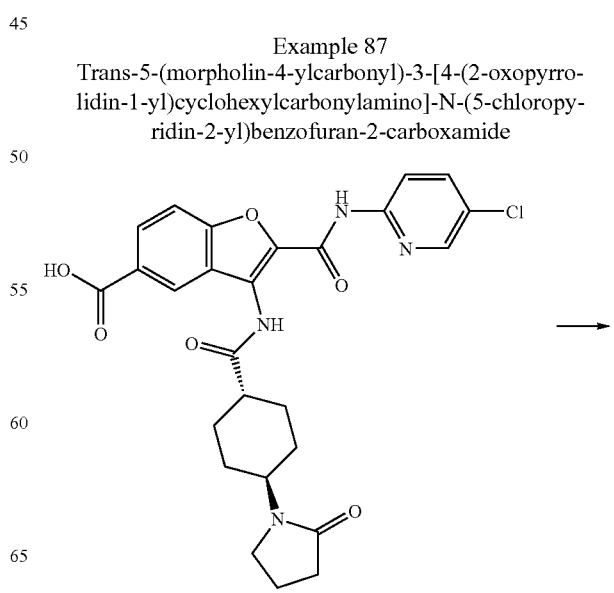 →

75
-continued

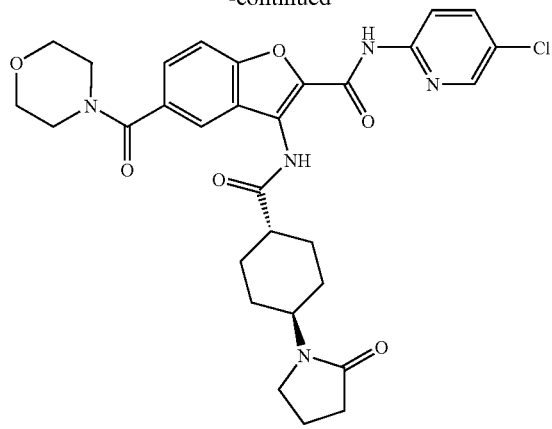

Trans-5-carboxy-3-[4-(2-oxopyrrolidin-1-yl)cyclohexyl-carbonylamino]-N-(5-chloropyridin-2-yl)benzofuran-2-carboxamide (830 mg) obtained in Example 77 is suspended in N,N-dimethylformamide-pyridine (1:1, 30 ml), and thereto are added successively morpholine (196 mg), 1-hydroxybenzotriazole (406 mg) and 1-ethyl-3-(3-dimethylaminopropyl) carbodiimide hydrochloride (576 mg) under ice-cooling, and the mixture is stirred at room temperature for 17 hours. To the reaction solution are poured ice-water and a saturated aqueous sodium hydrogen carbonate solution, and the mixture is extracted with ethyl acetate, washed with water and a saturated brine, and dried over sodium sulfate. The solvent is evaporated under reduced pressure, and the resulting residue is purified by NH-silica gel column chromatography (eluent: chloroform). The resulting residue is suspended in ethyl acetate-n-hexane, and the precipitates are collected by filtration, and dried to give the title compound (805 mg).

APCI-MS M/Z: 594/596 [M+H]$^+$

Examples 88-143

The corresponding compounds are treated in a similar manner to Example 87 to give the following compounds in a free form, which are further treated with hydrogen chloride to give hydrochlorides thereof.

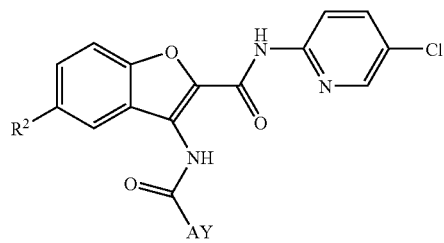

| Ex. No. | —R² | —AY | Physicochemical Properties |
|---|---|---|---|
| 88 | CH₃–N(CH₃)–C(=O)– | cyclohexyl-(2-oxopyrrolidin-1-yl) | APCI-MS M/Z: 552/554 [M + H]$^+$ |
| 89 | CH₃–O–CH₂CH₂–N(CH₃)–C(=O)– | cyclohexyl-(2-oxopyrrolidin-1-yl) | APCI-MS M/Z: 596/599 [M + H]$^+$ |

-continued
| | | | |
|---|---|---|---|
| 90 | 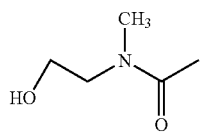 | 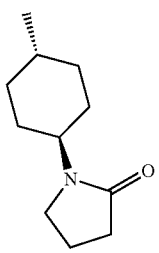 | APCI-MS M/Z: 582/584 [M + H]⁺ |
| 91 | 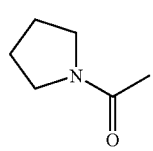 | 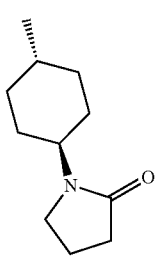 | APCI-MS M/Z: 578/580 [M + H]⁺ |
| 92 | 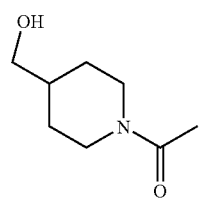 | 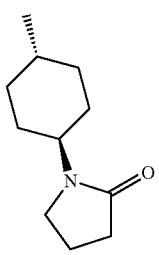 | APCI-MS M/Z: 622/624 [M + H]⁺ |
| 93 | 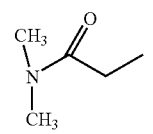 | 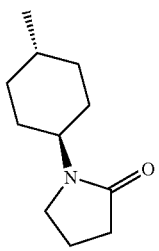 | APCI-MS M/Z: 566/568 [M + H]⁺ |
| 94 | 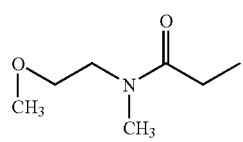 | 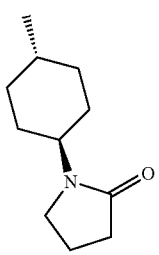 | APCI-MS M/Z: 610/612 [M + H]⁺ |

-continued
| | | | |
|---|---|---|---|
| 95 | 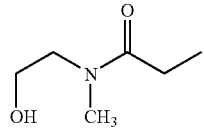 | 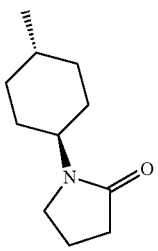 | APCI-MS M/Z: 596/598 [M + H]+ |
| 96 | 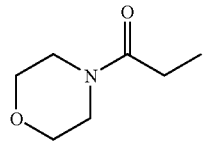 | 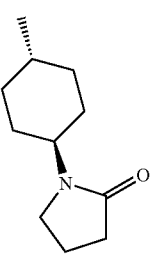 | APCI-MS M/Z: 608/610 [M + H]+ |
| 97 | 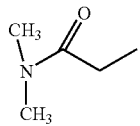 | 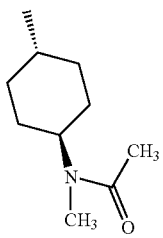 | APCI-MS M/Z: 554/556 [M + H]+ |
| 98 | 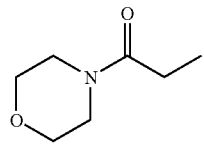 | 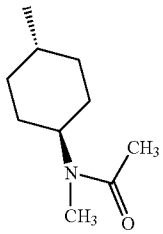 | APCI-MS M/Z: 596/598 [M + H]+ |
| 99 | 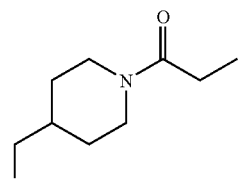 | 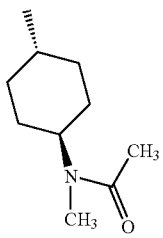 | APCI-MS M/Z: 624/626 [M + H]+ |

| 100 | 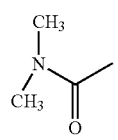 | 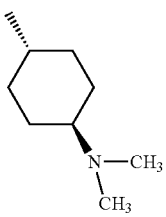 | APCI-MS M/Z: 512/514 [M + H]+ Dihydrochloride |
| Ex. No. | Structure | Physicochemical Properties |
|---|---|---|
| 101 | 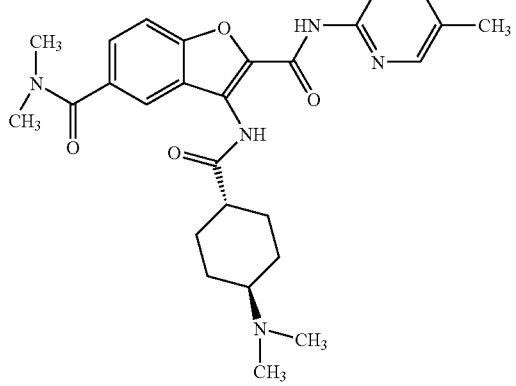 | APCI-MS M/Z: 492 [M + H]+ Hydrochloride |
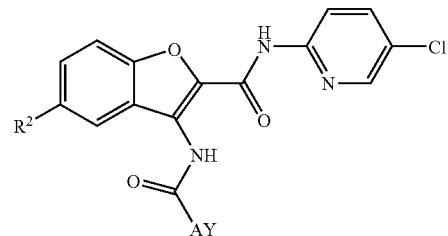
| Ex. No. | —R² | —AY | Physicochemical Properties |
|---|---|---|---|
| 102 | 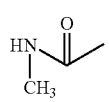 | 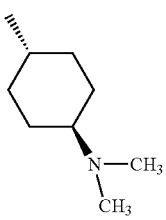 | APCI-MS M/Z: 498/500 [M + H]+ Dihydrochloride |
| 103 | 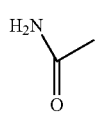 | 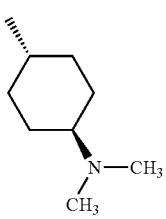 | APCI-MS M/Z: 484/486 [M + H]+ Dihydrochloride |

-continued
| | | | |
|---|---|---|---|
| 104 | 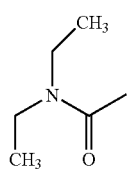 | 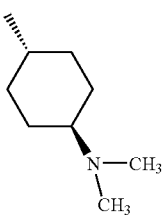 | APCI-MS M/Z: 540/542 [M + H]+ Hydrochloride |
| 105 | 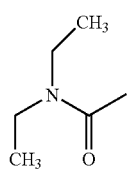 | 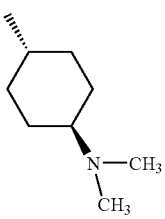 | APCI-MS M/Z: 528/530 [M + H]+ Hydrochloride |
| Ex. No. | Structure | Physicochemical Properties |
|---|---|---|
| 106 | 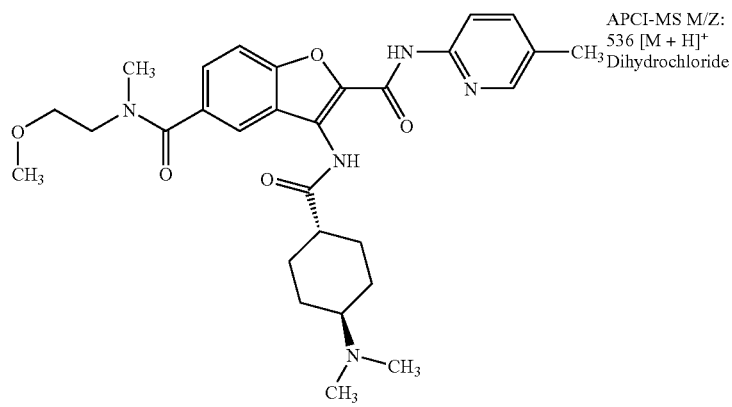 | APCI-MS M/Z: 536 [M + H]+ Dihydrochloride |
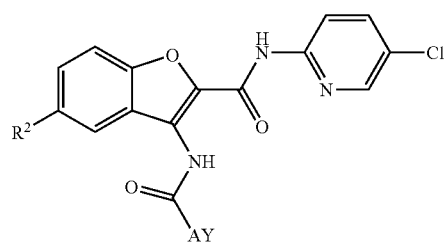
| Ex. No. | —R² | —AY | Physicochemical Properties |
|---|---|---|---|
| 107 | 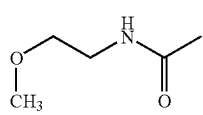 | 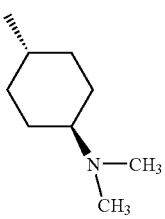 | APCI-MS M/Z: 542/544 [M + H]+ Dihydrochloride |

-continued
| | | | |
|---|---|---|---|
| 108 | 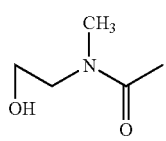 | 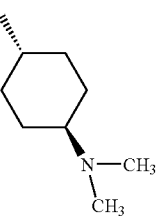 | APCI-MS M/Z: 542/544 [M + H]+ Hydrochloride |
| 109 | 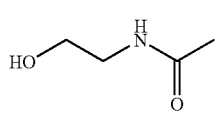 | 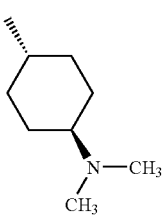 | APCI-MS M/Z: 528/530 [M + H]+ Dihydrochloride |
| 110 | 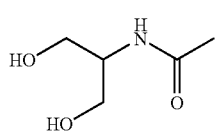 | 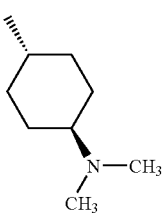 | APCI-MS M/Z: 558/560 [M + H]+ |
| 111 | 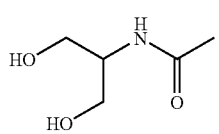 | 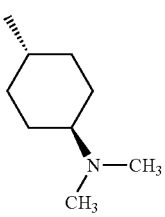 | APCI-MS M/Z: 558/560 [M + H]+ Dihydrochloride |
| 112 | 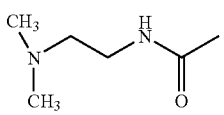 | 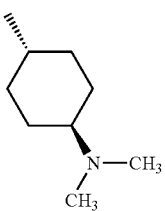 | APCI-MS M/Z: 555/557 [M + H]+ Trihydrochloride |
| 113 | 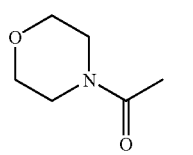 | 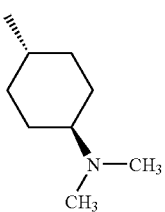 | APCI-MS M/Z: 554/556 [M + H]+ Dihydrochloride |
| 114 | 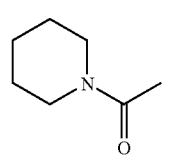 | 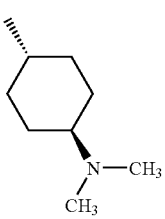 | APCI-MS M/Z: 552/554 [M + H]+ Dihydrochloride |

-continued
| | | | |
|---|---|---|---|
| 115 | 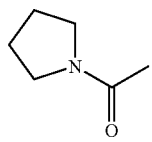 | 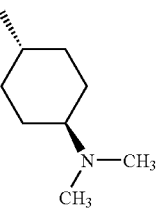 | APCI-MS M/Z: 538/540 [M + H]+ Dihydrochloride |
| 116 | 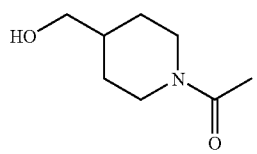 | 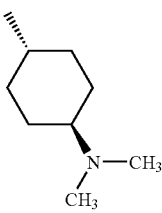 | APCI-MS M/Z: 582/584 [M + H]+ Dihydrochloride |
| 117 | 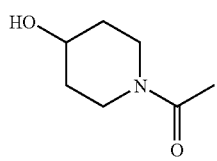 | 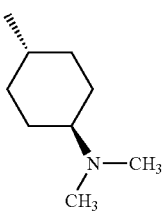 | APCI-MS M/Z: 568/570 [M + H]+ Dihydrochloride |
| 118 | 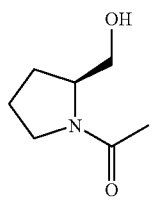 | 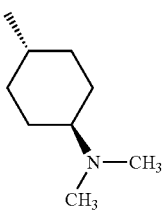 | APCI-MS M/Z: 568/570 [M + H]+ Hydrochloride |
| 119 | 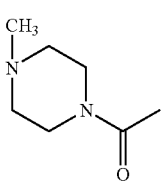 | 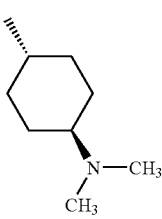 | APCI-MS M/Z: 567/569 [M + H]+ Trihydrochloride |
| 120 | 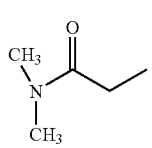 | 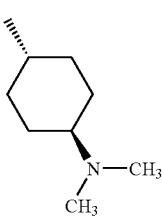 | APCI-MS M/Z: 526/528 [M + H]+ Hydrochloride |
| 121 | 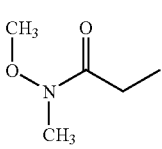 | 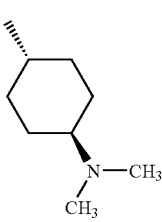 | APCI-MS M/Z: 542/544 [M + H]+ Hydrochloride |

-continued
| | | | |
|---|---|---|---|
| 122 | 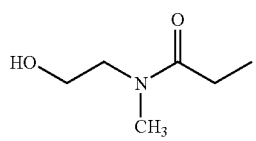 | 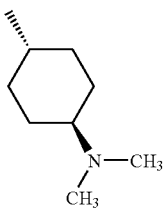 | APCI-MS M/Z: 556/558 [M + H]⁺ |
| 123 | 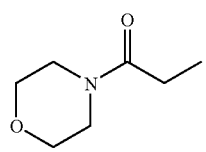 | 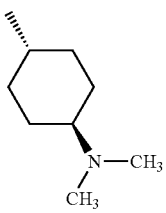 | APCI-MS M/Z: 568/570 [M + H]⁺ Hydrochloride |
| 124 | 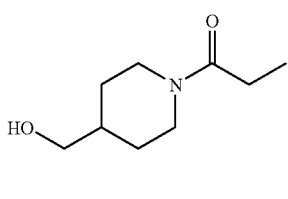 | 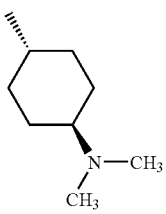 | APCI-MS M/Z: 596/598 [M + H]⁺ Hydrochloride |
| 125 | 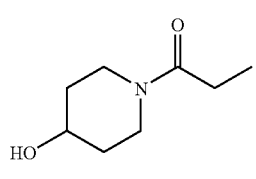 | 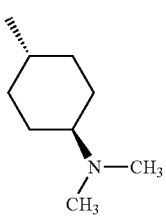 | APCI-MS M/Z: 582/584 [M + H]⁺ Hydrochloride |
| 126 | 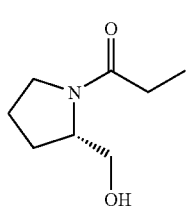 | 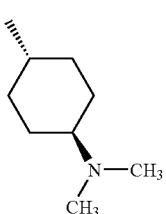 | APCI-MS M/Z: 582/584 [M + H]⁺ Hydrochloride |
| 127 | 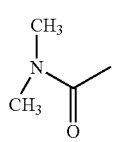 | 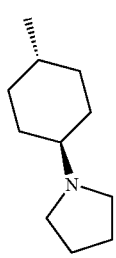 | APCI-MS M/Z: 538/540 [M + H]⁺ |
| 128 | 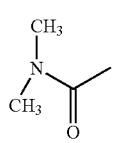 | 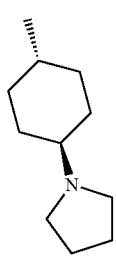 | APCI-MS M/Z: 538/540 [M + H]⁺ Hydrochloride |

-continued
| | | | |
|---|---|---|---|
| 129 | 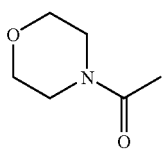 | 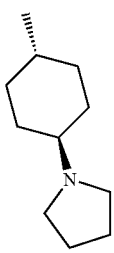 | APCI-MS M/Z: 580/582 [M + H]+ Dihydrochloride |
| 130 | 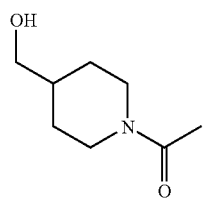 | 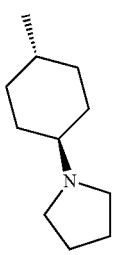 | APCI-MS M/Z: 608/610 [M + H]+ Dihydrochloride |
| 131 | 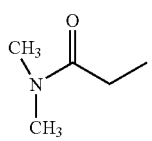 | 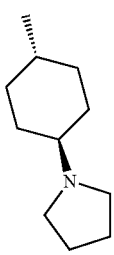 | APCI-MS M/Z: 552/554 [M + H]+ Dihydrochloride |
| 132 | 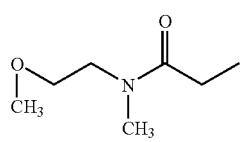 | 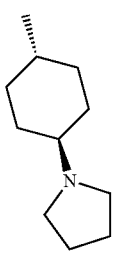 | APCI-MS M/Z: 596/598 [M + H]+ Dihydrochloride |
| 133 | 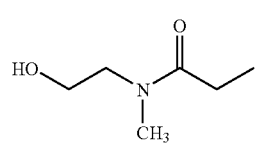 |  | APCI-MS M/Z: 582/584 [M + H]+ |
| 134 | 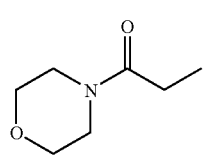 | 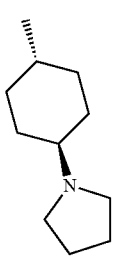 | APCI-MS M/Z: 594/596 [M + H]+ Dihydrochloride |

| | | |
|---|---|---|
| 135 | 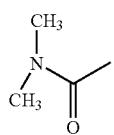 | 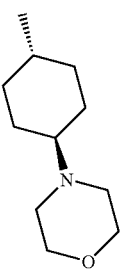 APCI-MS M/Z: 554/556 [M + H]+ Dihydrochloride |
| 136 | 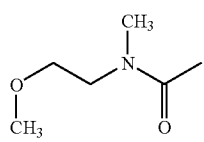 | 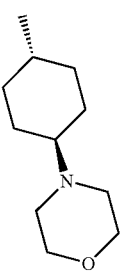 APCI-MS M/Z: 598/600 [M + H]+ |
| 137 | 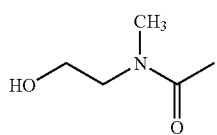 | 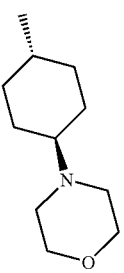 APCI-MS M/Z: 584/586 [M + H]+ |
| 138 | 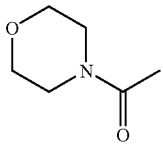 | 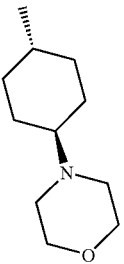 APCI-MS M/Z: 596/598 [M + H]+ |
| 139 | 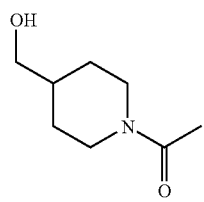 | 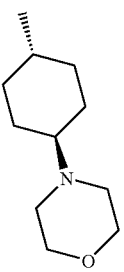 APCI-MS M/Z: 624/626 [M + H]+ |

-continued
| 140 | 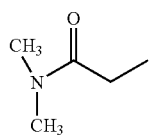 | 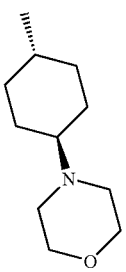 | APCI-MS M/Z: 568/570 [M + H]+ |
| 141 |  | 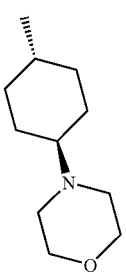 | APCI-MS M/Z: 612/614 [M + H]+ Hydrochloride |
| 142 | 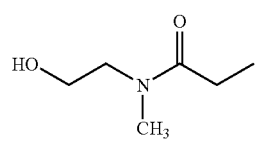 | 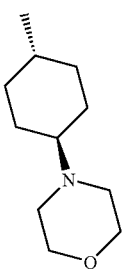 | APCI-MS M/Z: 598/600 [M + H]+ |
| 143 | 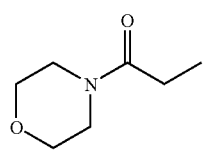 | 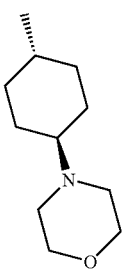 | APCI-MS M/Z: 610/612 [M + H]+ Hydrochloride |

Example 144

Trans-5-(4,5-dihydroxazol-2-yl)-3-[4-(dimethylamino)cyclohexylcarbonylamino]-N-(5-chloropyridin-2-yl)benzofuran-2-carboxamide

Example 145

Trans-3-[4-(N-acetyl-N-methylamino)cyclohexylcarbonylamino]-5-(2-hydroxyethyl)-N-(5-chloropyridin-2-yl)-benzofuran-2-carboxamide

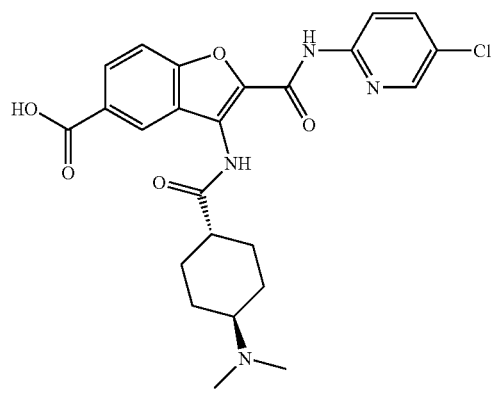

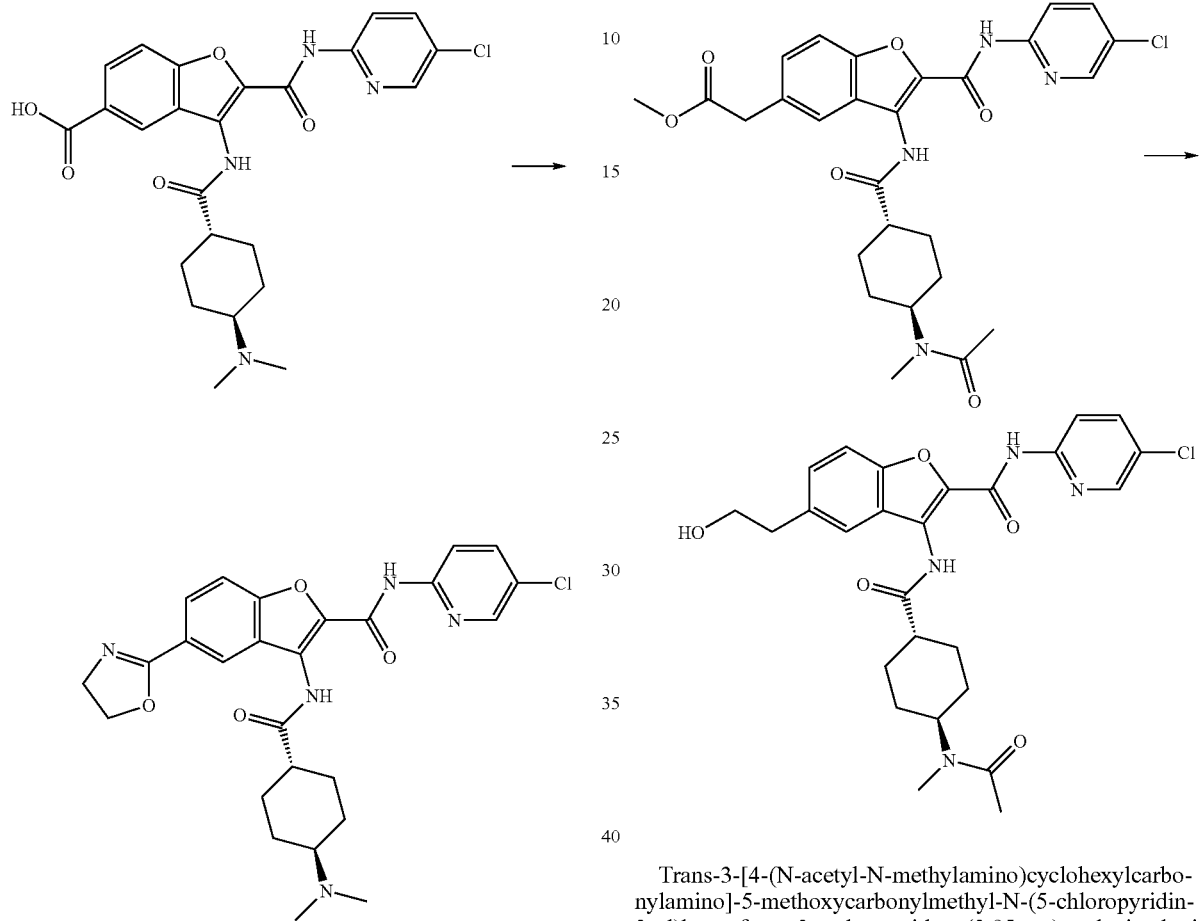

Trans-5-carboxy-3-[4-(dimethylamino)cyclohexyl-carbonylamino]-N-(5-chloropyridin-2-yl)benzofuran-2-carboxamide (220 mg) obtained in Example 78 is suspended in pyridine (3 ml), and thereto are added successively 2-bromoethylammonium bromide (125 mg), 1.0M 1-hydroxybenzotriazole-N,N-dimethylformamide solution (600 μl) and 1-ethyl-3-(3-dimethylaminopropyl)carbodiimide hydrochloride (115 mg) under ice-cooling, and the mixture is stirred at room temperature for 2.5 days. To the reaction solution are poured ice-water and a saturated aqueous sodium hydrogen carbonate solution, and the mixture is extracted with chloroform, dried over sodium sulfate, and the solvent is evaporated under reduced pressure. The resulting residue is purified by NH-silica gel column chromatography (eluent: chloroform, then chloroform/ethyl acetate=4/1), and the resulting residue is suspended in diisopropyl ether. The precipitates are collected by filtration, and dried to give the title compound (117 mg).

APCI-MS M/Z: 510/512 [M+H]$^+$

Trans-3-[4-(N-acetyl-N-methylamino)cyclohexylcarbonylamino]-5-methoxycarbonylmethyl-N-(5-chloropyridin-2-yl)benzofuran-2-carboxamide (2.95 g) obtained in Example 2 is suspended in tetrahydrofuran (65 ml), and thereto is added lithium borohydride (238 mg), and the mixture is stirred at room temperature for 12 hours. To the reaction solution is poured 10% hydrochloric acid under ice-cooling, and the mixture is stirred at room temperature for 15 minutes. Subsequently, the reaction solution is neutralized with a saturated aqueous sodium hydrogen carbonate solution, and extracted with ethyl acetate. The organic layer is washed with a saturated brine, dried over sodium sulfate, and the solvent is evaporated under reduced pressure. The resulting residue is purified by NH-silica gel column chromatography (eluent: ethyl acetate, then chloroform/methanol=40/1), and the resulting residue is suspended in diethyl ether. The precipitates are collected by filtration to give the title compound (2.24 g).

APCI-MS M/Z: 513/515 [M+H]$^+$

Examples 146-149

The corresponding compounds are treated in a similar manner to Example 145 to give the following compounds in a free form, which are further treated with hydrogen chloride to give hydrochlorides thereof.

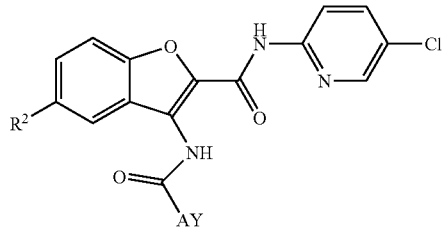

| Ex. No. | —R² | —AY | Physicochemical Properties |
|---|---|---|---|
| 146 | 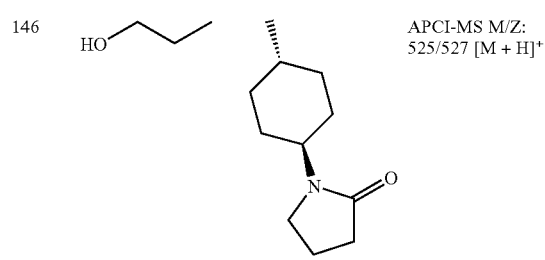 | | APCI-MS M/Z: 525/527 [M + H]⁺ |
| 147 | 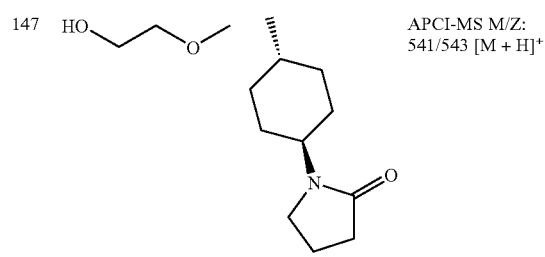 | | APCI-MS M/Z: 541/543 [M + H]⁺ |
| 148 | 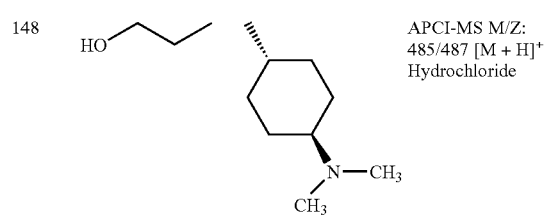 | | APCI-MS M/Z: 485/487 [M + H]⁺ Hydrochloride |
| 149 | 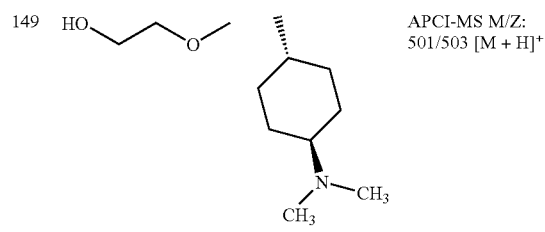 | | APCI-MS M/Z: 501/503 [M + H]⁺ |

Example 150

Trans-3-[4-(dimethylamino)cyclohexylcarbonyl-amino]-5-hydroxymethyl-N-(5-chloropyridin-2-yl)benzofuran-2-carboxamide hydrochloride

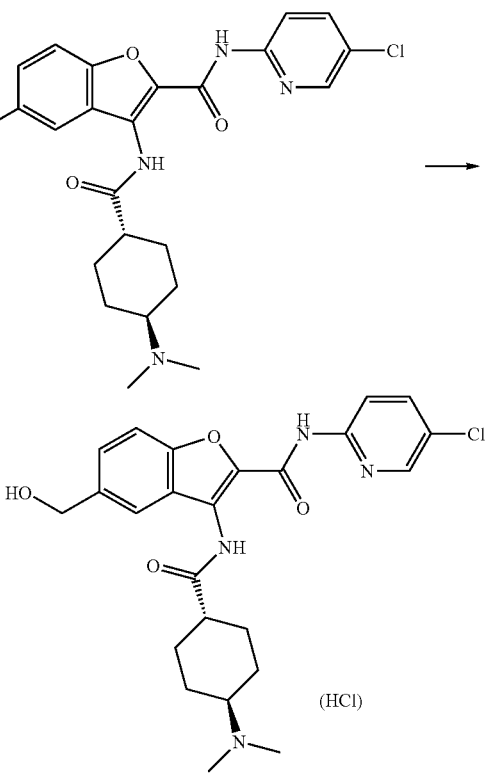

Trans-5-carboxy-3-[4-(dimethylamino)cyclohexyl-carbonylamino]-N-(5-chloropyridin-2-yl)benzofuran-2-carboxamide (243 mg) obtained in Example 78 is suspended in thionyl chloride (2.5 ml), and the mixture is stirred at room temperature for 10 minutes, then stirred at 50° C. for 10 minutes. The mixture is cooled to room temperature and stirred for one hour. The reaction solution is concentrated to dryness under reduced pressure. The resulting residue is suspended in tetrahydrofuran/chloroform (2:1, 15 ml), and thereto is added sodium borohydride (150 mg), and the mixture is stirred at room temperature overnight. To the reaction solution is poured 1N hydrochloric acid under ice-cooling, and the mixture is stirred for 0.5 hour. A saturated aqueous sodium hydrogen carbonate solution is further poured thereto, and the mixture is extracted with chloroform. The organic layer is washed with a saturated aqueous sodium hydrogen carbonate solution and a saturated brine, dried over sodium sulfate, and the solvent is evaporated under reduced pressure. The resulting residue is purified by NH-silica gel column chromatography (eluent: chloroform, then chloroform/methanol=200/1) to give trans-3-[4-(dimethylamino)cyclohexylcarbonylamino]-5-hydroxymethyl-N-(5-chloropyridin-2-yl)benzofuran-2-carboxamide (46 mg). This product is dissolved in chloroform (1 ml), and thereto is added 2N hydrogen chloride in methanol (0.1 ml), and the reaction solution is concentrated under reduced pressure. The resulting residue is suspended in ethyl acetate-methanol, and the precipitates are collected by filtration, and dried to give the title compound (45 mg).

APCI-MS M/Z: 471/473 [M+H]+

Example 151

Trans-3-[4-(dimethylamino)cyclohexylcarbonylamino]-6-hydroxy-N-(5-chloropyridin-2-yl)benzofuran-2-carboxamide hydrochloride

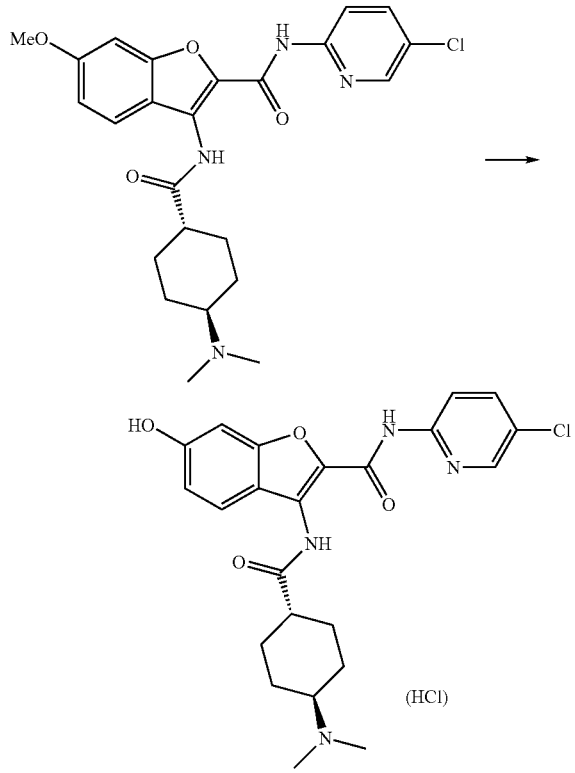

To a suspension of trans-3-[4-(dimethylamino)cyclohexylcarbonylamino]-6-methoxy-N-(5-chloropyridin-2-yl)-benzofuran-2-carboxamide (473 mg) obtained in Example 23 in dichloromethane (20 ml) is added dropwise boron tribromide (3.5 g) over 2 minutes at −78° C. The mixture is stirred at room temperature for 4 days, and the reaction solution is poured into ice-water, neutralized with a saturated aqueous sodium hydrogen carbonate solution, and extracted with a mixed solvent of ethyl acetate-tetrahydrofuran. The organic layer is washed with a saturated brine, dried over sodium sulfate, and the solvent is evaporated under reduced pressure. The resulting residue is suspended in chloroform/diethyl ether, and the precipitates are collected by filtration, and dried to give trans-3-[4-(dimethylamino)cyclohexylcarbonylamino]-6-hydroxy-N-(5-chloropyridin-2-yl)benzofuran-2-carboxamide (335 mg). This product (48 mg) is suspended in methanol and treated with 4N hydrogen chloride in dioxane to give the title compound (54 mg).

APCI-MS M/Z: 457/459 [M+H]+

Example 152

Trans-3-[4-(dimethylamino)cyclohexylcarbonylamino]-5-hydroxy-N-(5-chloropyridin-2-yl)benzofuran-2-carboxamide hydrochloride

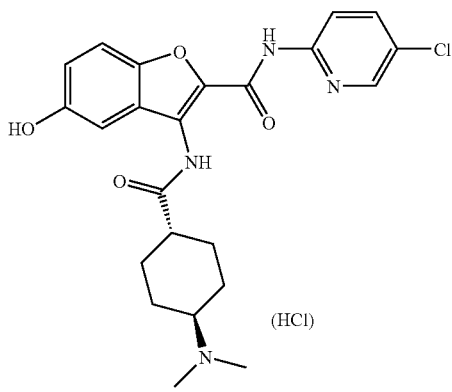

Trans-3-[4-(dimethylamino)cyclohexylcarbonylamino]-5-methyloxy-N-(5-chloropyridin-2-yl)benzofuran-2-carboxamide (473 mg) obtained in Example 19 is treated in a similar manner to Example 151 to give the title compound (33 mg).

APCI-MS M/Z: 457/459 [M+H]+

Example 153

Trans-6-t-butoxycarbonylmethoxy-3-[4-(dimethylamino)cyclohexylcarbonylamino]-N-(5-chloropyridin-2-yl)benzofuran-2-carboxamide

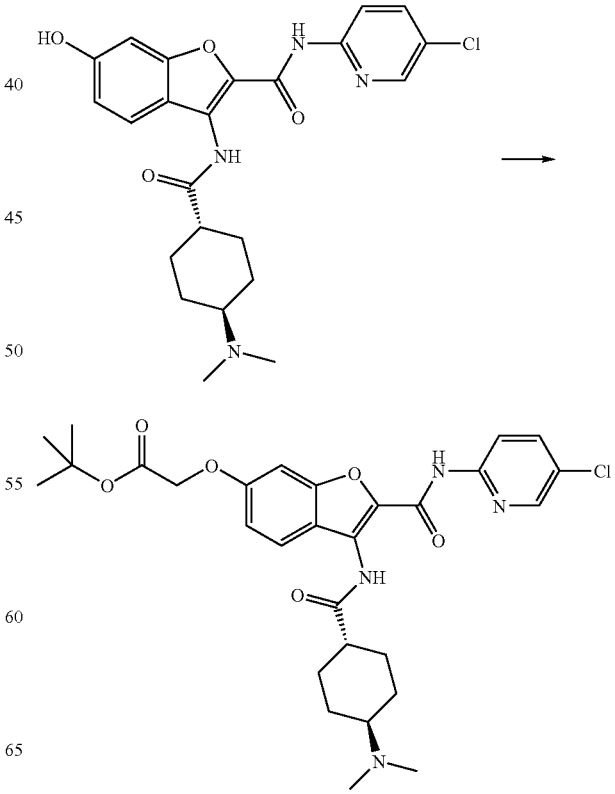

Trans-3-[4-(dimethylamino)cyclohexylcarbonylamino]-6-hydroxy-N-(5-chloropyridin-2-yl)benzofuran-2-carboxamide (90 mg) obtained in Example 151 is dissolved in N,N-dimethylformamide (2 ml), and thereto are added cesium carbonate (110 mg) and t-butyl bromoacetate (35.5 µl). The mixture is stirred at room temperature for 12 hours, and further stirred at 50° C. for 2.5 hours. The reaction solution is allowed to stand for cooling, and diluted with water, and extracted with ethyl acetate. The organic layer is concentrated under reduced pressure, and the resulting residue is purified by NH-silica gel column chromatography (eluent: hexane/ethyl acetate=1/1, then ethyl acetate) to give the title compound (21 mg).

APCI-MS M/Z: 571/573 [M+H]$^+$

Examples 154-155

Trans-3-[4-(dimethylamino)cyclohexylcarbonylamino]-6-hydroxy-N-(5-chloropyridin-2-yl)benzofuran-2-carboxamide obtained in Example 151 and the corresponding starting compounds are treated in a similar manner to Example 153 to give the following compounds in a free form, or which are further treated with hydrogen chloride to give hydrochlorides thereof.

| Ex. No. | Structure | Physicochemical properties |
|---|---|---|
| 154 | 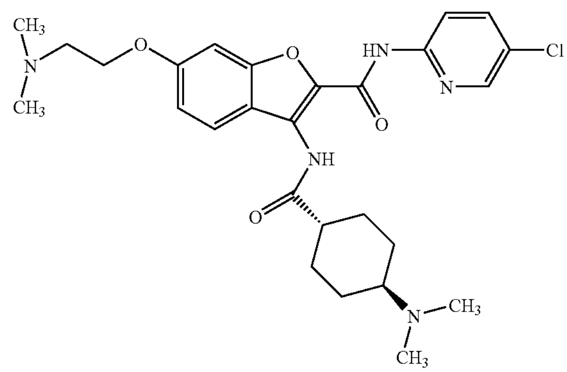 | APCI-MS M/Z: 528/530 [M + H]$^+$ Dihydrochloride |
| 155 | 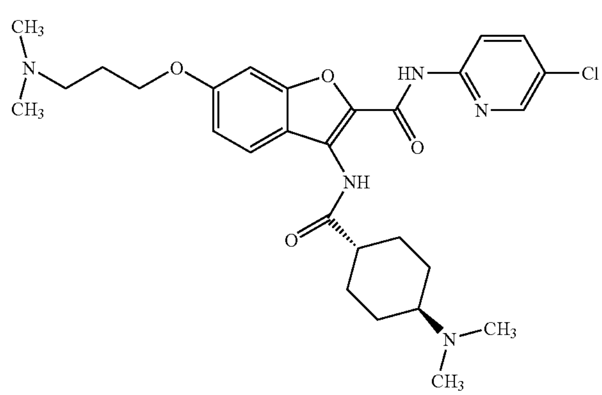 | APCI-MS M/Z: 542/544 [M + H]$^+$ Dihydrochloride |

Example 156

Trans-6-carboxymethyloxy-3-[4-(dimethylamino)-cyclohexylcarbonylamino]-N-(5-chloropyridin-2-yl)benzofuran-2-carboxamide hydrochloride

Example 157

Trans-5-carboxymethyloxy-3-[4-(dimethylamino)cyclohexylcarbonylamino]-N-(5-chloropyridin-2-yl)benzofuran-2-carboxamide hydrochloride

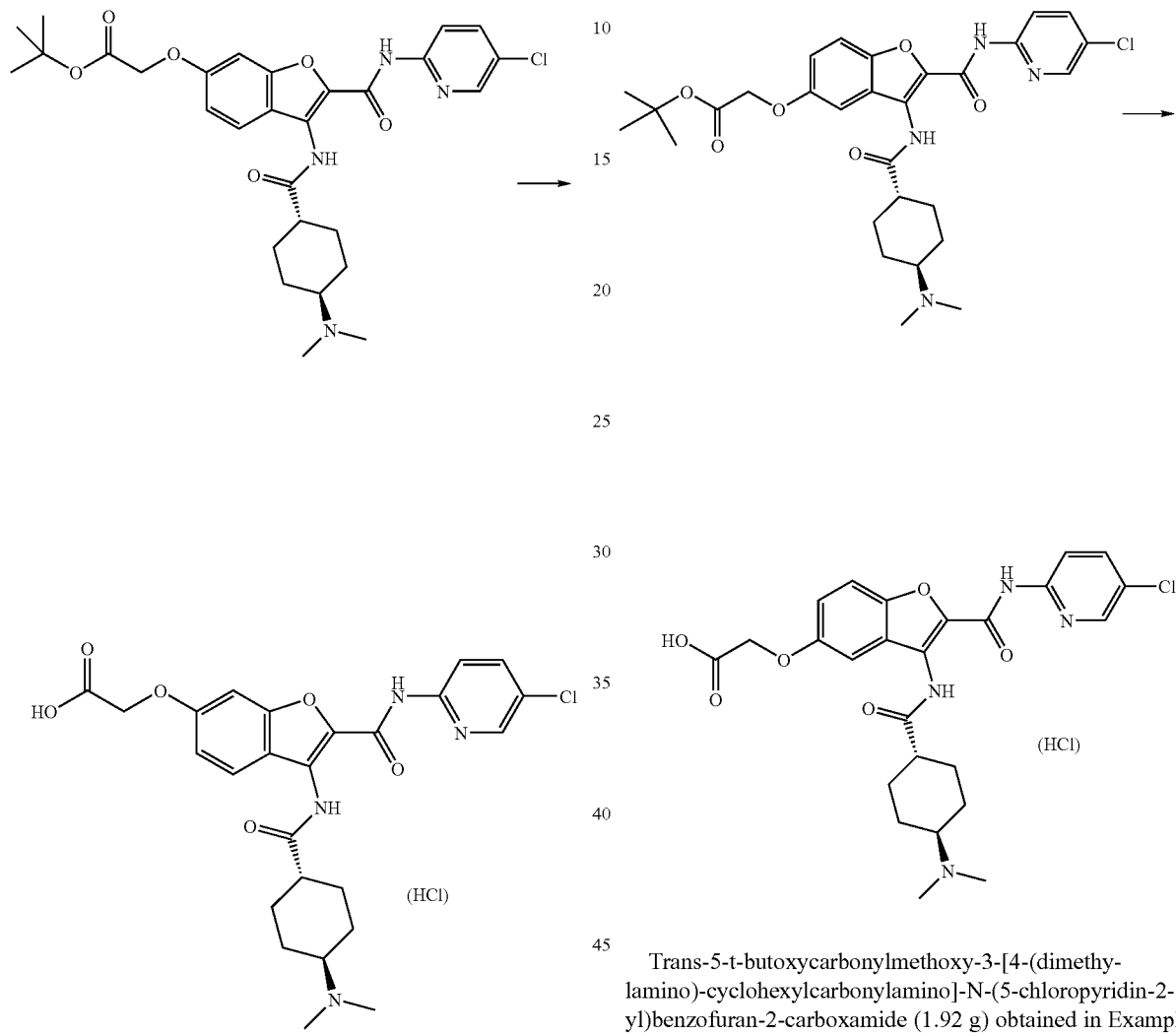

Trans-6-t-butoxycarbonylmethyloxy-3-[4-(dimethylamino)cyclohexylcarbonylamino]-N-(5-chloropyridin-2-yl)-benzofuran-2-carboxamide (21 mg) obtained in Example 153 is suspended in 4N hydrogen chloride in dioxane (8 ml), and the mixture is stirred at room temperature for 28 hours. The reaction solution is diluted with diethyl ether, and the precipitates are collected by filtration, washed several times with diethyl ether, and dried to give the title compound (17 mg).

APCI-MS M/Z: 515/517 [M+H]$^+$

Trans-5-t-butoxycarbonylmethoxy-3-[4-(dimethylamino)-cyclohexylcarbonylamino]-N-(5-chloropyridin-2-yl)benzofuran-2-carboxamide (1.92 g) obtained in Example 31 is dissolved in 6N hydrochloric acid (40 ml), and the mixture is stirred at room temperature for 2 hours. To the reaction solution is added isopropanol (100 ml), and the precipitated solid is collected by filtration, washed with isopropanol and diethyl ether, and dried under reduced pressure to give the title compound (1.86 g).

APCI-MS M/Z: 515/517 [M+H]$^+$

Examples 158-179

Trans-5-carboxymethyloxy-3-[4-(dimethylamino)cyclohexylcarbonylamino]-N-(5-chloropyridin-2-yl)benzofuran-2-carboxamide hydrochloride obtained in Example 157 and the corresponding starting compounds are treated in a similar manner to Example 87 to give the following compounds in a free form, or which are further treated with hydrogen chloride to give hydrochlorides thereof.

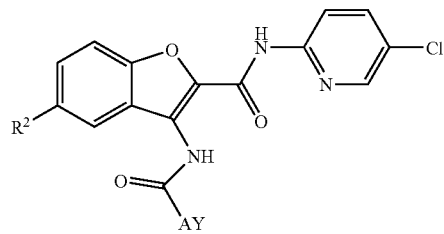

| Ex. No. | —R² | —AY | Physicochemical properties |
|---|---|---|---|
| 158 | N(CH₃)₂-CH₂-C(O)- with OCH₃ (N,N-dimethyl methoxyacetamide group) | trans-4-(dimethylamino)cyclohexyl | APCI-MS M/Z: 542/544 [M + H]⁺ Hydrochloride |
| 159 | CH₃NH-C(O)-CH₂-OCH₃ | trans-4-(dimethylamino)cyclohexyl | APCI-MS M/Z: 528/530 [M + H]⁺ Hydrochloride |
| 160 | H₂N-C(O)-CH₂-OCH₃ | trans-4-(dimethylamino)cyclohexyl | APCI-MS M/Z: 514/516 [M + H]⁺ Hydrochloride |
| 161 | CH₃O-CH₂CH₂-NH-C(O)-CH₂-OCH₃ | trans-4-(dimethylamino)cyclohexyl | APCI-MS M/Z: 572/574 [M + H]⁺ Hydrochloride |
| 162 | HO-CH₂CH₂-N(CH₃)-C(O)-CH₂-OCH₃ | trans-4-(dimethylamino)cyclohexyl | APCI-MS M/Z: 572/574 [M + H]⁺ Hydrochloride |
| 163 | HO-CH₂CH₂-NH-C(O)-CH₂-OCH₃ | trans-4-(dimethylamino)cyclohexyl | APCI-MS M/Z: 558/560 [M + H]⁺ Hydrochloride |

-continued

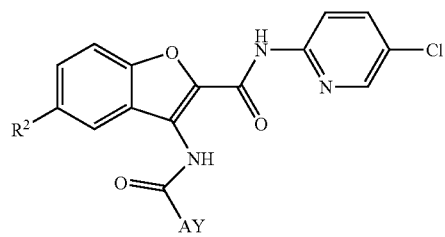

| Ex. No. | —R² | —AY | Physicochemical properties |
|---|---|---|---|
| 164 | HOCH₂CH₂CH₂NHC(O)CH₂OCH₃ (3-hydroxypropyl-NH-C(O)-CH₂-O-) | trans-4-(dimethylamino)cyclohexyl | APCI-MS M/Z: 572/574 [M + H]⁺ Hydrochloride |
| 165 | (CH₃OCH₂CH₂)₂N-C(O)-CH₂-O- | trans-4-(dimethylamino)cyclohexyl | APCI-MS M/Z: 630/632 [M + H]⁺ Hydrochloride |
| 166 | (S)-HOCH₂CH(CH₃)NH-C(O)-CH₂-O- | trans-4-(dimethylamino)cyclohexyl | APCI-MS M/Z: 572/574 [M + H]⁺ Hydrochloride |
| 167 | (R)-HOCH₂CH(CH₃)NH-C(O)-CH₂-O- | trans-4-(dimethylamino)cyclohexyl | APCI-MS M/Z: 572/574 [M + H]⁺ Hydrochloride |
| 168 | HOCH(CH₃)CH₂NH-C(O)-CH₂-O- | trans-4-(dimethylamino)cyclohexyl | APCI-MS M/Z: 572/574 [M + H]⁺ Hydrochloride |

-continued

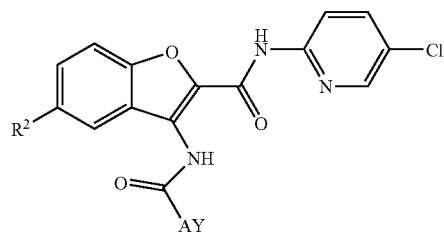

| Ex. No. | —R² | —AY | Physicochemical properties |
|---|---|---|---|
| 169 | (S)-CH₃-CH(OH)-CH₂-NH-C(O)-CH₂-OCH₃ | trans-4-(N,N-dimethylamino)cyclohexyl | APCI-MS M/Z: 572/574 [M + H]⁺ Hydrochloride |
| 170 | HOCH₂-C(CH₃)₂-NH-C(O)-CH₂-OCH₃ | trans-4-(N,N-dimethylamino)cyclohexyl | APCI-MS M/Z: 586/588 [M + H]⁺ Hydrochloride |
| 171 | (HOCH₂)₂CH-NH-C(O)-CH₂-OCH₃ | trans-4-(N,N-dimethylamino)cyclohexyl | APCI-MS M/Z: 588/590 [M + H]⁺ Hydrochloride |
| 172 | (CH₃)₂N-CH₂-CH₂-NH-C(O)-CH₂-OCH₃ | trans-4-(N,N-dimethylamino)cyclohexyl | APCI-MS M/Z: 585/587 [M + H]⁺ Dihydrochloride |
| 173 | morpholino-C(O)-CH₂-OCH₃ | trans-4-(N,N-dimethylamino)cyclohexyl | APCI-MS M/Z: 584/586 [M + H]⁺ Hydrochloride |
| 174 | piperidino-C(O)-CH₂-OCH₃ | trans-4-(N,N-dimethylamino)cyclohexyl | APCI-MS M/Z: 582/584 [M + H]⁺ Hydrochloride |

-continued

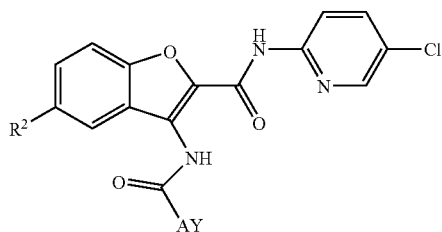

| Ex. No. | —R² | —AY | Physicochemical properties |
| --- | --- | --- | --- |
| 175 | pyrrolidine-N-C(O)-CH₂-OMe | trans-4-(N,N-dimethylamino)cyclohexyl | APCI-MS M/Z: 568/570 [M + H]⁺ Hydrochloride |
| 176 | 4-hydroxypiperidine-N-C(O)-CH₂-OMe | trans-4-(N,N-dimethylamino)cyclohexyl | APCI-MS M/Z: 598/600 [M + H]⁺ Hydrochloride |
| 177 | 4-(hydroxymethyl)piperidine-N-C(O)-CH₂-OMe | trans-4-(N,N-dimethylamino)cyclohexyl | APCI-MS M/Z: 612/614 [M + H]⁺ Hydrochloride |
| 178 | 2-(hydroxymethyl)pyrrolidine-N-C(O)-CH₂-OMe | trans-4-(N,N-dimethylamino)cyclohexyl | APCI-MS M/Z: 598/600 [M + H]⁺ Hydrochloride |
| 179 | 4-methylpiperazine-N-C(O)-CH₂-OMe | trans-4-(N,N-dimethylamino)cyclohexyl | APCI-MS M/Z: 597/599 [M + H]⁺ Dihydrochloride |

Example 180

Trans-5-amino-3-[4-(dimethylamino)cyclohexylcarbonylamino]-N-(5-chloropyridin-2-yl)benzofuran-2-carboxamide dihydrochloride

Example 181

Trans-3-[4-(dimethylamino)cyclohexylcarbonylamino]-5-methylamino-N-(5-chloropyridin-2-yl)benzofuran-2-carboxamide dihydrochloride

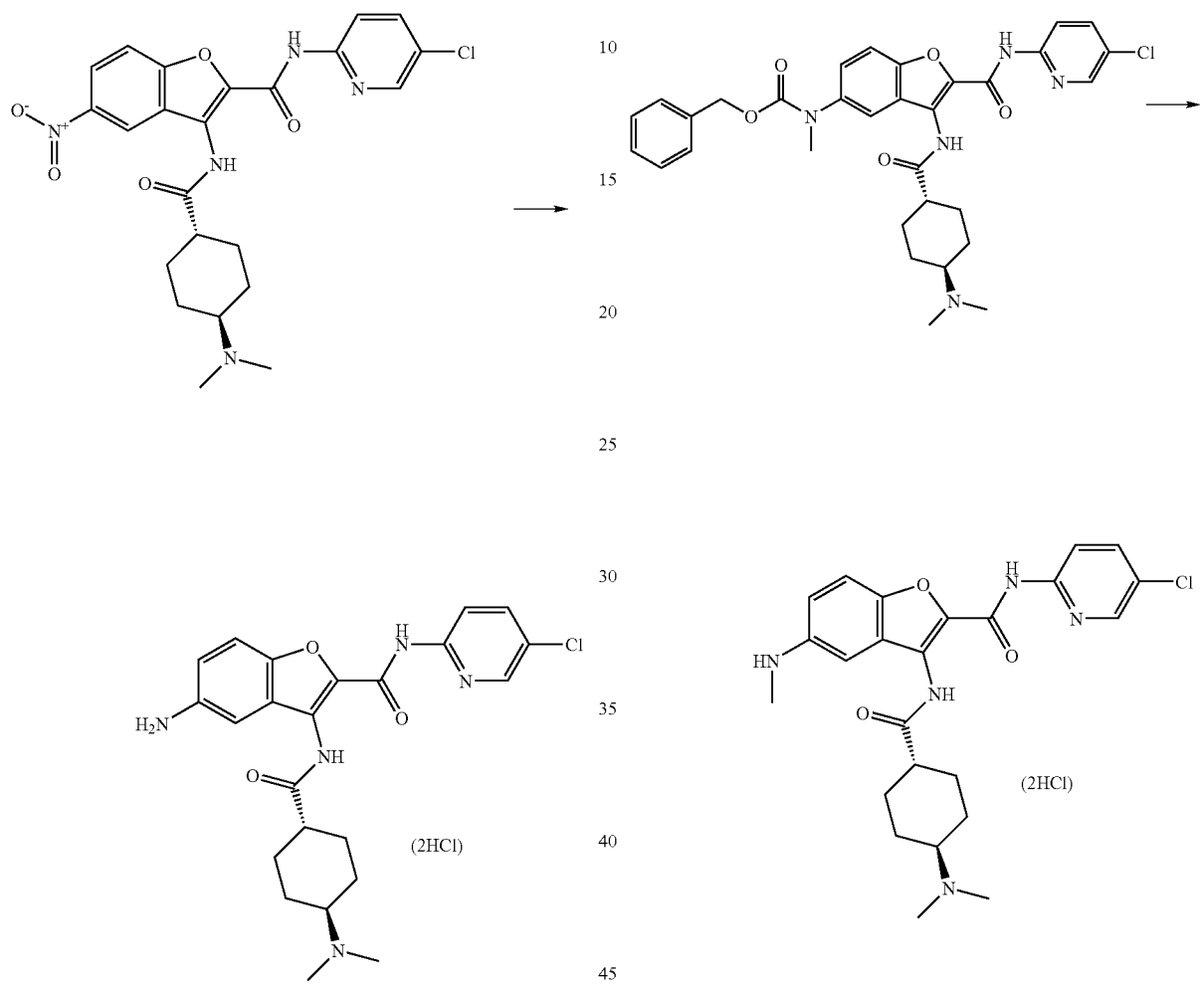

Trans-3-[4-(dimethylamino)cyclohexylcarbonylamino]-5-nitro-N-(5-chloropyridin-2-yl)benzofuran-2-carboxamide (3.00 g) obtained in Example 18 is suspended in ethanol (100 ml), and thereto are added tin(II) chloride (anhydrous) (7.02 g) and water (1.0 ml). The mixture is heated under reflux for 7 hours, and allowed to stand for cooling. To the reaction solution are added 10% aqueous sodium hydroxide solution (30 ml) and tetrahydrofuran (200 ml), and the mixture is stirred at room temperature for one hour. The insoluble materials are filtered on celite, and the filtrate is concentrated under reduced pressure, and purified by silica gel column chromatography (eluent: n-hexane/ethyl acetate=1/1, then chloroform/ethyl acetate=1/1). The resulting residue is suspended in ethyl acetate/n-hexane, and the precipitates are collected by filtration and dried to give trans-5-amino-3-[4-(dimethylamino)cyclohexylcarbonylamino]-N-(5-chloropyridin-2-yl)-benzofuran-2-carboxamide (1.43 g). This product (35 mg) is dissolved in ethanol, and treated with 4N hydrogen chloride/ethyl acetate to give the title compound (43 mg).

APCI-MS M/Z: 456/458 [M+H]$^+$

To trans-5-[N-(benzyloxycarbonyl)-N-methylamino]-3-[4-(dimethylamino)cyclohexylcarbonylamino]-N-(5-chloropyridin-2-yl)benzofuran-2-carboxamide (100 mg) obtained in Example 22 is added 30% hydrogen bromide in acetic acid (2 ml), and the mixture is stirred at room temperature for 2 hours. To the reaction solution is added diethyl ether (20 ml), and the precipitates are collected by filtration, and suspended in a saturated aqueous sodium hydrogen carbonate solution, and extracted with ethyl acetate. The organic layer is washed with a saturated brine, dried over sodium sulfate, and the solvent is evaporated under reduced pressure to give trans-3-[4-(dimethylamino)cyclohexylcarbonylamino]-5-methylamino-N-(5-chloropyridin-2-yl)benzofuran-2-carboxamide. Subsequently, this product is dissolved in ethanol, and treated with 4N hydrogen chloride in ethyl acetate to give the title compound (88 mg).

APCI-MS M/Z: 470/472 [M+H]$^+$

Example 182

Trans-3-[4-(dimethylamino)cyclohexylcarbonylamino]-5-(2-methylaminoethoxy)-N-(5-chloropyridin-2-yl)-benzofuran-2-carboxamide trihydrochloride

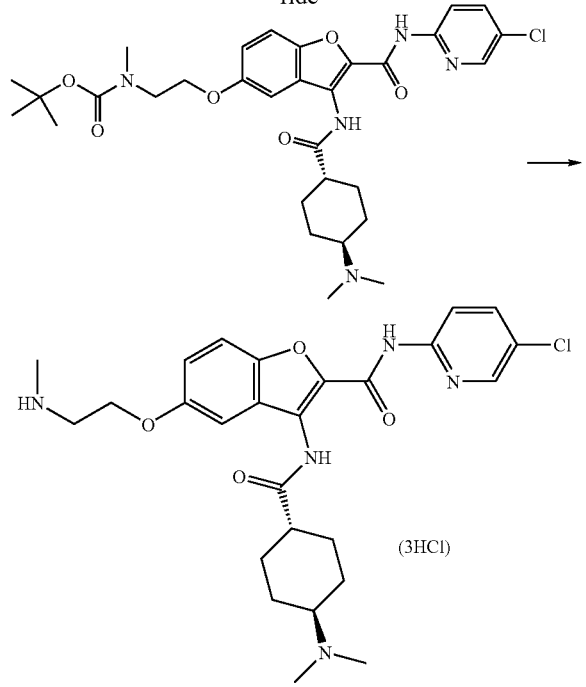

(3HCl)

Trans-5-[2-(N-t-butoxycarbonyl-N-methylamino)ethoxy]-3-[4-(dimethylamino)cyclohexylcarbonylamino]-N-(5-chloropyridin-2-yl)benzofuran-2-carboxamide (300 mg) obtained in Example 36 is dissolved in dioxane (5 ml), and thereto is added 4N hydrogen chloride in dioxane (10 ml), and the mixture stirred at room temperature for 5 hours. The reaction solution is concentrated under reduced pressure, and the resulting residue is suspended in diethyl ether. The precipitates are collected by filtration, and dried to give the title compound (301 mg).

APCI-MS M/Z: 514/516 [M+H]$^+$

Example 183

Trans-5-(2-aminoxyethoxy)-3-[4-(2-oxopyrrolidine-1-yl)cyclohexylcarbonylamino]-N-(5-chloropyridin-2-yl)benzofuran-2-carboxamide dihydrochloride

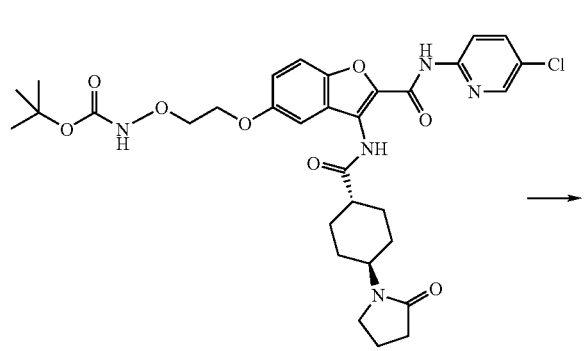

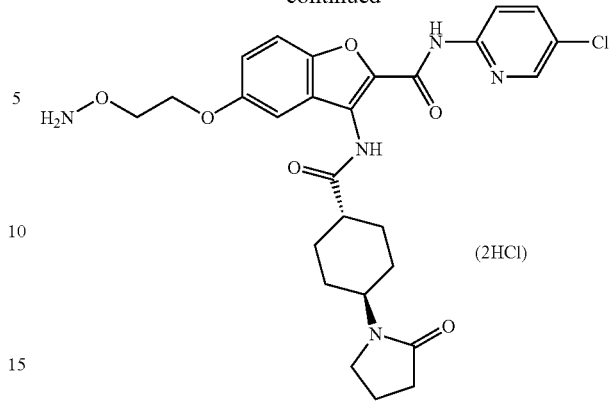

(2HCl)

Trans-5-[2-(t-butoxycarbonylaminoxy)ethoxy]-3-[4-(2-oxopyrrolidine-1-yl)cyclohexylcarbonylamino]-N-(5-chloropyridin-2-yl)benzofuran-2-carboxamide (250 mg) obtained in Example 10 is treated in a similar manner to Example 182 to give the title compound (334 mg).

APCI-MS M/Z: 556/558 [M+H]$^+$

Example 184

Trans-5-methoxyacetylamino-3-[4-(dimethylamino)cyclohexylcarbonylamino]-N-(5-chloropyridin-2-yl)-benzofuran-2-carboxamide hydrochloride

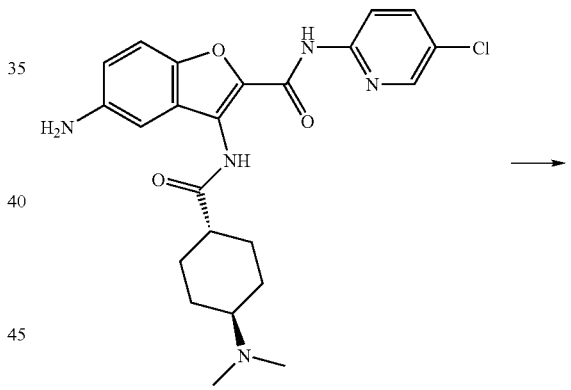

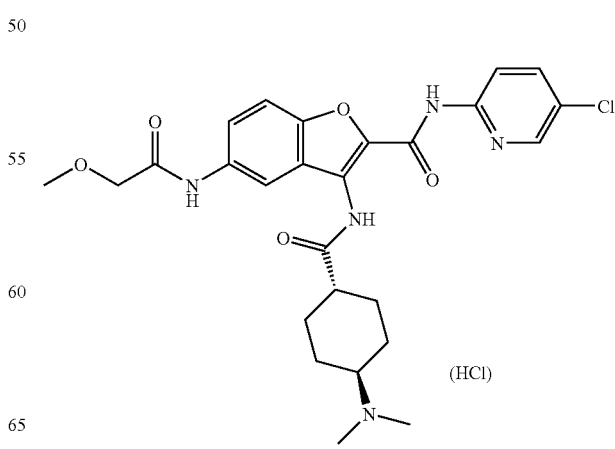

(HCl)

Trans-5-amino-3-[4-(dimethylamino)cyclohexylcarbonylamino]-N-(5-chloropyridin-2-yl)benzofuran-2-carboxamide (100 mg) obtained in Example 180 is suspended in N,N-dimethylformamide (6 ml), and thereto are added successively methoxyacetic acid (23 mg), 1-hydroxybenzotriazole (39 mg) and 1-ethyl-3-(3-dimethylaminopropyl)-carbodiimide hydrochloride (55 mg) under ice-cooling, and the mixture is stirred at room temperature for 17 hours. To the reaction solution is poured a saturated aqueous sodium hydrogen carbonate solution, and the mixture is extracted with chloroform. The organic layer is washed with a saturated brine, and dried over sodium sulfate. The solvent is evaporated under reduced pressure, and the resulting residue is purified by NH-silica gel column chromatography (eluent: chloroform, then chloroform/methanol=30/1) to give trans-5-methoxyacetylamino-3-[4-(dimethylamino)cyclohexylcarbonylamino]-N-(5-chloropyridin-2-yl)benzofuran-2-carboxamide. Subsequently, this product is dissolved in ethanol, and treated with 4N hydrogen chloride in ethyl acetate to give the title compound (84 mg).

APCI-MS M/Z: 528/530 [M+H]$^+$

Examples 185-188

Trans-5-amino-3-[4-(dimethylamino)cyclohexylcarbonylamino]-N-(5-chloropyridin-2-yl)benzofuran-2-carboxamide obtained in Example 180 and the corresponding starting compounds are treated in a similar manner to Example 184 to the compounds in a free form, or which are further treated with hydrogen chloride to give hydrochlorides thereof.

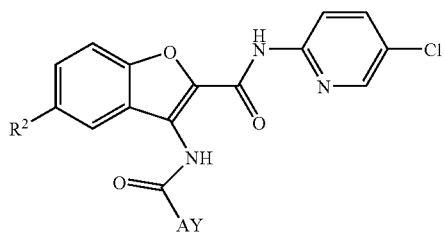

| Ex. No. | —R² | —AY | Physicochemical properties |
|---|---|---|---|
| 185 | (3-methoxypropanamide-N-methyl) | (trans-4-dimethylaminocyclohexyl) | APCI-MS M/Z: 542/544 [M + H]$^+$ Hydrochloride |
| 186 | (2-(dimethylamino)-N-methylacetamide) | (trans-4-dimethylaminocyclohexyl) | APCI-MS M/Z: 541/543 [M + H]$^+$ Dihydrochloride |
| 187 | (4-(dimethylamino)-N-methylbutanamide) | (trans-4-dimethylaminocyclohexyl) | APCI-MS M/Z: 569/571 [M + H]$^+$ Dihydrochloride |
| 188 | (2-acetamido-N-methylacetamide) | (trans-4-dimethylaminocyclohexyl) | APCI-MS M/Z: 555/557 [M + H]$^+$ Hydrochloride |

Example 189

Trans-5-acetoxyacetylamino-3-[4-(dimethylamino)cyclohexylcarbonylamino]-N-(5-chloropyridin-2-yl)-benzofuran-2-carboxamide hydrochloride

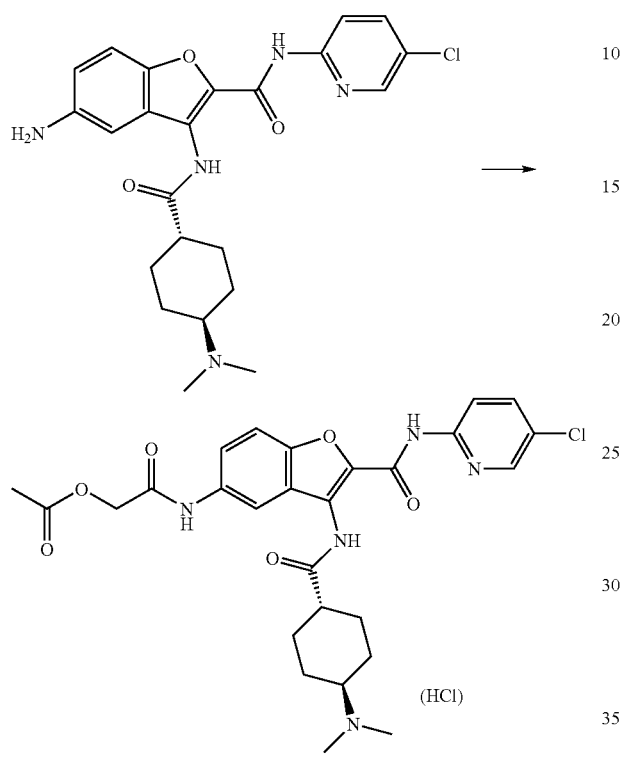

Trans-5-amino-3-[4-(dimethylamino)cyclohexylcarbonylamino]-N-(5-chloropyridin-2-yl)benzofuran-2-carboxamide (100 mg) obtained in Example 180 is dissolved in dichloromethane (8 ml), and thereto are added acetoxy acetylchloride (36 mg) and pyridine (36 μl) under ice-cooling, and the mixture is stirred at room temperature for 17 hours. To the reaction solution is poured a saturated aqueous sodium hydrogen carbonate solution, and the mixture is extracted with chloroform. The organic layer is washed with a saturated brine, dried over sodium sulfate, and the solvent is evaporated under reduced pressure. The resulting residue is purified by NH-silica gel column chromatography (eluent: chloroform, then chloroform/methanol=50/1) to give trans-5-acetoxyacetylamino-3-[4-(dimethylamino)cyclohexylcarbonylamino]-N-(5-chloropyridin-2-yl)benzofuran-2-carboxamide (110 mg). A portion of this product is dissolved in ethanol, and treated with 4N hydrogen chloride in ethyl acetate to give the title compound (16 mg).

APCI-MS M/Z: 556/558 [M+H]$^+$

Examples 190-196

The corresponding compounds are treated in a similar manner to Example 189 to give the following compounds in a free form, or which are further treated with hydrogen chloride to give hydrochlorides thereof.

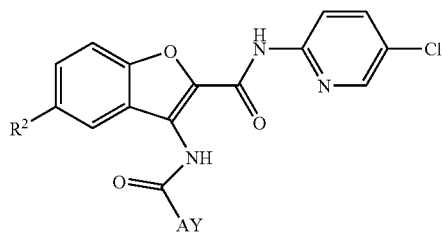

| Ex. No. | —R$^2$ | —AY | Physicochemical properties |
|---|---|---|---|
| 190 | -N(CH₃)H-) | ₂) | APCI-MS M/Z: 498/500 [M + H]$^+$ Hydrochloride |

-continued

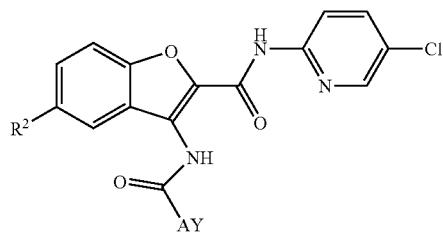

| Ex. No. | —R² | —AY | Physicochemical properties |
|---|---|---|---|
| 191 | ethyl N-methylcarbamate group (CH₃CH₂-O-C(O)-N(H)-CH₃... N-methyl) | trans-4-(dimethylamino)cyclohexyl | APCI-MS M/Z: 528/530 [M + H]⁺ Hydrochloride |
| 192 | 1,3-dimethyl-3-methylurea group | trans-4-(dimethylamino)cyclohexyl | APCI-MS M/Z: 527/529 [M + H]⁺ Hydrochloride |
| 193 | N-methylmethanesulfonamide | trans-4-(dimethylamino)cyclohexyl | APCI-MS M/Z: 534/536 [M + H]⁺ Hydrochloride |
| 194 | 3-morpholinopropyl-N-methylsulfonamide | trans-4-(dimethylamino)cyclohexyl | APCI-MS M/Z: 647/649 [M + H]⁺ Dihydrochloride |
| 195 | N,N-dimethyl-methanesulfonamide | trans-4-(dimethylamino)cyclohexyl | APCI-MS M/Z: 548/550 [M + H]⁺ Hydrochloride |
| 196 | N-methyl-N-(2-methoxyethyl)acetamide | trans-4-(dimethylamino)cyclohexyl | APCI-MS M/Z: 556/558 [M + H]⁺ Dihydrochloride |

Example 197
Trans-3-[4-(dimethylamino)cyclohexylcarbonylamino]-5-hydroxyacetylamino-N-(5-chloropyridin-2-yl)benzofuran-2-carboxamide hydrochloride

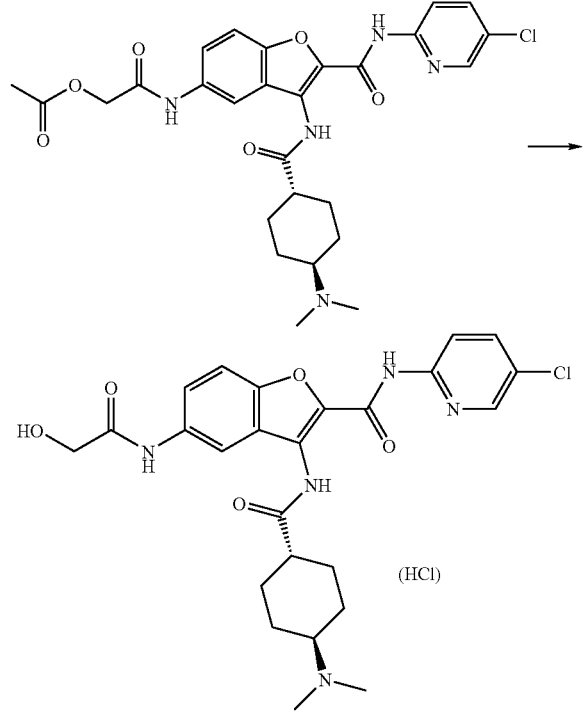

Trans-5-acetoxyacetylamino-3-[4-(dimethylamino)-cyclohexylcarbonylamino]-N-(5-chloropyridin-2-yl)benzofuran-2-carboxamide (70 mg) obtained in Example 189 is dissolved in tetrahydrofuran/methanol (1:1, 8 ml), and thereto is added potassium carbonate (5 mg), and the mixture is stirred at room temperature for 48 hours. The reaction solution is concentrated under reduced pressure, and the resulting residue is purified by silica gel column chromatography (eluent: chloroform/methanol=30/1). The resulting trans-3-[4-(dimethylamino)cyclohexylcarbonylamino]-5-hydroxyacetylamino-N-(5-chloropyridin-2-yl)-benzofuran-2-carboxamide is dissolved in ethanol, and treated with 4N hydrogen chloride in ethyl acetate to give the title compound (46 mg).
APCI-MS M/Z: 514 [M+H]$^+$

Example 198
Trans-5-dimethylamino-3-[4-(dimethylamino)-cyclohexylcarbonylamino]-N-(5-chloropyridin-2-yl)benzofuran-2-carboxamide dihydrochloride

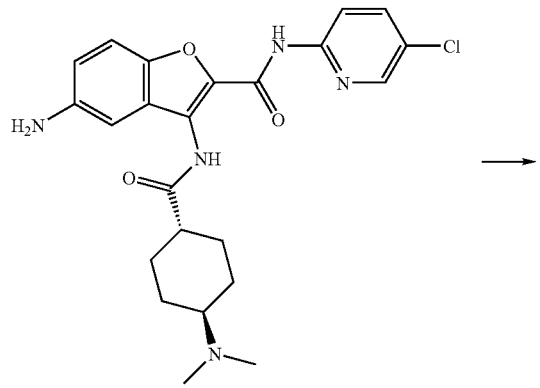

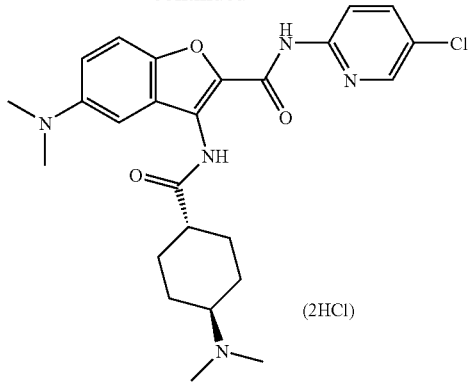

Trans-5-amino-3-[4-(dimethylamino)cyclohexylcarbonylamino]-N-(5-chloropyridin-2-yl)benzofuran-2-carboxamide (50 mg) obtained in Example 180 is suspended in dichloromethane (3 ml), and thereto are added successively 35% aqueous formaldehyde solution (82 μl) and sodium triacetoxy borohydride (70 mg) under ice-cooling. The reaction solution is warmed to room temperature, and stirred for 11.5 hours. To the reaction solution is poured a saturated aqueous sodium hydrogen carbonate solution under ice-cooling, and the mixture is extracted with dichloromethane. The organic layer is washed with a saturated brine, dried over sodium sulfate, and the solvent is evaporated under reduced pressure. The resulting residue is purified by NH-silica gel column chromatography (eluent: ethyl acetate) to give trans-5-dimethylamino-3-[4-(dimethylamino)cyclohexylcarbonylamino]-N-(5-chloropyridin-2-yl)benzofuran-2-carboxamide (44 mg). This product is suspended in methanol, and treated with 4N hydrogen chloride in ethyl acetate to give the title compound (49 mg).
APCI-MS M/Z: 528/530 [M+H]$^+$

Examples 199-200

Trans-5-amino-3-[4-(dimethylamino)cyclohexylcarbonylamino]-N-(5-chloropyridin-2-yl)benzofuran-2-carboxamide obtained in Example 180 and the corresponding starting compounds are treated in a similar manner to Example 198 to give the following compounds in a free form, or which are further treated with hydrogen chloride to give hydrochlorides thereof.

| Ex. No. | —R$^2$ | —AY | Physicochemical properties |
|---|---|---|---|
| 199 | -CH2-CH2-CH2-O-CH3) | ![cyclohexyl-N(CH3)2] | APCI-MS M/Z: 600/602 [M + H]$^+$ Dihydrochloride |

-continued

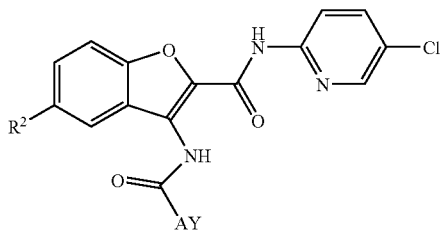

| Ex. No. | —R² | —AY | Physicochemical properties |
|---|---|---|---|
| 200 | HO\~\~\~N(CH₃)(CH₂CH₂OH) attached | trans-cyclohexyl-N(CH₃)₂ | APCI-MS M/Z: 544/546 [M + H]⁺ Dihydrochloride |

Example 201

Trans-3-[4-(dimethylamino)cyclohexylcarbonylamino]-5-(2-hydroxy-1-hydroxymethylethoxy)-N-(5-chloropyridin-2-yl)benzofuran-2-carboxamide dihydrochloride

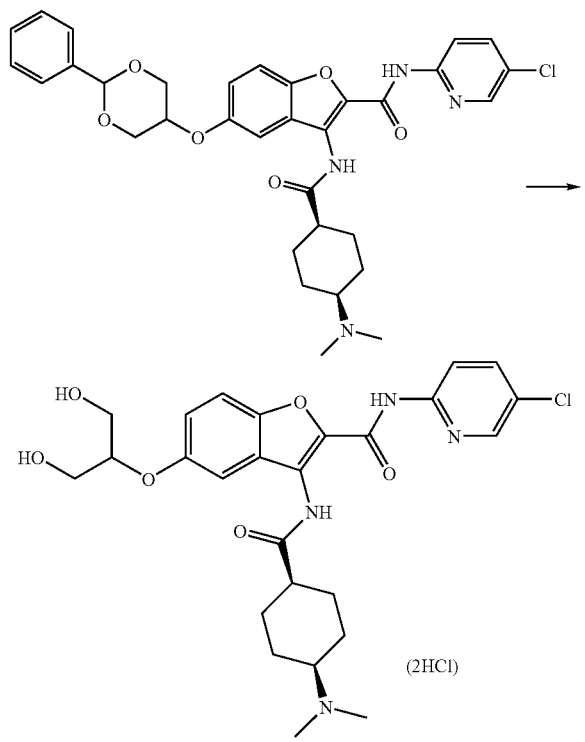

Trans-3-[4-(dimethylamino)cyclohexylcarbonylamino]-5-(2-phenyl-[1,3]dioxan-5-yloxy)-N-(5-chloropyridin-2-yl)-benzofuran-2-carboxamide (200 mg) obtained in Example 35 is dissolved in tetrahydrofuran (5 ml), and thereto is added 2N hydrochloric acid (5 ml), and the mixture is stirred at room temperature for 3 hours. The reaction solution is basified with a saturated aqueous sodium hydrogen carbonate solution and potassium carbonate, and extracted with chloroform. The organic layer is washed with a saturated brine, dried over sodium sulfate, and the solvent is evaporated under reduced pressure. The resulting residue is purified by NH-silica gel column chromatography (eluent: methanol/ethyl acetate=1/20→methanol/ethyl acetate=1/5) to give trans-3-[4-(dimethylamino)cyclohexylcarbonylamino]-5-(2-hydroxy-1-hydroxymethylethoxy)-N-(5-chloropyridin-2-yl)benzofuran-2-carboxamide (162 mg). This product is dissolved in methanol, and thereto is added 4N hydrogen chloride in ethyl acetate (1 ml). The solvent is evaporated under reduced pressure, and the resulting residue is suspended in diethyl ether, and the precipitates are collected by filtration to give the title compound (141 mg).

APCI-MS M/Z: 531/533 [M+H]⁺

Example 202

Trans-3-[4-(N-t-butoxycarbonyl-N-methylamino)-cyclohexylcarbonylamino]-5-methoxycarbonyl-N-(5-chloropyridin-2-yl)benzofuran-2-carboxamide

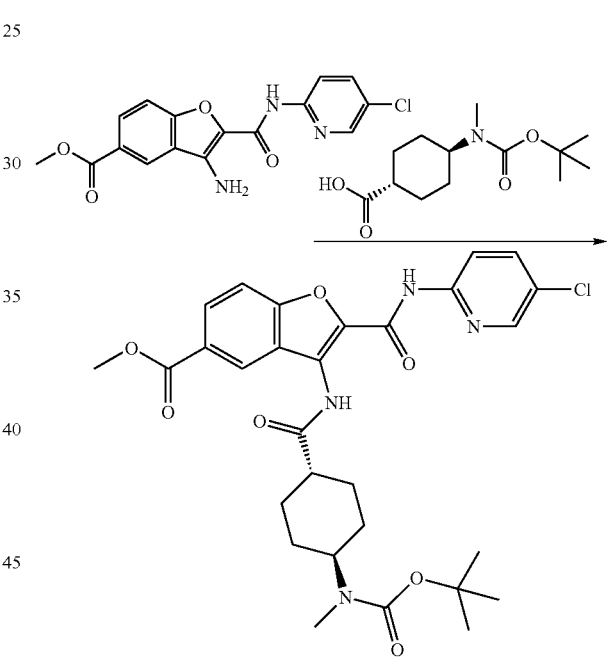

Trans-4-(N-t-butoxycarbonyl-N-methylamino)cyclohexanecarboxylic acid (4.12 g) obtained in Reference Example 115 is dissolved in dichloromethane (80 ml), and thereto is added pyridine (7.9 ml). To the mixture is added dropwise thionyl chloride (1.04 ml) under ice-cooling, and the mixture is stirred at room temperature for 3 hours. The reaction solution is concentrated, and to the resulting residue are added successively pyridine (80 ml), 3-amino-5-methoxycarbonyl-N-(5-chloropyridin-2-yl)benzofuran-2-carboxamide (2.76 g) obtained in Reference Example 72, and 4-dimethylaminopyridine (195 mg) under ice-cooling. The reaction solution is warmed to room temperature, and stirred for 17 hours. To the reaction solution is poured a saturated aqueous sodium hydrogen carbonate solution, and the precipitates are collected by filtration, washed successively with water and diethyl ether, and dried to give the title compound (4.63 g).

APCI-MS M/Z: 585 [M+H]⁺

Example 203

Trans-3-[4-(t-butoxycarbonylamino)cyclohexylcarbonylamino]-N-(5-chloropyridin-2-yl)benzofuran-2-carboxamide

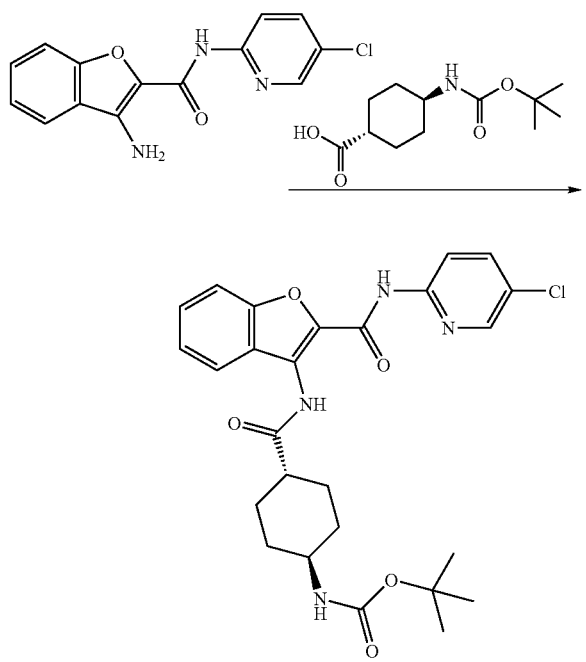

Trans-4-(t-butoxycarbonylamino)cyclohexanecarboxylic acid (2.54 g) obtained in Reference Example 116 is dissolved in dichloromethane (50 ml), and thereto is added pyridine (4.22 ml), and the mixture is cooled with ice. To the mixture is added dropwise thionyl chloride (0.76 ml), and the mixture is stirred at room temperature for 5 hours. The reaction solution is cooled again with ice, and thereto are added 3-amino-N-(5-chloropyridin-2-yl)benzofuran-2-carboxamide (2.00 g) obtained in Reference Example 74 and dichloromethane (20 ml), and the mixture is stirred at room temperature for 15 hours. To the reaction solution is poured water, and the mixture is extracted with chloroform. The organic layer is washed successively with water, 5% aqueous citric acid solution, water, a saturated aqueous sodium hydrogen carbonate solution and a saturated brine, dried over sodium sulfate, and the solvent is evaporated under reduced pressure. The resulting residue is purified by silica gel column chromatography (eluent: chloroform) and suspended in diethyl ether. The precipitates are collected by filtration to give the title compound (2.94 g).

APCI-MS M/Z: 513/515 [M+H]$^+$

Examples 204-217

The corresponding starting compounds are treated in a similar manner to Example 202 or Example 203 to give the following compounds.

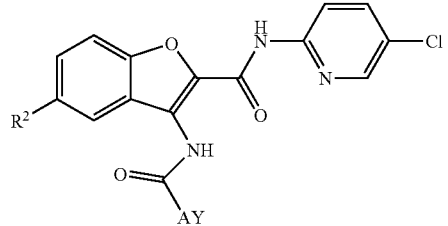

| Ex. No. | —R$^2$ | —AY | Physicochemical properties |
|---|---|---|---|
| 204 | —H | ![structure] | APCI-MS M/Z: 527/529 [M + H]$^+$ |

-continued
| | | |
|---|---|---|
| 205 | 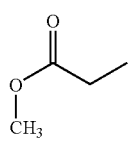 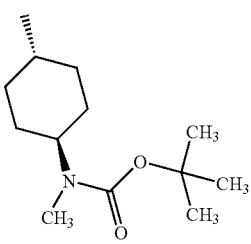 | APCI-MS M/Z: 616/618 [M + NH$_4$]$^+$ |
| 206 | 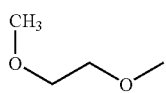 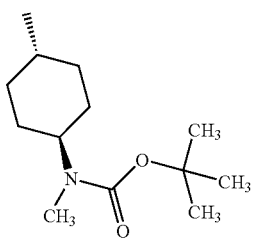 | APCI-MS M/Z: 601/603 [M + H]$^+$ |
| 207 | 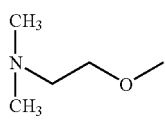 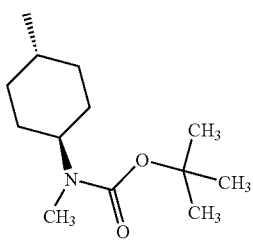 | APCI-MS M/Z: 614/616 [M + H]$^+$ |
| Ex. No. | Structure | Physicochemical properties |
|---|---|---|
| 208 | 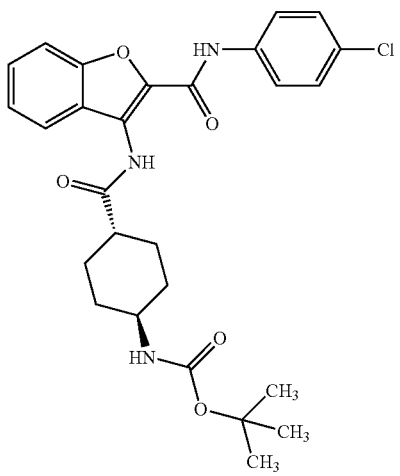 | APCI-MS M/Z: 512/514 [M + H]$^+$ |
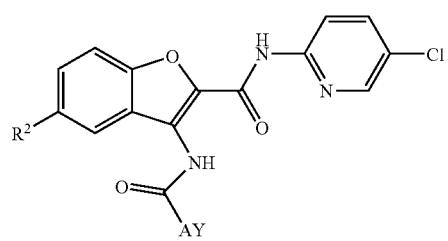
| Ex. No. | —R$^2$ | —AY | Physicochemical properties |
|---|---|---|---|

-continued
| | | |
|---|---|---|
| 209 |  | APCI-MS M/Z: 588/590 [M + H]+ |
| | 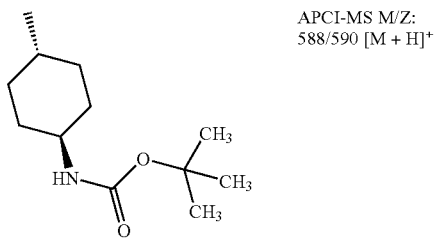 | |
| 210 | —H | APCI-MS M/Z: 527/529 [M + H]+ |
| | 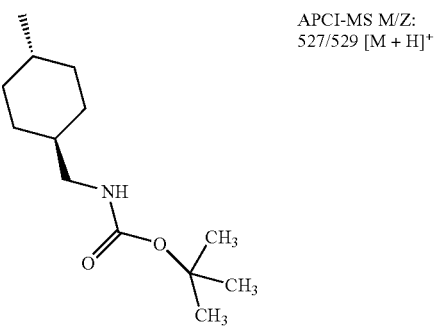 | |
| 211 | —H | APCI-MS M/Z: 499/501 [M + H]+ |
| | 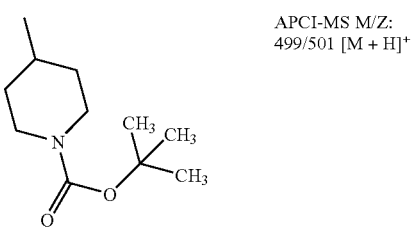 | |
| 212 | —H | APCI-MS M/Z: 513/515 [M + H]+ |
| | 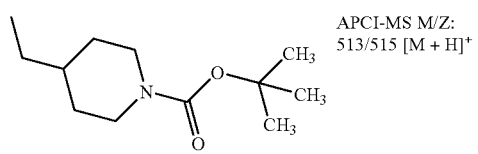 | |
| 213 | —H | APCI-MS M/Z: 527/529 [M + H]+ |
| | 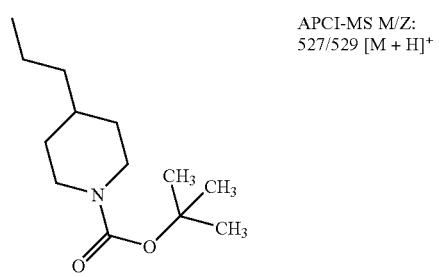 | |
| 214 | —H | APCI-MS M/Z: 511/513 [M + H]+ |
| | 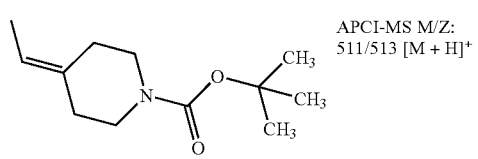 | |
| 215 | —H | APCI-MS M/Z: 487/489 [M + H]+ |
| | 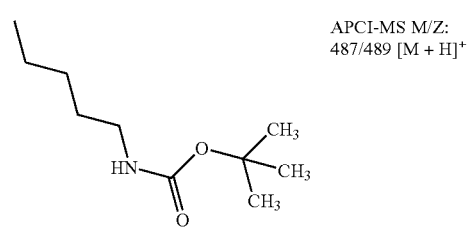 | |

| 216 | —H | 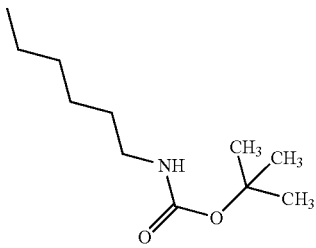 | APCI-MS M/Z: 501/503 [M + H]+ |
| 217 | —H | 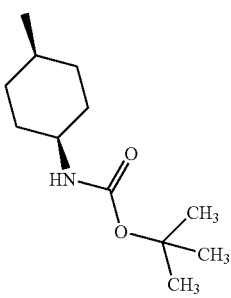 | APCI-MS M/Z: 513 [M + H]+ |

Example 218

Trans-5-methoxycarbonyl-3-[4-(methylamino)-cyclohexylcarbonylamino]-N-(5-chloropyridin-2-yl)benzofuran-2-carboxamide hydrochloride

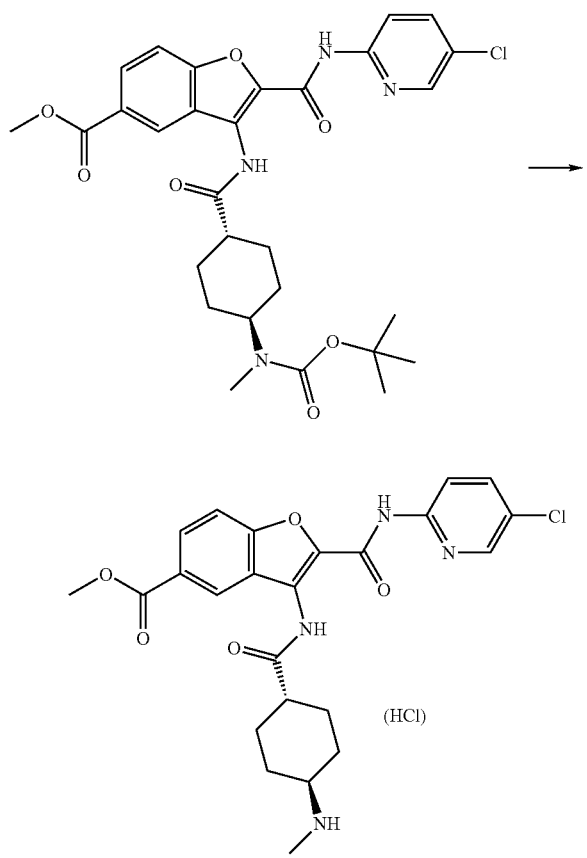

Trans-3-[4-(N-t-butoxycarbonyl-N-methylamino)cyclohexylcarbonylamino]-5-methoxycarbonyl-N-(5-chloropyridin-2-yl)benzofuran-2-carboxamide (4.60 g) obtained in Example 202 is dissolved in dioxane (20 ml), and thereto is added 4N hydrogen chloride in dioxane (10 ml), and the mixture is stirred at room temperature for 48 hours. The reaction solution is diluted with diethyl ether, and the precipitates are collected by filtration, washed several times with diethyl ether and dried to give the title compound (4.02 g).

APCI-MS M/Z: 485/487 [M+H]+

Example 219

Trans-3-(4-aminocyclohexylcarbonylamino)-N-(5-chloropyridin-2-yl)benzofuran-2-carboxamide dihydrochloride

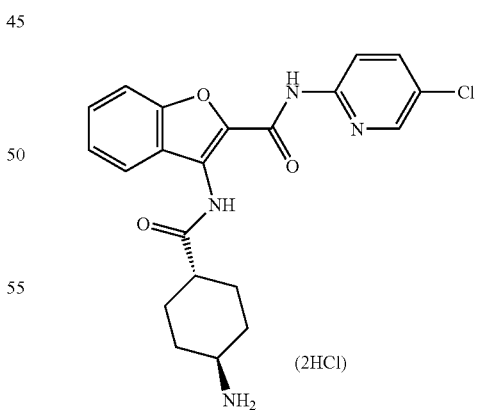

Trans-3-[4-(t-butoxycarbonylamino)cyclohexylcarbonylamino]-N-(5-chloropyridin-2-yl)benzofuran-2-carboxamide (10.70 g) obtained in Example 203 is dissolved in dioxane (150 ml), and thereto is added 4N hydrogen chloride in dioxane (150 ml). The mixture is stirred at room temperature for 12 hours, and concentrated under reduced pressure. The residue is crushed in diethyl ether, and collected by filtration to give the title compound (9.80 g).

APCI-MS M/Z: 412/414 [M+H]⁺

Example 220

3-[2-(piperidin-4-yl)acetylamino]-N-(5-chloropyridin-2-yl)benzofuran-2-carboxamide

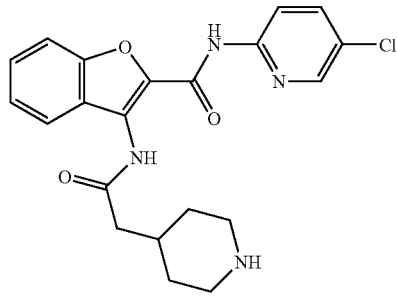

3-[2-(1-t-Butoxycarbonylpiperidin-4-yl)acetylamino]-N-(5-chloropyridin-2-yl)benzofuran-2-carboxamide (2.34 g) obtained in Example 212 is suspended in ethyl acetate (30 ml), and thereto is added 2.6N hydrogen chloride in ethyl acetate (30 ml), and the mixture is stirred at room temperature for 5 hours. The reaction solution is concentrated under reduced pressure, and to the resulting residue are added chloroform and an aqueous sodium hydrogen carbonate solution. The precipitates are collected by filtration to give the title compound (1.47 g).

APCI-MS M/Z: 413/415 [M+H]⁺

Examples 221-233

The corresponding starting compounds are treated in a similar manner to Example 218, Example 219 or Example 220 to give the following compounds in a free form, or which are further treated with hydrogen chloride to give hydrochlorides thereof.

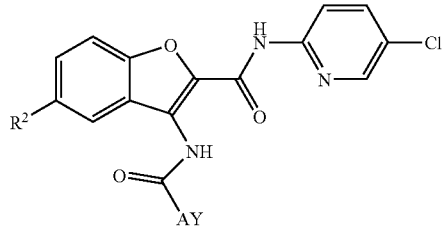

| Ex. No. | —R² | —AY | Physicochemical properties |
|---|---|---|---|
| 221 | —H | ▨cyclohexyl-NH-CH₃ | APCI-MS M/Z: 427/429 [M + H]⁺ |
| 222 | O=C(OCH₃)CH₂CH₃ (propanoate) | ▨cyclohexyl-NH-CH₃ | APCI-MS M/Z: 499/501 [M + H]⁺ Dihydrochloride |
| 223 | CH₃-O-CH₂-CH₂-O- | ▨cyclohexyl-NH-CH₃ | APCI-MS M/Z: 501/503 [M + H]⁺ Dihydrochloride |
| 224 | (CH₃)₂N-CH₂-CH₂-O- | ▨cyclohexyl-NH-CH₃ | APCI-MS M/Z: 514/516 [M + H]⁺ Trihydrochloride |

| Ex. No. | Structure | Physicochemical properties |
|---|---|---|
| 225 | [benzofuran-2-carboxamide with 4-Cl-phenyl-NH and 4-aminocyclohexyl amide] | APCI-MS M/Z: 412/414 [M + H]⁺ Hydrochloride |

| Ex. No. | —R² | —AY | Physicochemical properties |
|---|---|---|---|
| 226 | CH₃-O-C(=O)- | ▨cyclohexyl-NH₂ | APCI-MS M/Z: 471/473 [M + H]⁺ Hydrochloride |

-continued

| | | | |
|---|---|---|---|
| 227 | —H | 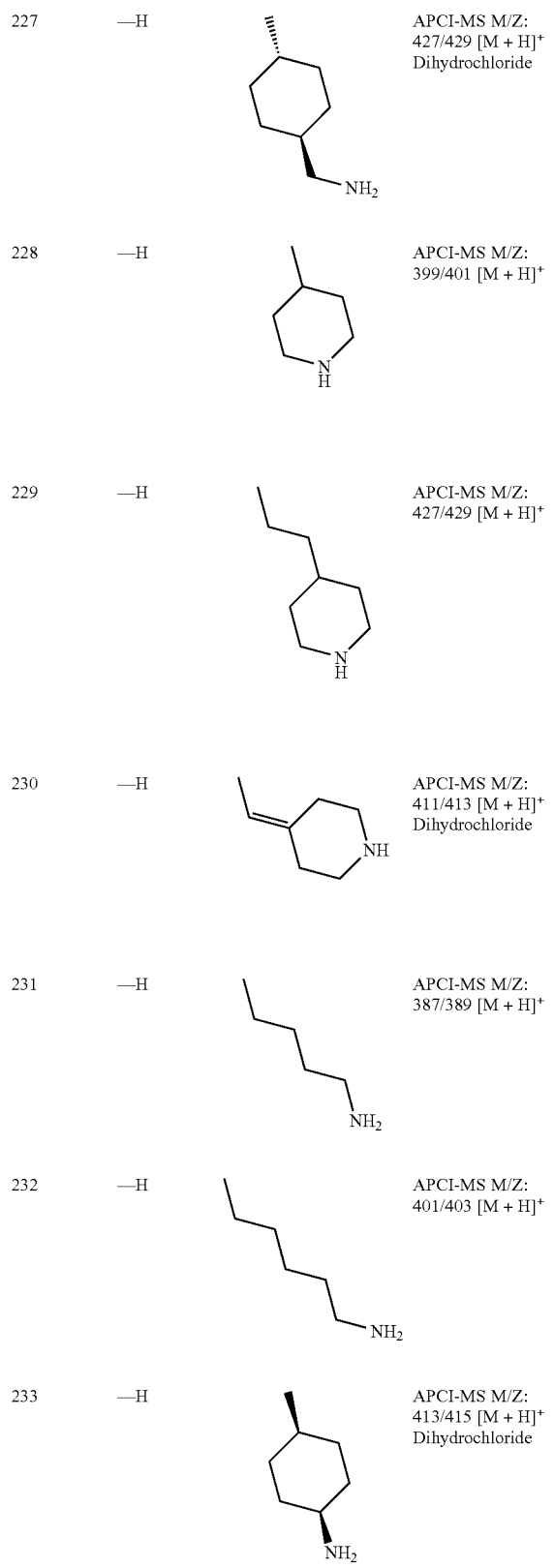 | APCI-MS M/Z: 427/429 [M + H]+ Dihydrochloride |
| 228 | —H | | APCI-MS M/Z: 399/401 [M + H]+ |
| 229 | —H | | APCI-MS M/Z: 427/429 [M + H]+ |
| 230 | —H | | APCI-MS M/Z: 411/413 [M + H]+ Dihydrochloride |
| 231 | —H | | APCI-MS M/Z: 387/389 [M + H]+ |
| 232 | —H | | APCI-MS M/Z: 401/403 [M + H]+ |
| 233 | —H | | APCI-MS M/Z: 413/415 [M + H]+ Dihydrochloride |

Example 234

Trans-3-[4-(N-formyl-N-methylamino)cyclohexyl-carbonylamino]-5-methoxycarbonyl-N-(5-chloropyridin-2-yl)-benzofuran-2-carboxamide

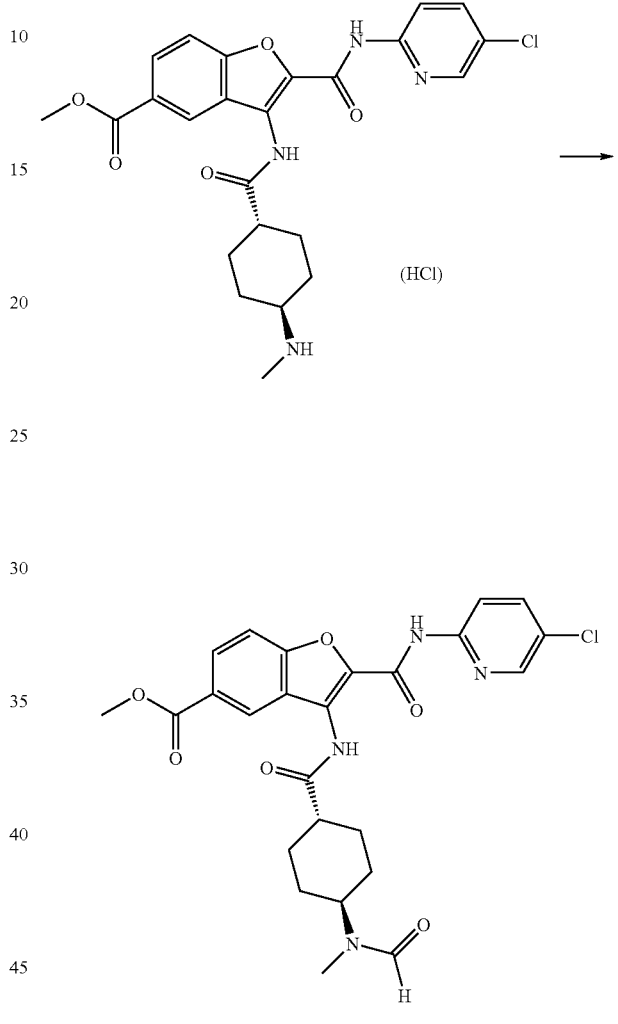

To a solution of imidazole (783 mg) and triethylamine (2.41 ml) in chloroform (80 ml) is added dropwise formic acid (709 μl) with stirring under ice-cooling. Oxalyl chloride (1.00 ml) in chloroform (10 ml) is further added thereto, and the mixture is stirred at room temperature for 0.5 hour. The reaction solution is cooled again with ice, and thereto is added trans-5-methoxycarbonyl-3-[4-(methylamino)cyclohexyl-carbonylamino]-N-(5-chloropyridine-2-yl)benzofuran-2-carboxamide hydrochloride (1.50 g) obtained in Example 218. The mixture is warmed to room temperature and stirred for 3 hours. To the reaction solution are poured ice-water and a saturated aqueous sodium hydrogen carbonate solution, and the mixture is extracted with chloroform. The extract is washed with a saturated brine, and dried over sodium sulfate. The solvent is evaporated under reduced pressure, and the resulting residue is purified by NH-silica gel column chromatography (eluent: chloroform) to give the title compound (1.45 g).

APCI-MS M/Z: 513/515 [M+H]+

Examples 235-238

The corresponding starting compounds are treated in a similar manner to Example 234 to give the following compounds.

| Ex. No. | —R² | —AY | Physicochemical properties |
|---|---|---|---|
| 235 | (methyl propanoate ester group) | (trans-cyclohexyl-N(CH₃)CHO) | APCI-MS M/Z: 527 [M + H]⁺ |
| 236 | —H | (trans-cyclohexyl-N(CH₃)CHO) | APCI-MS M/Z: 455/457 [M + H]⁺ |
| 237 | —OCH₃ | (trans-cyclohexyl-N(CH₃)CHO) | APCI-MS M/Z: 485/487 [M + H]⁺ |
| 238 | CH₃OCH₂CH₂O— | (trans-cyclohexyl-N(CH₃)CHO) | APCI-MS M/Z: 529/531 [M + H]⁺ |

Example 239

Trans-3-[4-(N-acetyl-N-methylamino)cyclohexylcarbonylamino]-5-methoxycarbonyl-N-(5-chloropyridin-2-yl)-benzofuran-2-carboxamide

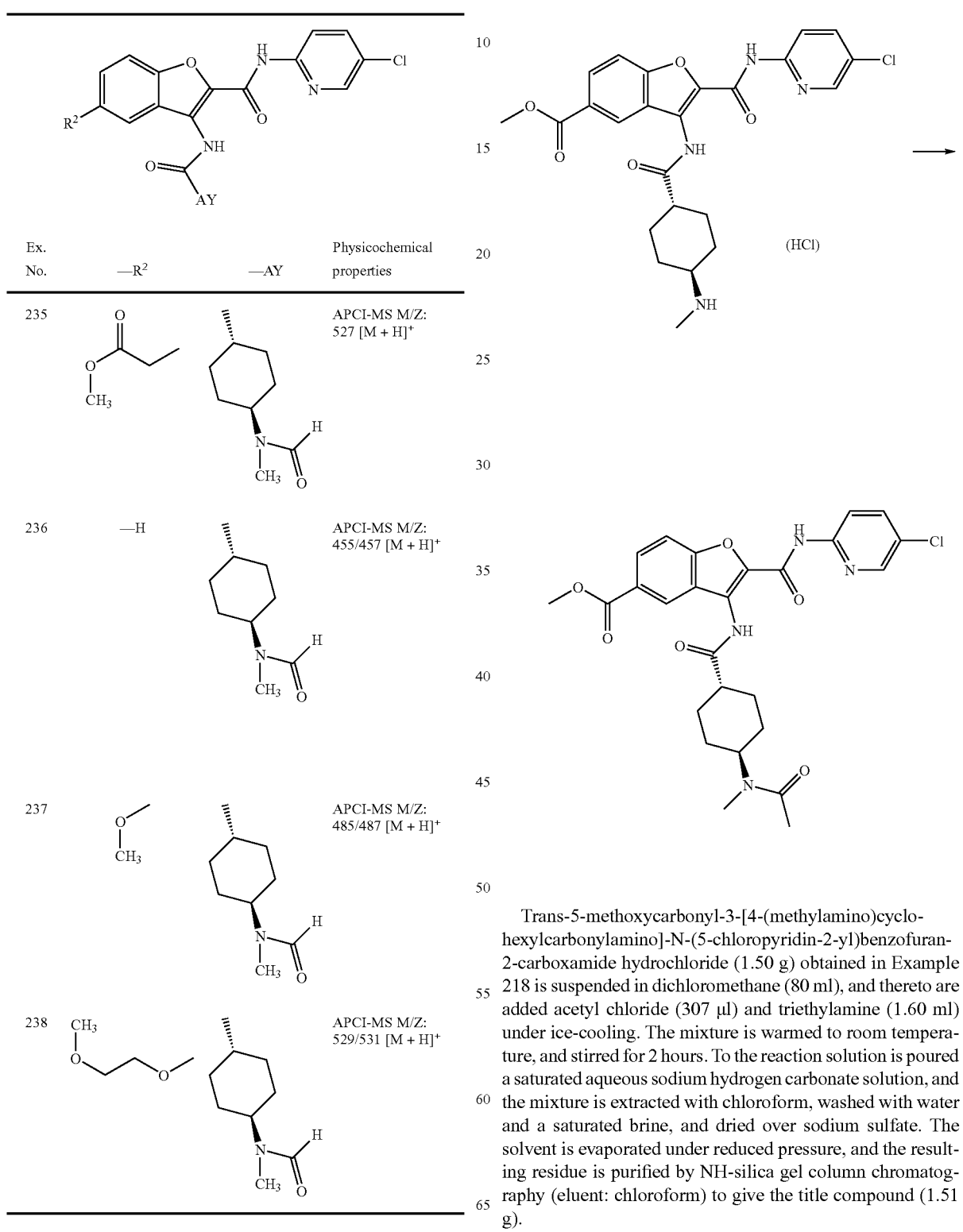

Trans-5-methoxycarbonyl-3-[4-(methylamino)cyclohexylcarbonylamino]-N-(5-chloropyridin-2-yl)benzofuran-2-carboxamide hydrochloride (1.50 g) obtained in Example 218 is suspended in dichloromethane (80 ml), and thereto are added acetyl chloride (307 μl) and triethylamine (1.60 ml) under ice-cooling. The mixture is warmed to room temperature, and stirred for 2 hours. To the reaction solution is poured a saturated aqueous sodium hydrogen carbonate solution, and the mixture is extracted with chloroform, washed with water and a saturated brine, and dried over sodium sulfate. The solvent is evaporated under reduced pressure, and the resulting residue is purified by NH-silica gel column chromatography (eluent: chloroform) to give the title compound (1.51 g).

APCI-MS M/Z: 527/529 [M+H]⁺

Example 240

3-[(1-Acetylpiperidin-4-yl)carbonylamino]-N-(5-chloropyridin-2-yl)benzofuran-2-carboxamide

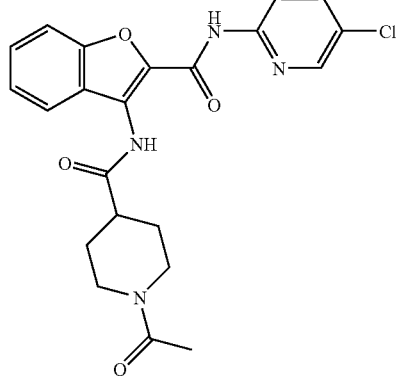

3-[(Piperidin-4-yl)carbonylamino]-N-(5-chloropyridin-2-yl)benzofuran-2-carboxamide (140 mg) obtained in Example 228 is suspended in dichloromethane (10 ml), and thereto are added acetyl chloride (30 μl) and triethylamine (74 μl) under ice-cooling, and the mixture is stirred at room temperature for 6 hours. The reaction solution is diluted with chloroform, washed successively with water, 5% aqueous citric acid solution, a saturated aqueous sodium hydrogen carbonate solution and a saturated brine, and dried over sodium sulfate. The solvent is evaporated under reduced pressure, and the resulting residue is dissolved in ethyl acetate, and treated with activated carbon. The resulting residue is recrystallized from ethyl acetate to give the title compound (38 mg).

APCI-MS M/Z: 441/443 [M+H]$^+$

Example 241-245

The corresponding starting compounds are treated in a similar manner to Example 239 or Example 240 to give the following compounds in a free form, or which are further treated with hydrogen chloride to give hydrochlorides thereof.

| Ex. No. | —R² | —AY | Physicochemical properties |
|---|---|---|---|
| 241 | —H | (trans-4-methylcyclohexyl)-N(CH₃)-C(O)-CH₂CH₃ | APCI-MS M/Z: 483/485 [M + H]⁺ |
| 242 | —H | (trans-4-methylcyclohexyl)-N(CH₃)-C(O)-cyclopropyl | APCI-MS M/Z: 496/498 [M + H]⁺ |
| 243 | —H | (trans-4-methylcyclohexyl)-N(CH₃)-C(O)-CH(CH₃)₂ | APCI-MS M/Z: 497/499 [M + H]⁺ |
| 244 | —H | (trans-4-methylcyclohexyl)-N(CH₃)-C(O)-C(CH₃)₃ | APCI-MS M/Z: 511/513 [M + H]⁺ |
| 245 | —H | 4-methylpiperidin-1-yl-SO₂-CH₃ | APCI-MS M/Z: 477/479 [M + H]⁺ |

Example 246

Trans-3-[4-(N-acetyl-N-methylamino)cyclohexylcarbonylamino]-5-(2-methoxyethoxy)-N-(5-chloropyridin-2-yl)benzofuran-2-carboxamide

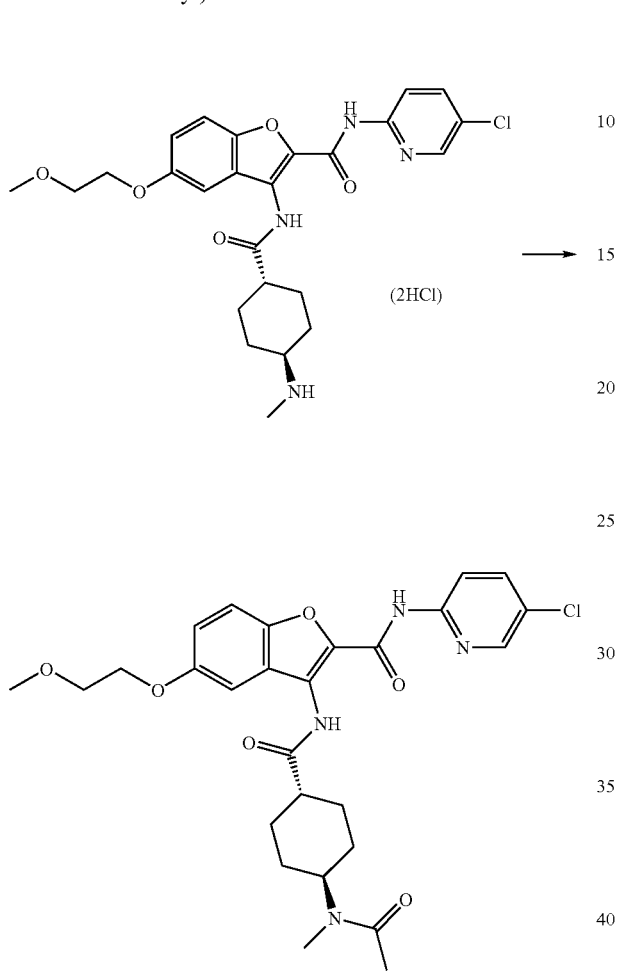

(2HCl)

Trans-5-(2-methoxyethoxy)-3-[4-(methylamino)cyclohexylcarbonylamino]-N-(5-chloropyridin-2-yl)benzofuran-2-carboxamide dihydrochloride (110 mg) obtained in Example 223 is suspended in N,N-dimethylformamide (5 ml), and thereto are added successively acetic acid (13.2 µl), 1-hydroxybenzotriazole (31 mg), triethylamine (80 µl) and 1-ethyl-3-(3-dimethylaminopropyl)carbodiimide hydrochloride (44 mg), and the mixture is stirred at room temperature for 15 hours. To the reaction solution are added acetic acid (8.2 µl), 1-hydroxybenzotriazole (20 mg), triethylamine (67 µl) and 1-ethyl-3-(3-dimethylaminopropyl)carbodiimide hydrochloride (28 mg), and the mixture is further stirred at room temperature for 20 hours. To the reaction solution is poured a saturated aqueous sodium hydrogen carbonate solution, and the mixture is extracted with chloroform. The organic layer is washed with a saturated brine, dried over sodium sulfate, and the solvent is evaporated under reduced pressure. The resulting residue is purified by NH-silica gel column chromatography (eluent: n-hexane/ethyl acetate=1/1, then ethyl acetate). The obtained solid is suspended in n-hexane/diisopropyl ether, and collected by filtration to give the title compound (42 mg).

APCI-MS M/Z: 543/545 [M+H]+

Example 247

3-[1-((Pyridin-3-yl)carbonyl)piperidin-4-ylcarbonylamino]-N-(5-chloropyridin-2-yl)benzofuran-2-carboxamide dihydrochloride

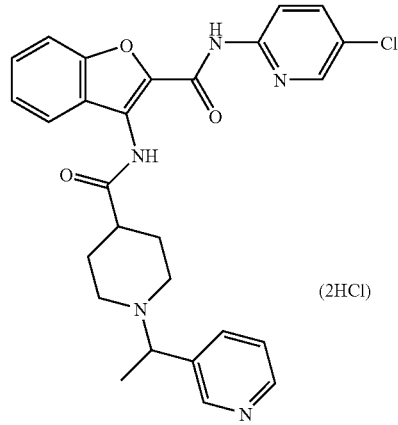

(2HCl)

3-[(Piperidin-4-yl)carbonylamino]-N-(5-chloropyridin-2-yl)benzofuran-2-carboxamide (100 mg) obtained in Example 228 is dissolved in N,N-dimethylformamide (3 ml), and thereto are added successively nicotinic acid (34 mg), 1-hydroxybenzotriazole (37 mg) and 1-ethyl-3-(3-dimethylaminopropyl)carbodiimide hydrochloride (53 mg), and the mixture is stirred at room temperature for 4 hours. To the reaction solution are poured a saturated aqueous sodium hydrogen carbonate solution and water, and the precipitates are collected by filtration, washed with chloroform, and dried to give 3-[1-((pyridin-3-yl)carbonyl)piperidin-4-ylcarbonylamino]-N-(5-chloropyridin-2-yl)benzofuran-2-carboxamide (103 mg). This product is treated with hydrogen chloride in dioxane to give the title compound (115 mg).

APCI-MS M/Z: 504/506 [M+H]+

Examples 248-257

The corresponding starting compounds are treated in a similar manner to Example 246 or Example 247 to give the following compounds in a free form, or which are treated with hydrogen chloride to give hydrochlorides thereof.

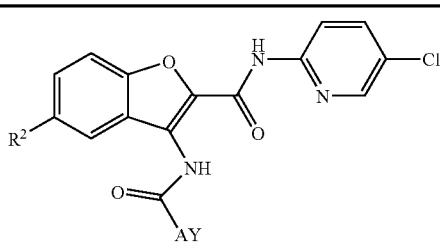

| Ex. No. | —R² | —AY | Physico-chemical properties |
|---|---|---|---|
| 248 | —H | 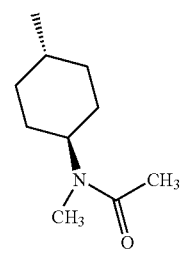 | APCI-MS M/Z: 469/471 [M + H]+ |

147
-continued
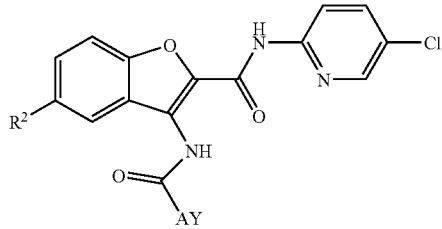
| Ex. No. | —R² | —AY | Physico-chemical properties |
|---|---|---|---|
| 249 | 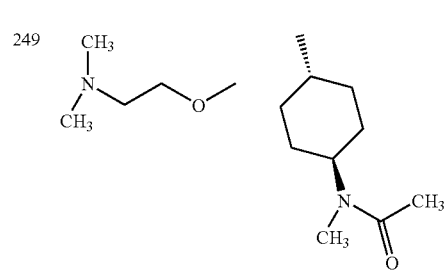 | | APCI-MS M/Z: 556/558 [M + H]⁺ Dihydrochloride |
| 250 | —H | 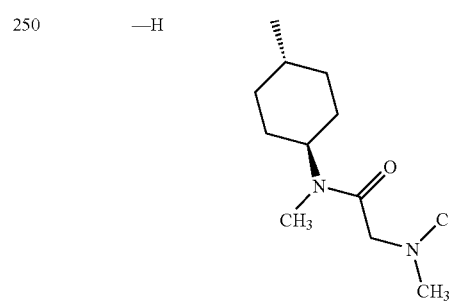 | APCI-MS M/Z: 512/514 [M + H]⁺ |
| 251 | —H | 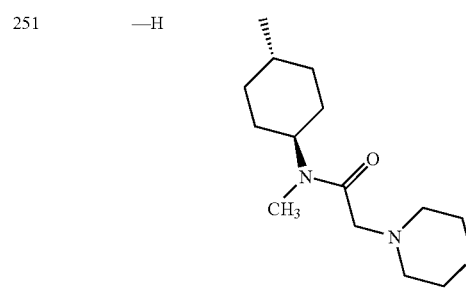 | APCI-MS M/Z: 554/556 [M + H]⁺ |
| 252 | —H | 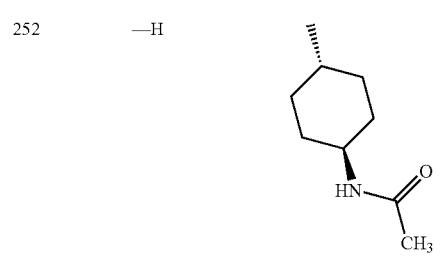 | APCI-MS M/Z: 455/457 [M + H]⁺ |
148
-continued
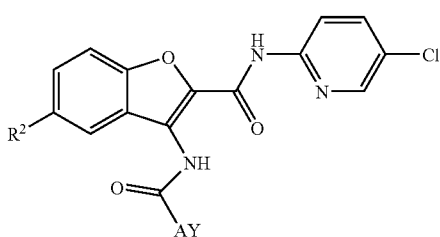
| Ex. No. | —R² | —AY | Physico-chemical properties |
|---|---|---|---|
| 253 | —H | 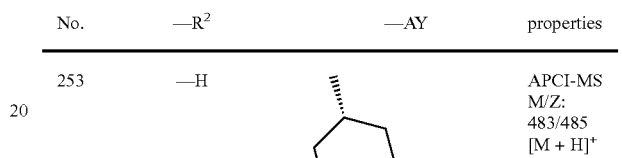 | APCI-MS M/Z: 483/485 [M + H]⁺ |
| 254 | —H | 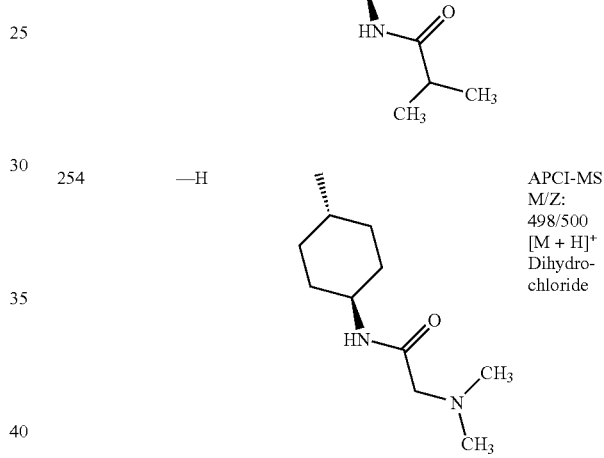 | APCI-MS M/Z: 498/500 [M + H]⁺ Dihydrochloride |
| 255 | —H | 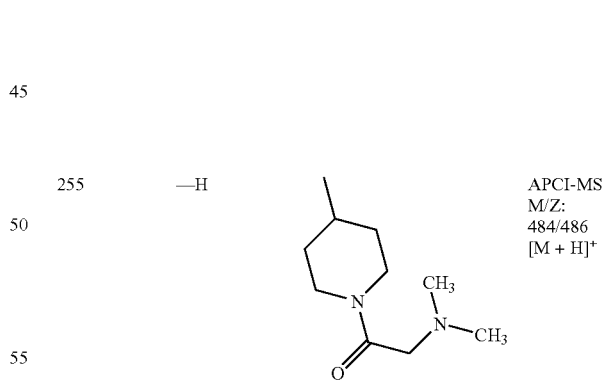 | APCI-MS M/Z: 484/486 [M + H]⁺ |
| 256 | —H | 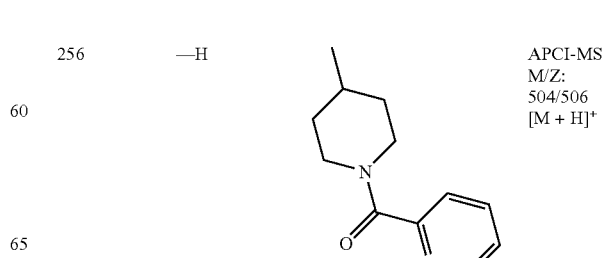 | APCI-MS M/Z: 504/506 [M + H]⁺ |

-continued

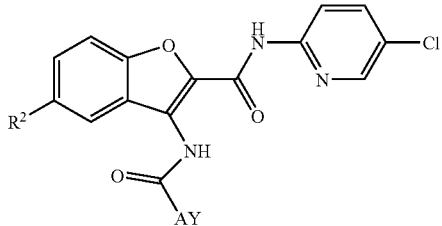

| Ex. No. | —R² | —AY | Physico-chemical properties |
|---|---|---|---|
| 257 | —H | (4-methylpiperidinyl-N-C(O)-4-pyridyl) | APCI-MS M/Z: 504/506 [M + H]⁺ Dihydrochloride |

Example 258

Trans-5-carboxy-3-[4-(N-formyl-N-methylamino)-cyclohexylcarbonylamino]-N-(5-chloropyridin-2-yl)benzofuran-2-carboxamide

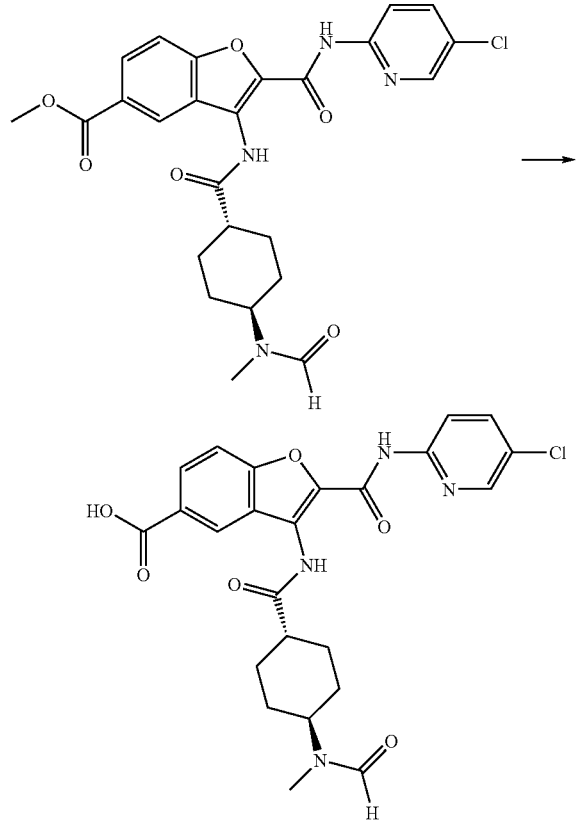

Trans-3-[4-(N-formyl-N-methylamino)cyclohexylcarbonylamino]-5-methoxycarbonyl-N-(5-chloropyridin-2-yl)benzofuran-2-carboxamide (1.90 g) obtained in Example 234 is suspended in tetrahydrofuran/methanol (1:1, 50 ml), and thereto is added 4N aqueous sodium hydroxide solution (5 ml) under ice-cooling. The mixture is warmed to room temperature, and stirred for 17 hours. The reaction solution is concentrated under reduced pressure, and to the residue is poured ice-water, and the mixture is neutralized with 10% hydrochloric acid. The precipitates are collected by filtration, washed successively with water and tetrahydrofuran, and dried to give the title compound (1.59 g).

ESI-MS M/Z: 497/499 [M−H]⁻

Examples 259-260

The corresponding starting compounds are treated in a similar manner to Example 258 to give the following compounds in a free form, or which are treated with hydrogen chloride to give hydrochlorides thereof.

| No. Ex. | —R² | —AY | Physicochemical properties |
|---|---|---|---|
| 259 | HOOC-CH₂- | trans-cyclohexyl-N(CHO)(CH₃) | ESI-MS M/Z: 511/513 [M − H]⁻ |
| 260 | HOOC-CH(CH₃)- | trans-cyclohexyl-N(CH₃)(COCH₃) | ESI-MS M/Z: 511/513 [M − H]⁻ |

Example 261

Trans-5-dimethylaminocarbonyl-3-[4-(N-formyl-N-methylamino)cyclohexylcarbonylamino]-N-(5-chloropyridin-2-yl)benzofuran-2-carboxamide

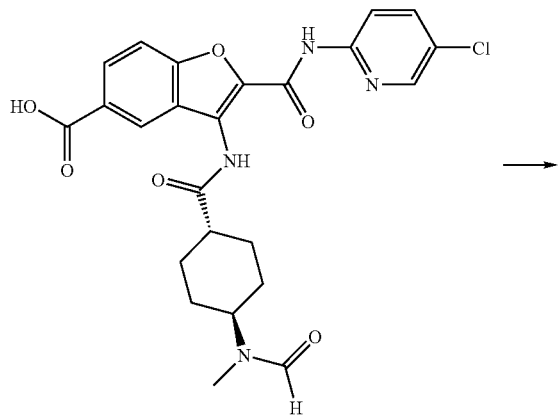

Trans-5-carboxy-3-[4-(N-formyl-N-methylamino)cyclhexylcarbonylamino]-N-(5-chloropyridin-2-yl)benzofuran-2-carboxamide (196 mg) obtained in Example 258 is suspended in N,N-dimethylformamide/pyridine (1:1, 8 ml), and thereto are added successively dimethylamine hydrochloride (49 mg), 1-hydroxybenzotriazole (108 mg) and 1-ethyl-3-(3-dimethylaminopropyl)carbodiimide hydrochloride (153 mg) under ice-cooling, and the mixture is stirred at room temperature for 48 hours. To the reaction solution is poured a saturated aqueous sodium hydrogen carbonate solution, and the mixture is extracted with ethyl acetate. The extract is washed with water and a saturated brine, dried over sodium sulfate. The solvent is evaporated under reduced pressure, and the resulting residue is purified by NH-silica gel column chromatography (eluent: ethyl acetate). The resulting residue is suspended in diethyl ether/n-hexane, and the precipitates are collected by filtration to give the title compound (141 mg).

APCI-MS M/Z: 526/528 [M+H]$^+$

Examples 262-275

The corresponding starting compounds are treated in a similar manner to Example 261 to give the following compounds in a free form, or which are further treated with hydrogen chloride to give hydrochlorides thereof.

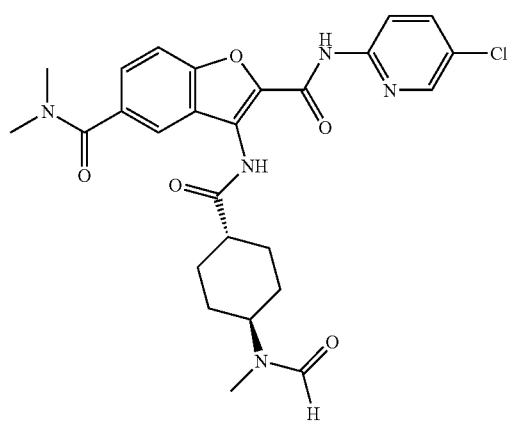

| Ex. No. | —R$^2$ | —AY | Physicochemical properties |
|---|---|---|---|
| 262 | 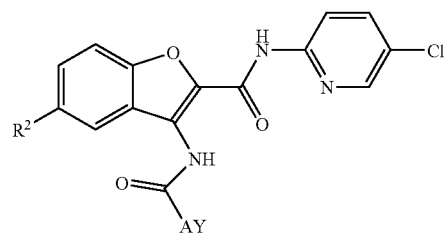 | | APCI-MS M/Z: 568/570 [M + H]$^+$ |

-continued

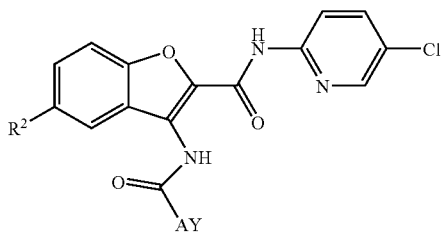

| Ex. No. | —R² | —AY | Physicochemical properties |
|---|---|---|---|
| 263 | (1-acetylpyrrolidin-3-yl) | (trans-4-(N-methylformamido)cyclohexyl) | APCI-MS M/Z: 552/554 [M + H]⁺ |
| 264 | N-(2-methoxyethyl)-N-methylacetamide | (trans-4-(N-methylformamido)cyclohexyl) | APCI-MS M/Z: 570/572 [M + H]⁺ |
| 265 | N-(2-hydroxyethyl)-N-methylacetamide | (trans-4-(N-methylformamido)cyclohexyl) | APCI-MS M/Z: 556/558 [M + H]⁺ |
| 266 | 1-acetyl-4-(hydroxymethyl)piperidine | (trans-4-(N-methylformamido)cyclohexyl) | APCI-MS M/Z: 596/598 [M + H]⁺ |
| 267 | N,N-dimethylpropanamide | (trans-4-(N-methylformamido)cyclohexyl) | APCI-MS M/Z: 540/542 [M + H]⁺ |

-continued

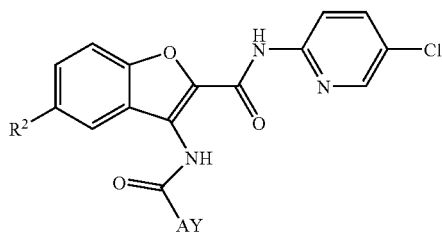

| Ex. No. | —R² | —AY | Physicochemical properties |
|---|---|---|---|
| 268 | 1-(morpholin-4-yl)propan-1-one group | trans-4-(N-methyl-N-formylamino)cyclohexyl | APCI-MS M/Z: 582/584 [M + H]⁺ |
| 269 | 1-[4-(hydroxymethyl)piperidin-1-yl]propan-1-one group | trans-4-(N-methyl-N-formylamino)cyclohexyl | APCI-MS M/Z: 610/612 [M + H]⁺ |
| 270 | N,N-dimethylacetamide group | trans-4-(N-methyl-N-acetylamino)cyclohexyl | APCI-MS M/Z: 540/542 [M + H]⁺ |
| 271 | 1-(morpholin-4-yl)acetyl group | trans-4-(N-methyl-N-acetylamino)cyclohexyl | APCI-MS M/Z: 582/584 [M + H]⁺ |

-continued
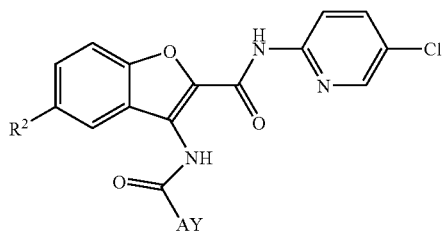
| Ex. No. | —R² | —AY | Physicochemical properties |
|---|---|---|---|
| 272 | 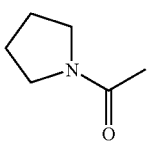 |  | APCI-MS M/Z: 566/568 [M + H]⁺ |
| 273 | 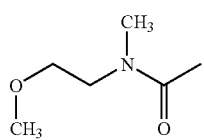 | 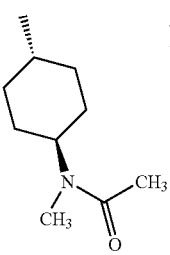 | APCI-MS M/Z: 584/586 [M + H]⁺ |
| 274 | 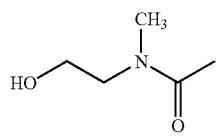 | 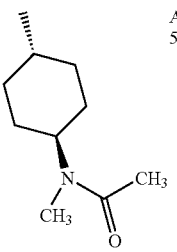 | APCI-MS M/Z: 570/572 [M + H]⁺ |
| 275 | 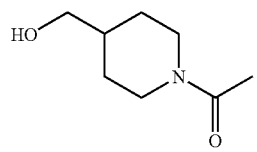 | 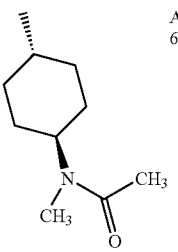 | APCI-MS M/Z: 610/612 [M + H]⁺ |

Examples 276-277

The corresponding starting compounds are treated in a similar manner to Example 145 to give the following compounds.

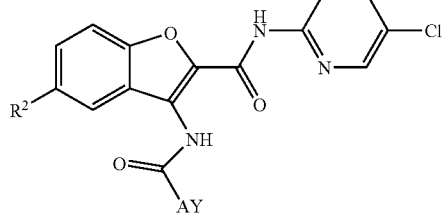

| Ex. No. | —R² | —AY | Physicochemical properties |
|---|---|---|---|
| 276 | HO~~~ | 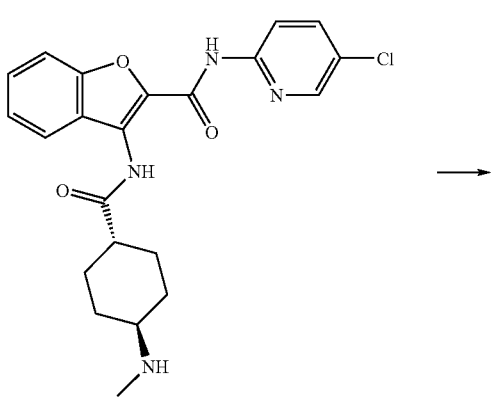 | APCI-MS M/Z: 499/501 [M + H]⁺ |
| 277 | HO~ | | APCI-MS M/Z: 499/501 [M + H]⁺ |

Example 278

Trans-3-[4-(N-(2-hydroxyethyl)-N-methylamino)-cyclohexylcarbonylamino]-N-(5-chloropyridin-2-yl)benzofuran-2-carboxamide dihydrochloride

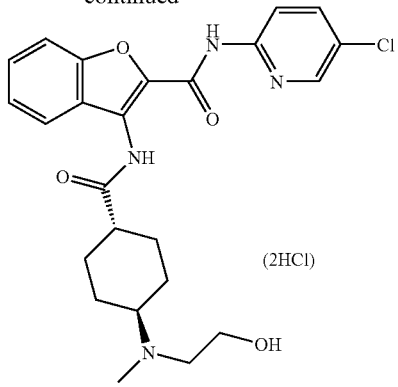

(2HCl)

Trans-3-[4-(methylamino)cyclohexylcarbonylamino]-N-(5-chloropyridin-2-yl)benzofuran-2-carboxamide (125 mg) obtained in Example 221 is suspended in ethanol (5 ml), and thereto are added 2-iodo-ethanol (105 μl) and sodium carbonate (57 mg), and the mixture is stirred at 50° C. for 15 hours. To the mixture is further added 2-iodo-ethanol (53 μl), and the mixture is further stirred at 80° C. for 6 hours. Again, 2-iodo-ethanol (53 μl) is added thereto, and the mixture is stirred at 80° C. for 24 hours. The reaction solution is concentrated under reduced pressure, and to the residue is poured a saturated aqueous sodium hydrogen carbonate solution, and the mixture is extracted with chloroform. The organic layer is washed with water, a saturated brine, dried over sodium sulfate, and the solvent is evaporated under reduced pressure. The resulting residue is purified by NH-silica gel column chromatography (eluent: n-hexane/ethyl acetate=1/2, then ethyl acetate) to give trans-3-[4-(N-(2-hydroxyethyl)-N-methylamino)cyclohexylcarbonylamino]-N-(5-chloropyridin-2-yl)benzofuran-2-carboxamide (53 mg). Subsequently, this product is dissolved in chloroform/methanol (5/1, 6 ml), and thereto is added 4N hydrogen chloride in ethyl acetate (1 ml). The solvent is evaporated under reduced pressure. The resulting residue is suspended in diethyl ether, and collected by filtration to give the title compound (55 mg).
APCI-MS M/Z: 471/473 [M+H]⁺

Example 279

3-[[1-((Pyridin-4-yl)methyl)piperidin-4-yl]-carbonylamino]-N-(5-chloropyridin-2-yl)benzofuran-2-carboxamide

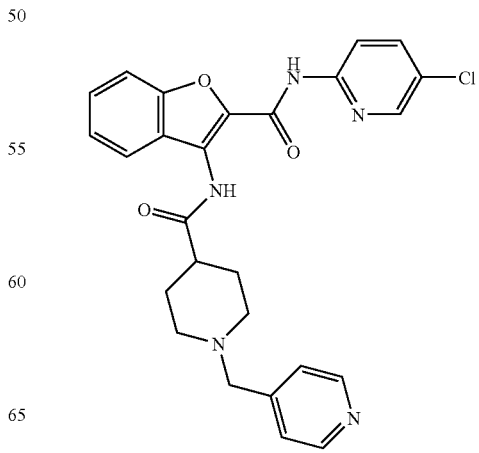

3-((Piperidin-4-yl)carbonylamino)-N-(5-chloropyridin-2-yl)benzofuran-2-carboxamide (100 mg) obtained in Example 228 is suspended in N,N-dimethylacetamide (3 ml), and thereto are added 4-(chloromethyl)pyridine hydrochloride (45 mg), sodium carbonate (80 mg) and sodium iodide (41 mg), and the mixture is stirred at room temperature for 12 hours. To the reaction solution is poured a saturated aqueous sodium hydrogen carbonate solution, and the mixture is extracted with ethyl acetate. The organic layer is washed with water and a saturated brine, and dried over sodium sulfate. The solvent is evaporated under reduced pressure, and the resulting residue is purified by NH-silica gel column chromatography (eluent: n-hexane/ethyl acetate=2/1, then 1/1) to give the title compound (109 mg).

APCI-MS M/Z: 490/492 [M+H]$^+$

Examples 280-289

The corresponding starting compounds are treated in a similar manner to Example 278 or Example 279 to give the following compounds in a free form, or which are further treated with hydrogen chloride to give hydrochlorides thereof.

-continued

| | | | |
|---|---|---|---|
| 285 | —H |  | APCI-MS M/Z: 518/520 [M + H]+ Trihydrochloride |
| 286 | —H |  | APCI-MS M/Z: 518/520 [M + H]+ Trihydrochloride |
| 287 | —H |  | APCI-MS M/Z: 517/519 [M + H]+ Dihydrochloride |
| 288 | —H |  | APCI-MS M/Z: 490/492 [M + H]+ Trihydrochloride |
| 289 | — |  | APCI-MS M/Z: 490/492 [M + H]+ Trihydrochloride |

Example 290

Trans-3-[4-(2-hydroxyethylamino)cyclohexylcarbonylamino]-N-(4-chlorophenyl)benzofuran-2-carboxamide hydrochloride

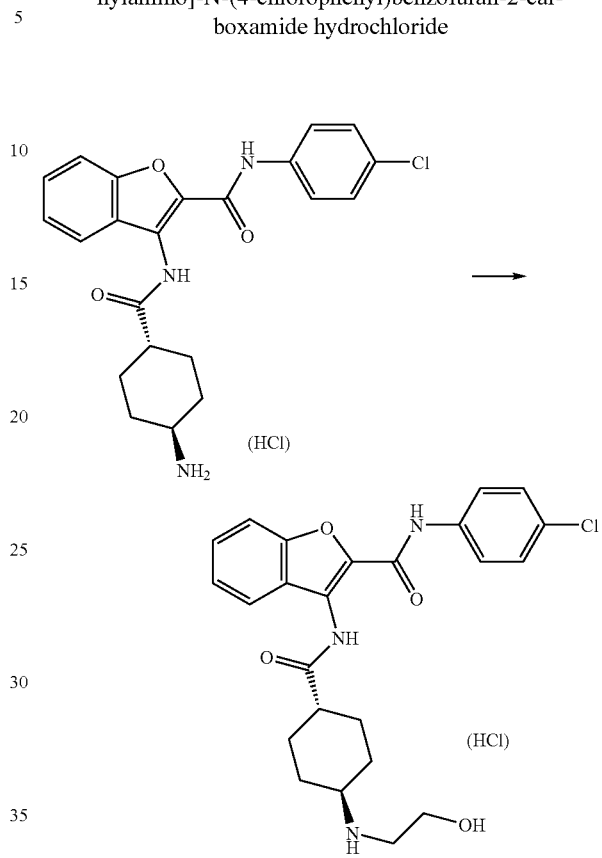

Trans-3-[4-aminocyclohexylcarbonylamino]-N-(4-chlorophenyl)benzofuran-2-carboxamide hydrochloride (150 mg) obtained in Example 225 is suspended in acetonitrile/methanol (5/1, 6 ml), and thereto is added triethylamine (93 μl), and the mixture is stirred at room temperature for several minutes. The reaction solution is cooled with ice, and thereto is added 2-iodo-ethanol (29 μl), and the mixture is stirred at 50° C. for 3 hours. 2-Iodo-ethanol (58 μl) is further added thereto, and the mixture is stirred at 50° C. for 3 hours. Again, 2-iodo-ethanol (58 μl) is added thereto, and the mixture is further stirred at 50° C. for 15 hours. The reaction solution is concentrated under reduced pressure, and to the residue are poured water and a saturated aqueous sodium hydrogen carbonate solution, and the mixture is extracted with chloroform. The organic layer is washed with water and a saturated brine, dried over sodium sulfate, and the solvent is evaporated under reduced pressure. The resulting residue is purified by NH-silica gel column chromatography (eluent: ethyl acetate, then ethyl acetate/methanol=20/1) to give trans-3-[4-(2-hydroxyethylamino)cyclohexylcarbonylamino]-N-(4-chlorophenyl)benzofuran-2-carboxamide (104 mg). This product (104 mg) is dissolved in chloroform/methanol (5/1, 6 ml), and thereto is added 4N hydrogen chloride in ethyl acetate (1 ml). The solvent is evaporated under reduced pressure, and the resulting residue is suspended in diethyl ether, and collected by filtration to give the title compound (95 mg).

APCI-MS M/Z: 456/458 [M+H]+

Examples 291-296

The corresponding starting compounds are treated in a similar manner to Example 290 to give the following compounds in a free form, or which are further treated with hydrogen chloride to give hydrochlorides thereof.

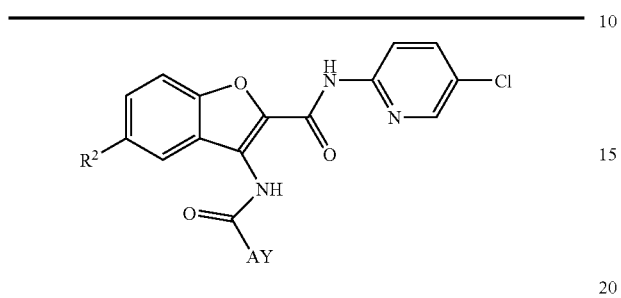

| Ex. No. | Structure | Physico-chemical properties |
|---|---|---|
| 291 | 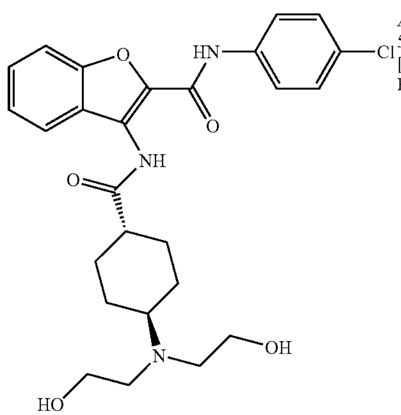 | APCI-MS M/Z: 500/502 [M + H]+ Hydrochloride |

| Ex. No. | —R² | —AY | Physicochemical properties |
|---|---|---|---|
| 292 | —H | | APCI-MS M/Z: 469/471 [M + H]+ Dihydrochloride |
| 293 | —H | 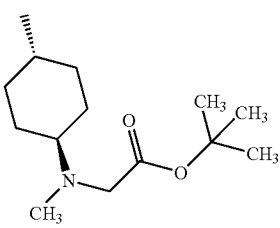 | APCI-MS M/Z: 541/543 [M + H]+ |
| 294 | —H | 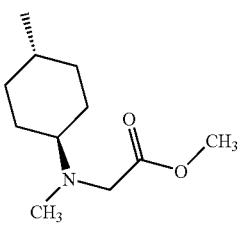 | APCI-MS M/Z: 499/501 [M + H]+ Dihydrochloride |
| 295 | —H | 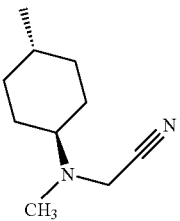 | APCI-MS M/Z: 466/468 [M + H]+ |
| 296 | —H | 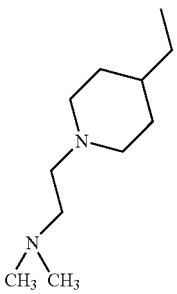 | APCI-MS M/Z: 484/486 [M + H]+ |

Example 297

Trans-3-[4-(morpholin-4-yl)cyclohexylcarbonylamino]-N-(5-chloropyridin-2-yl)benzofuran-2-carboxamide dihydrochloride

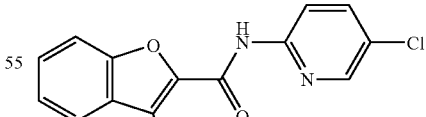
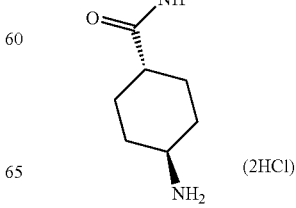

(2HCl)

-continued

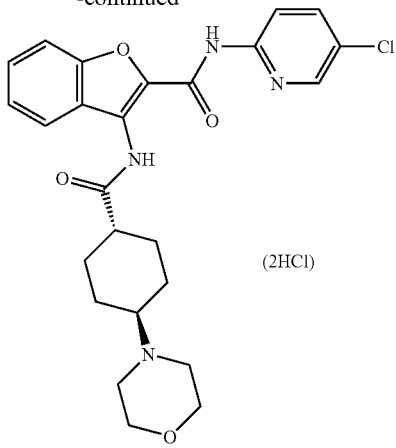

(2HCl)

Trans-3-[4-aminocyclohexylcarbonylamino]-N-(5-chloropyridin-2-yl)benzofuran-2-carboxamide dihydrochloride (200 mg) obtained in Example 219 is suspended in N,N-dimethyl acetamide (10 ml), and thereto are added bis(2-chloroethyl) ether (73 μl), sodium iodide (185 mg), and sodium carbonate (131 mg), and the mixture is stirred at 50° C. for 5 hours, and then stirred at 80° C. for 3 hours. Bis(2-chloroethyl) ether (73 μl) is further added thereto, and the mixture is stirred at 80° C. for 15 hours. The reaction solution is concentrated under reduced pressure, and to the residue is poured a saturated aqueous sodium hydrogen carbonate solution, and the mixture is extracted with chloroform. The organic layer is washed with water and a saturated brine, dried over sodium sulfate, and the solvent is evaporated under reduced pressure. The resulting residue is purified by NH-silica gel column chromatography (eluent: n-hexane/ethyl acetate=5/1, then 1/1) to give trans-3-[4-(morpholin-4-yl)cyclohexylcarbonylamino]-N-(5-chloropyridin-2-yl)benzofuran-2-carboxamide (70 mg). Subsequently, this product is dissolved in chloroform/methanol (5/1, 6 ml), and thereto is added 4N hydrogen chloride in ethyl acetate (1 ml), and the solvent is evaporated under reduced pressure. The resulting residue is suspended in diethyl ether, and collected by filtration to give the title compound (65 mg).

APCI-MS M/Z: 483/485 [M+H]$^+$

Examples 298-301

The corresponding starting compounds are treated in a similar manner to Example 297 to give the following compounds in a free form, or which are further treated with hydrogen chloride to give hydrochlorides thereof.

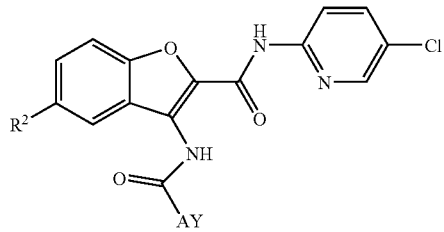

| Ex. No. | —R$^2$ | —AY | Physicochemical properties |
|---|---|---|---|

-continued

| | | | |
|---|---|---|---|
| 298 | —H |  | APCI-MS M/Z: 467 [M + H]$^+$ Dihydrochloride |
| 299 | —H | 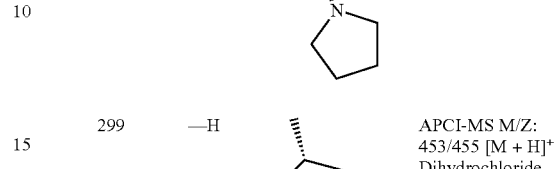 | APCI-MS M/Z: 453/455 [M + H]$^+$ Dihydrochloride |

| Ex. No. | Structure | Physicochemical properties |
|---|---|---|
| 300 | 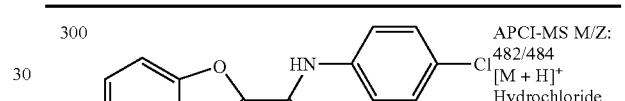 | APCI-MS M/Z: 482/484 [M + H]$^+$ Hydrochloride |
| 301 | 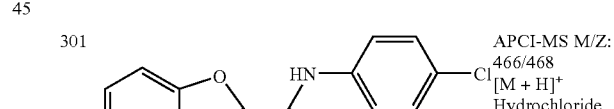 | APCI-MS M/Z: 466/468 [M + H]$^+$ Hydrochloride |

Example 302

Trans-3-[4-(N-carboxymethyl-N-methylamino)-cyclohexylcarbonylamino]-N-(5-chloropyridin-2-yl)-benzofuran-2-carboxamide dihydrochloride

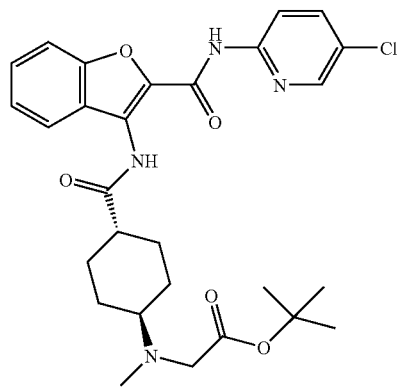

Trans-3-[4-(N-t-butoxycarbonylmethyl-N-methylamino)-cyclohexylcarbonylamino]-N-(5-chloropyridin-2-yl)benzofuran-2-carboxamide (820 mg) obtained in Example 293 is treated in a similar manner to Example 156 to give the title compound (778 mg).

ESI-MS M/Z: 507/509 [M+Na]⁺

Examples 303-305

Trans-3-[4-(N-carboxymethyl-N-methylamino)cyclohexylcarbonylamino]-N-(5-chloropyridin-2-yl)benzofuran-2-carboxamide dihydrochloride obtained in Example 302 istreated in a similar manner to Example 87 to give the following compounds in a free form, or which are further treated with hydrogen chloride to give hydrochlorides thereof.

| Ex. No. | —R² | —AY | Physicochemical properties |
|---|---|---|---|
| 303 | —H | (trans-cyclohexyl-N(CH₃)-CH₂-C(O)-NH₂) | APCI-MS M/Z: 484/486 [M + H]⁺ Dihydrochloride |
| 304 | —H | (trans-cyclohexyl-N(CH₃)-CH₂-C(O)-NHCH₃) | APCI-MS M/Z: 498/500 [M + H]⁺ Dihydrochloride |
| 305 | —H | (trans-cyclohexyl-N(CH₃)-CH₂-C(O)-N(CH₃)₂) | APCI-MS M/Z: 512/514 [M + H]⁺ Dihydrochloride |

Example 306

Trans-3-[4-(dimethylamino)cyclohexylcarbonylamino]-N-(5-chloropyridin-2-yl)benzofuran-2-carboxamide hydrochloride

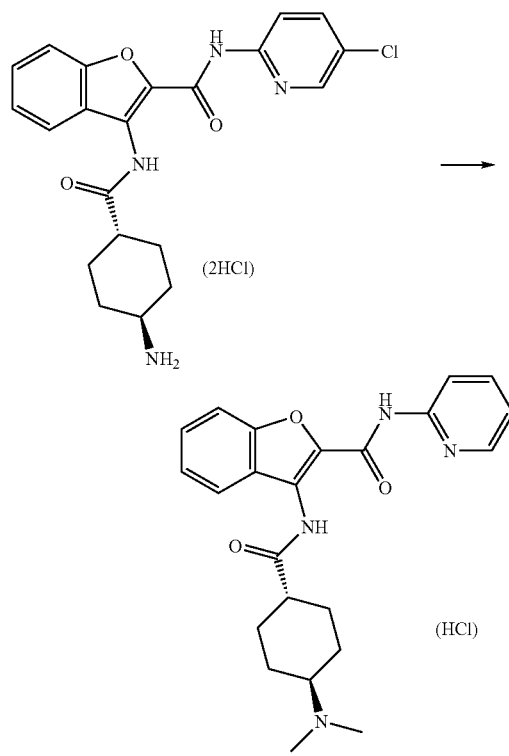

Trans-3-(4-aminocyclohexylcarbonylamino)-N-(5-chloropyridin-2-yl)benzofuran-2-carboxamide dihydrochloride (9.30 g) obtained in Example 219 is suspended in dichloromethane (430 ml), and thereto is added triethylamine (7.99 ml) under ice-cooling, and the mixture is stirred for several minutes. Then, 35% aqueous formaldehyde solution (7.59 ml) and sodium triacetoxy borohydride (12.10 g) are successively added thereto, and the reaction solution is warmed to room temperature, and stirred for 12 hours. To the reaction solution is poured a saturated aqueous sodium hydrogen carbonate solution under ice-cooling, and the mixture is extracted with chloroform. The organic layer is washed successively with water and a saturated brine, dried over sodium sulfate, and the solvent is evaporated under reduced pressure. The residue is purified by NH-silica gel column chromatography (eluent: n-hexane/ethyl acetate=3/1, then ethyl acetate) to give trans-3-[4-(dimethylamino)-cyclohexylcarbonylamino]-N-(5-chloropyridin-2-yl)benzofuran-2-carboxamide (6.92 g). This product is dissolved in chloroform/methanol (5/1, 60 ml), and thereto is added 4N hydrogen chloride in ethyl acetate (50 ml) under ice-cooling. The reaction solution is concentrated under reduced pressure, and the resulting residue is suspended in diethyl ether, and collected by filtration to give the title compound (7.83 g).

APCI-MS M/Z: 441/443 [M+H]$^+$

Example 307

Trans-3-[4-[N-[3-(t-butoxycarbonylamino)-propyl]-N-methylamino]cyclohexylcarbonylamino]-N-(5-chloropyridin-2-yl)benzofuran-2-carboxamide

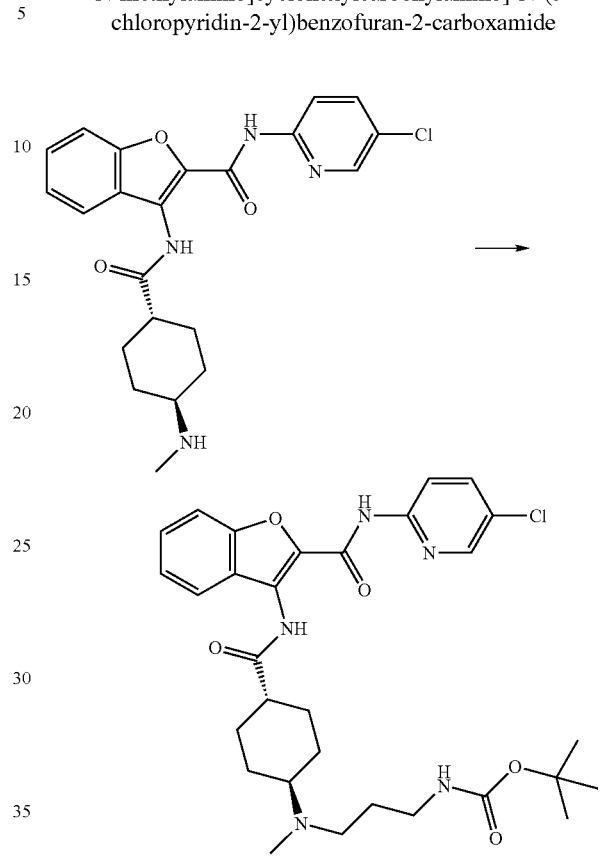

Trans-3-[4-(methylamino)cyclohexylcarbonylamino]-N-(5-chloropyridin-2-yl)benzofuran-2-carboxamide (250 mg) obtained in Example 221 is suspended in dichloromethane (8 ml), and thereto are added 3-t-butoxycarbonylaminopropanal (198 mg) and triethylamine (160 μl) under ice-cooling, and the mixture is stirred for several minutes. Then, sodium triacetoxy borohydride (243 mg) and the reaction solution is warmed to room temperature, and stirred for 4 hours. To the reaction solution is poured a saturated aqueous sodium hydrogen carbonate solution under ice-cooling, and the mixture is extracted with chloroform. The organic layer is washed successively with water and a saturated brine, dried over sodium sulfate, and the solvent is evaporated under reduced pressure. The resulting residue is purified by NH-silica gel column chromatography (eluent: n-hexane/ethyl acetate=3/1, then 1/1) to give the title compound (312 mg).

APCI-MS M/Z: 584/586 [M+H]$^+$

Examples 308-326

The corresponding starting compounds are treated in a similar manner to Example 306 or Example 307 to give the following compounds in a free form, or which are further treated with hydrogen chloride to give hydrochlorides thereof.

| Ex. No. | Structure | Physicochemical properties |
|---|---|---|
| 308 | 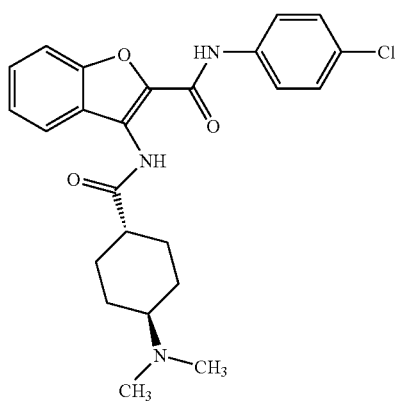 | APCI-MS M/Z: 440/442 [M + H]+ Hydrochloride |
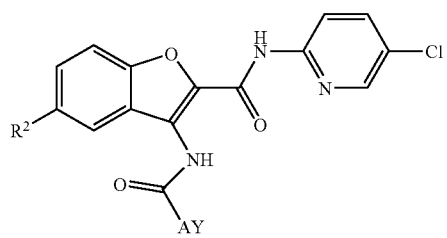
| Ex. No. | —R² | —AY | Physicochemical properties |
|---|---|---|---|
| 309 | —H | 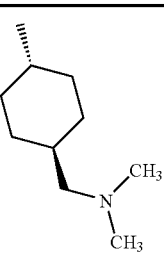 | APCI-MS M/Z: 455/457 [M + H]+ Dihydrochloride |
| 310 | —H | 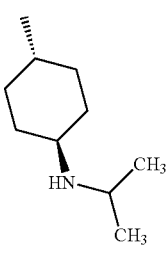 | APCI-MS M/Z: 455/457 [M + H]+ Dihydrochloride |
| 311 | 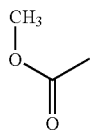 | 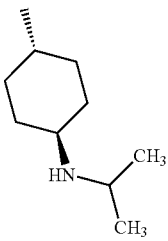 | APCI-MS M/Z: 513/515 [M + H]+ |

-continued
| | | | |
|---|---|---|---|
| 312 | —H | 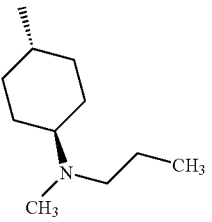 | APCI-MS M/Z: 469/471 [M + H]+ Dihydrochloride |
| 313 | —H | 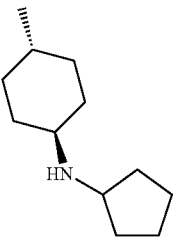 | APCI-MS M/Z: 481/483 [M + H]+ Dihydrochloride |
| 314 | —H | 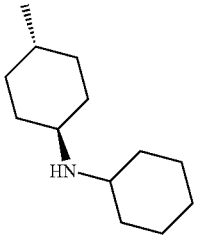 | APCI-MS M/Z: 495/497 [M + H]+ Dihydrochloride |
| 315 | —H | 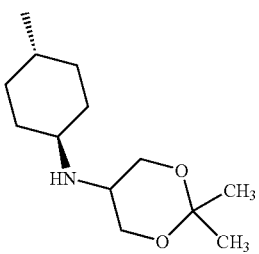 | APCI-MS M/Z: 527/529 [M + H]+ |
| 316 | —H | 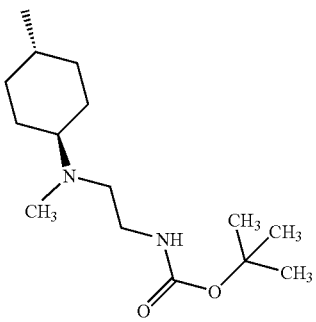 | APCI-MS M/Z: 570/572 [M + H]+ |
| 317 | —H | 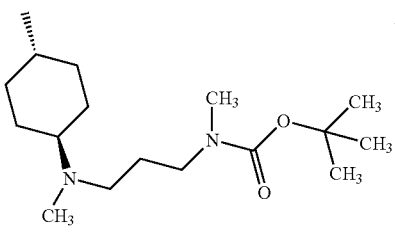 | APCI-MS M/Z: 598/600 [M + H]+ |

| 318 | —H | 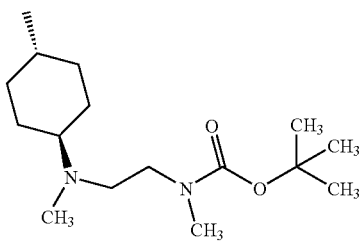 | APCI-MS M/Z: 584/586 [M + H]+ |
| 319 | —H | 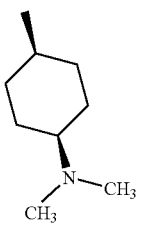 | APCI-MS M/Z: 441/443 [M + H]+ Dihydrochloride |
| 320 | —H | 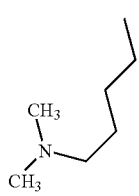 | APCI-MS M/Z: 415/417 [M + H]+ Hydrochloride |
| 321 | —H | 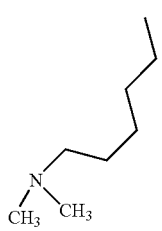 | APCI-MS M/Z: 429/431 [M + H]+ Hydrochloride |
| 322 | —H | 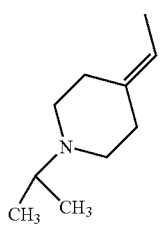 | APCI-MS M/Z: 453/455 [M + H]+ Dihydrochloride |
| 323 | —H | 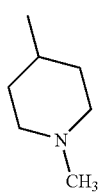 | APCI-MS M/Z: 413/415 [M + H]+ Dihydrochloride |

-continued
| 324 | —H | 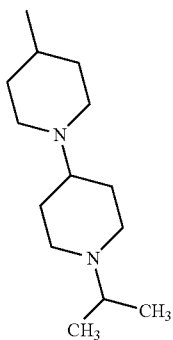 | APCI-MS M/Z: 524/526 [M + H]+ Trihydrochloride |
| 325 | —H | 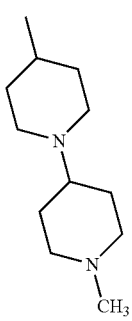 | APCI-MS M/Z: 496/498 [M + H]+ Trihydrochloride |
| 326 | —H | 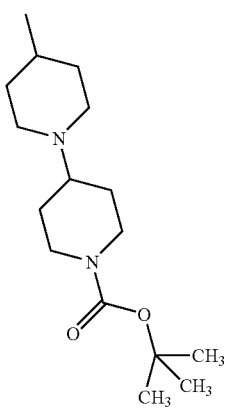 | APCI-MS M/Z: 582/584 [M + H]+ |

Example 327

Trans-3-[4-[N-[3-(dimethylamino)propyl]-N-methylamino]cyclohexylcarbonylamino]-N-(5-chloropyridin-2-yl)benzofuran-2-carboxamide trihydrochloride

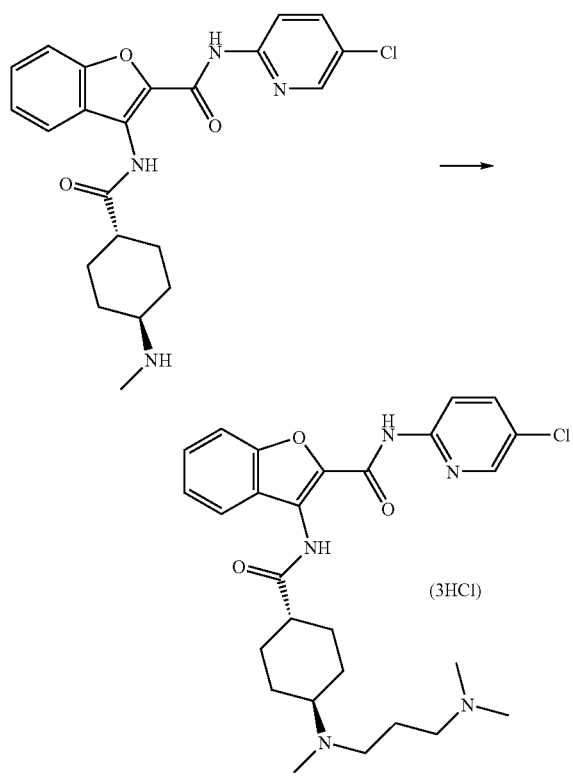

(1) 3-Aminopropionaldehyde diethyl acetal (5.00 g) is dissolved in dichloromethane (70 ml), and thereto are added successively 35% aqueous formaldehyde solution (13.5 ml) and sodium triacetoxy borohydride (18.0 g) under ice-cooling, and the reaction solution is warmed to room temperature and stirred for 6 hours. To the reaction solution is poured a saturated aqueous sodium hydrogen carbonate solution under ice-cooling, and further thereto is added potassium carbonate. The mixture is extracted with chloroform, and the organic layer is washed with a saturated brine, dried over sodium sulfate, and the solvent is evaporated under reduced pressure to give crude 3-(dimethylamino)propionaldehyde diethyl acetal (5.31 g).

(2) 3-(Dimethylamino)propionaldehyde diethyl acetal (284 mg) obtained in Example 327-(1) is dissolved in tetrahydrofuran (3 ml), and thereto is added conc. hydrochloric acid (3 ml), and the mixture is stirred at room temperature for 15 hours. The reaction solution is concentrated to dryness under reduced pressure, and the resulting residue is dissolved in dichloromethane (7 ml). Trans-3-[4-(methylamino)cyclohexylcarbonylamino]-N-(5-chloropyridin-2-yl)benzofuran-2-carboxamide (150 mg) obtained in Example 221 and triethylamine (226 μl) are added thereto, and the mixture is stirred for several minutes. Then, sodium triacetoxy borohydride (137 mg) is added thereto, and the reaction solution is warmed to room temperature, and stirred for 15 hours. To the reaction solution is added a saturated aqueous sodium hydrogen carbonate solution under ice-cooling, and the mixture is extracted with chloroform. The organic layer is washed successively with water and a saturated brine, dried over sodium sulfate, and the solvent is evaporated under reduced pressure. The resulting residue is purified by NH-silica gel column chromatography (eluent: ethyl acetate, then ethyl acetate/methanol=20/1) to give trans-3-[4-[N-[3-(dimethylamino)propyl]-N-methylamino]cyclohexylcarbonylamino]-N-(5-chloropyridin-2-yl)benzofuran-2-carboxamide (99 mg). Subsequently, this product is dissolved in chloroform/methanol (5/1, 6 ml), and thereto is added 4N hydrogen chloride in ethyl acetate (1 ml), and the solvent is evaporated under reduced pressure. The resulting residue is suspended in diethyl ether, and collected by filtration to give the title compound (106 mg).

APCI-MS M/Z: 512/514 [M+H]$^+$

Examples 328-332

The corresponding starting compounds are treated in a similar manner to Example 327 to give the following compounds in a free form, or which are further treated with hydrogen chloride to give hydrochlorides thereof.

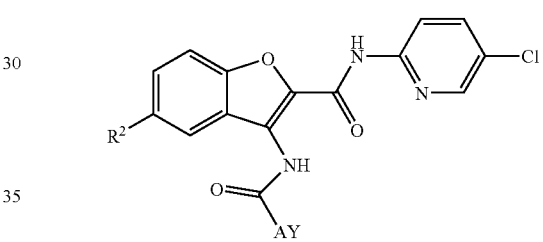

| Ex. | —R$^2$ | —AY | Physicochemical properties |
|---|---|---|---|
| 328 | —H | 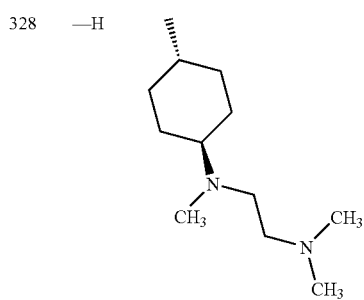 | APCI-MS M/Z: 498/500 [M + H]$^+$ Trihydrochloride |
| 329 | —H | 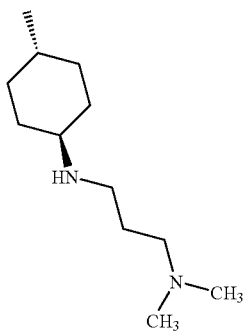 | APCI-MS M/Z: 498/500 [M + H]$^+$ Trihydrochloride |

183
-continued

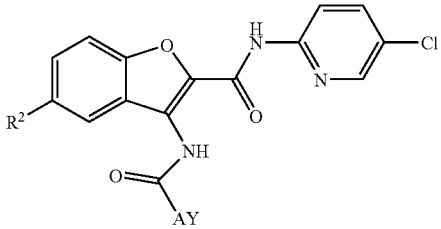

| Ex. Ex. | —R² | —AY | Physicochemical properties |
|---|---|---|---|
| 330 | —H | (structure) | APCI-MS M/Z: 583/585 [M + H]⁺ Tetrahydrochloride |
| 331 | —H | 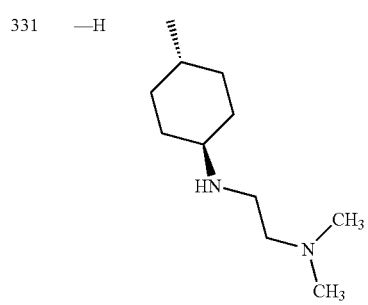 | APCI-MS M/Z: 484/486 [M + H]⁺ Trihydrochloride |
| 332 | —H | 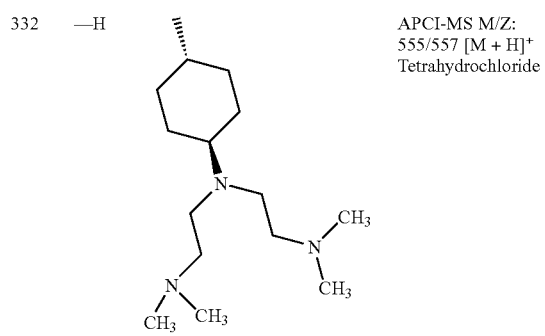 | APCI-MS M/Z: 555/557 [M + H]⁺ Tetrahydrochloride |

184

Example 333

Trans-3-[4-(piperidin-1-yl)cyclohexylcarbonylamino]-N-(5-chloropyridin-2-yl)benzofuran-2-carboxamide dihydrochloride

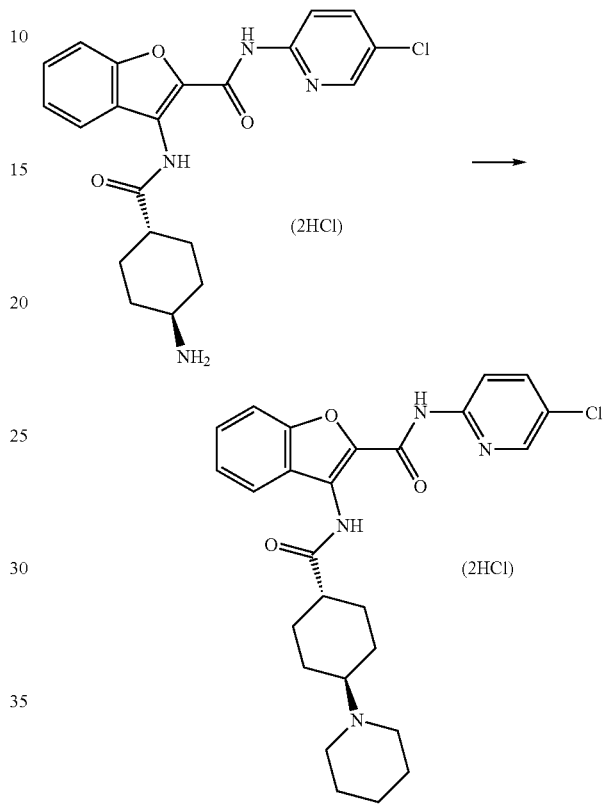

Trans-3-(4-aminocyclohexylcarbonylamino)-N-(5-chloropyridin-2-yl)benzofuran-2-carboxamide dihydrochloride (125 mg) obtained in Example 219 is suspended in dichloromethane (10 ml), and thereto is added triethylamine (102 µl) under ice-cooling, and the mixture is stirred for several minutes. Then, about 25% aqueous glutaraldehyde solution (150 mg) and sodium triacetoxy borohydride (155 mg) are added successively, and the mixture is stirred under ice-cooling for 2 hours. To the reaction solution is poured a saturated aqueous sodium hydrogen carbonate solution, and the mixture is extracted with chloroform. The organic layer is washed successively with water and a saturated brine, dried over sodium sulfate, and the solvent is evaporated under reduced pressure. The resulting residue is purified by NH-silica gel column chromatography (eluent: n-hexane/ethyl acetate=3/1, then 1/1) to give trans-3-[4-(piperidin-1-yl)cyclohexylcarbonylamino]-N-(5-chloropyridin-2-yl)benzofuran-2-carboxamide (106 mg). Subsequently, this product is dissolved in chloroform/methanol (5/1, 6 ml), and 4N hydrogen chloride in ethyl acetate (5 ml) is added thereto under ice-cooling. The reaction solution is concentrated under reduced pressure, and the resulting residue is suspended in diethyl ether, and collected by filtration to give the title compound (107 mg).

APCI-MS M/Z: 481/483 [M+H]⁺

Example 334

Trans-3-[4-(N-acetyl-N-isopropylamino)cyclohexyl-carbonylamino]-N-(5-chloropyridin-2-yl)benzofuran-2-carboxamide

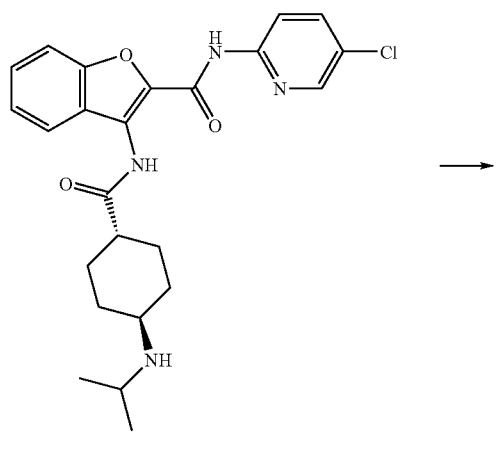

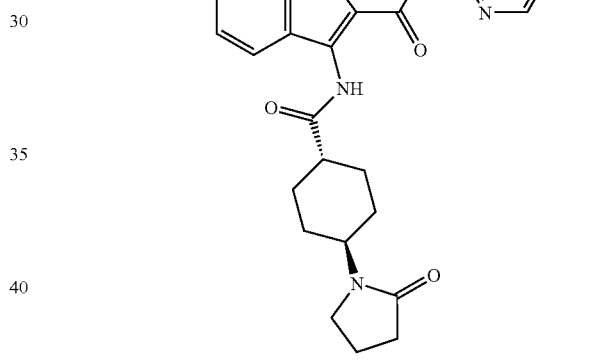

Trans-3-[4-(isopropylamino)cyclohexylcarbonylamino]-N-(5-chloropyridin-2-yl)benzofuran-2-carboxamide (100 mg) obtained in Example 310 and triethylamine (61 μl) is dissolved in chloroform (5 ml), and thereto is added acetyl chloride (24 μl). The mixture is stirred at room temperature for one hour, and thereto is poured a saturated aqueous sodium hydrogen carbonate solution, and the mixture is extracted with chloroform. The organic layer is washed successively with water and a saturated brine, dried over sodium sulfate, and the solvent is evaporated under reduced pressure. The resulting residue is purified by silica gel column chromatography (eluent: n-hexane/ethyl acetate=1/1, then ethyl acetate). The resulting residue is suspended in n-hexane, and collected by filtration to give the title compound (60 mg).

APCI-MS M/Z: 497/499 [M+H]$^+$

Example 335

Trans-3-[4-(2-oxopyrrolidin-1-yl)cyclohexylcarbonylamino]-N-(5-chloropyridin-2-yl)benzofuran-2-carboxamide

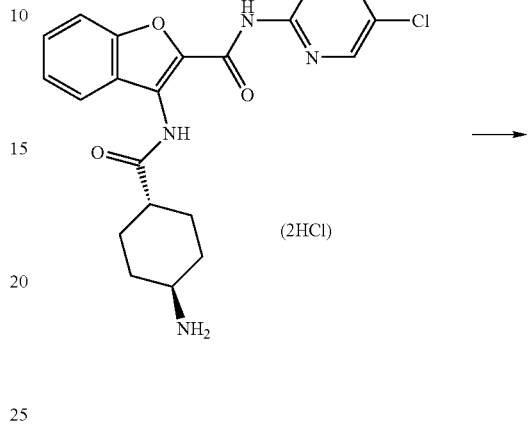

(2HCl)

Trans-3-(4-aminocyclohexylcarbonylamino)-N-(5-chloropyridin-2-yl)benzofuran-2-carboxamide dihydrochloride (150 mg) obtained in Example 219 is suspended in dichloromethane (5 ml), and thereto is added triethylamine (129 μl) under ice-cooling, and the mixture is stirred for several minutes. Then, 15% aqueous succinic semialdehyde solution (290 μl) and sodium triacetoxy borohydride (131 mg) are successively added thereto, and under ice-cooling, the mixture is stirred for 0.5 hour. Then, 1-hydroxybenzotriazole (63 mg), 1-ethyl-3-(3-dimethylaminopropyl)carbodiimide hydrochloride (118 mg) and N,N-dimethylformamide (3 ml) are successively added thereto, and the mixture is stirred at room temperature for 15 hours. The reaction solution is concentrated under reduced pressure, and thereto is poured chloroform. The mixture is washed successively with a saturated aqueous sodium hydrogen carbonate solution, water, and a saturated brine, dried over sodium sulfate, and the solvent is evaporated under reduced pressure. The resulting residue is purified by NH-silica gel column chromatography (eluent: n-hexane/ethyl acetate=1/1, then ethyl acetate), and the resulting residue is suspended in n-hexane, and collected by filtration to give the title compound (29 mg).

APCI-MS M/Z: 481/483 [M+H]$^+$

Example 336

Trans-3-[4-(t-butoxycarbonylamino)cyclohexylcarbonylamino]-5-carboxy-N-(5-chloropyridin-2-yl)benzofuran-2-carboxamide

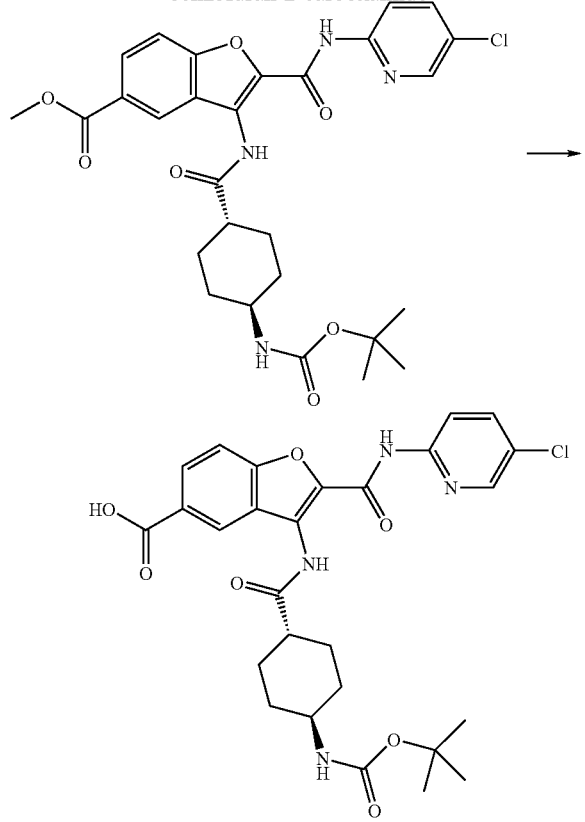

Trans-3-[4-(t-butoxycarbonylamino)cyclohexylcarbonylamino]-5-methoxycarbonyl-N-(5-chloropyridine-2-yl)benzofuran-2-carboxamide (540 mg) obtained in Example 209 is treated in a similar manner to Example 77 to give the title compound (475 mg).

ESI-MS M/Z: 555/557 [M−H]⁻

Example 337

Trans-3-[4-(N-t-butoxycarbonyl-N-methylamino)-cyclohexylcarbonylamino]-5-carboxy-N-(5-chloropyridin-2-yl)benzofuran-2-carboxamide

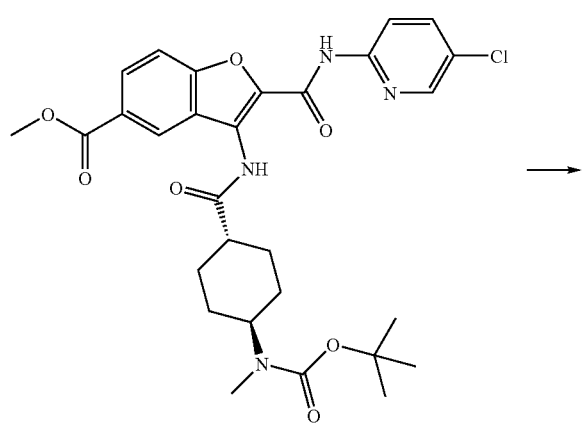

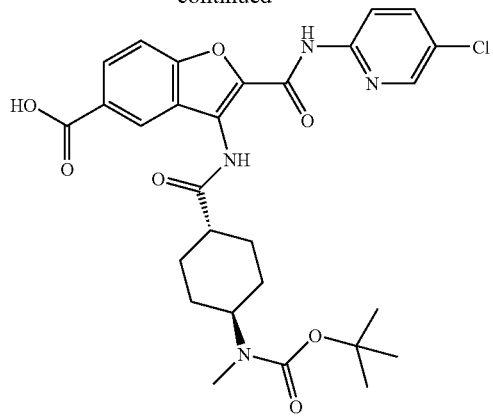

Trans-3-[4-(N-t-butoxycarbonyl-N-methylamino)cyclohexylcarbonyl]-5-methoxycarbonyl-N-5-chloropyridin-2-yl)benzofuran-2-carboxamide (3.52 g) obtained in Example 202 is treated in a similar manner to Example 77 to give the title compound (3.19 g).

ESI-MS M/Z: 569/571 [M−H]⁻

Examples 338-340

The corresponding starting compounds are treated in a similar manner to Example 87 to give the following compounds.

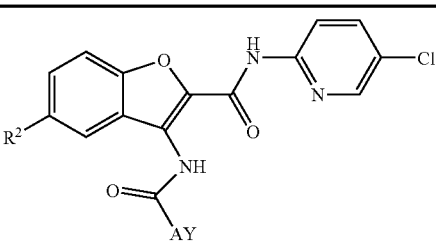

| Ex. No. | —R² | —AY | Physico-chemical properties |
|---|---|---|---|
| 338 | CH₃—N(CH₃)—C(=O)— | trans-cyclohexyl-NH-C(=O)-O-C(CH₃)₃ | ESI-MS M/Z: 582/584 [M − H]⁻ |
| 339 | CH₃—NH—C(=O)— | trans-cyclohexyl-N(CH₃)-C(=O)-O-C(CH₃)₃ | APCI-MS M/Z: 601/603 [M + NH₄]⁺ |
| 340 | CH₃—N(CH₃)—C(=O)— | trans-cyclohexyl-N(CH₃)-C(=O)-O-C(CH₃)₃ | APCI-MS M/Z: 615/617 [M + NH₄]⁺ |

Examples 341-344

The corresponding starting compounds are treated in a similar manner to Example 218 to give the following compounds in a free form, or which are further treated with hydrogen chloride to give hydrochlorides thereof.

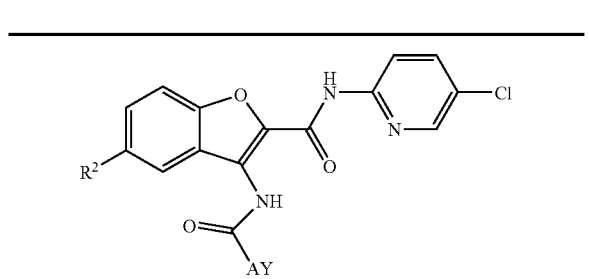

| Ex. No. | —R² | —AY | Physicochemical properties |
|---|---|---|---|
| 341 | 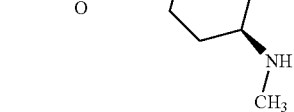 | | ESI-MS M/Z: 471/473 [M + H]⁺ Dihydrochloride |
| 342 | 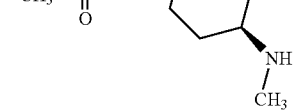 | | APCI-MS M/Z: 484/486 [M + H]⁺ Dihydrochloride |
| 343 | 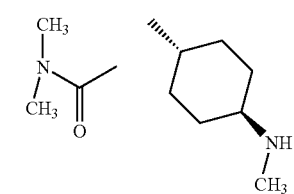 | | APCI-MS M/Z: 498/500 [M + H]⁺ Dihydrochloride |
| 344 | 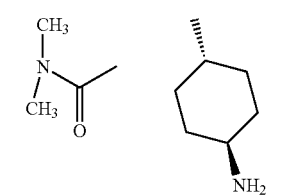 | | APCI-MS M/Z: 484/486 [M + H]⁺ Hydrochloride |

Example 345

Trans-5-dimethylaminocarbonyl-3-[4-(isopropylamino)cyclohexylcarbonylamino]-N-(5-chloropyridin-2-yl)-benzofuran-2-carboxamide hydrochloride

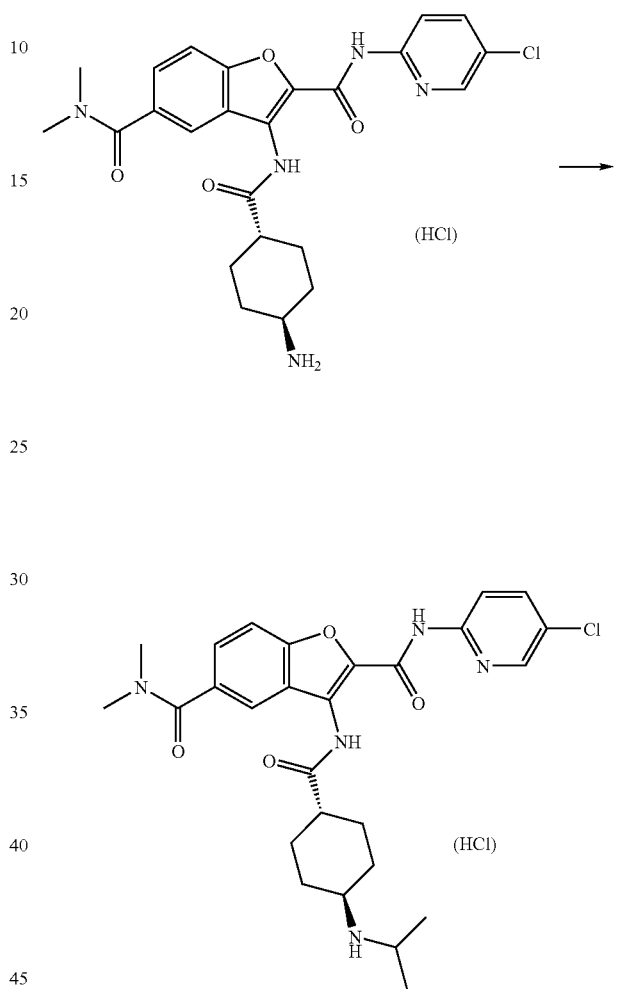

Trans-3-(4-aminocyclohexylcarbonylamino)-5-dimethylaminocarbonyl-N-(5-chloropyridin-2-yl)benzofuran-2-carboxamide hydrochloride (160 mg) obtained in Example 344 is suspended in dichloromethane (8 ml), and thereto are added successively triethylamine (129 μl), acetone (113 μl), and sodium triacetoxy borohydride (130 mg) under ice-cooling, and the reaction solution is warmed to room temperature, and stirred for 17 hours. Under ice-cooling, to the reaction solution is poured a saturated aqueous sodium hydrogen carbonate solution, and the mixture is extracted with chloroform. The organic layer is washed with a saturated brine, dried over sodium sulfate, and the solvent is evaporated under reduced pressure. The resulting residue is purified by NH-silica gel column chromatography (eluent: ethyl acetate, then chloroform/methanol=30/1). The resulting residue is dissolved in ethanol, and thereto is added 4N hydrogen chloride in ethyl acetate. The reaction solution is concentrated and the resulting residue is suspended in diethyl ether. The precipitates are collected by filtration to give the title compound (94 mg).

APCI-MS M/Z: 526/528 [M+H]⁺

Example 346

Trans-5-carboxy-3-[4-(isopropylamino)cyclohexyl-carbonylamino]-N-(5-chloropyridin-2-yl)benzofuran-2-carboxamide

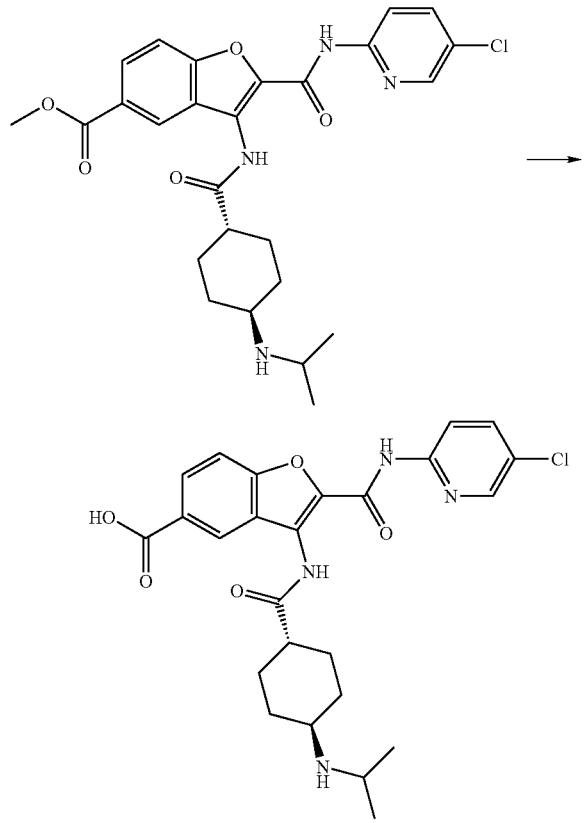

Trans-3-[4-(isopropylamino)cyclohexylcarbonylamino]-5-methoxycarbonyl-N-(5-chloropyridin-2-yl)benzofuran-2-carboxamide (690 mg) obtained in Example 311 is suspended in tetrahydrofuran/methanol (1:1, 10 ml), and under ice-cooling, thereto is added 4N aqueous sodium hydroxide solution (3 ml). The mixture is warmed to room temperature, and stirred for 18 hours. The reaction solution is concentrated under reduced pressure, and poured into ice-water. The mixture is neutralized with 10% hydrochloric acid, and the precipitates are collected by filtration, washed successively with water, tetrahydrofuran, and diethyl ether, and dried to give the title compound (702 mg).

ESI-MS M/Z: 497/499 [M−H]−

Examples 347-349

Trans-5-carboxy-3-[4-(isopropylamino)cyclohexylcarbonylamino]-N-(5-chloropyridin-2-yl)benzofuran-2-carboxamide obtained in Example 346 is treated in a similar manner to Example 87 to give the following compounds in a free form, or which are further treated with hydrogen chloride to give hydrochlorides thereof.

| Ex. No. | —R² | —AY | Physico-chemical properties |
|---|---|---|---|
| 347 | morpholino-C(O)CH< | trans-cyclohexyl-NH-CH(CH₃)₂ | APCI-MS M/Z: [M + H]⁺ Hydrochloride |
| 348 | pyrrolidino-C(O)CH< | trans-cyclohexyl-NH-CH(CH₃)₂ | APCI-MS M/Z: 552/554 [M + H]⁺ Hydrochloride |
| 349 | HO-CH₂-piperidino-C(O)CH< | trans-cyclohexyl-NH-CH(CH₃)₂ | APCI-MS M/Z: 596/598 [M + H]⁺ Hydrochloride |

Examples 350-354

The corresponding starting compounds are treated in a similar manner to Example 218 to give the following compounds in a free form, or which are further treated with hydrogen chloride to give hydrochlorides thereof.

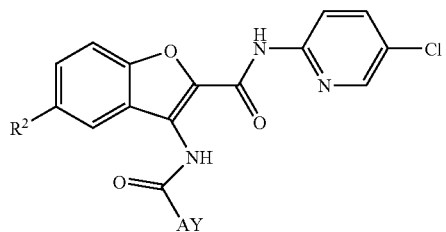

Examples 355-362

The corresponding starting compounds are treated in a similar manner to Example 239 or Example 246 to give the following compounds in a free form, or which are further treated with hydrogen chloride to give hydrochlorides thereof.

| Ex. No. | —R² | —AY | Physicochemical properties |
|---|---|---|---|
| 350 | —H | (trans-4-methylcyclohexyl)-N(CH₃)-CH₂CH₂CH₂-NH₂ | APCI-MS M/Z: 484/486 [M + H]⁺ Trihydrochloride |
| 351 | —H | (trans-4-methylcyclohexyl)-N(CH₃)-CH₂CH₂CH₂-NH-CH₃ | APCI-MS M/Z: 498/500 [M + H]⁺ Trihydrochloride |
| 352 | —H | (trans-4-methylcyclohexyl)-N(CH₃)-CH₂CH₂-NH₂ | APCI-MS M/Z: 470/472 [M + H]⁺ Trihydrochloride |
| 353 | —H | (trans-cyclohexyl)-N(CH₃)-CH₂CH₂-NH-CH₃ | APCI-MS M/Z: 484/486 [M + H]⁺ Trihydrochloride |
| 354 | —H | 4-(piperidin-4-yl)piperidinyl | APCI-MS M/Z: 482/484 [M + H]⁺ Trihydrochloride |

| Ex. No. | —R² | —AY | Physico-chemical properties |
|---|---|---|---|
| 355 | —H | (trans-4-methylcyclohexyl)-N(CH₃)-CH₂CH₂CH₂-NH-C(O)CH₃ | APCI-MS M/Z: 526/528 [M + H]⁺ Dihydrochloride |
| 356 | —H | (trans-4-methylcyclohexyl)-N(CH₃)-CH₂CH₂CH₂-N(CH₃)-C(O)CH₃ | APCI-MS M/Z: 540/542 [M + H]⁺ Dihydrochloride |
| 357 | —H | (trans-4-methylcyclohexyl)-N(CH₃)-CH₂CH₂-NH-C(O)CH₃ | APCI-MS M/Z: 512/514 [M + H]⁺ Dihydrochloride |
| 358 | —H | (trans-4-methylcyclohexyl)-N(CH₃)-CH₂CH₂-N(CH₃)-C(O)CH₃ | APCI-MS M/Z: 526/528 [M + H]⁺ Dihydrochloride |

-continued

| Ex. No. | —R² | —AY | Physico-chemical properties |
|---|---|---|---|
| 359 | —H | (trans-4-(N-methyl-N-methylaminocyclohexyl)propyl-NH-C(O)-CH₂-N(CH₃)₂ group) | APCI-MS M/Z: 569/571 [M + H]⁺ Trihydrochloride |
| 360 | —H | (trans-4-(N-methyl-N-methylaminocyclohexyl)propyl-N(CH₃)-C(O)-CH₂-N(CH₃)₂ group) | APCI-MS M/Z: 583/585 [M + H]⁺ Trihydrochloride |
| 361 | —H | (trans-4-(N-methyl-N-methylaminocyclohexyl)ethyl-NH-C(O)-CH₂-N(CH₃)₂ group) | APCI-MS M/Z: 555/557 [M + H]⁺ Trihydrochloride |
| 362 | —H | (trans-4-(N-methyl-N-methylaminocyclohexyl)ethyl-N(CH₃)-C(O)-CH₂-N(CH₃)₂ group) | APCI-MS M/Z: 569/571 [M + H]⁺ Trihydrochloride |

Examples 363-364

The corresponding starting compounds are treated in a similar manner to Example 306 to give the following compounds in a free form, or which are further treated with hydrogen chloride to give hydrochlorides thereof.

| Ex. No. | —R² | —AY | Physicochemical properties |
|---|---|---|---|
| 363 | —H | (trans-4-(N-methyl-N-cyclopentylamino)cyclohexyl group) | APCI-MS M/Z: 495/497 [M + H]⁺ Dihydrochloride |
| 364 | —H | (trans-4-[N-methyl-N-(2,2-dimethyl-1,3-dioxan-5-yl)amino]cyclohexyl group) | APCI-MS M/Z: 541/543 [M + H]⁺ |

Examples 365-366

The corresponding starting compounds are treated in a similar manner to Example 201 to give the following compounds in a free form, or which are further treated with hydrogen chloride to give hydrochlorides thereof.

| Ex. No. | —R² | —AY | Physicochemical properties |
|---|---|---|---|
| 365 | —H | (trans-4-[(1,3-dihydroxyprop-2-yl)amino]cyclohexyl group) | APCI-MS M/Z: 487/489 [M + H]⁺ Dihydrochloride |

-continued

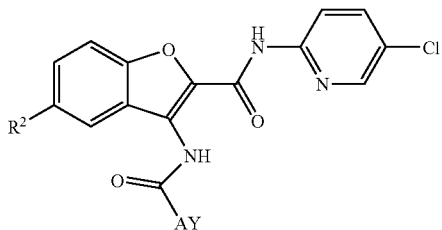

| Ex. No. | —R² | —AY | Physicochemical properties |
|---|---|---|---|
| 366 | —H | 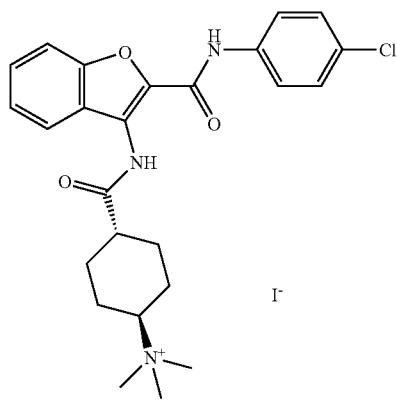 | APCI-MS M/Z: 501/503 [M + H]⁺ Dihydrochloride |

Example 367

[4-[2-(4-Chlorophenylcarbamoyl)benzofuran-3-yl-carbamoyl]cyclohexyl]trimethylammonium iodide

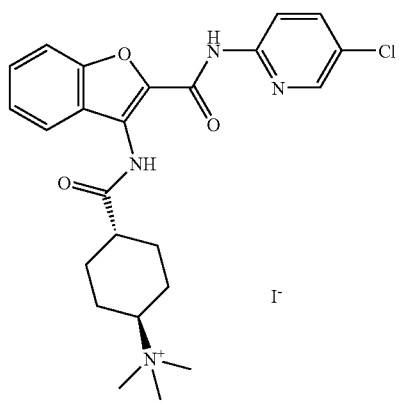

Trans-3-[4-(dimethylamino)cyclohexylcarbonylamino]-N-(4-chlorophenyl)benzofuran-2-carboxamide (106 mg) obtained in Example 308 is dissolved in dichloromethane (5 ml), and thereto is added methyl iodide (30 μl), and the mixture is stirred at room temperature for 5 hours. To the reaction solution is poured dichloromethane diethyl ether (1/5, 25 ml), and the precipitates are collected by filtration to give the title compound (126 mg).

ESI-MS M/Z: 454/456 [M–I]⁺

Example 368

[4-[2-(5-Chloropyridin-2-ylcarbamoyl)benzofuran-3-ylcarbamoyl]cyclohexyl]trimethylammonium iodide

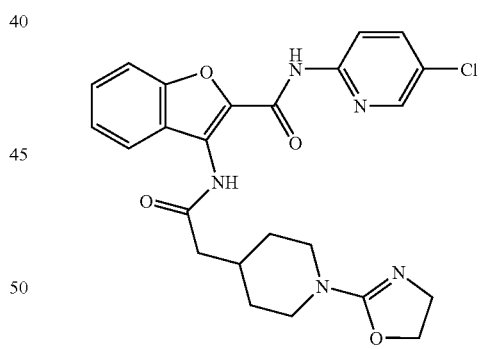

Trans-3-[4-(dimethylamino)cyclohexylcarbonylamino]-N-(5-chloropyridin-2-yl)benzofuran-2-carboxamide (150 mg) obtained in Example 306 and methyl iodide (21 μl) are treated in a similar manner to Example 367 to give the title compound (137 mg).

ESI-MS M/Z: 455/457 [M–I]⁺

Example 369

3-[2-[1-(4,5-Dihydroxazol-2-yl)piperidin-4-yl]acetylamino]-N-(5-chloropyridin-2-yl)benzofuran-2-carboxamide 3-[2-(Piperidin-4-yl)acetylamino]-N-(5-chloropyridin-2-yl)benzofuran-2-carboxamide (103 mg) obtained in Example 220 is suspended in tetrahydrofuran (5 ml), and thereto is added 2-bromoethyl isocyanate (27 μl), and the mixture is stirred at room temperature for one hour. Triethylamine (280 μl) is added thereto, and the mixture is further stirred at room temperature for 6 hours. To the reaction solution are poured water and ethyl acetate, and the precipitates are collected by filtration, washed with ethyl acetate, and dried to give the title compound (50 mg).

APCI-MS M/Z: 482/484 [M+H]⁺

Examples 370-372

The corresponding starting compounds are treated in a similar manner to Example 369 to give the following compounds.

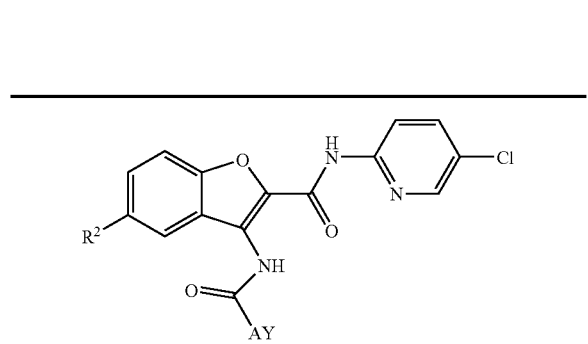

| Ex. No. | —R² | —AY | Physicochemical properties |
|---|---|---|---|
| 370 | —H | 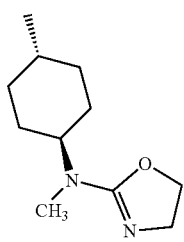 | APCI-MS M/Z: 496/498 [M + H]⁺ |
| 371 | —H | 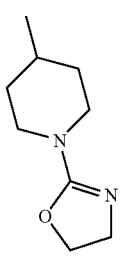 | APCI-MS M/Z: 468/470 [M + H]⁺ |
| 372 | —H | 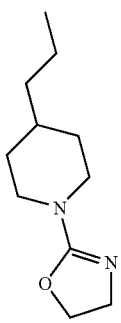 | APCI-MS M/Z: 496/498 [M + H]⁺ |

Example 373

3-[[1-(2-Thiazolyl)piperidin-4-yl]carbonylamino]-N-(5-chloropyridin-2-yl)benzofuran-2-carboxamide hydrochloride

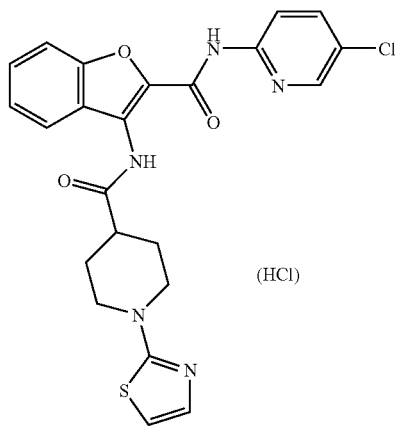

3-[(Piperidin-4-yl)carbonylamino]-N-(5-chloropyridin-2-yl)benzofuran-2-carboxamide (100 mg) obtained in Example 228 is suspended in 2-butanol (5 ml), and thereto are added 2-bromothiazole (113 µl) and N,N-diisopropylethylamine (131 µl), and the mixture is heated under reflux for 24 hours. To the reaction solution are added 2-bromothiazole (57 µl) and N,N-dimethylacetamide (2 ml), and the mixture is further heated under reflux for 24 hours. To the reaction solution is poured a saturated aqueous sodium hydrogen carbonate solution, and the mixture is extracted with chloroform. The organic layer is washed with water and a saturated brine, and dried over sodium sulfate. The solvent is evaporated under reduced pressure, and the resulting residue is purified by silica gel column chromatography (eluent: n-hexane/ethyl acetate=3/1, then ethyl acetate) to give 3-[[1-(2-thiazolyl) piperidin-4-yl]-carbonylamino]-N-(5-chloropyridin-2-yl) benzofuran-2-carboxamide (38 mg). This product is further treated with hydrogen chloride in dioxane to give the title compound (25 mg).
APCI-MS M/Z: 482/484 [M+H]⁺

Example 374

Trans-3-[4-((pyrimidin-2-yl)amino)cyclohexylcarbonylamino]-N-(5-chloropyridin-2-yl)benzofuran-2-carboxamide dihydrochloride

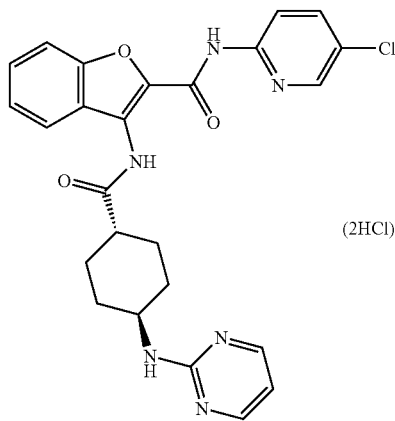

Trans-3-[4-aminocyclohexylcarbonylamino]-N-(5-chloropyridin-2-yl)benzofuran-2-carboxamide dihydrochloride (350 mg) obtained in Example 219 and 2-chloropyrimidine (99 mg) are treated in a similar manner to Example 373 to give the title compound (65 mg).

APCI-MS M/Z: 491/493 [M+H]+

Example 375

Trans-3-[4-(pyrrol-1-yl)cyclohexylcarbonylamino]-N-(5-chloropyridin-2-yl)benzofuran-2-carboxamide

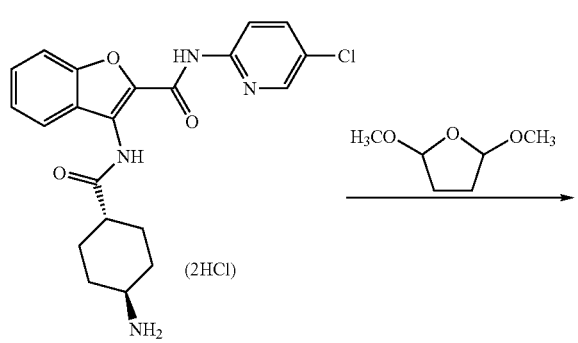

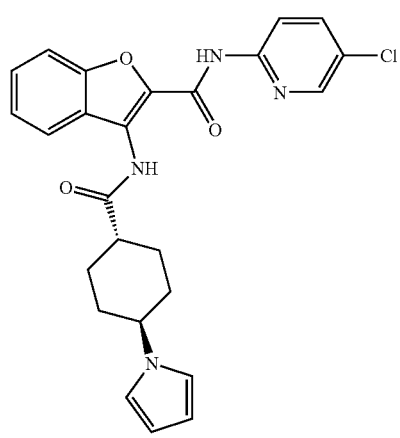

Trans-3-(4-aminocyclohexylcarbonylamino)-N-(5-chloropyridin-2-yl)benzofuran-2-carboxamide dihydrochloride (200 mg) obtained in Example 219, tetrahydro-2,5-dimethoxyfuran (53 µl), sodium acetate (68 mg) are stirred at 80° C. for 2 hours in acetic acid (3 ml). To the mixture is added tetrahydro-2,5-dimethoxyfuran (26 µl), and the mixture is further stirred at 80° C. for 2 hours. After cooling, the reaction solution is poured into ice-water, and the mixture is extracted with chloroform. The organic layer is washed with a saturated aqueous sodium hydrogen carbonate solution, a saturated brine, and dried over sodium sulfate, and the solvent is evaporated under reduced pressure. The resulting residue is purified by NH-silica gel column chromatography (eluent: ethyl acetate/hexane=1/5→ethyl acetate/hexane=1/3) to give the title compound (96 mg).

APCI-MS M/Z: 463/465 [M+H]+

Example 376

3-[(1-t-Butoxycarbonylpiperidin-4-yl)oxy-carbonylamino]-N-(5-chloropyridin-2-yl)benzofuran-2-carboxamide

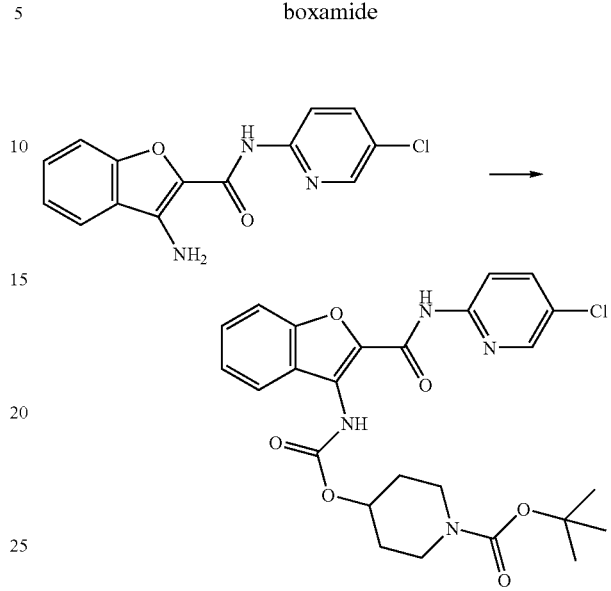

t-Butyl 4-hydroxy-1-piperidinecarboxylate (175 mg) and triphosgene (90 mg) are dissolved in dichloromethane (5 ml), and thereto is added pyridine (77 µl) with stirring under ice-cooling. The reaction solution is stirred at room temperature for 3 hours, and then cooled again with ice. To the mixture is added 3-amino-N-(5-chloropyridin-2-yl)-benzofuran-2-carboxamide (250 mg) obtained in Reference Example 74, and the mixture is stirred for several minutes. Pyridine (105 µl) is added to the mixture, and the mixture is stirred at room temperature for 3 hours. The reaction solution is poured into water, and the mixture is extracted with chloroform. The organic layer is washed successively with 5% aqueous citric acid solution, water, a saturated aqueous sodium hydrogen carbonate solution and a saturated brine, dried over sodium sulfate, and the solvent is evaporated under reduced pressure. The resulting residue is purified by NH-silica gel column chromatography (eluent: n-hexane/ethyl acetate=10/1, then 5/1) to give the title compound (406 mg).

APCI-MS M/Z: 515/517 [M+H]+

Example 377

Trans-3-[4-(t-butoxycarbonylamino)cyclohexyloxycarbonylamino]-N-(5-chloropyridin-2-yl)benzofuran-2-carboxamide

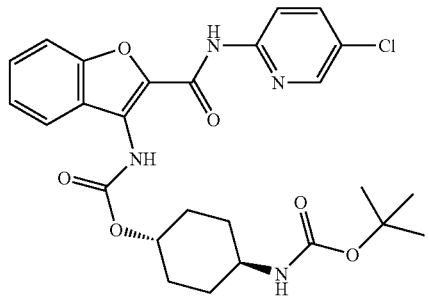

3-Amino-N-(5-chloropyridin-2-yl)benzofuran-2-carboxamide (500 mg) obtained in Reference Example 74 and t-butyl trans-(4-hydroxycyclohexyl)carbamate (375 mg) is treated in a similar manner to Example 376 to give the title compound (680 mg).

APCI-MS M/Z: 529/531 [M+H]⁺

Examples 378-379

The compound obtained in Example 376 or Example 377 is treated in a similar manner to Example 220 to give the following compounds.

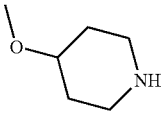

| Ex. No. | —R² | —AY | Physicochemical properties |
|---|---|---|---|
| 378 | —H | 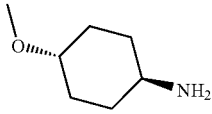 | APCI-MS M/Z: 415/417 [M + H]⁺ Dihydrochloride |
| 379 | —H | 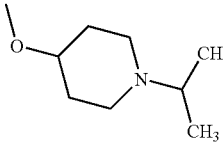 | APCI-MS M/Z: 429/431 [M + H]⁺ Dihydrochloride |

Examples 380-381

The compound obtained in Example 378 or Example 379 is treated in a similar manner to Example 345 to give the following compounds in a free form, or which are further treated with hydrogen chloride to give hydrochlorides thereof.

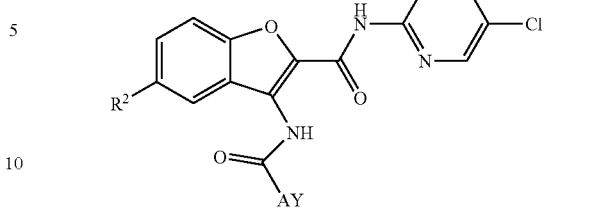

| Ex. No. | —R² | —AY | Physicochemical properties |
|---|---|---|---|
| 380 | —H | 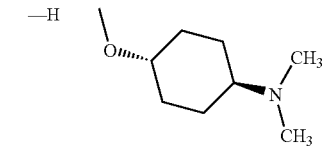 | APCI-MS M/Z: 457/459 [M + H]⁺ Dihydrochloride |
| 381 | —H | 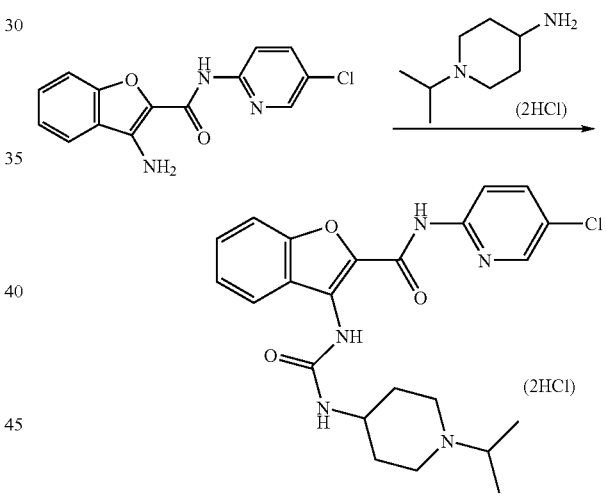 | APCI-MS M/Z: 457/459 [M + H]⁺ Dihydrochloride |

Example 382

3-[3-(1-Isopropylpiperidin-4-yl)ureido]-N-(5-chloro-pyridin-2-yl)benzofuran-2-carboxamide dihydrochloride

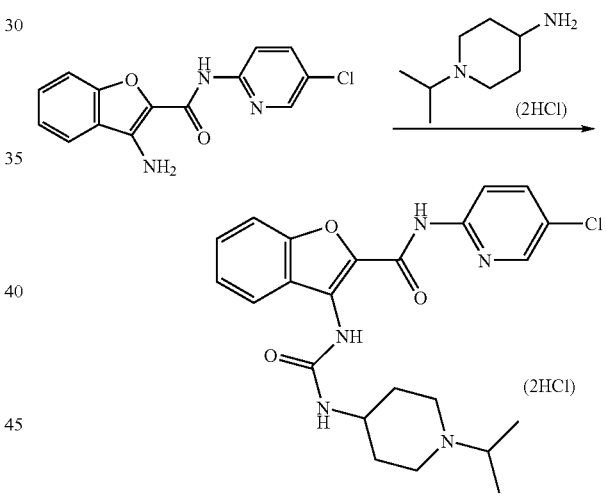

(1) 1-Isopropylpiperidine-4-carboxylic acid hydrochloride (3.00 g) obtained in Reference Example 130 is suspended in toluene (180 ml), and thereto are added triethylamine (5.0 ml) and diphenylphophoryl azide (4.0 ml), and the mixture is heated at 100° C. for 2 hours. After cooling, to the reaction solution is added benzyl alcohol (4.5 ml) at room temperature, and the mixture is heated under reflux for 4 hours. The reaction solution is concentrated under reduced pressure, and the resulting residue is diluted with ethyl acetate, and washed successively with a saturated aqueous sodium hydrogen carbonate solution, water and a saturated brine. The resultant is dried over sodium sulfate, and the solvent is evaporated under reduced pressure. The residue is purified by NH-silica gel column chromatography (eluent: n-hexane/diethyl ether=2/1, then n-hexane/ethyl acetate=2/1) to give a crude product (6.32 g) containing benzyl(1-isopropylpiperidin-4-yl)carbamate.

APCI-MS M/Z: 277 [M+H]⁺

(2) The crude product (6.32 g) containing benzyl(1-isopropylpiperidin-4-yl)carbamate obtained in Example 382-(1) is dissolved in ethanol (100 ml), and thereto is added 10% palladium on carbon (600 mg), and the mixture is stirred at ambient temperature under hydrogen atmosphere overnight. The insoluble materials are removed by filtration, and the filtrate is concentrated under reduced pressure, and subjected to azeotropic distillation with toluene. The resulting residue is purified by NH-silica gel column chromatography (eluent: n-hexane/ethyl acetate=1/1, then chloroform/methanol=20/1, and further 10/1) to give 4-amino-1-isopropylpiperidine (1.90 g). The resulting 4-amino-1-isopropylpiperidine is treated with 4N hydrogen chloride in dioxane to give 4-amino-1-isopropylpiperidine dihydrochloride.

APCI-MS M/Z: 143 [M+H]$^+$ (3) 4-Amino-1-isopropylpiperidine dihydrochloride (112 mg) obtained in Example 382-(2) and triphosgene (54 mg) are suspended in dichloromethane (3 ml), and thereto is added pyridine (253 µl) with stirring under ice-cooling. The reaction solution is stirred at room temperature for 3 hours, and 3-amino-N-(5-chloropyridin-2-yl)benzofuran-2-carboxamide (150 mg) obtained in Reference Example 74 is added thereto, and the mixture is stirred at room temperature for 12 hours, then further heated under reflux for 15 hours. To the reaction solution are poured water and a saturated aqueous sodium hydrogen carbonate solution, and the mixture is extracted with chloroform. The organic layer is washed with a saturated brine, dried over sodium sulfate, and the solvent is evaporated under reduced pressure. The resulting residue is purified by NH-silica gel column chromatography (eluent: n-hexane/ethyl acetate=4/1, then 2/1) to give 3-[3-(1-isopropylpiperidin-4-yl)-ureido]-N-(5-chloropyridin-2-yl)benzofuran-2-carboxamide (112 mg). Subsequently, this product is treated with 4N hydrogen chloride in ethyl acetate (2 ml) to give the title compound (114 mg).

APCI-MS M/Z: 456/458 [M+H]$^+$

Example 383

Trans-3-(4-methylhomopiperazin-1-ylcarbonylamino)-N-(5-chloropyridin-2-yl)benzofuran-2-carboxamide dihydrochloride

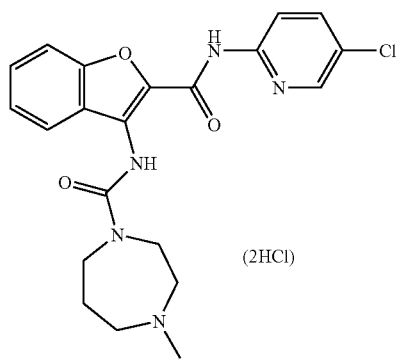

3-Amino-N-(5-chloropyridin-2-yl)benzofuran-2-carboxamide (200 mg) obtained in Reference Example 74 and 1-methylhomopiperazine (86 µl) are treated in a similar manner to Example 382-(3) to give the title compound (110 mg).

APCI-MS M/Z: 428/430 [M+H]$^+$

Example 384
Trans-3-[4-(2-oxopiperidin-1-yl)cyclohexylcarbonylamino]-N-(5-chloropyridin-2-yl)benzofuran-2-carboxamide

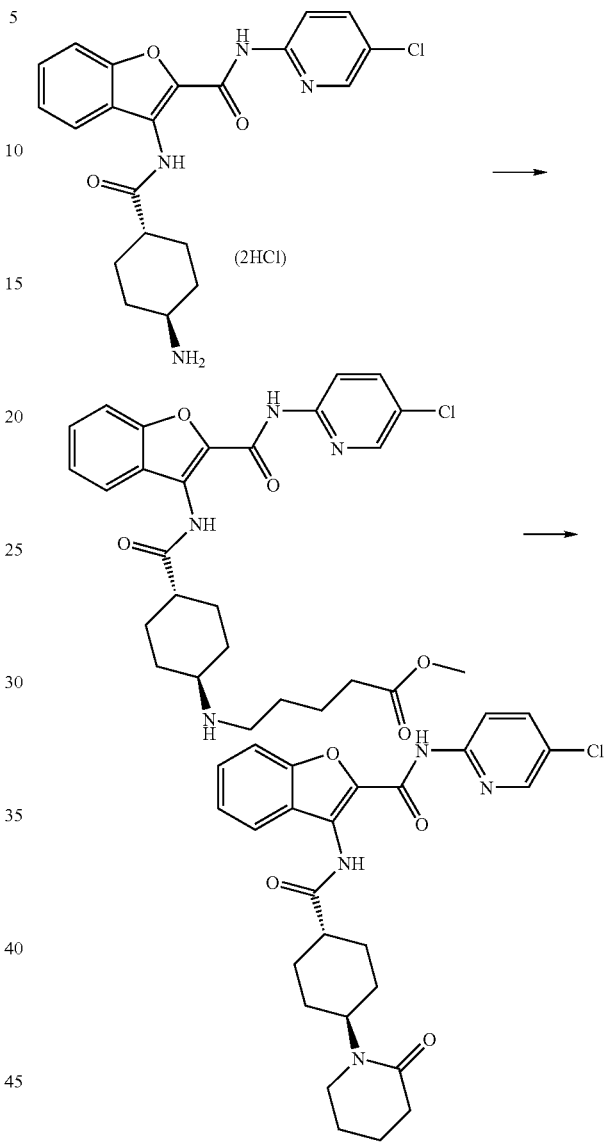

(1) Trans-3-(4-aminocyclohexylcarbonylamino)-N-(5-chloropyridin-2-yl)benzofuran-2-carboxamide dihydrochloride (300 mg) obtained in Example 219 is suspended in N,N-dimethylacetamide (5 ml), and thereto are added methyl 5-bromovalerate (106 µl), N,N-diisopropylethylamine (537 µl), and potassium iodide (111 mg), and the mixture is stirred at 100° C. for 24 hours. Methyl 5-bromovalerate (106 µl), N,N-diisopropylethylamine (537 µl) and potassium iodide (111 mg) are further added thereto, and the mixture is stirred at 100° C. for 12 hours. The reaction solution is diluted with ethyl acetate, and washed successively with a saturated aqueous sodium hydrogen carbonate solution, water, a saturated brine, and dried over sodium sulfate. The solvent is evaporated under reduced pressure, and the resulting residue is purified by NH-silica gel column chromatography (eluent: n-hexane/ethyl acetate=1/1, then ethyl acetate) to give trans-3-[4-(4-methoxycarbonylbutylamino)cyclohexylcarbonylamino]-N-(5-chloropyridin-2-yl)-benzofuran-2-carboxamide (101 mg).

APCI-MS M/Z: 527/529 [M+H]$^+$ (2) Trans-3-[4-(4-methoxycarbonylbutylamino)cyclohexylcarbonylamino]-N-(5-chloropyridin-2-yl)benzofuran-2-carboxamide (95 mg) obtained in the above (1) is dissolved in tetrahydrofuran (3 ml), and thereto is added 1N aqueous sodium hydroxide solution (216 µl), and the mixture is stirred at room temperature for 4 hours. To the mixture is added 1N aqueous sodium hydroxide solution (684 µl), and the mixture is further stirred for 2 days. The reaction solution is concentrated to dryness under reduced pressure, and to the resulting residue are added N,N-dimethylformamide (3 ml), 1-hydroxybenzotriazole (73 mg) and 1-ethyl-3-(3-dimethylaminopropyl)carbodiimide hydrochloride (104 mg). The mixture is stirred at room temperature for one day, and further thereto are added 1-hydroxybenzotriazole (73 mg) and 1-ethyl-3-(3-dimethylaminopropyl)carbodiimide hydrochloride (104 mg), and the mixture is further stirred for one day. To the reaction solution is poured a saturated aqueous sodium hydrogen carbonate solution, and the mixture is extracted with ethyl acetate. The organic layer is washed with water and a saturated brine, and dried over sodium sulfate, and the solvent is evaporated under reduced pressure. The resulting residue is purified by silica gel column chromatography (eluent: ethyl acetate) to give the title compound (40 mg).

APCI-MS M/Z: 495/497 [M+H]$^+$

Example 385

Trans-5-(N$^2$-hydroxy)amidino-3-[4-(2-oxopyrrolidin-1-yl)cyclohexylcarbonylamino]-N-(5-chloropyridin-2-yl)benzofuran-2-carboxamide

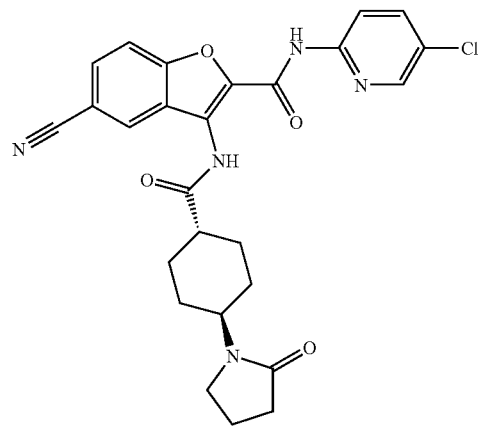

-continued

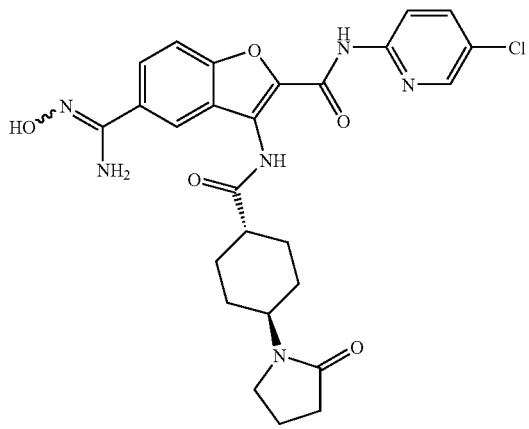

Trans-5-cyano-3-[4-(2-oxopyrrolidin-1-yl)cyclohexylcarbonylamino]-N-(5-chloropyridin-2-yl)benzofuran-2-carboxamide (107 mg) obtained in Example 6 is suspended in dimethyl sulfoxide (2 ml), and thereto are added hydroxyammonium chloride (36 mg) and a 28% sodium methoxide in methanol (100 µl). The mixture is heated at 50° C. for 2 hours, and further at 80° C. for 2 hours. The reaction solution is poured into ice-water, and the precipitates are collected by filtration, and purified by recycle HPLC to give the title compound (25 mg; APCI-MS M/Z: 539/541 [M+H]$^+$) and trans-5-aminocarbonyl-3-[4-(2-oxopyrrolidin-1-yl)cyclohexylcarbonylamino]-N-(5-chloropyridin-2-yl)benzofuran-2-carboxamide (18 mg; APCI-MS M/Z: 524/526 [M+H]$^+$).

Example 386

Trans-5-[2-(guanidinoxy)ethoxy]-3-[4-(2-oxopyrrolidin-1-yl)cyclohexylcarbonylamino]-N-(5-chloropyridin-2-yl)benzofuran-2-carboxamide dihydrochloride

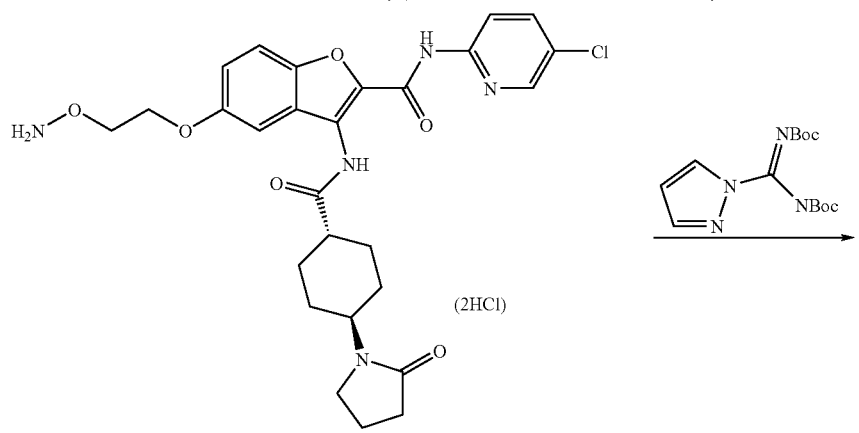

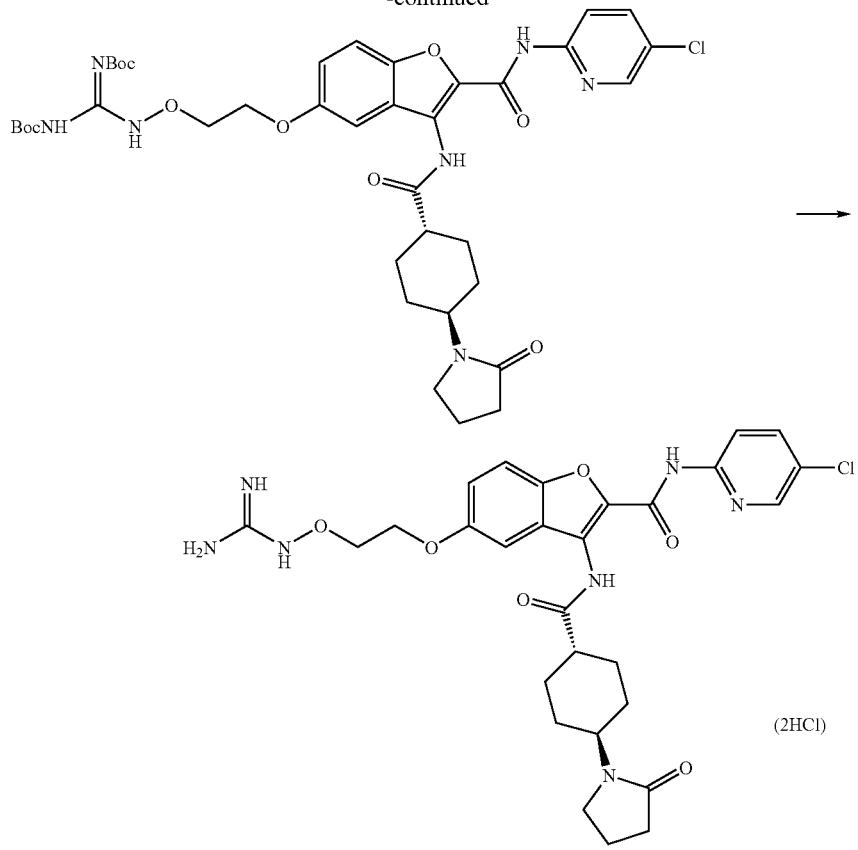

(1) Trans-5-(2-aminoxyethoxy)-3-[4-(2-oxopyrrolidin-1-yl)cyclohexylcarbonylamino]-N-(5-chloropyridin-2-yl)benzofuran-2-carboxamide dihydrochloride (90 mg) obtained in Example 183 is dissolved in N,N-dimethyl formamide (3 ml), and thereto are added N,N-diisopropylethylamine (38 μl) and N,N'-bis(t-butoxycarbonyl)-1H-pyrazole-1-carboxamidine (57 mg), and the mixture is stirred at room temperature for one day. The reaction solution is concentrated under reduced pressure, and the residue is poured into water, and extracted with chloroform. The organic layer is dried over sodium sulfate, and the solvent is evaporated under reduced pressure. The resulting residue is purified by NH-silica gel column chromatography (eluent: n-hexane/ethyl acetate=1/1, then ethyl acetate) to give trans-5-{2-[N,N'-bis(t-butoxycarbonyl)-guadinoxy]ethoxy}-3-[4-(2-oxopyrrolidin-1-yl)cyclohexylcarbonylamino]-N-(5-chloropyridin-2-yl)benzofuran-2-carboxamide (82 mg).

ESI-MS M/Z: 820/822 [M+Na]⁺, 798/800 [M+H]⁺

(2) To trans-5-{2-[N,N'-bis(t-butoxycarbonyl)guadinoxy]-ethoxy}-3-[4-(2-oxopyrrolidin-1-yl)cyclohexylcarbonylamino]-N-(5-chloropyridin-2-yl)benzofuran-2-carboxamide (73 mg) obtained in the above (1) is added trifluoroacetic acid (2 ml), and the mixture is stirred at room temperature for 12 hours. The reaction solution is concentrated under reduced pressure, and the residue is neutralized with a saturated aqueous potassium carbonate solution, and extracted with chloroform. The organic layer is dried over sodium sulfate, and the solvent is evaporated under reduced pressure. The residue is purified by NH-silica gel column chromatography (eluent: chloroform, then chloroform/methanol=97/3) to give trans-5-[2-(guanidinoxy)ethoxy]-3-[4-(2-oxopyrrolidin-1-yl)cyclohexylcarbonylamino]-N-(5-chloropyridin-2-yl)benzofuran-2-carboxamide (15 mg). Subsequently, this product (15 mg) is suspended in methanol (0.5 ml), and thereto is added 4N hydrogen chloride in dioxane (25 μl). To the mixture is poured diethyl ether, and the precipitates are washed with diethyl ether, and dried to give the title compound (17 mg).

ESI-MS M/Z: 598/600 [M+H]⁺

Examples 387-391

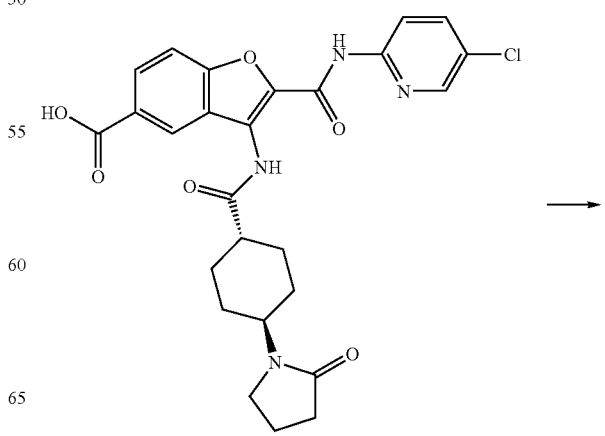

211

-continued

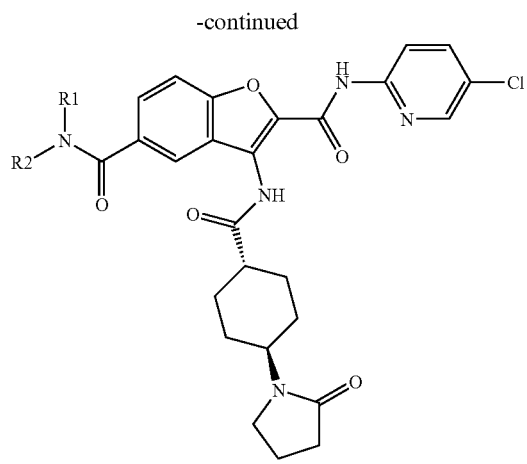

Trans-5-carboxy-3-[4-(2-oxopyrrolidin-1-yl)cyclohexyl-carbonylamino]-N-(5-chloropyridin-2-yl)benzofuran-2-carboxamide obtained in Example 77 and the corresponding starting compounds are treated in a similar manner to Example 87 to give the following compounds.

| No. Ex. | —R² | —AY | Physico-chemical properties |
|---|---|---|---|
| 387 | | | APCI-MS M/Z: 610/612 [M + H]⁺ |
| 388 | | | APCI-MS M/Z: 614/616 [M + H]⁺ |
| 389 | | | APCI-MS M/Z: 628/630 [M + H]⁺ |

212

-continued

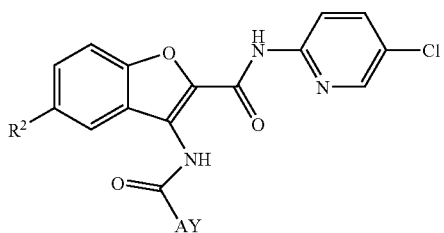

| No. Ex. | —R² | —AY | Physico-chemical properties |
|---|---|---|---|
| 390 | | | APCI-MS M/Z: 615/617 [M + H]⁺ |
| 391 | | | APCI-MS M/Z: 615/617 [M + H]⁺ |

Examples 392-393

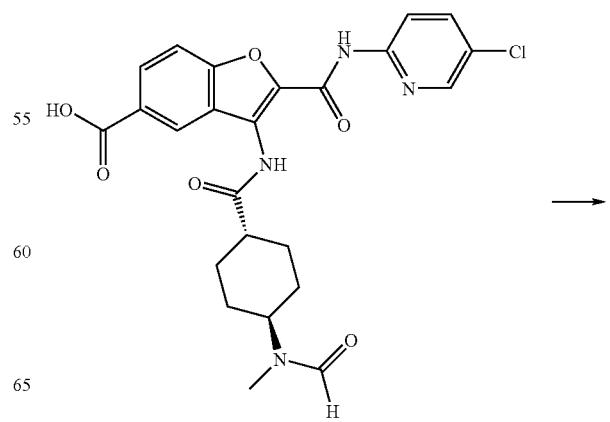

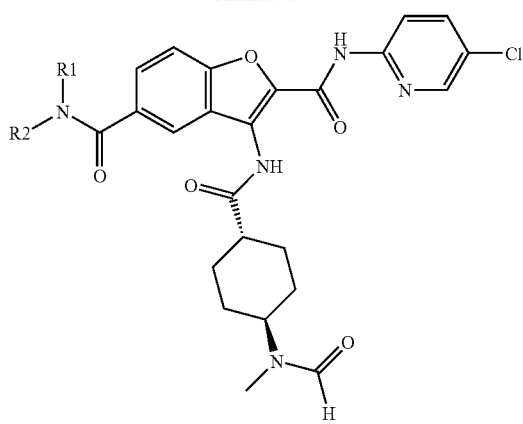

Trans-5-carboxy-3-[4-(N-formyl-N-methylamino) cyclohexylcarbonylamino]-N-(5-chloropyridin-2-yl)benzofuran-2-carboxamide obtained in Example 258 and amino compounds are treated in a similar manner to Example 261 to give the following compounds in a free form, or which are further treated with hydrogen chloride to give hydrochlorides thereof.

| Ex. No. | —R² | —AY | Physico-chemical properties |
|---|---|---|---|
| 392 | H₃C–N(piperazine)–C(=O)– | trans-cyclohexyl-N(CH₃)–CHO | APCI-MS M/Z: 581/583 [M + H]⁺ Hydrochloride |
| 393 | (CH₃)₂N–CH₂CH₂–N(CH₃)–C(=O)– | trans-cyclohexyl-N(CH₃)–CHO | APCI-MS M/Z: 583/585 [M + H]⁺ Hydrochloride |

Examples 394-399

Trans-5-dimethylaminocarbonyl-3-[4-(methylamino) cyclohexylcarbonylamino]-N-(5-chloropyridin-2-yl)benzofuran-2-carboxamide dihydrochloride obtained in Example 343 and acid chloride compounds are treated in a similar manner to Example 239 to give the following compounds.

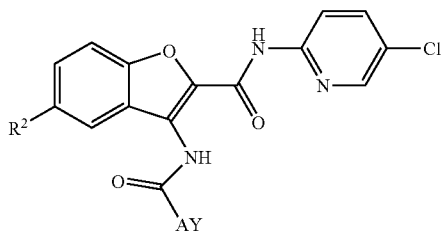
| Ex. No. | —R² | —AY | Physicochemical properties |
|---|---|---|---|
| 394 | CH₃-N(CH₃)-C(=O)- | trans-4-[N(CH₃)SO₂CH₃]-cyclohexyl | APCI-MS M/Z: 576/578 [M + H]⁺ |
| 395 | CH₃-N(CH₃)-C(=O)- | trans-4-[N(CH₃)C(=O)OCH₃]-cyclohexyl | APCI-MS M/Z: 556/558 [M + H]⁺ |
| 396 | CH₃-N(CH₃)-C(=O)- | trans-4-[N(CH₃)C(=O)N(CH₃)₂]-cyclohexyl | APCI-MS M/Z: 569/571 [M + H]⁺ |
| 397 | CH₃-N(CH₃)-C(=O)- | trans-4-[N(CH₃)C(=O)CH₂OCH₃]-cyclohexyl | APCI-MS M/Z: 570/572 [M + H]⁺ |
| 398 | CH₃-N(CH₃)-C(=O)- | trans-4-[N(CH₃)C(=O)CH₂OC(=O)CH₃]-cyclohexyl | APCI-MS M/Z: 598/600 [M + H]⁺ |

-continued

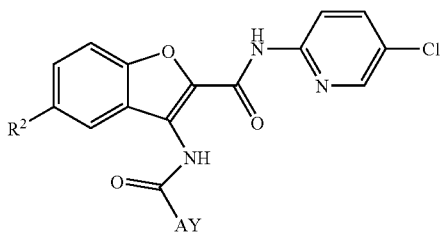

| Ex. No. | —R² | —AY | Physicochemical properties |
|---|---|---|---|
| 399 | (CH₃)₂N-C(=O)- | 4-[N-methyl-N-(acetoxyacetyl)amino]cyclohexyl | APCI-MS M/Z: 602/604 [M + H]⁺ |

Example 400

Trans-5-dimethylaminocarbonyl-3-[4-(N-hydroxy-acetyl-N-methylamino)cyclohexylcarbonylamino]-N-(5-chloropyridin-2-yl)benzofuran-2-carboxamide

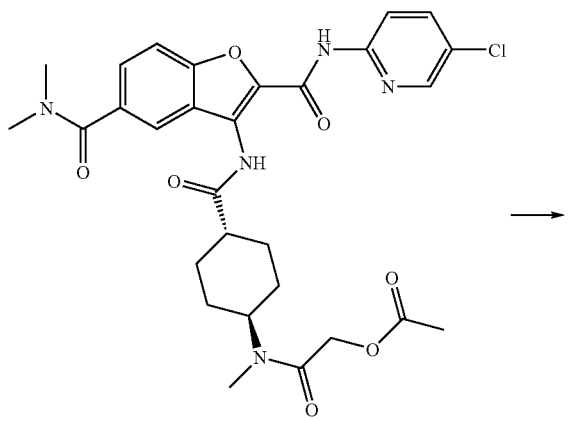

Trans-3-[4-(N-acetoxyacetyl-N-methylamino)cyclohexylcarbonylamino]-5-dimethylaminocarbonyl-N-(5-chloropyridin-2-yl)benzofuran-2-carboxamide (91 mg) obtained in Example 398 is dissolved in tetrahydrofuran/methanol (2:3, 5 ml), and thereto is added at room temperature 2N aqueous sodium hydroxide solution (300 μl), and the mixture is stirred for 4 hours. The reaction solution is acidified with diluted hydrochloric acid, and the mixture is diluted with chloroform. The mixture is dried over sodium sulfate, and the solvent is evaporated under reduced pressure. The resulting residue is purified by recycle HPLC to give the title compound (44 mg).

APCI-MS M/Z: 556/558 [M+H]⁺

Examples 401-403

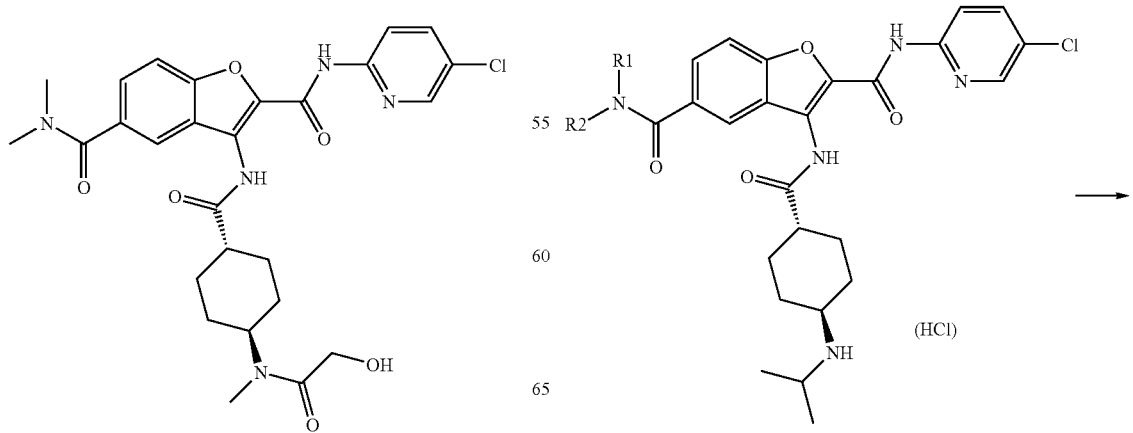

-continued

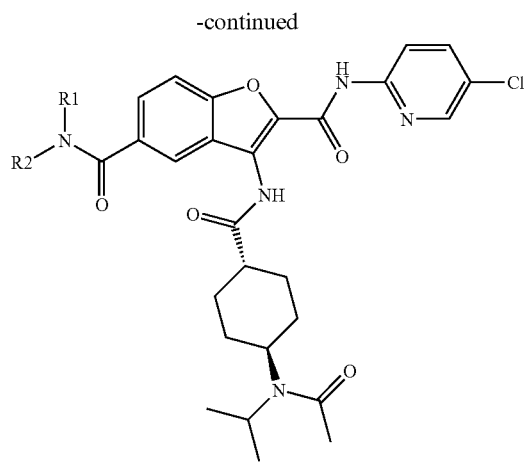

The compound obtained in Example 345, 347 or 348 and acetyl chloride are treated in a similar manner to Example 334 to give the following compounds.

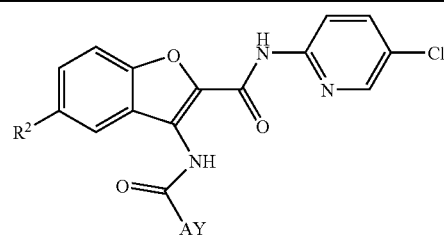

| Ex. No. | —R² | —AY | Physicochemical properties |
|---|---|---|---|
| 401 | 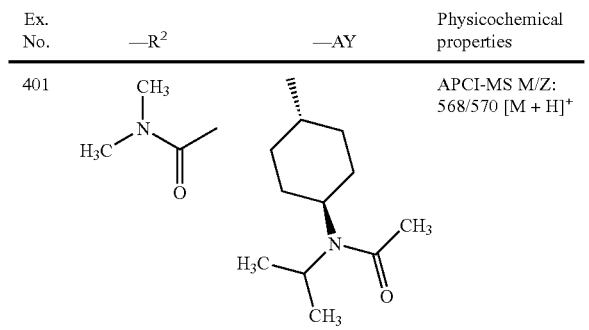 | | APCI-MS M/Z: 568/570 [M + H]⁺ |
| 402 | 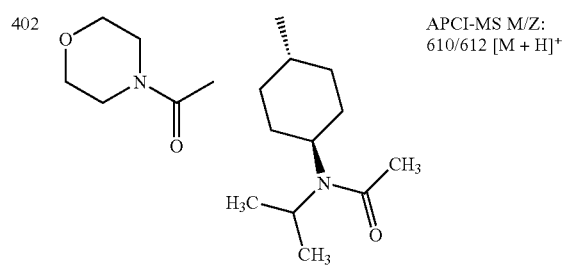 | | APCI-MS M/Z: 610/612 [M + H]⁺ |

-continued

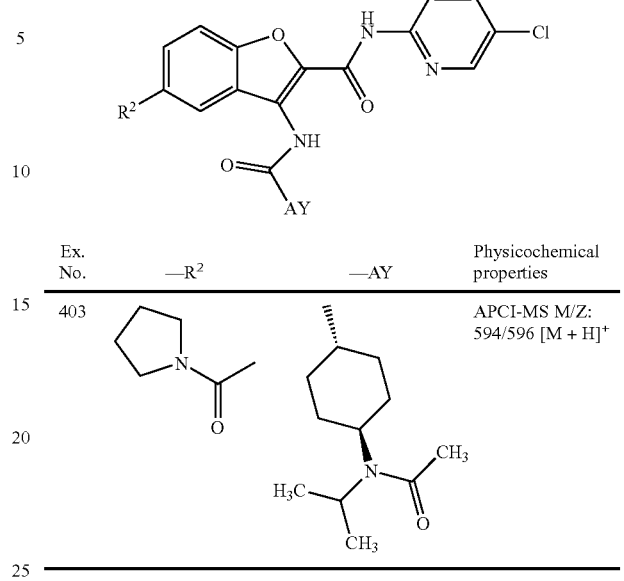

| Ex. No. | —R² | —AY | Physicochemical properties |
|---|---|---|---|
| 403 | | | APCI-MS M/Z: 594/596 [M + H]⁺ |

Examples 404-405

3-Amino-5-nitro-N-(5-chloropyridin-2-yl)benzofuran-2-carboxamide obtained in Reference Example 86 and a carboxylic acid are treated in a similar manner to Example 1 or Example 2 to give the following compounds.

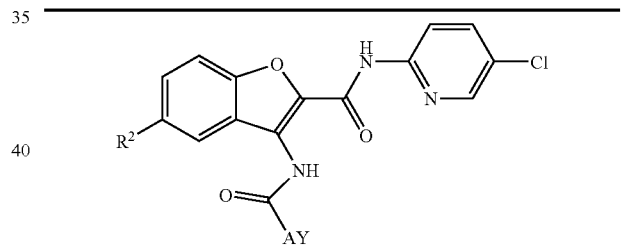

| Ex. No. | —R² | —AY | Physicochemical properties |
|---|---|---|---|
| 404 | 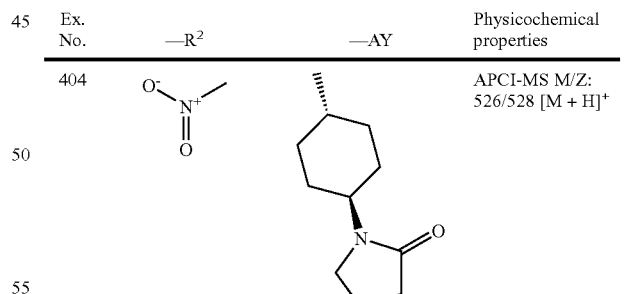 | | APCI-MS M/Z: 526/528 [M + H]⁺ |
| 405 | 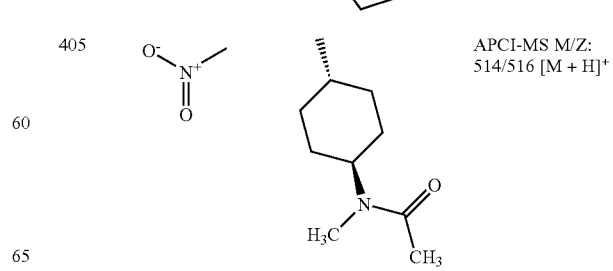 | | APCI-MS M/Z: 514/516 [M + H]⁺ |

Example 406

Trans-5-amino-3-[4-(2-oxopyrrolidin-1-yl)-cyclohexylcarbonylamino]-N-(5-chloropyridin-2-yl)-benzofuran-2-carboxamide hydrochloride

Example 407

Trans-3-[4-(N-acetyl-N-methylamino) cyclohexylcarbonylamino]-5-amino-N-(5-chloropyridin-2-yl) benzofuran-2-carboxamide hydrochloride

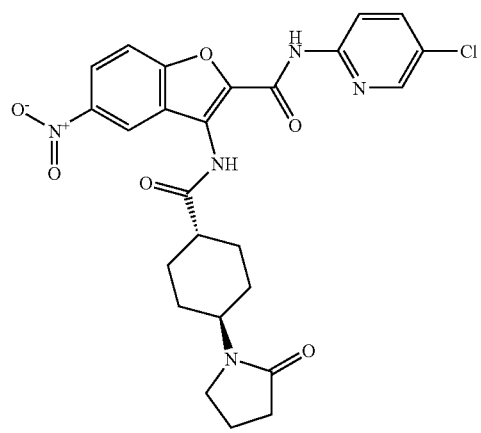

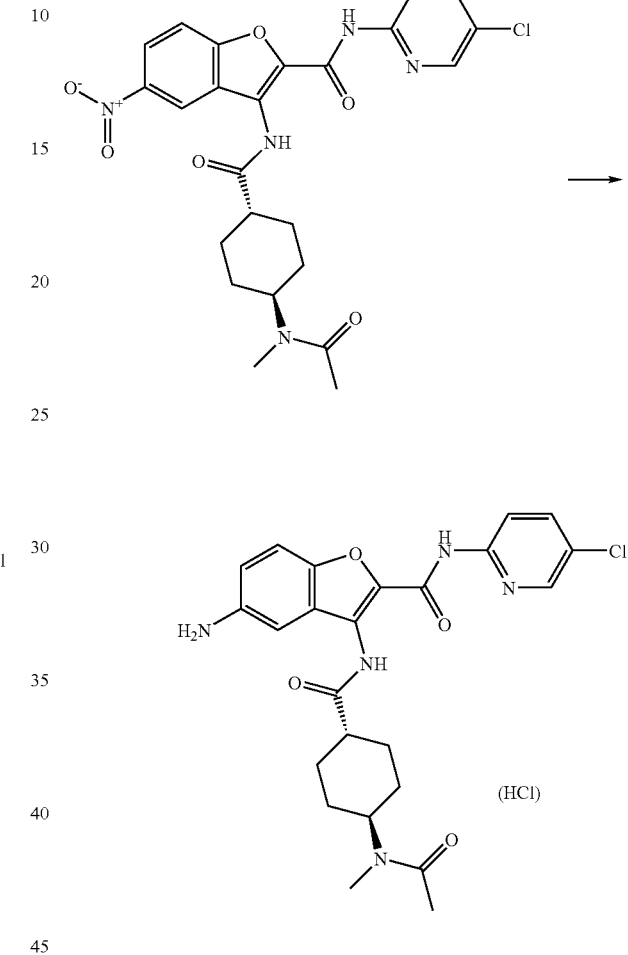

Trans-5-nitro-3-[4-(2-oxopyrrolidin-1-yl)cyclohexylcarbonylamino]-N-(5-chloropyridin-2-yl)benzofuran-2-carboxamide (2.50 g) obtained in Example 404 is suspended in ethanol/tetrahydrofuran (1:1, 400 ml), and thereto is added Raney nickel, and the mixture is stirred at room temperature under atmospheric hydrogen pressure for 12 hours. To the resulting yellow suspension is poured chloroform (200 ml), and the mixture is stirred at room temperature for 0.5 hour. The insoluble materials are removed by filtration, and the filtrate is concentrated under reduced pressure. The residue is purified by silica gel column chromatography (eluent: chloroform to chloroform/methanol=4/1), suspended in ethyl acetate/diethyl ether. The precipitates are collected by filtration, washed with diethyl ether, and dried to give trans-5-amino-3-[4-(2-oxopyrrolidin-1-yl)cyclohexylcarbonylamino]-N-(5-chloropyridin-2-yl)benzofuran-2-carboxamide (1.94 g). This product (150 mg) is suspended in methanol, and the mixture is treated with 4N hydrogen chloride in dioxane to give the title compound (158 mg).

APCI-MS M/Z: 496/498 [M+H]$^+$

Trans-3-[4-(N-acetyl-N-methylamino)cyclohexylcarbonylamino]-5-nitro-N-(5-chloropyridin-2-yl)benzofuran-2-carboxamide (2.27 g) obtained in Example 405 is treated in a similar manner to Example 406 to give trans-3-[4-(N-acetyl-N-methylamino)cyclohexylcarbonylamino]-5-amino-N-(5-chloropyridin-2-yl)benzofuran-2-carboxamide (1.62 g). The resulting free compound (150 mg) is suspended in methanol, and treated with 4N hydrogen chloride in dioxane to give the title compound (158 mg).

APCI-MS M/Z: 484/486 [M+H]$^+$

Examples 408-409

Trans-5-amino-3-[4-(2-oxopyrrolidin-1-yl)cyclohexylcarbonylamino]-N-(5-chloropyridin-2-yl)benzofuran-2-carboxamide hydrochloride obtained in Example 406 or trans-3-[4-(N-acetyl-N-methylamino)cyclohexylcarbonylamino]-5-amino-N-(5-chloropyridin-2-yl)benzofuran-2- carboxamide hydrochloride obtained in Example 407 is treated in a similar manner to Example 198 to give the following compounds in a free form, or which are further treated with hydrogen chloride to give hydrochlorides thereof.

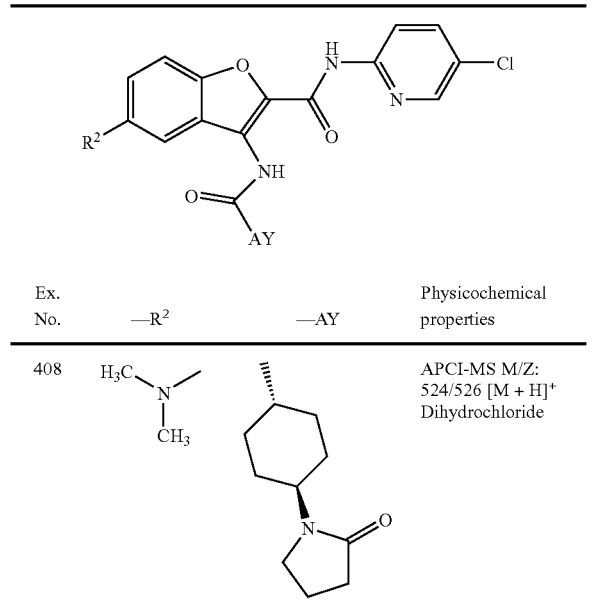

| Ex. No. | —R² | —AY | Physicochemical properties |
|---|---|---|---|
| 408 | H₃C−N(CH₃)− | (cyclohexyl-pyrrolidinone) | APCI-MS M/Z: 524/526 [M + H]⁺ Dihydrochloride |

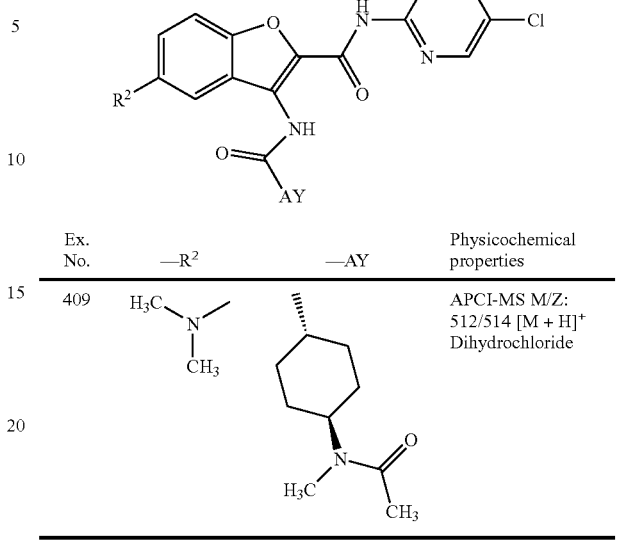

| Ex. No. | —R² | —AY | Physicochemical properties |
|---|---|---|---|
| 409 | H₃C−N(CH₃)− | (cyclohexyl-N-methylacetamide) | APCI-MS M/Z: 512/514 [M + H]⁺ Dihydrochloride |

Example 410

Trans-5-dimethylaminocarbonyl-3-[4-(3-oxomorpholin-4-yl)cyclohexylcarbonylamino]-N-(5-chloropyridin-2-yl)benzofuran-2-carboxamide

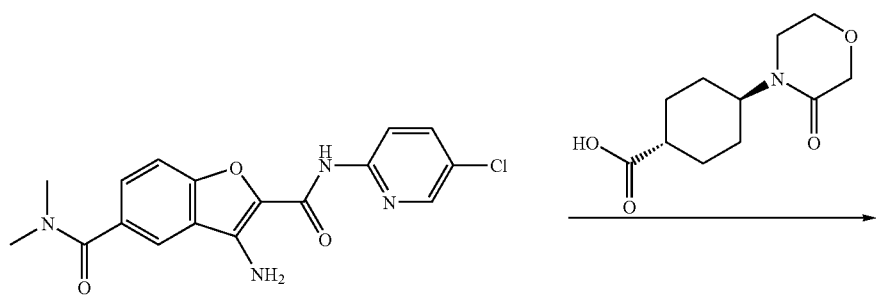

Trans-4-(3-oxomorpholin-4-yl)cyclohexanecarboxylic acid (85 mg) obtained in Reference Example 141 is dissolved in chloroform (3 ml), and thereto are added thionyl chloride (30 µl) and a drop of N,N-dimethylformamide, and the mixture is stirred at room temperature for 15 hours. To the resulting reaction solution is added 3-amino-5-dimethylaminocarbonyl-N-(5-chloropyridin-2-yl)benzofuran-2-carboxamide (96 mg) obtained in Reference Example 156 and pyridine (2 ml), and the mixture is stirred at room temperature for 2 hours. To the reaction solution is poured a saturated aqueous sodium hydrogen carbonate solution, and the mixture is extracted with chloroform. The organic layer is dried over sodium sulfate, and the solvent is evaporated under reduced pressure. The resulting residue is purified by NH-silica gel column chromatography (eluent: n-hexane/ethyl acetate=2/1, then ethyl acetate), and further purified by recycle HPLC to give the title compound (28 mg).

APCI-MS M/Z: 568/570 [M+H]$^+$

Examples 411-417

The amino compounds obtained in Reference Example 156-158 and corresponding carboxylic acids are treated in a similar manner to Example 410 to give the following compounds.

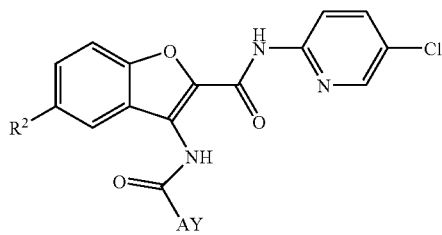

| Ex. No. | —R² | —AY | Physicochemical properties |
|---|---|---|---|
| 411 | N(CH₃)₂C(O)— | trans-cyclohexyl-oxazolidin-2-one | APCI-MS M/Z: 554/556 [M + H]$^+$ |
| 412 | N(CH₃)₂C(O)— | trans-cyclohexyl-CH₂-pyrrolidin-2-one | APCI-MS M/Z: 566/568 [M + H]$^+$ |
| 413 | N(CH₃)₂C(O)— | trans-cyclohexyl-CH₂-N(CH₃)C(O)CH₃ | APCI-MS M/Z: 554/556 [M + H]$^+$ |
| 414 | N(CH₃)₂C(O)— | -(CH₂)₄-pyrrolidin-2-one | APCI-MS M/Z: 526/528 [M + H]$^+$ |

| Ex. No. | Structure | Physicochemical properties |
|---|---|---|

-continued
| 415 | 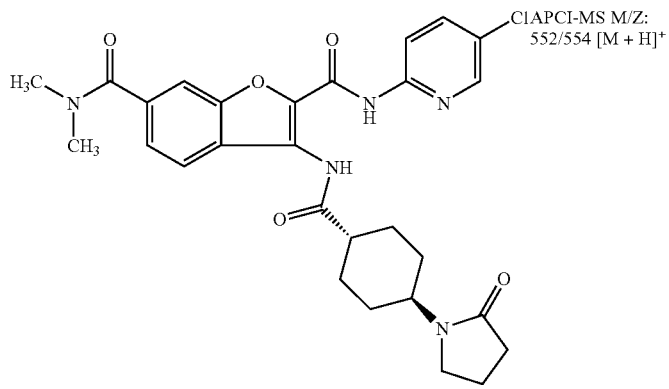 | ClAPCI-MS M/Z: 552/554 [M + H]⁺ |
| 416 | 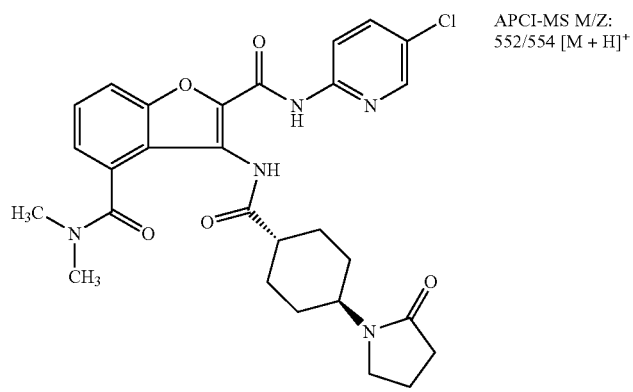 | APCI-MS M/Z: 552/554 [M + H]⁺ |
| 417 | 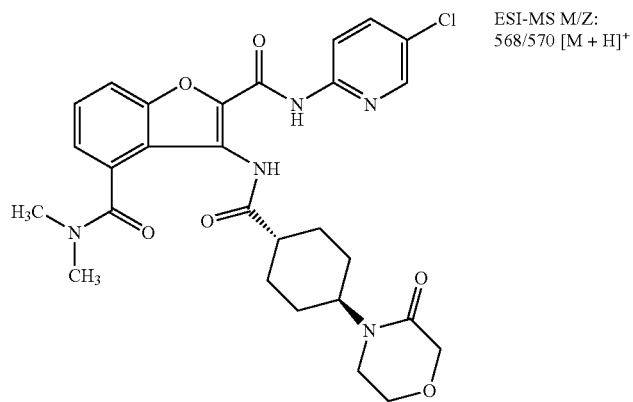 | ESI-MS M/Z: 568/570 [M + H]⁺ |
Example 418
Trans-4-methoxycarbonyl-3-[4-(2-oxo-oxazolidin-3-yl)cyclohexylcarbonylamino]-N-(5-chloropyridin-2-yl)benzofuran-2-carboxamide
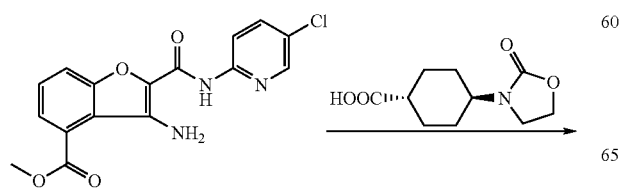

-continued

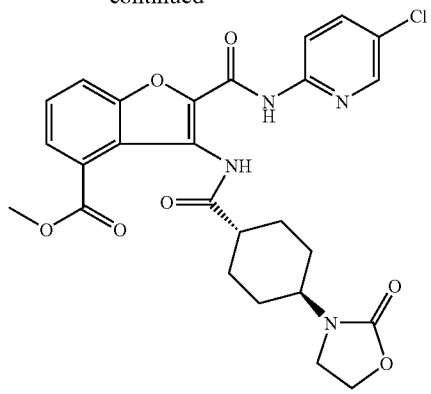

3-Amino-4-methoxycarbonyl-N-(5-chloropyridin-2-yl)-benzofuran-2-carboxamide (351 mg) obtained in Reference Example 152 and trans-4-(2-oxo-oxazolidin-3-yl)cyclohexanecarboxylic acid (432 mg) obtained in Reference Example 142 are treated in a similar manner to Example 1 to give the title compound (129 mg).
APCI-MS M/Z: 541/543 [M+H]$^+$ Example 419

Trans-4-carboxy-3-[4-(2-oxo-oxazolidin-3-yl)-cyclohexylcarbonylamino]-N-(5-chloropyridin-2-yl)benzofuran-2-carboxamide

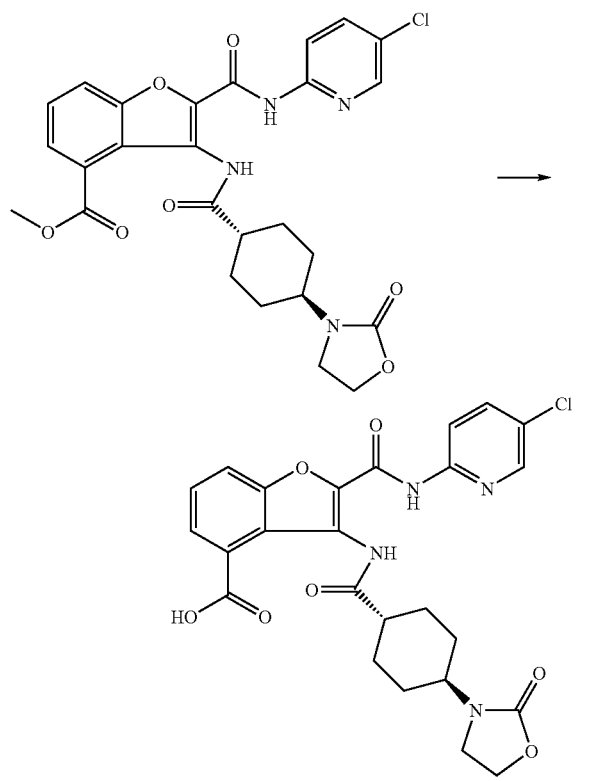

Trans-4-methoxycarbonyl-3-[4-(2-oxo-oxazolidin-3-yl) cyclohexylcarbonylamino]-N-(5-chloropyridin-2-yl)benzofuran-2-carboxamide (107 mg) obtained in Example 418 is treated in a similar manner to Example 77 to give the title compound (80.4 mg).

ESI-MS M/Z: 525/527 [M−H]$^-$

Example 420

Trans-4-dimethylaminocarbonyl-3-[4-(2-oxo-oxazolidin-3-yl)cyclohexylcarbonylamino]-N-(5-chloropyridin-2-yl)benzofuran-2-carboxamide

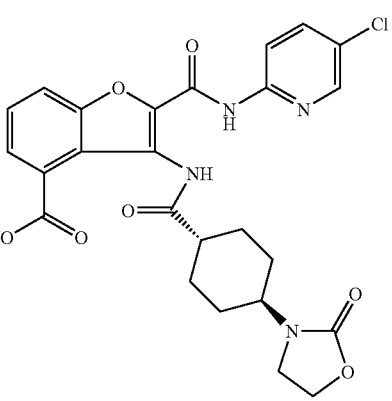

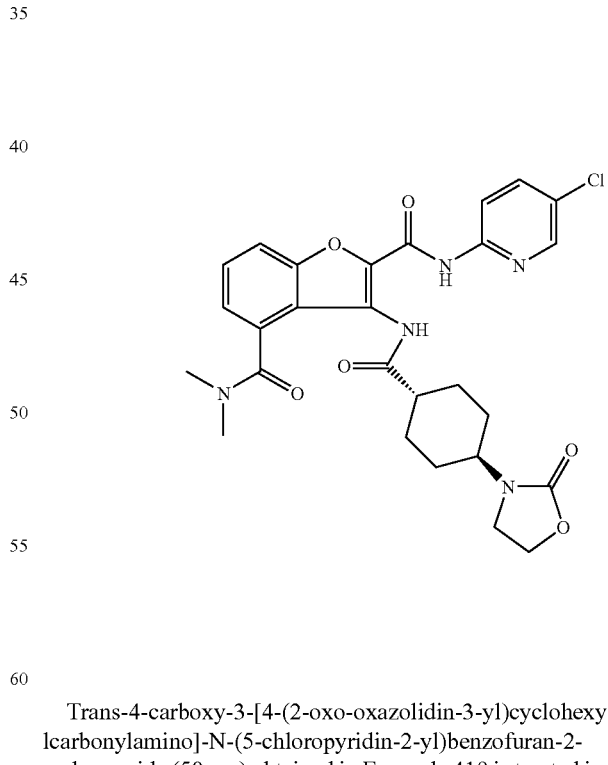

Trans-4-carboxy-3-[4-(2-oxo-oxazolidin-3-yl)cyclohexylcarbonylamino]-N-(5-chloropyridin-2-yl)benzofuran-2-carboxamide (50 mg) obtained in Example 419 is treated in a similar manner to Example 87 to give the title compound (36.4 mg).
APCI-MS M/Z: 554/556 [M+H]$^+$

Example 421

Trans-4-methoxycarbonyl-3-[4-(2-oxopyrrolidin-1-yl)cyclohexylcarbonylamino]-N-(5-chloropyridin-2-yl)-benzofuran-2-carboxamide

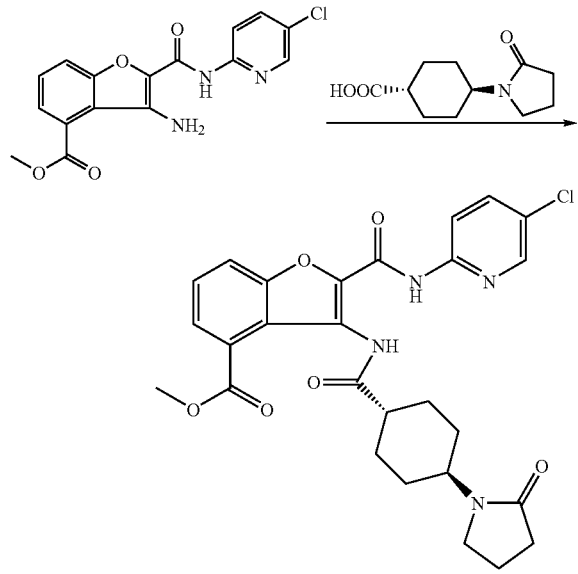

3-Amino-4-methoxycarbonyl-N-(5-chloropyridin-2-yl)-benzofuran-2-carboxamide (2.33 g) obtained in Reference Example 152 and trans-4-(2-oxopyrrolidin-1-yl)cyclohexanecarboxylic acid (2.06 g) obtained in Reference Example 142 are treated in a similar manner to Example 1 to give the title compound (1.90 g).

APCI-MS M/Z: 539/541 [M+H]+

Example 422

Trans-4-carboxy-3-[4-(2-oxopyrrolidin-1-yl)-cyclohexylcarbonylamino]-N-(5-chloropyridin-2-yl)benzofuran-2-carboxamide

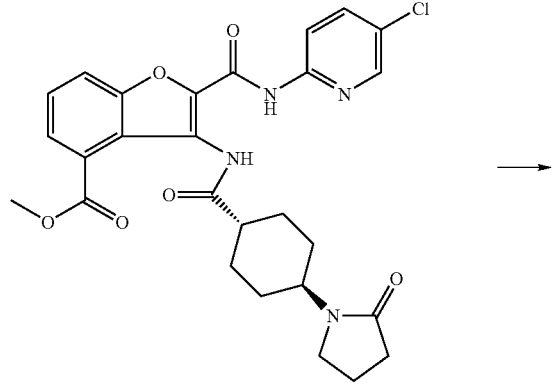

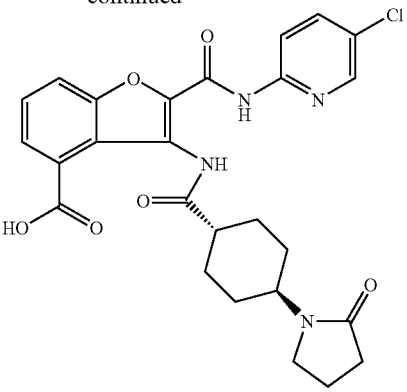

Trans-4-methoxycarbonyl-3-[4-(2-oxopyrrolidin-1-yl)cyclohexylcarbonylamino]-N-(5-chloropyridin-2-yl)benzofuran-2-carboxamide (880 mg) obtained in Example 421 is treated in a similar manner to Example 77 to give the title compound (623 mg).

ESI-MS M/Z: 523/525 [M−H]−

Example 423

Trans-4-hydroxymethyl-3-[4-(2-oxopyrrolidin-1-yl)cyclohexylcarbonylamino]-N-(5-chloropyridin-2-yl)benzofuran-2-carboxamide

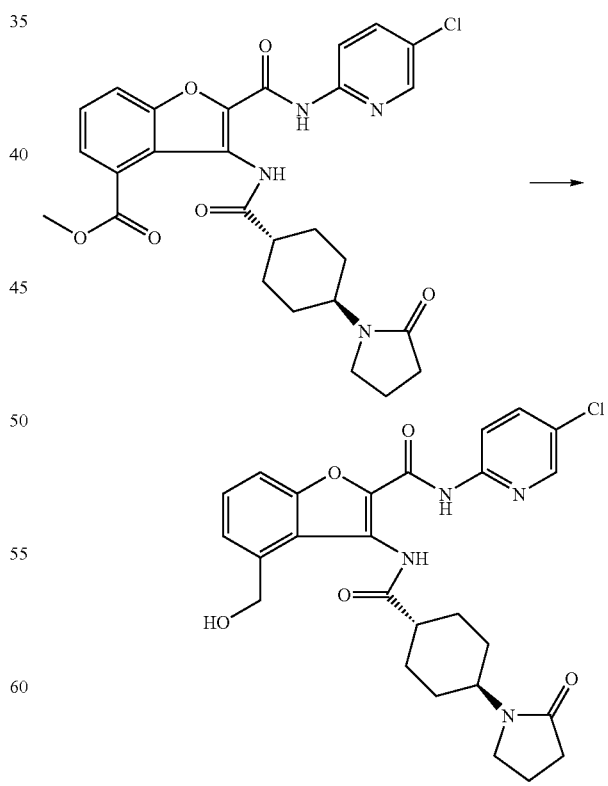

Trans-4-methoxycarbonyl-3-[4-(2-oxopyrrolidin-1-yl)-cyclohexylcarbonylamino]-N-(5-chloropyridin-2-yl)benzofuran-2-carboxamide (350 mg) obtained in Example 421 is treated in a similar manner to Example 145 to give the title compound (40.9 mg).

ESI-MS M/Z: 511/513[M+H]+

Example 424

Trans-4-[N-(2-dimethylaminoethyl)-N-methyl]-aminocarbonyl-3-[4-(2-oxopyrrolidin-1-yl)cyclohexylcarbonylamino]-N-(5-chloropyridin-2-yl)benzofuran-2-carboxamide dihydrochloride

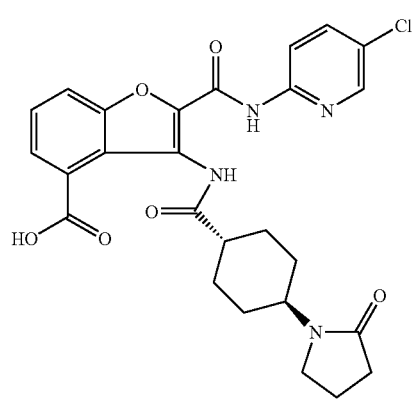

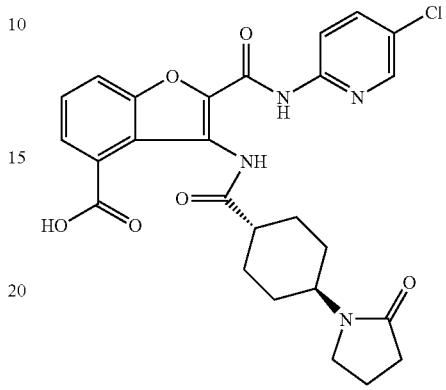

Trans-4-carboxy-3-[4-(2-oxopyrrolidin-1-yl)cyclohexylcarbonylamino]N-(5-chloropyridin-2-yl)benzofuran-2-carboxamide (70 mg) obtained in Example 422 is treated in a similar manner to Example 87 to give trans-4-[N-(2-dimethylaminoethyl)-N-methyl]aminocarbonyl-3-[4-(2-oxopyrrolidin-1-yl)cyclohexylcarbonylamino]-N-(5-chloropyridin-2-yl)benzofuran-2-carboxamide (40.7 mg). This product is dissolved in methanol, and treated with 4N hydrogen chloride in dioxane (50 µl) to give the title compound (35.7 mg).

APCI-MS M/Z: 609/611 [M+H]+

Example 425

Trans-4-t-butoxycarbonylamino-3-[4-(2-oxopyrrolidin-1-yl)cyclohexylcarbonylamino]-N-(5-chloropyridin-2-yl)benzofuran-2-carboxamide

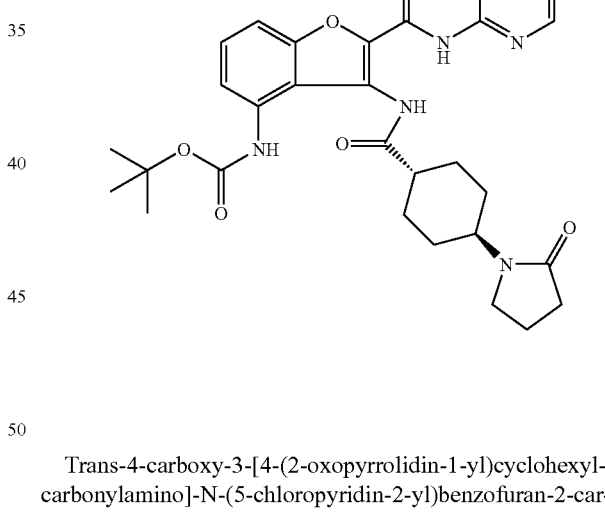

Trans-4-carboxy-3-[4-(2-oxopyrrolidin-1-yl)cyclohexylcarbonylamino]-N-(5-chloropyridin-2-yl)benzofuran-2-carboxamide (325 mg) obtained in Example 422 is dissolved in t-butanol (8 ml), and thereto are added at room temperature triethylamine (91 µl) and diphenylphosphoryl azide (140 µl), and the mixture is stirred at 60° C. for 1.5 hour, and then heated under reflux for 5.5 hours. The reaction solution is diluted with a saturated aqueous sodium hydrogen carbonate solution, and extracted with chloroform. The organic layer is washed with a saturated brine, dried over sodium sulfate, and the solvent is evaporated under reduced pressure. The resulting residue is purified by silica gel column chromatography (eluent: chloroform/methanol=100/1, then 10/1) to give the title compound (141.7 mg).

ESI-MS M/Z: 596/598 [M+H]+

Example 426
Trans-4-amino-3-[4-(2-oxopyrrolidin-1-yl)-cyclohexylcarbonylamino]-N-(5-chloropyridin-2-yl)benzofuran-2-carboxamide

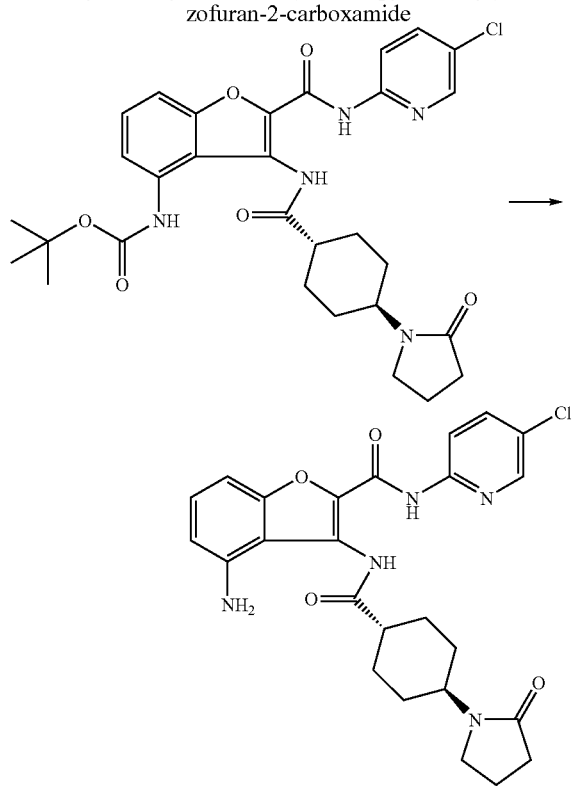

Trans-4-t-butoxycarbonylamino-3-[4-(2-oxopyrrolidin-1-yl)cyclohexylcarbonylamino]-N-(5-chloropyridin-2-yl)benzofuran-2-carboxamide (108 mg) obtained in Example 425 is dissolved in trifluoroacetic acid (2 ml), and the mixture is stirred at room temperature for 2 hours. The reaction solution is concentrated under reduced pressure, and the resulting residue is neutralized with a saturated aqueous sodium hydrogen carbonate solution, and extracted with chloroform. The organic layer is dried over sodium sulfate, and the solvent is evaporated under reduced pressure. The resulting residue is purified by NH-silica gel column chromatography (eluent: n-hexane/ethyl acetate=1/1, then ethyl acetate) to give the title compound (85.4 mg).

ESI-MS M/Z: 496/498 [M+H]$^+$

Example 427
Trans-4-dimethylamino-3-[4-(2-oxopyrrolidin-1-yl)cyclohexylcarbonylamino]-N-(5-chloropyridin-2-yl)benzofuran-2-carboxamide

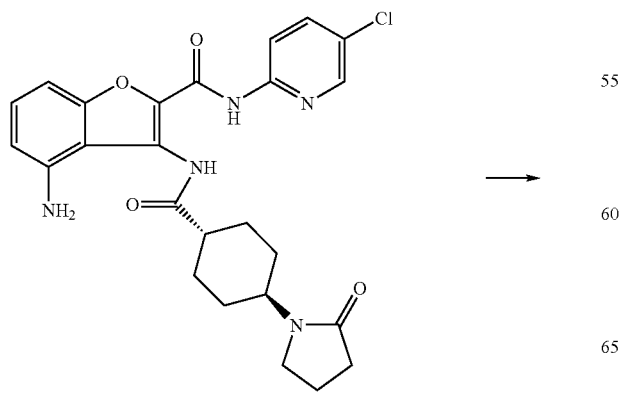

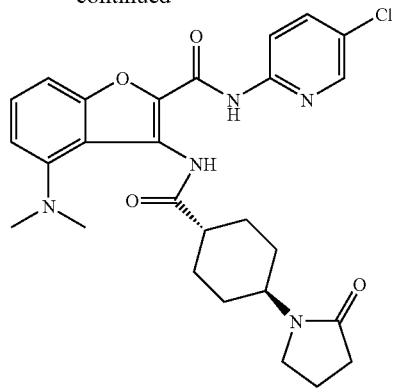

Trans-4-amino-3-[4-(2-oxopyrrolidin-1-yl)cyclohexylcarbonylamino]-N-(5-chloropyridin-2-yl)benzofuran-2-carboxamide (41.7 mg) obtained in Example 426 is treated in a similar manner to Example 198 to give the title compound (8.0 mg).

APCI-MS M/Z: 524/526 [M+H]$^+$

Example 428
Trans-4-methanesulfonylamino-3-[4-(2-oxopyrrolidin-1-yl)cyclohexylcarbonylamino]-N-(5-chloropyridin-2-yl)benzofuran-2-carboxamide

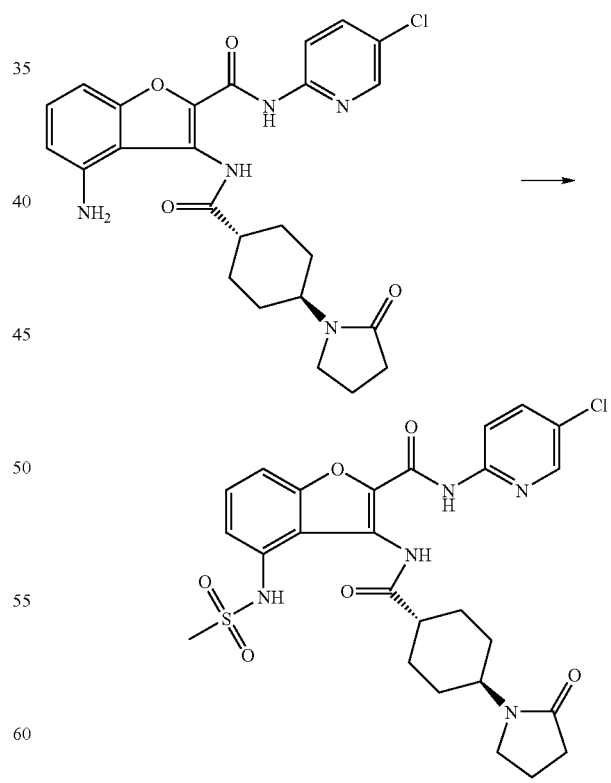

Trans-4-amino-3-[4-(2-oxopyrrolidin-1-yl)cyclohexylcarbonylamino]-N-(5-chloropyridin-2-yl)benzofuran-2-carboxamide (27 mg) obtained in Example 426 is dissolved in pyridine (2 ml), and thereto is added methanesulfonyl chloride (7 μl) under ice-cooling. The mixture is stirred at room temperature overnight, and thereto are further added pyridine (3 ml) and methanesulfonyl chloride (500 μl) under ice-cooling. The mixture is stirred at room temperature for 6 hours. Water is added to the reaction solution, and the mixture is extracted with chloroform. The solvent is evaporated under reduced pressure, and the resulting residue is purified by silica gel column chromatography (eluent: chloroform, then chloroform/methanol=9/1) to give the title compound (21.2 mg).

APCI-MS M/Z: 574/576 [M+H]$^+$

Example 429

Trans-3-[4-(3-oxo-morpholin-4-yl)cyclohexylcarbonylamino]-N-(5-chloropyridin-2-yl)benzofuran-2-carboxamide

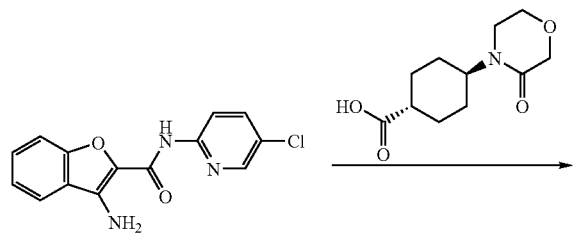

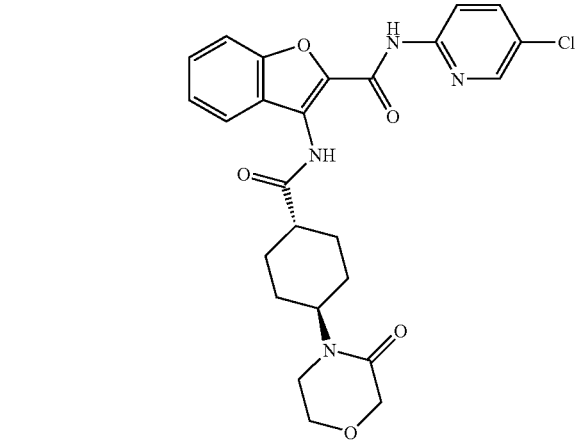

3-Amino-N-(5-chloropyridin-2-yl)benzofuran-2-carboxamide (66 mg) obtained in Reference Example 74 and trans-4-(3-oxo-morpholin-4-yl)cyclohexanecarboxylic acid (68 mg) obtained in Reference Example 141 are treated in a similar manner to Example 410 to give the title compound (74 mg).

APCI-MS M/Z: 497/499 [M+H]$^+$

Reference Example 1

Methyl 3-formyl-4-hydroxybenzoate

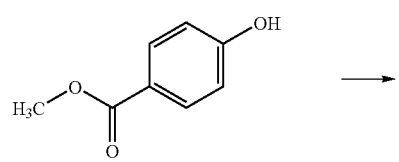

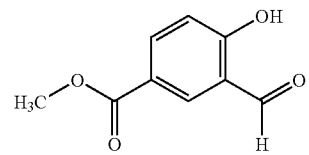

Methyl 4-hydroxybenzoate (1.52 g) is dissolved in trifluoroacetic acid (20 ml), thereto is added hexamethylenetetramine (700 mg) and the mixture is heated under reflux for 2 hours. The reaction solution is concentrated under reduced pressure, thereto is poured ice-water, and then the mixture is extracted with ethyl acetate. The organic layer is washed with saturated aqueous sodium hydrogen carbonate solution and saturated brine, dried over sodium sulfate and the solvent is evaporated under reduced pressure. The resulting residue is dissolved in chloroform, and then filtered to remove the insoluble materials. The filtrate is concentrated under reduced pressure, and then purified by silica gel column chromatography (eluent: n-hexane/ethyl acetate=4/1) to give the title compound (540 mg).

ESI-MS M/Z:179[M−H]$^-$.

Reference Example 2

Methyl(3-formyl-4-hydroxyphenyl)-acetate

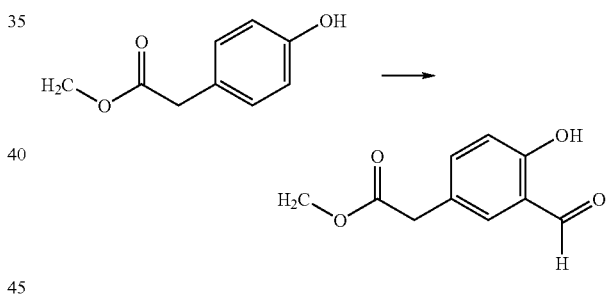

Methyl(4-hydroxyphenyl)acetate (1.66 g) is dissolved in trifluoroacetic acid (20 ml), thereto is added hexamethylenetetramine (700 mg) and the mixture is heated under reflux for 2 hours. The reaction solution is concentrated under reduced pressure, thereto is poured ice-water, and then the mixture is extracted with ethyl acetate. The organic layer is washed with saturated aqueous sodium hydrogen carbonate solution and saturated brine, dried over sodium sulfate and evaporated to remove the solvent under reduced pressure. The resulting residue is purified by silica gel column chromatography (eluent: n-hexane/ethyl acetate=9/1 followed by 4/1) to give the title compound (1.08 g).

ESI-MS M/Z:193[M−H]$^-$.

Reference Examples 3-4

The corresponding compounds are treated in a similar manner to Reference Example 1 or Reference Example 2 to give the following compounds.

| Ref. Ex. No. | Structure | Physicochemical Properties |
|---|---|---|
| 3 | 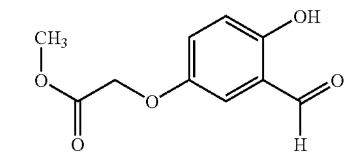 | APCI-MS M/Z: 225 [M + H + MeOH − H₂O]⁺ |
| 4 | 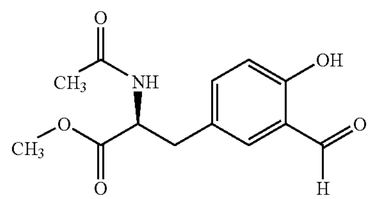 | EI-MS M/Z: 265 [M]⁺ |

Reference Example 5

Methyl 3-cyano-4-hydroxybenzoate

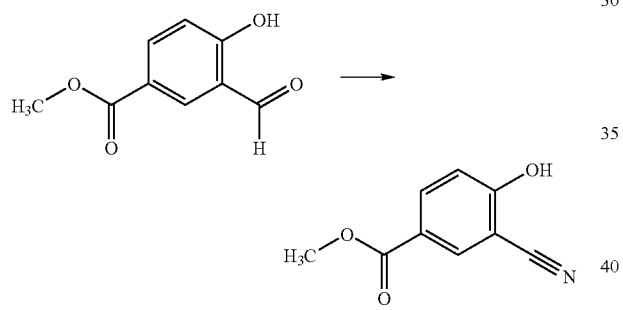

Methyl 3-formyl-4-hydroxybenzoate (28.60 g) obtained in Reference Example 1 is dissolved in formic acid (120 ml), thereto is added hydroxylammonium chloride (14.30 g) and the mixture is heated under reflux for 15 hours. The reaction solution is concentrated under reduced pressure, diluted with ethyl acetate, washed successively with water and saturated brine, dried over sodium sulfate and the solvent is evaporated under reduced pressure to give the title compound (24.25 g).

ESI-MS M/Z:176[M−H]⁻.

Reference Example 6

Methyl(3-cyano-4-hydroxyphenyl)-acetate

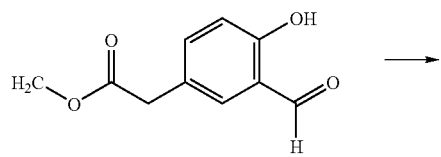

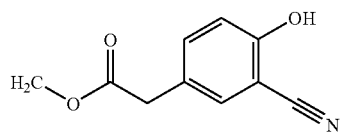

Methyl(3-formyl-4-hydroxyphenyl)acetate (1.05 g) obtained in Reference Example 2 is dissolved in formic acid (15 ml), and thereto are added hydroxylammonium chloride (0.49 g) and sodium formate (0.81 g) and the mixture is heated under reflux for 8 hours. The reaction solution is concentrated under reduced pressure, diluted with ethyl acetate, washed successively with water and saturated brine, dried over sodium sulfate and the solvent is evaporated under reduced pressure to give the title compound (520 mg).

ESI-MS M/Z:190[M−H]⁻.

Reference Examples 7-19

The corresponding compounds are treated in a similar manner to Reference Example 5 or Reference Example 6 to give the following compounds.

| Ref. Ex. No. | Structure | Physicochemical Properties |
|---|---|---|
| 7 | 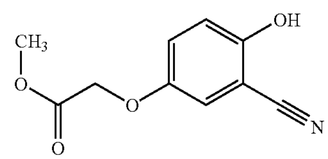 | ESI-MS M/Z: 192 [M − H]⁻ |
| 8 | 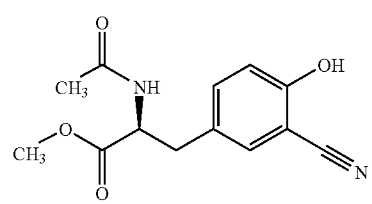 | APCI-MS M/Z: 263 [M + H]⁺ |
| 9 | 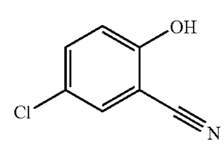 | ESI-MS M/Z: 152/154 [M − H]⁻ |
| 10 | 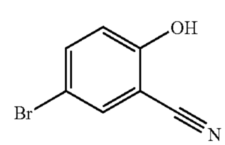 | ESI-MS M/Z: 196/198 [M − H]⁻ |
| 11 | 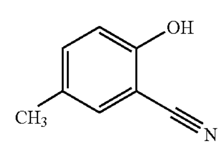 | ESI-MS M/Z: 132 [M − H]⁻ |

241

-continued

| Ref. Ex. No. | Structure | Physicochemical Properties |
|---|---|---|
| 12 | 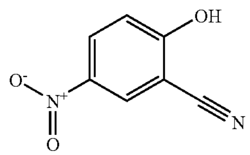 | ESI-MS M/Z: 163 [M − H]⁻ |
| 13 | 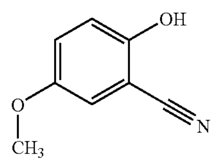 | ESI-MS M/Z: 148 [M − H]⁻ |
| 14 | 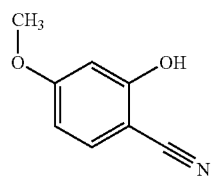 | ESI-MS M/Z: 148 [M − H]⁻ |
| 15 | 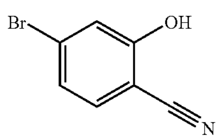 | ESI-MS M/Z: 196/198 [M − H]⁻ |
| 16 | 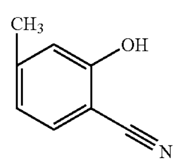 | ESI-MS M/Z: 132 [M − H]⁻ |
| 17 | 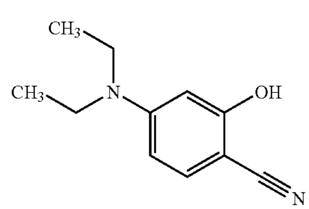 | This compound is used at the next step without purification. |
| 18 | 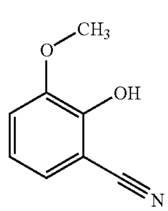 | ESI-MS M/Z: 148 [M − H]⁻ |
| 19 | 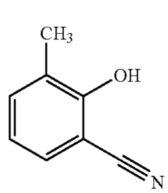 | This compound is used at the next step without purification. |

242

Reference Example 20

2-(4-Methoxycarbonyl-2-cyanophenoxy)-N-(5-chloropyridin-2-yl)acetamide

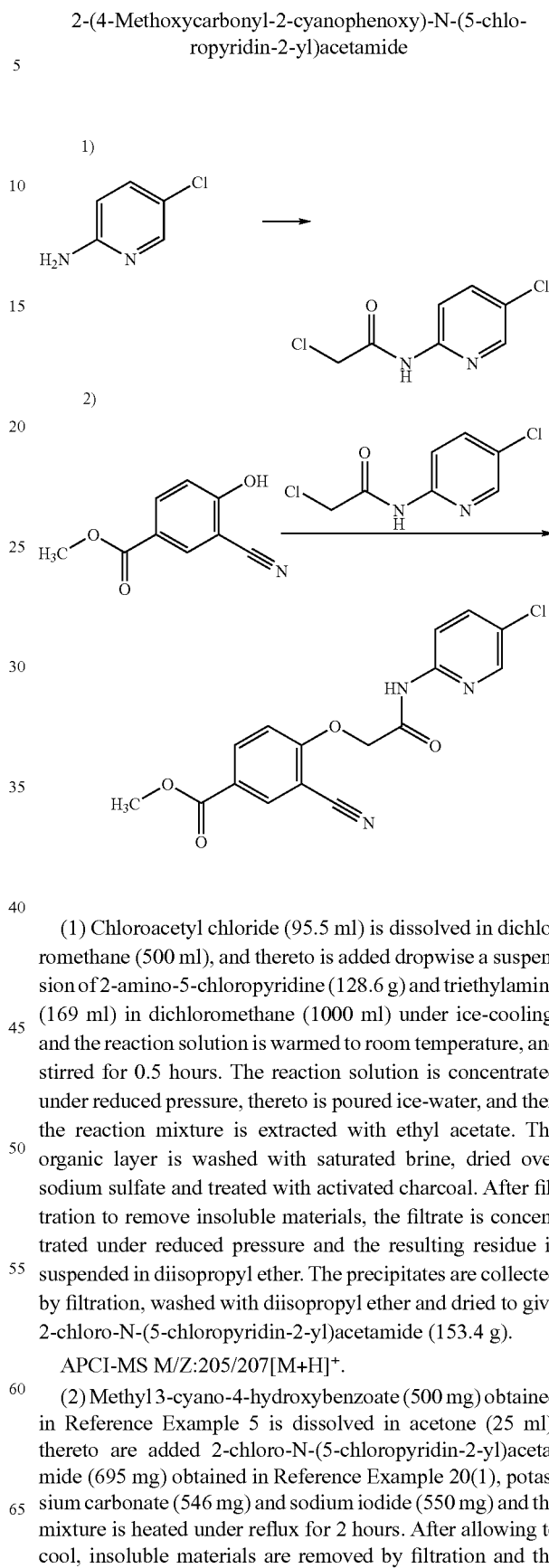

(1) Chloroacetyl chloride (95.5 ml) is dissolved in dichloromethane (500 ml), and thereto is added dropwise a suspension of 2-amino-5-chloropyridine (128.6 g) and triethylamine (169 ml) in dichloromethane (1000 ml) under ice-cooling, and the reaction solution is warmed to room temperature, and stirred for 0.5 hours. The reaction solution is concentrated under reduced pressure, thereto is poured ice-water, and then the reaction mixture is extracted with ethyl acetate. The organic layer is washed with saturated brine, dried over sodium sulfate and treated with activated charcoal. After filtration to remove insoluble materials, the filtrate is concentrated under reduced pressure and the resulting residue is suspended in diisopropyl ether. The precipitates are collected by filtration, washed with diisopropyl ether and dried to give 2-chloro-N-(5-chloropyridin-2-yl)acetamide (153.4 g).

APCI-MS M/Z:205/207[M+H]⁺.

(2) Methyl 3-cyano-4-hydroxybenzoate (500 mg) obtained in Reference Example 5 is dissolved in acetone (25 ml), thereto are added 2-chloro-N-(5-chloropyridin-2-yl)acetamide (695 mg) obtained in Reference Example 20(1), potassium carbonate (546 mg) and sodium iodide (550 mg) and the mixture is heated under reflux for 2 hours. After allowing to cool, insoluble materials are removed by filtration and the insolubles are washed with acetone several times. The filtrate and the washing are combined and concentrated under reduced pressure, and then purified by silica gel column chromatography (eluent: chloroform followed by chloroform/ethyl acetate=4/1). The resulting residue is suspended in diethyl ether, and then the precipitates are collected by filtration to give the title compound (660 mg).

APCI-MS M/Z:346/348[M+H]$^+$.

Reference Example 21

2-[2-Cyano-4-(methoxycarbonylmethyl)phenoxy]-N-(5-chloropyridin-2-yl)acetamide

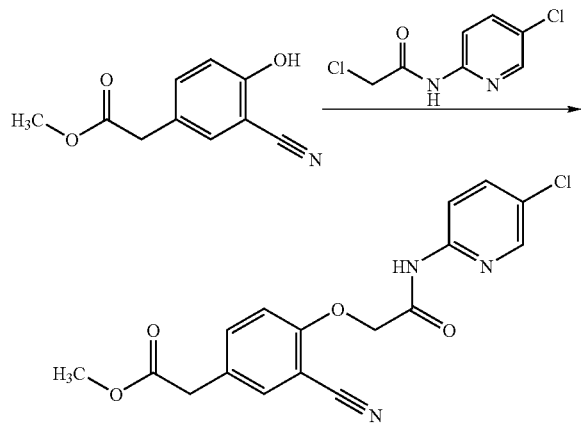

Methyl(3-cyano-4-hydroxyphenyl)acetate (500 mg) obtained in Reference Example 6 is dissolved in acetone (25 ml), thereto are added 2-chloro-N-(5-chloropyridin-2-yl)acetamide (640 mg) obtained in Reference Example 20(1), cesium carbonate (1.20 g) and sodium iodide (510 mg) and the mixture is heated under reflux for 5 hours. After allowing to cool, the insoluble materials are removed by filtration and the insoluble materials are washed with acetone several times. The filtrate and the washing are combined, concentrated under reduced pressure, to the residue is poured water and extracted with ethyl acetate. The organic layer is washed with saturated brine, dried over sodium sulfate and evaporated to remove solvent under reduced pressure. The resulting residue is purified by silica gel column chromatography (eluent: n-hexane/ethyl acetate/chloroform=3/1/1). The resulting residue is suspended in diethyl ether-n-hexane, and then the precipitates are collected by filtration to give the title compound (570 mg).

APCI-MS M/Z:360/362[M+H]$^+$.

Reference Examples 22-23

The corresponding compounds are treated in a similar manner to Reference Example 20 or Reference Example 21 to give the following compounds.

| Ref. Ex. No. | Structure | Physicochemical Properties |
|---|---|---|
| 22 | 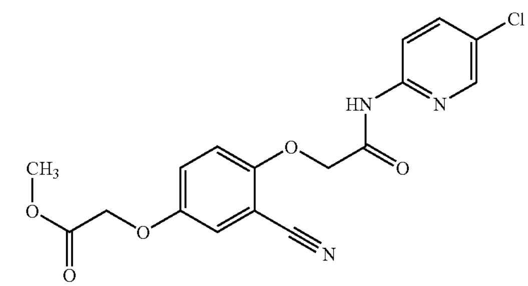 | APCI-MS M/Z: 376/378 [M + H]$^+$ |
| 23 | 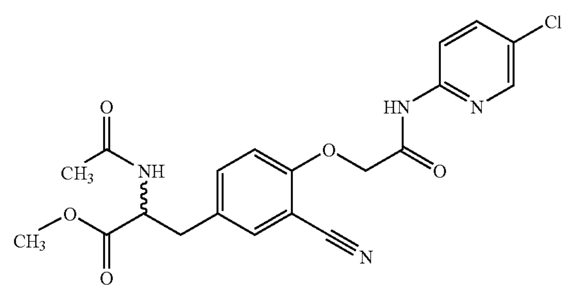 | APCI-MS M/Z: 431/433 [M + H]$^+$ |

Reference Example 24 t-Butyl(2-cyanophenoxy)acetate

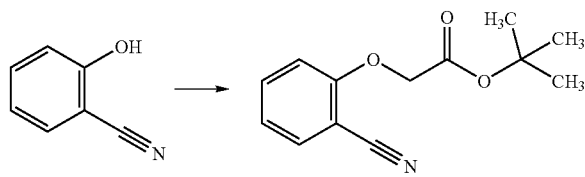

2-Cyanophenol (107.1 g) is dissolved in acetone (1000 ml) and is added t-butyl bromoacetate (200.0 g). Furthermore, potassium carbonate (141.6 g) is added, and then the reaction solution is heated under reflux for 2 hours. After allowing to cool, the insoluble materials are removed by filtration, and then the insoluble materials are washed with acetone several times. The filtrate and the washing are combined, concentrated under reduced pressure and treated with diisopropyl ether azeotropically. The resulting residue is crystallized from n-hexane-diisopropyl ether (5/1) (600 ml), and then stirred under ice-cooling. The precipitates are collected by filtration, washed with cold n-hexane-diisopropyl ether (10/1) (600 ml) several times and dried to give the title compounds (194.5 g).

APCI-MS M/Z:251[M+NH$_4$]$^+$.

Reference Examples 25-36

The corresponding compounds are treated in a similar manner to Reference Example 24 to give the following compounds.

| Ref. Ex. No. | Structure | Physicochemical Properties |
|---|---|---|
| 25 | 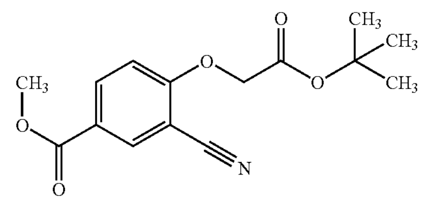 | APCI-MS M/Z: 309 [M + NH$_4$]$^+$ |
| 26 | 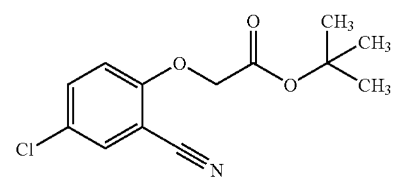 | APCI-MS M/Z: 285/287 [M + NH$_4$]$^+$ |
| 27 | 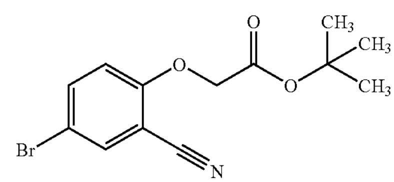 | APCI-MS M/Z: 329/331 [M + NH$_4$]$^+$ |
| 28 | 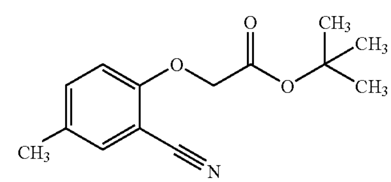 | APCI-MS M/Z: 265 [M + NH$_4$]$^+$ |
| 29 | 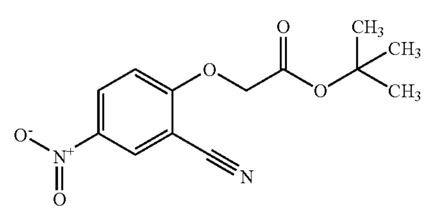 | APCI-MS M/Z: 296 [M + NH$_4$]$^+$ |

-continued

| Ref. Ex. No. | Structure | Physicochemical Properties |
|---|---|---|
| 30 | [structure] | APCI-MS M/Z: 282 [M + NH₄]⁺ |
| 31 | [structure] | APCI-MS M/Z: 281 [M + NH₄]⁺ |
| 32 | [structure] | APCI-MS M/Z: 329/331 [M + NH₄]⁺ |
| 33 | [structure] | APCI-MS M/Z: 265 [M + NH₄]⁺ |
| 34 | [structure] | APCI-MS M/Z: 305 [M + H]⁺ |
| 35 | [structure] | APCI-MS M/Z: 281 [M + NH₄]⁺ |
| 36 | [structure] | APCI-MS M/Z: 265 [M + NH₄]⁺ |

Reference Example 37

(2-Cyanophenoxy)acetic acid

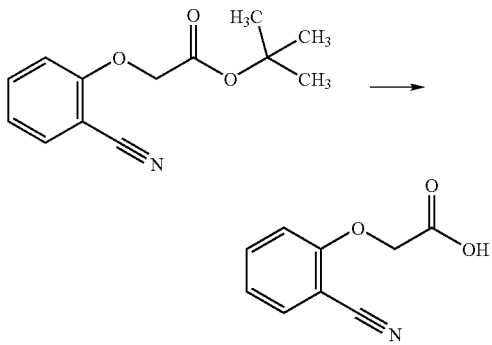

t-Butyl(2-cyanophenoxy)acetate (300.0 g) obtained in Reference Example 24 is dissolved in dichloromethane (400 ml), and thereto is added trifluoroacetic acid (990 ml) and the mixture is stirred at room temperature for 4 hours. The reaction solution is concentrated under reduced pressure, the resulting residue is suspended in diethyl ether (100 ml) and diisopropyl ether (500 ml) is poured thereto. The precipitates are collected by filtration, washed with diisopropyl ether several times and dried to give the title compound (198.4 g).
ESI-MS M/Z:176[M−H]$^-$.

Reference Examples 38-49

The corresponding compounds are treated in a similar manner to Reference Example 37 to give the following compounds.

| Ref. Ex. No. | Structure | Physico-chemical Properties |
|---|---|---|
| 38 | methyl 4-(carboxymethoxy)-3-cyanobenzoate | ESI-MS M/Z: 234 [M − H]$^-$ |
| 39 | (4-chloro-2-cyanophenoxy)acetic acid | ESI-MS M/Z: 210/212 [M − H]$^-$ |
| 40 | (4-bromo-2-cyanophenoxy)acetic acid | ESI-MS M/Z: 254/256 [M − H]$^-$ |
| 41 | (2-cyano-4-methylphenoxy)acetic acid | ESI-MS M/Z: 190 [M − H]$^-$ |
| 42 | (2-cyano-4-nitrophenoxy)acetic acid | ESI-MS M/Z: 221 [M − H]$^-$ |
| 43 | (2-cyano-4-methoxyphenoxy)acetic acid | ESI-MS M/Z: 206 [M − H]$^-$ |
| 44 | (2-cyano-5-methoxyphenoxy)acetic acid | ESI-MS M/Z: 206 [M − H]$^-$ |
| 45 | (5-bromo-2-cyanophenoxy)acetic acid | ESI-MS M/Z: 254/256 [M − H]$^-$ |
| 46 | (2-cyano-5-methylphenoxy)acetic acid | ESI-MS M/Z: 190 [M − H]$^-$ |
| 47 | (2-cyano-5-(diethylamino)phenoxy)acetic acid | ESI-MS M/Z: 247 [M − H]$^-$ |

-continued

| Ref. Ex. No. | Structure | Physico-chemical Properties |
|---|---|---|
| 48 | ![structure] | ESI-MS M/Z: 206 [M − H]⁻ |
| 49 | ![structure] | ESI-MS M/Z: 190 [M − H]⁻ |

Reference Example 50

[4-(N-Benzyloxycarbonyl-N-methylamino)-2-cyanophenoxy]acetic acid

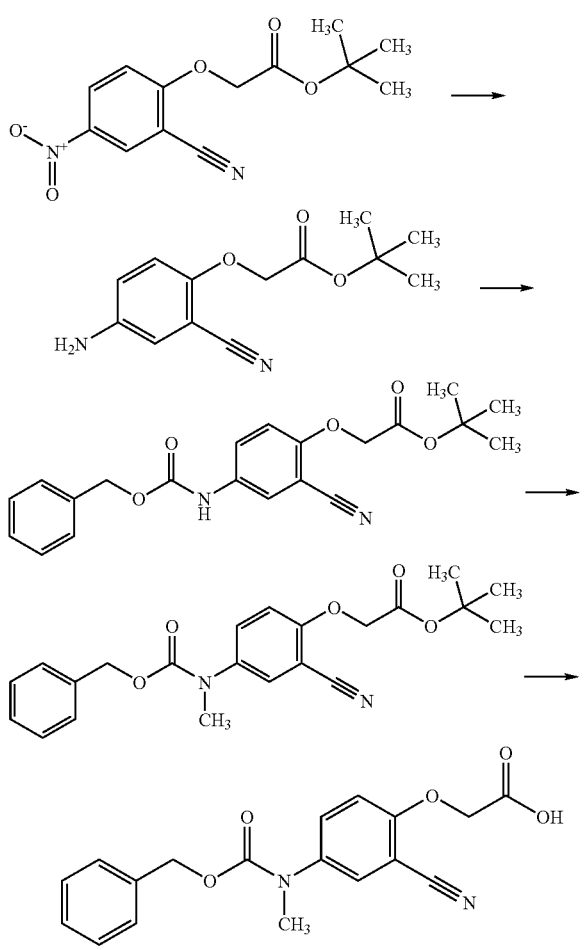

(1) t-Butyl 2-(4-nitro-2-cyanophenoxy)acetate (500 mg) obtained in Reference Example 29 is dissolved in tetrahydrofuran (20 ml), thereto is added 10% palladium-carbon (100 mg) and the mixture is stirred for 2 hours under atmospheric hydrogen pressure. The insolubles are removed by filtration, and then the filtrate is concentrated under reduced pressure to give t-butyl (4-amino-2-cyanophenoxy)acetate (440 mg).
APCI-MS M/Z:249[M+H]⁺.

(2) t-Butyl(4-amino-2-cyanophenoxy)acetate (430 mg) obtained in Reference Example 50(1) is dissolved in tetrahydrofuran (10 ml), is added saturated sodium hydrogen carbonate solution (10 ml), and then is added benzyl chloroformate (355 mg) under ice-cooling. Under ice-cooling, the reaction solution is stirred for 1 hour and extracted with ethyl acetate. The organic layer is washed with saturated brine, dried over sodium sulfate, evaporated to remove the solvent under reduced pressure. The resulting residue is purified by silica gel column chromatography (eluent: n-hexane/ethyl acetate=9/1 followed by 3/1) to give t-butyl(4-benzyloxycarbonylamino-2-cyanophenoxy)acetate (540 mg).
APCI-MS M/Z:383[M+H]⁺.

(3) t-Butyl(4-benzyloxycarbonylamino-2-cyanophenoxy) acetate (100 mg) obtained in Reference Example 50(2) is dissolved in N,N-dimethylformamide (3 ml) and thereto is added 60% oleaginous sodium hydride (12.5 mg). After the mixture is stirred for 20 minutes at room temperature, methyl iodide (24.4 μl) is added thereto dropwise and the mixture is further stirred for one hour. To the reaction solution is poured saturated aqueous ammonium chloride solution and extracted with ethyl acetate. The organic layer is washed successively with water and saturated brine, dried over sodium sulfate and evaporated to remove the solvent. The resulting residue is purified by silica gel column chromatography (eluent: n-hexane/ethyl acetate=9/1 followed by 3/1) to give t-butyl[4-(N-benzyloxycarbonyl-N-methylamino)-2-cyanophenoxy]acetate (91 mg).
APCI-MS M/Z:414[M+NH₄]⁺.

(4) t-Butyl[4-(N-benzyloxycarbonyl-N-methylamino)-2-cyanophenoxy]acetate (2.42 g) obtained in Reference Example 50(3) is treated in a similar manner to Reference Example 37 to give the title compound (2.06 g).
ESI-MS M/Z:339[M−H]⁻.

Reference Example 51

(2-Cyanophenoxy)-N-(5-chloropyridin-2-yl)acetamide (2-Cyanophenoxy)acetic acid (48.63 g) obtained in Reference Example 37 is dissolved in dichloromethane (1000 ml), thereto are added oxalyl chloride (26.34 ml) and N,N-dimethylformamide (10 drops) and the mixture is stirred at room temperature for 3.5 hours. The reaction solution is cooled on ice-bath, thereto is added 2-amino-5-chloropyridine (32.08 g), and then pyridine (60.54 ml) is added. After 5 minutes, the reaction solution is warmed to room temperature and stirred overnight. To the reaction solution is added ice-water, and the solution is adjusted to about pH 4 with 10% hydrochloric acid, and then is extracted with chloroform. The organic layer is washed successively with water, saturated aqueous sodium hydrogen carbonate and saturated brine, dried over sodium sulfate and evaporated to remove the solvent. The resulting residue is suspended in chloroform-ethyl acetate and collected by filtration to give (2-cyanophenoxy)-N-(5-chloropyridin-2-yl)acetamide (51.58 g). Furthermore, the filtrate is concentrated under reduced pressure, and then purified by silica gel column chromatography (eluent: chloroform) to give the title compound (11.50 g).

APCI-MS M/Z:288/290[M+H]$^+$.

Reference Example 52-66

The corresponding compounds are treated in a similar manner to Reference Example 51 to give the following compounds.

| Ref. Ex. No. | Structure | Physicochemical Properties |
|---|---|---|
| 52 | 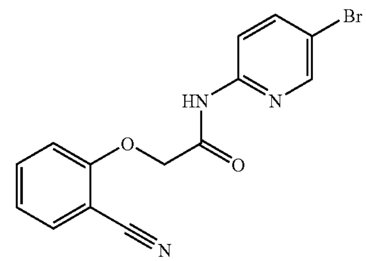 | APCI-MS M/Z: 332/334 [M + H]$^+$ |
| 53 | 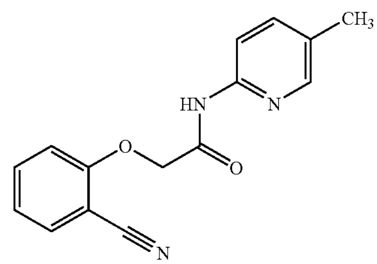 | APCI-MS M/Z: 268 [M + H]$^+$ |
| 54 | 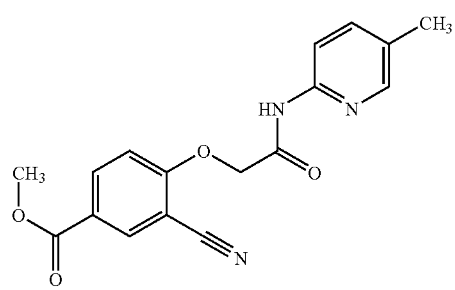 | APCI-MS M/Z: 326 [M + H]$^+$ |
| 55 | 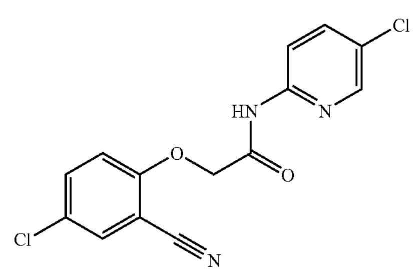 | APCI-MS M/Z: 332/334 [M + H]$^+$ |

-continued

| Ref. Ex. No. | Structure | Physicochemical Properties |
|---|---|---|
| 56 | 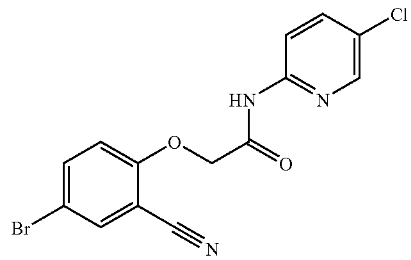 | APCI-MS M/Z: 366/368 [M + H]⁺ |
| 57 | 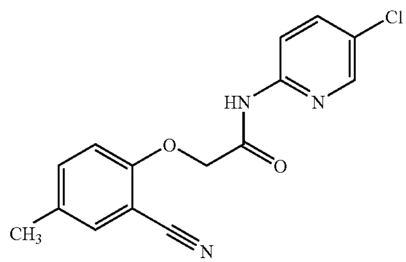 | APCI-MS M/Z: 302/304 [M + H]⁺ |
| 58 | 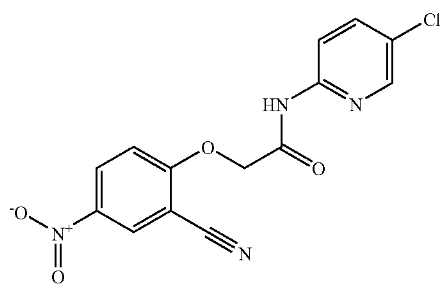 | APCI-MS M/Z: 329/331 [M + H]⁺ |
| 59 | 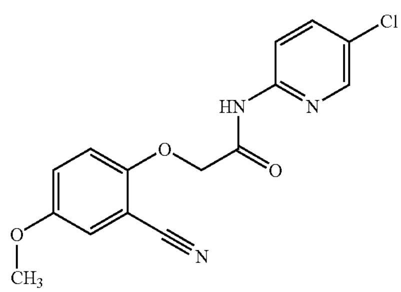 | APCI-MS M/Z: 318/320 [M + H]⁺ |
| 60 | 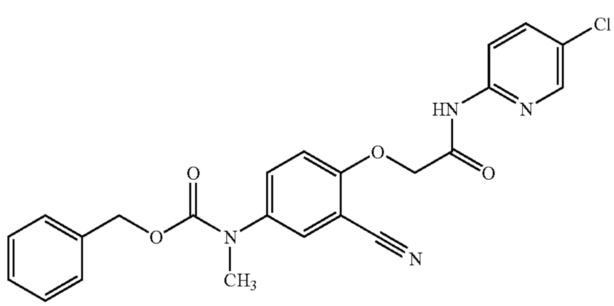 | APCI-MS M/Z: 451/453 [M + H]⁺ |

-continued
| Ref. Ex. No. | Structure | Physicochemical Properties |
|---|---|---|
| 61 | 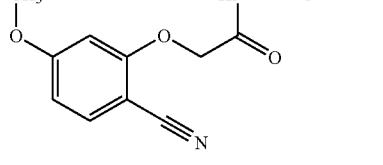 | APCI-MS M/Z: 318/320 [M + H]+ |
| 62 | 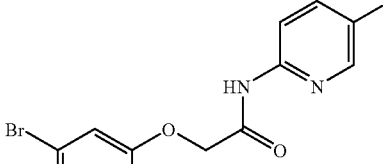 | APCI-MS M/Z: 366/368 [M + H]+ |
| 63 | 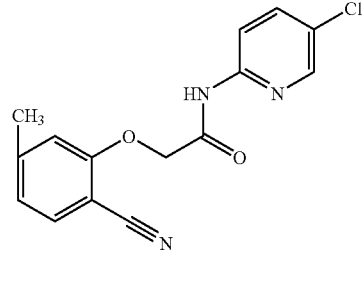 | APCI-MS M/Z: 302/304 [M + H]+ |
| 64 | 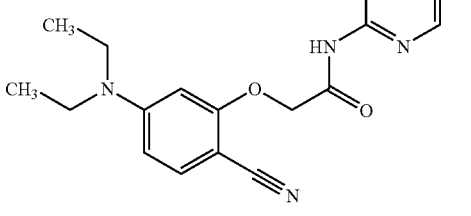 | APCI-MS M/Z: 359/361 [M + H]+ |
| 65 | 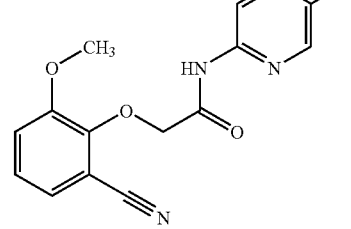 | APCI-MS M/Z: 318/320 [M + H]+ |

| Ref. Ex. No. | Structure | Physicochemical Properties |
|---|---|---|
| 66 | 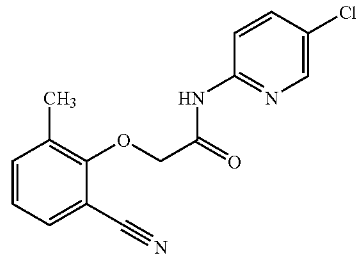 | APCI-MS M/Z: 302/304 [M + H]⁺ |

Reference Example 67

(2-Cyanophenoxy)-N-(4-chlorophenyl)-acetamide

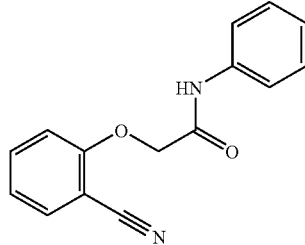

(2-Cyanophenoxy)acetic acid (30.00 g) obtained in Reference Example 37 is dissolved in N,N-dimethylformamide (300 ml), thereto are added 4-chloroaniline (25.9 g), 4-dimethylaminopyridine (22.7 g) and 1-ethyl-3-(3-dimethylaminopropyl)carbodiimide hydrochloride (35.6 g) successively and the mixture is stirred for 3 hours at room temperature. The reaction solution is concentrated under reduced pressure and the resulting residue is diluted with ethyl acetate-tetrahydrofuran, washed successively with water, 5% hydrochloric acid, water and saturated brine, dried over sodium sulfate and evaporated to remove the solvent. The resulting residue is suspended in diisopropyl ether, and then the precipitates are collected by filtration to give the title compound (44.00 g).

APCI-MS M/Z:287/289[M+H]⁺.

Reference Examples 68-71

The corresponding compounds are treated in a similar manner to Reference Example 67 to give the following compounds.

| Ref. Ex. No. | Structure | Physicochemical Properties |
|---|---|---|
| 68 | | APCI-MS M/Z: 331/333 [M + H]⁺ |
| 69 | 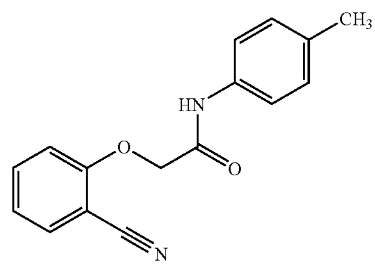 | APCI-MS M/Z: 267 [M + H]⁺ |
| 70 | 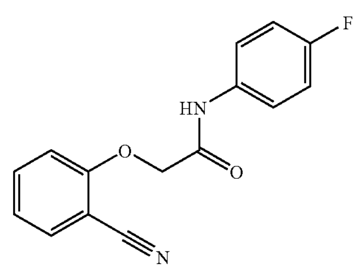 | APCI-MS M/Z: 271 [M + H]⁺ |
| 71 | 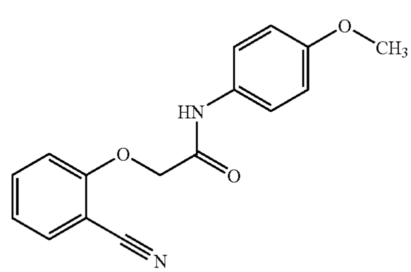 | APCI-MS M/Z: 283 [M + H]⁺ |

Reference Example 72

3-Amino-5-methoxycarbonyl-N-(5-chloropyridin-2-yl)benzofuran-2-carboxamide

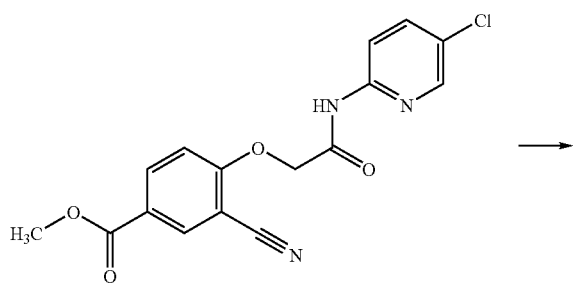

↓

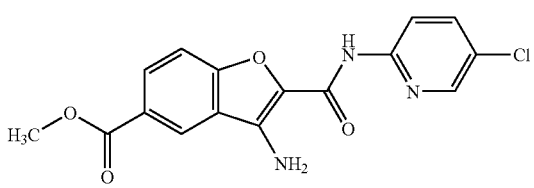

2-(4-Methoxycarbonyl-2-cyanophenoxy)-N-(5-chloropyridin-2-yl)acetamide (1.73 g) obtained in Reference Example 20 is dissolved in N,N-dimethylacetamide (15 ml), thereto is added sodium carbonate (160 mg) and the mixture is stirred at 100° C. for 2 hours. After allowing to cool, to the reaction solution is poured ice-water, and the resulting precipitates are collected by filtration, washed successively with water, tetrahydrofuran and diethyl ether and dried to give the title compound (1.20 g).

APCI-MS M/Z:346/348[M+H]$^+$.

Reference Example 73

3-Amino-5-methoxycarbonylmethyl-N-(5-chloropyridin-2-yl)benzofuran-2-carboxamide

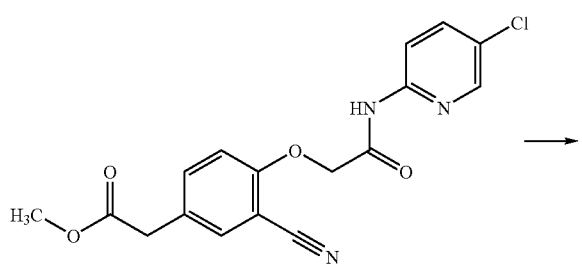

↓

-continued

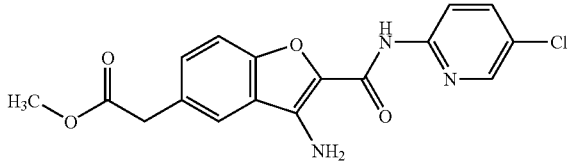

2-[2-Cyano-4-(methoxycarbonylmethyl)phenoxy]-N-(5-chloropyridin-2-yl)acetamide (500 mg) obtained in Reference Example 21 is dissolved in N,N-dimethylacetamide (15 ml), thereto is added sodium carbonate (74 mg) and the mixture is stirred at 100° C. for 16 hours. After allowing to cool, to the reaction solution is poured ice-water and extracted with ethyl acetate. The organic layer is washed successively with water and saturated brine, dried over sodium sulfate and evaporated to remove the solvent. The resulting residue is purified by silica gel column chromatography (eluent: n-hexane/ethyl acetate/chloroform=3/1/1), suspended in diethyl ether-n-hexane, and then the precipitates are collected by filtration to give title compound (180 mg).

APCI-MS M/Z:360/362[M+H]$^+$.

Reference Example 74

3-Amino-N-(5-chloropyridin-2-yl)benzofuran-2-carboxamide

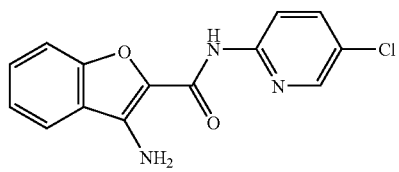

(2-Cyanophenoxy)-N-(5-chloropyridin-2-yl)acetamide (150.00 g) obtained in Reference Example 51 is dissolved in N,N-dimethylacetamide (1500 ml), thereto is added sodium carbonate (60.8 g) and the mixture is stirred at 70° C. for 7 hours. After allowing to cool, the reaction solution is poured to ice-water, and the resulting precipitates are collected by filtration and washed with water several times. The precipitates are dissolved in ethyl acetate, washed with water and saturated brine, dried over sodium sulfate and the organic layer is treated with activated charcoal. The insoluble materials are filtered, and then the filtrate is concentrated under reduced pressure and the resulting residue is suspended in diethyl ether-ethyl acetate. The precipitates are collected by filtration, washed with diethyl ether, and dried to give the title compound (119.33 g).

APCI-MS M/Z: 288/290[M+H]$^+$.

Reference Examples 75-96

The corresponding compounds are treated in a similar manner to Reference Example 72, 73 or 74 to give the following compounds.

| Ref. Ex. No. | Structure | Physicochemical Properties |
|---|---|---|
| 75 | benzofuran-2-carboxamide, 3-amino, N-(5-bromopyridin-2-yl) | APCI-MS M/Z: 332/334 [M + H]$^+$ |
| 76 | benzofuran-2-carboxamide, 3-amino, N-(5-methylpyridin-2-yl) | APCI-MS M/Z: 268 [M + H]$^+$ |
| 77 | benzofuran-2-carboxamide, 3-amino, N-(4-chlorophenyl) | APCI-MS M/Z: 287/289 [M + H]$^+$ |
| 78 | benzofuran-2-carboxamide, 3-amino, N-(4-bromophenyl) | APCI-MS M/Z: 331/333 [M + H]$^+$ |
| 79 | benzofuran-2-carboxamide, 3-amino, N-(4-methylphenyl) | APCI-MS M/Z: 267 [M + H]$^+$ |
| 80 | benzofuran-2-carboxamide, 3-amino, N-(4-fluorophenyl) | APCI-MS M/Z: 271 [M + H]$^+$ |
| 81 | benzofuran-2-carboxamide, 3-amino, N-(4-methoxyphenyl) | APCI-MS M/Z: 283 [M + H]$^+$ |
| 82 | methyl 3-amino-2-[(5-methylpyridin-2-yl)carbamoyl]benzofuran-5-carboxylate | APCI-MS M/Z: 326 [M + H]$^+$ |

-continued
| Ref. Ex. No. | Structure | Physicochemical Properties |
|---|---|---|
| 83 | 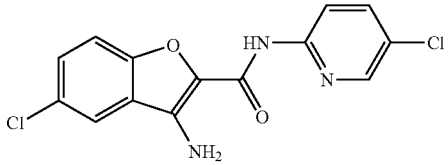 | APCI-MS M/Z: 322/324 [M + H]+ |
| 84 | 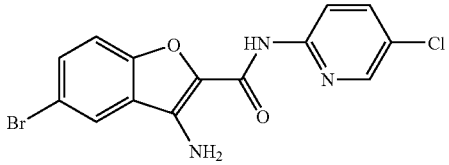 | APCI-MS M/Z: 366/368 [M + H]+ |
| 85 | 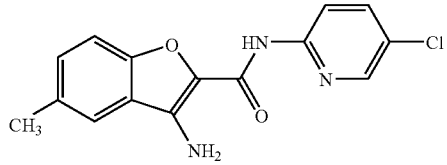 | APCI-MS M/Z: 302/304 [M + H]+ |
| 86 | 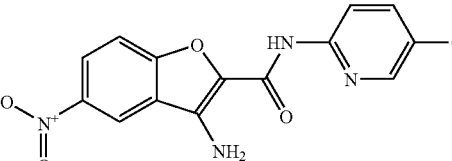 | APCI-MS M/Z: 333/335 [M + H]+ |
| 87 | 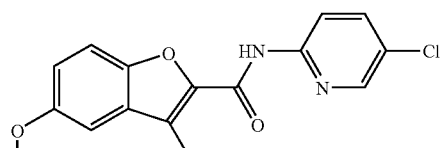 | APCI-MS M/Z: 318/320 [M + H]+ |
| 88 | 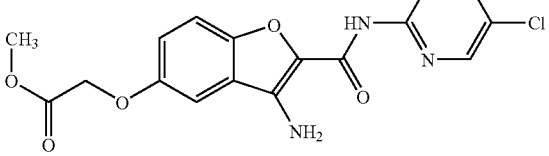 | APCI-MS M/Z: 376/378 [M + H]+ |
| 89 | 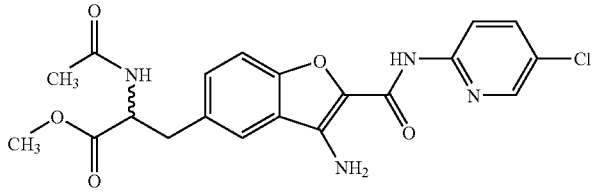 | APCI-MS M/Z: 431/433 [M + H]+ |
| 90 | 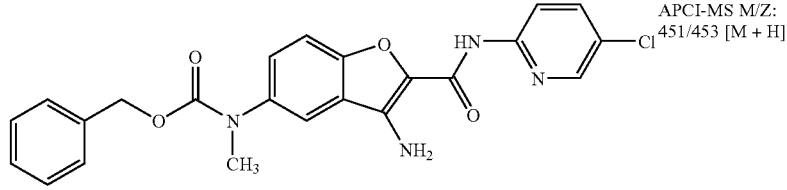 | APCI-MS M/Z: 451/453 [M + H]+ |

-continued

| Ref. Ex. No. | Structure | Physicochemical Properties |
|---|---|---|
| 91 | 6-methoxy-benzofuran with 3-NH₂, 2-C(O)NH-(5-chloropyridin-2-yl) | APCI-MS M/Z: 318/320 [M + H]⁺ |
| 92 | 6-bromo-benzofuran with 3-NH₂, 2-C(O)NH-(5-chloropyridin-2-yl) | APCI-MS M/Z: 366/368 [M + H]⁺ |
| 93 | 6-methyl-benzofuran with 3-NH₂, 2-C(O)NH-(5-chloropyridin-2-yl) | APCI-MS M/Z: 302/304 [M + H]⁺ |
| 94 | 6-(diethylamino)-benzofuran with 3-NH₂, 2-C(O)NH-(5-chloropyridin-2-yl) | APCI-MS M/Z: 359/361 [M + H]⁺ |
| 95 | 7-methoxy-benzofuran with 3-NH₂, 2-C(O)NH-(5-chloropyridin-2-yl) | APCI-MS M/Z: 318/320 [M + H]⁺ |
| 96 | 7-methyl-benzofuran with 3-NH₂, 2-C(O)NH-(5-chloropyridin-2-yl) | APCI-MS M/Z: 302/304 [M + H]⁺ |

Reference Example 97

(2-Cyano-4-hydroxyphenoxy)-N-(5-chloropyridin-2-yl)acetamide

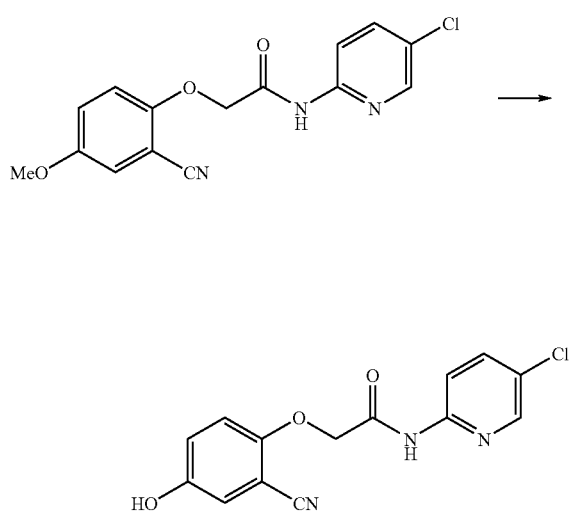

To the suspension of (2-cyano-4-methoxyphenoxy)-N-(5-chloropyridin-2-yl)acetamide (40.0 g) obtained in Reference Example 59 in dichloromethane (2000 ml), boron tribromide (173 g) is added at −58° C. dropwise over 40 minutes. The reaction solution is stirred for 26 hours with keeping the internal temperature between −20° C. and 0° C., and then poured to an ice-water. The precipitated solid is collected by filtration, washed with water, and then dried under reduced pressure. A part of the resulting solid (37.2 g), i.e. 24.3 g thereof is purified by silica gel column chromatography (eluent: chloroform/methanol=50/1-10/1) to give the title compound (17.0 g).

APCI-MS M/Z:304/306[M+H]$^+$.

Reference Example 98

3-Amino-5-hydroxy-N-(5-chloropyridin-2-yl)benzofuran-2-carboxamide

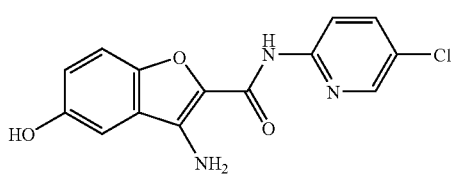

(2-Cyano-4-hydroxyphenoxy)-N-(5-chloropyridin-2-yl)acetamide (321 mg) obtained in Reference Example 97 is treated in a similar manner to Reference Example 73 to give the title compound (274 mg).

APCI-MS M/Z:304/306[M+H]$^+$.

Reference Example 99

(4-t-Buthoxycarbonylmethoxy-2-cyanophenoxy)-N-(5-chloropyridin-2-yl)acetamide

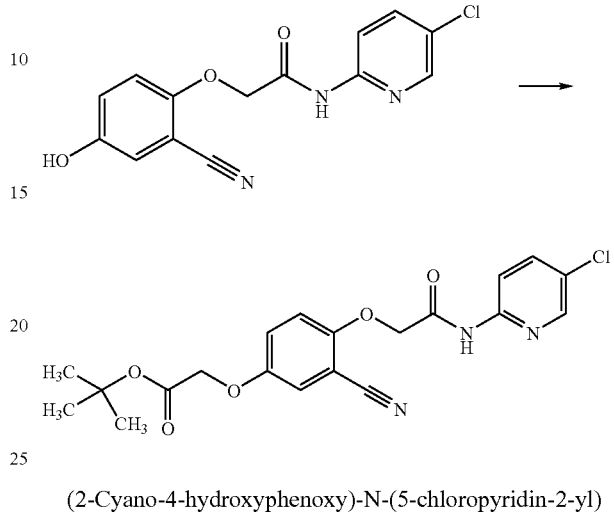

(2-Cyano-4-hydroxyphenoxy)-N-(5-chloropyridin-2-yl)acetamide (5.75 g) obtained in Reference Example 97 is dissolved in acetone (160 ml) and to the solution, are added cesium carbonate (8.08 g), t-butyl bromoacetate (4.58 g) and sodium iodide (3.64 g). The reaction solution is heated under reflux for 8 hour, thereto are added additional cesium carbonate (1.89 g), t-butyl bromoacetate (840 µl) and sodium iodide (875 mg) and the mixture is heated under reflux for additional 14 hours. After allowing to cool, the reaction solution is poured to an ice-water, adjusted pH 1-2 with 10% hydrochloric acid and extracted with ethyl acetate. The organic layer is dried over sodium sulfate and evaporated to remove the solvent. The resulting residue is purified by silica gel column chromatography (eluent: hexane/ethyl acetate=3/1, 2/1 followed by 1/1) and furthermore, purified by NH-silica gel column chromatography (eluent: hexane/ethyl acetate=2/1 followed by 1/1) to give the title compound (4.02 g).

APCI-MS M/Z:418/420[M+H]$^+$.

Reference Example 100

3-Amino-5-t-butoxycarbonylmethoxy-N-(5-chloropyridin-2-yl)benzofuran-2-carboxamide

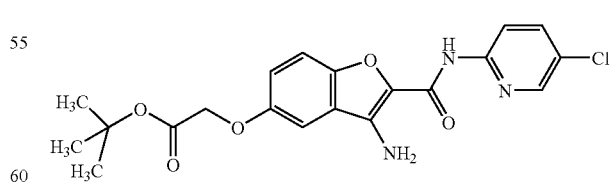

(4-t-Buthoxycarbonylmethoxy-2-cyanophenoxy)-N-(5-chloropyridin-2-yl)acetamide (8.18 g) obtained in Reference Example 99 is treated in a similar manner to Reference Example 73 to give the title compound (5.72 g).

APCI-MS M/Z:418/420[M+H]$^+$.

Reference Example 101

3-Amino-5-(2-methoxyethoxy)-N-(5-chloropyridin-2-yl)benzofuran-2-carboxamide

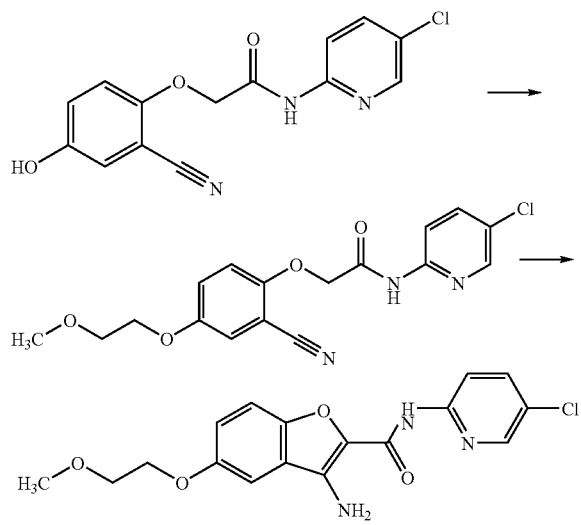

(1) (2-Cyano-4-hydroxyphenoxy)-N-(5-chloropyridin-2-yl)acetamide (100 mg) obtained in Reference Example 97 is dissolved in tetrahydrofuran, and thereto are added 2-methoxyethanol (9.30 ml) and triphenylphosphine (31.0 g), and further diethyl azodicarboxylate (22.2 ml) is added dropwise under ice-cooling. The reaction solution is warmed to room temperature and stirred for 17 hours and concentrated under reduced pressure. To the resulting residue is poured diisopropyl ether, and the insoluble materials are removed by filtration, and then the filtrate is concentrated under reduced pressure. The resulting residue is purified by silica gel column chromatography (eluent: chloroform/ethyl acetate=10/1) to give [4-(2-methoxyethoxy)-2-cyanophenoxy]-N-(5-chloropyridin-2-yl)acetamide (71.48 g) as a crude material, which is used for next step without further purification.

APCI-MS M/Z:362/364[M+H]$^+$.

(2) The crude material containing [4-(2-methoxyethoxy)-2-cyanophenoxy]-N-(5-chloropyridin-2-yl)acetamide (71.48 g) obtained in Reference Example 101(1) is treated in a similar manner to Reference Example 72 to give the title compound (24.40 g).

APCI-MS M/Z:362/364[M+H]$^+$.

Reference Examples 102-106

(2-Cyano-4-hydroxyphenoxy)-N-(5-chloropyridin-2-yl)acetamide obtained in Reference Example 97 and the corresponding alcohol are treated in a similar manner to Reference Example 101 to give the following compounds.

| Ref. Ex. No. | Structure | Physicochemical Properties |
|---|---|---|
| 102 | 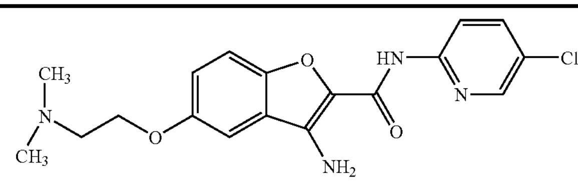 | APCI-MS M/Z: 375/377 [M + H]$^+$ |
| 103 | 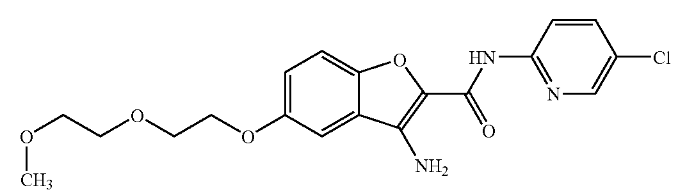 | APCI-MS M/Z: 406/408 [M + H]$^+$ |
| 104 | 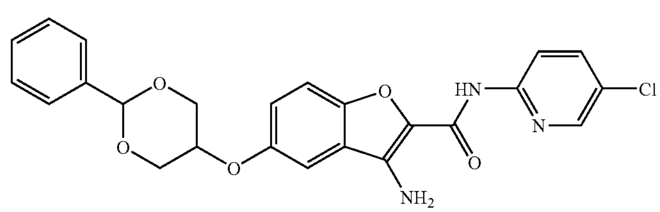 | APCI-MS M/Z: 466/468 [M + H]$^+$ |
| 105 | 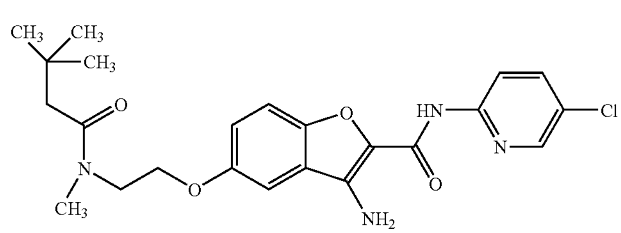 | APCI-MS M/Z: 461/463 [M + H]$^+$ |

| Ref. Ex. No. | Structure | Physicochemical Properties |
|---|---|---|
| 106 | 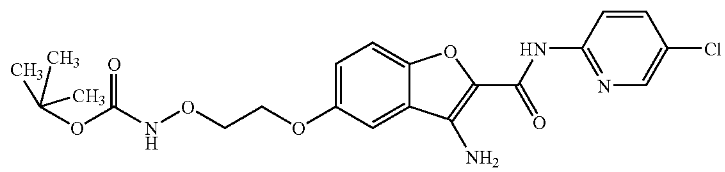 | APCI-MS M/Z: 463/465 [M + H]⁺ |

Reference Example 107

(2,4-Dicyanophenoxy)-N-(5-chloropyridin-2-yl)acetamide

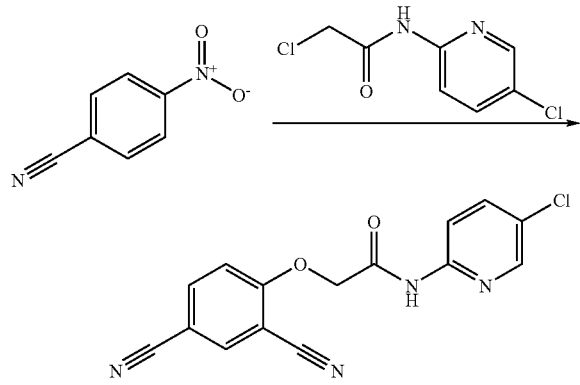

4-Nitrobenzonitrile (3.02 g) and potassium cyanide (2.02 g) are dissolved in dimethyl sulfoxide (100 ml) and stirred at 100° C. for an hour. The reaction solution is allowed to cool until room temperature and, thereto are added potassium carbonate (1.49 g), 2-chloro-N-(5-chloropyridin-2-yl)acetamide (10.42 g) obtained in Reference Example 20(1) and sodium iodide (8.76 g), and the mixture is stirred at 60° C. for 4.5 hours. The reaction solution is poured to water, and the precipitated solids are collected by filtration, washed with water and dried in air. The resulting solid is dissolved in ethyl acetate, dried over sodium sulfate, evaporated to remove the solvent under reduced pressure. The resulting residue is purified by silica gel column chromatography (eluent: hexane/ethyl acetate=5/1 to 1/1), and then the resulting residue is suspended in ethyl acetate-diisopropyl ether. The precipitates are collected by filtration and dried to give the title compound (2.81 g).

APCI-MS M/Z:313/315[M+H]⁺.

Reference Example 108

3-Amino-5-cyano-N-(5-chloropyridin-2-yl)benzofuran-2-carboxamide

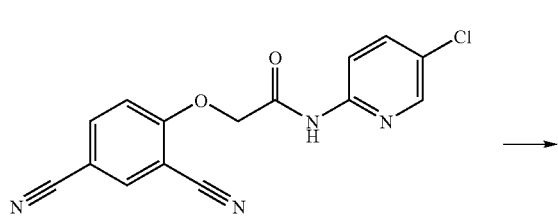

(2,4-Dicyanophenoxy)-N-(5-chloropyridin-2-yl)acetamide (1.02 g) obtained in Reference Example 107 is treated in a similar manner to Reference Example 73 to give the title compound (0.96 g).

APCI-MS M/Z:313/315[M+H]⁺.

Reference Example 109

(3-Chloro-2-cyanophenoxy)-N-(5-chloropyridin-2-yl)acetamide

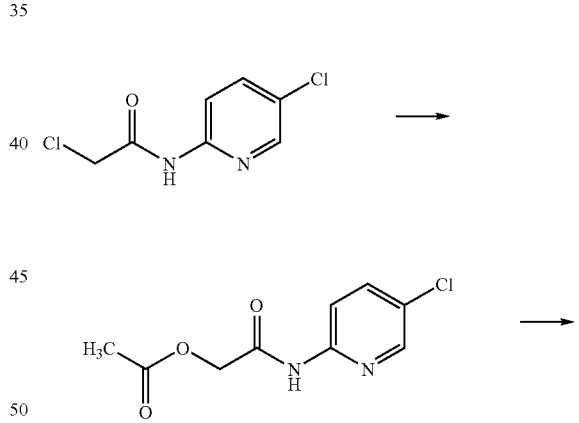

-continued

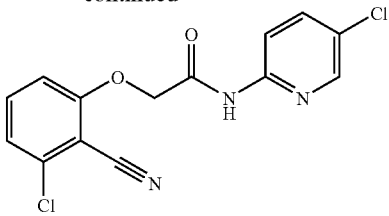

(1) 2-Cloro-N-(5-chloropyridin-2-yl)acetamide (30.68 g) obtained in Reference Example 20(1) is dissolved in N,N-dimethylformamide (500 ml), thereto is added sodium acetate (24.55 g) and the mixture is stirred at 60° C. for 5 hours. The reaction solution is diluted with ethyl acetate, washed successively with water and saturated brine. The solution is dried over magnesium sulfate, treated with activated charcoal, and the filtrate is concentrated under reduced pressure. The resulting residue is suspended in n-hexane and the resulting crystals are collected by filtration, washed with n-hexane, and dried to give N-(5-chloropyridin-2-yl)-2-acetoxyacetamide (30.58 g).

APCI-MS M/Z:229/231[M+H]$^+$.

(2) 2-Acetoxy-N-(5-chloropyridin-2-yl)acetamide (30.36 g) obtained in Reference Example 109(1) is suspended in methanol (1200 ml) and thereto is added potassium carbonate (22.0 g) under ice-cooling. The reaction solution is warmed to room temperature, stirred for 0.5 hours and concentrated under reduced pressure. To the resulting residue are poured ethyl acetate (1500 ml) and ice-water (1000 ml), and then the mixture is extracted with ethyl acetate. The organic layer is washed with saturated brine, dried over sodium sulfate and evaporated to remove the solvent under reduced pressure. The resulting residue is suspended in a small amount of ethyl acetate, thereto is added diisopropyl ether and the precipitated crystals are collected by filtration, washed with diisopropyl ether and dried to give 2-hydroxy-N-(5-chloropyridin-2-yl)acetamide (22.85 g).

APCI-MS M/Z:187/189[M+H]$^+$.

(3) 2-Chloro-6-nitrobenzonitrile (187 mg) and 2-hydroxy-N-(5-chloropyridin-2-yl)acetamide (183 mg) obtained in Reference Example 109(2) are dissolved in N,N-dimethylformamide (2 ml) and thereto is added 60% oleaginous sodium hydride (80 mg) under ice-cooling. After stirring for 6 hours with cooling, to the reaction solution is poured saturated aqueous ammonium chloride solution and extracted with ethyl acetate. The organic layer is washed with water and saturated brine, dried over sodium sulfate and evaporated to remove the solvent under reduced pressure. The resulting residue is suspended in n-hexane-diisopropyl ether, the resulting product is collected by filtration and dried to give the title compound (286 mg).

APCI-MS M/Z:322/324[M+H]$^+$.

Reference Example 110

3-Amino-4-chloro-N-(5-chloropyridin-2-yl)benzofuran-2-carboxamide

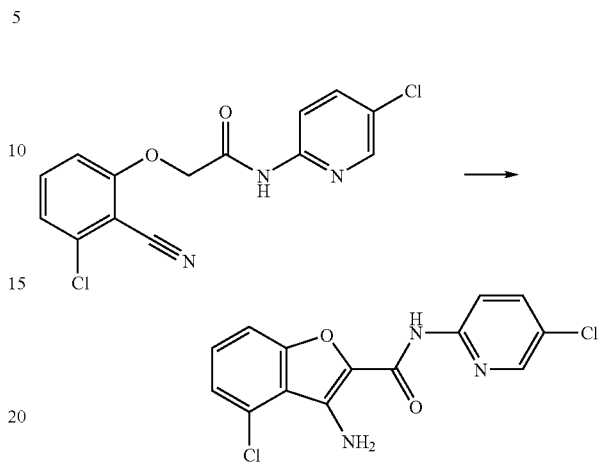

(3-Cloro-2-cyanophenoxy)-N-(5-chloropyridin-2-yl)acetamide (274 mg) obtained in Reference Example 109 is dissolved in N,N-dimethylacetamide (10 ml), thereto is added cesium carbonate (333 mg) and the mixture is stirred at 100° C. for 8 hours. After allowing to cool, to the reaction solution is added ice-water, the precipitates are collected by filtration and washed with water. The precipitates are dissolved in hot ethyl acetate, washed with saturated brine and dried over sodium sulfate. To the organic layer are added activated charcoal and NH-silica gel (5 g) and the mixture is filtered to remove the insoluble materials. The filtrate is concentrated under reduced pressure, the resulting residue is suspended in ethyl acetate-diethyl ether and the resulting product is collected by filtration to give the title compound (112 mg).

APCI-MS M/Z:322/324[M+H]$^+$.

Reference Example 111

3-Amino-4-methoxy-N-(5-chloropyridin-2-yl)benzofuran-2-carboxamide

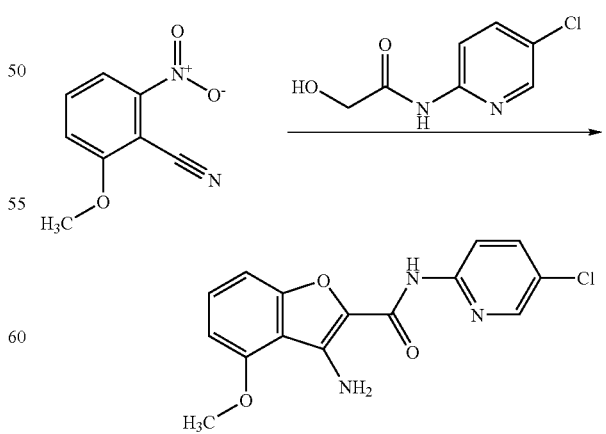

2-Methoxy-6-nitrobenzonitrile (589 mg) and 2-hydroxy-N-(5-chloropyridin-2-yl)acetamide (560 mg) obtained in Reference Example 109(2) are dissolved in N,N-dimethylacetamide (10 ml) and thereto is added potassium carbonate (810 mg). The reaction solution is stirred at 60° C. overnight, thereto is added additional potassium carbonate (810 mg) and the mixture is stirred at 100° C. for 4 hours. After allowing to cool, to the reaction solution is poured ice-water and extracted with ethyl acetate. The organic layer is washed with water and saturated brine, dried over sodium sulfate and treated with activated charcoal. The insoluble materials are removed by filtration, washed with chloroform-methanol, and the filtrate and the washing are combined and concentrated under reduced pressure. The resulting residue is suspended in diisopropyl ether, and then the resulting product is collected by filtration to give the title compound (104 mg).

APCI-MS M/Z:317/319[M+H]$^+$.

Reference Example 112

Methyl trans-4-(t-butoxycarbonylamino)cyclohexanecarboxylate

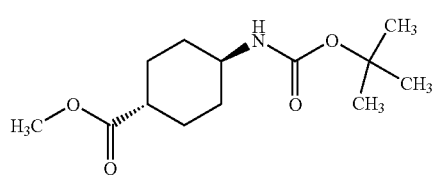

(1) Thionyl chloride (254 ml) is added dropwise to methanol (1500 ml) under cooling to −30° C. over a period of about one hour. After the addition, the reaction mixture is stirred at room temperature for 0.5 hours, thereto is added trans-cyclohexane-1,4-dicarboxylic acid (500.0 g) and the mixture is stirred at room temperature for 17 hours. The reaction solution is concentrated under reduced pressure, the residue is diluted with chloroform, and then washed with saturated aqueous sodium hydrogen carbonate solution and saturated brine. The organic layer is dried over sodium sulfate and evaporated to remove the solvent under reduced pressure. The resulting residue is crystallized from n-hexane, the resulting product is collected by filtration, dried to give dimethyl trans-cyclohexane-1,4-dicarboxylate (545.0 g).

APCI-MS M/Z:201[M+H]$^+$.

(2) Dimethyl trans-cyclohexane-1,4-dicarboxylate (150.0 g) obtained in Reference Example 112(1) is dissolved in tetrahydrofuran (1500 ml) and to the solution is added dropwise a mixture of 28% sodium methoxide-in methanol (149 g) and water (13.2 g) under ice-cooling. The reaction solution warmed to room temperature, stirred for 3.5 hours, thereto is added n-hexane (1500 ml) and the mixture is filtrated to collect the precipitates. The resulting solid is added to a mixture of conc. hydrochloric acid (50 ml), water (450 ml) and chloroform (1000 ml) under ice-cooling, and stirred at room temperature for 20 minutes. The chloroform layer is separated and the aqueous layer is extracted with chloroform. The organic layers are combined, dried over sodium sulfate and evaporated to remove the solvent under reduced pressure. The resulting residue is crystallized from n-hexane, the resulting product is collected by filtration and dried to give monomethyl trans-cyclohexane-1,4-dicarboxylate (106.0 g).

ESI-MS M/Z:185[M−H]$^-$.

(3) Monomethyl trans-cyclohexane-1,4-dicarboxylate (100.0 g) obtained in Reference Example 112(2) is dissolved in t-buthanol (1000 ml), thereto are added diphenylphosphoryl azide (155 g) and triethylamine (78.6 ml). The mixture is heated at about 60° C. for one hour and further heated under reflux for additional 17 hours. After allowing to cool, to the reaction solution is added ice-water, and the mixture is extracted with ethyl acetate. The organic layer is washed with saturated aqueous sodium hydrogen carbonate solution and saturated brine, dried over sodium sulfate and evaporated to remove the solvent under reduced pressure. The resulting residue is dissolved in methanol (250 ml), thereto is added water (750 ml) and the mixture is stirred under ice-cooling. After 0.5 hours, the precipitates are collected by filtration, washed with water-methanol (3:1, 1000 ml) and n-hexane successively and dried to give the title compound (117.0 g).

APCI-MS M/Z: 275[M+H]$^+$.

Reference Example 113

Trans-4-(2-oxo-pyrrolidin-1-yl)cyclohexanecarboxylic acid

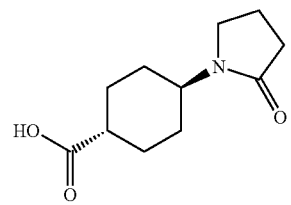

(1) Methyl trans-4-(t-butoxycarbonylamino)-cyclohexanecarboxylate (234.0 g) obtained in Reference Example 112 is dissolved in dioxane (500 ml), and thereto is added 4 N hydrogen chloride-dioxane (500 ml), and the mixture is stirred at room temperature for 19 hours. The reaction solution is concentrated under reduced pressure, and the resulting residue is suspended in diethyl ether, and then the precipitates are collected by filtration to give methyl trans-4-aminocyclohexanecarboxylate hydrochloride (121.9 g).

APCI-MS M/Z:158[M+H]$^+$.

(2) Methyl trans-4-aminocyclohexanecarboxylate hydrochloride (45.31 g) is suspended in dichloromethane (1000 ml), thereto is added 4-chlorobutyryl chloride (31.5 ml) under ice-cooling and to the mixture is added dropwise a solution of triethylamine (81.5 ml) in dichloromethane (80 ml). The reaction solution is warmed to room temperature, stirred for 3 hours and the reaction solution is concentrated under reduced pressure. To the resulting residue are poured ethyl acetate and 5% hydrochloric acid, and the organic layer is separated, washed with saturated aqueous sodium hydrogen carbonate solution and saturated brine. The organic layer is dried over sodium sulfate and treated with activated carbon, and the filtrate is concentrated under reduced pressure. The resulting residue is suspended in diisopropyl ether, filtered to collect the precipitates, dried to give methyl trans-4-(4-chlorobutyrylamino)cyclohexanecarboxylate (38.81 g).

APCI-MS M/Z:262/264[M+H]$^+$.

(3) Sixty % sodium hydride in oil (9.60 g) is suspended in N,N-dimethyacetamide (500 ml), to this mixture is added methyl trans-4-(4-chlorobutyrylamino)-cyclohexanecarboxylate (52.32 g) obtained in Reference Example 113(2) gradually under ice-cooling. The reaction solution is warmed to room temperature, stirred for 24 hours, and thereto are poured saturated aqueous ammonium chloride solution and ice-water, and the mixture is extracted with chloroform. The organic layer is washed with saturated brine, dried over magnesium sulfate and evaporated to remove the solvent under reduced pressure. The resulting residue is purified by silica gel column chromatography (eluent: ethyl acetate) and the obtained solid is suspended in n-hexane-diisopropyl ether. The resulting crystals are collected by filtration and dried to give methyl trans-4-(2-oxo-pyrrolidin-1-yl)cyclohexanecarboxylate (39.20 g).

APCI-MS M/Z:226[M+H]$^+$.

(4) Methyl trans-4-(2-oxo-pyrrolidin-1-yl)cyclohexanecarboxylate (39.15 g) obtained in Reference Example 113 (3) dissolved in methanol (400 ml), and thereto is added 2 N aqueous sodium hydroxide solution (60 ml) and the mixture is stirred at room temperature for 3 hours. The reaction solution is adjusted to pH 1-2 by pouring 10% hydrochloric acid under ice-cooling, saturated with sodium chloride, and then extracted with chloroform. The organic layer is dried over sodium sulfate, and then evaporated to remove the solvent under reduced pressure. The resulting residue is suspended in a small amount of ethyl acetate, and diisopropyl ether is poured thereto, and the resulting crystals are collected by filtration. The crystals are washed with diisopropyl ether several times and dried to give the title compound (35.94 g).

ESI-MS M/Z:210[M−H]$^-$.

Reference Example 114

Trans-4-(N-acetyl-N-methylamino)-cyclohexanecarboxylic acid

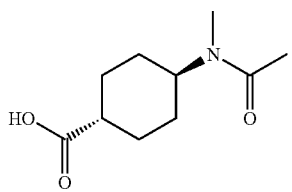

(1) Methyl trans-4-(t-butoxycarbonylamino)-cyclohexanecarboxylate (30.00 g) is dissolved in N,N-dimethylformamide (150 ml) and thereto is added 60% sodium hydride in oil (5.60 g) under ice-cooling. After stirring for 0.5 hours under cooling, to the reaction solution are added methyl iodide (14.5 ml) and methanol (0.15 ml) successively, and the reaction solution is warmed to room temperature and stirred for 4 hours. Under ice-cooling, to the reaction solution are poured saturated ammonium chloride and ice-water, and the mixture is extracted with ethyl acetate. The organic layer is washed with water and saturated brine successively, dried over sodium sulfate and evaporated to remove the solvent under reduced pressure. The resulting residue is purified by silica gel column chromatography (eluent: n-hexane/ethyl acetate=10/1, followed by 7/1) to give methyl trans-4-(N-t-butoxycarbonyl-N-methylamino)cyclohexanecarboxylate (26.33 g).

APCI-MS M/Z:272[M+H]$^+$.

(2) Methyl trans-4-(N-t-butoxycarbonyl-N-methylamino) cyclohexanecarboxylate (26.32 g) obtained in Reference Example 114(1) is dissolved in dioxane (100 ml) and thereto is added 4 N hydrogen chloride-dioxane solution (100 ml). The reaction solution is stirred at room temperature for 4 hours and to the solution is poured diisopropyl ether (500 ml). The precipitates are collected by filtration, washed with diisopropyl ether and dried to give methyl trans-4-(methylamino) cyclohexanecarboxylate hydrochloride (19.01 g).

APCI-MS M/Z:172[M+H]$^+$.

(3) Methyl trans-4-(methylamino)cyclohexanecarboxylate hydrochloride (18.93 g) obtained in Reference Example 114(2) is suspended in dichloromethane (400 ml), to the solution is added acetyl chloride (8.42 ml) under ice-cooling, and then a solution of triethylamine (38.1 ml) in dichloromethane (40 ml) is added dropwise. The reaction solution is warmed to room temperature, stirred for 2 hours, thereto is added 5% hydrochloric acid and the mixture is extracted with dichloromethane. The organic layer is washed with saturated brine, dried over sodium sulfate and evaporated to remove the solvent under reduced pressure. The resulting residue is purified by NH-silica gel column chromatography (eluent: ethyl acetate) to give methyl trans-4-(N-acetyl-N-methylamino) cyclohexanecarboxylate (19.05 g).

APCI-MS M/Z:214[M+H]$^+$.

(4) Methyl trans-4-(N-acetyl-N-methylamino)-cyclohexanecarboxylate (19.00 g) obtained in Reference Example 114 (3) is dissolved in methanol (200 ml), thereto is added aqueous 2 N sodium hydroxide solution (60 ml) and the mixture is stirred at room temperature for 3 hours. Under ice-cooling, the reaction solution is adjusted to pH 1-2 with 10% hydrochloric acid, saturated with sodium chloride, and then extracted with chloroform. The organic layer is dried over sodium sulfate, and then evaporated to remove the solvent under reduced pressure. The resulting residue is suspended in a small amount of ethyl acetate, to the mixture is poured diisopropyl ether and the crystals are collected by filtration. The crystals are washed with diisopropyl ether several times and dried to give the title compound (16.31 g).

ESI-MS M/Z:198[M−H]$^-$.

Reference Example 115

Trans-4-(N-t-butoxycarbonyl-N-methylamino)cyclohexanecarboxylic acid

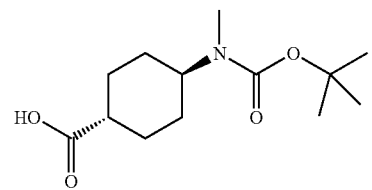

Methyl trans-4-(N-t-butoxycarbonyl-N-methylamino)-cyclohexanecarboxylate (44.78 g) obtained in Reference Example 114(1) is dissolved in methanol (300 ml), thereto is added aqueous 2 N sodium hydroxide solution (100 ml) and the mixture is stirred at room temperature for 6 hours. The reaction solution is concentrated under reduced pressure, to the residue are added ice-water, ethyl acetate and 10% hydrochloric acid under ice-cooling and then the mixture is extracted with ethyl acetate. The organic layer is washed with water and saturated brine successively, dried over sodium sulfate and evaporated to remove the solvent under reduced pressure. The resulting residue is suspended in a small amount of ethyl acetate, to the mixture is poured n-hexane and the crystals are collected by filtration. The crystals are washed with n-hexane-diisopropyl ether several times and dried to give the title compound (39.20 g).

ESI-MS M/Z:256[M–H]⁻

Reference Example 116

Trans-4-(t-butoxycarbonylamino)cyclohexanecarboxylic acid

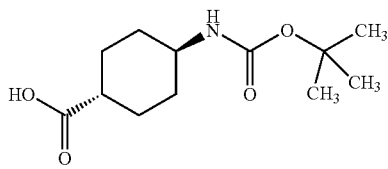

Methyl trans-4-(t-butoxycarbonylamino)cyclohexanecarboxylate (44.78 g) obtained in Reference Example 112 is treated in a similar manner to Reference Example 115 to give the title compound (24.04 g).

ESI-MS M/Z:242[M–H]⁻.

Reference Example 117

Trans-4-dimethylaminocyclohexane-carboxylic acid hydrochloride

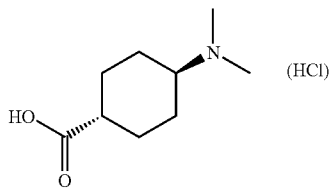

(1) Methyl trans-4-aminocyclohexanecarboxylate hydrochloride (93.0 g) obtained in Reference Example 113(1) is dissolved in methanol (1000 ml), thereto are added aqueous 35% formaldehyde solution (95.4 ml), sodium acetate (39.4 g) and 10% palladium-carbon (10 g), and the mixture is stirred for 3.5 hours under atmospheric hydrogen pressure. The insoluble materials are removed by filtration, the filtrate is concentrated under reduced pressure, to the resulting residue is added aqueous 20% potassium carbonate solution (500 ml), and the reaction mixture is extracted with chloroform. The organic layer is dried over sodium sulfate and potassium carbonate and evaporated to remove the solvent under reduced pressure. The resulting residue is purified by NH-silica gel column chromatography (eluent: n-hexane/ethyl acetate=2/1) to give methyl trans-4-dimethylaminocyclohexanecarboxylate (87.3 g).

APCI-MS M/Z:186[M+H]⁺.

(2) Methyl trans-4-dimethylaminocyclohexanecarboxylate (27.6 g) obtained in Reference Example 117(1) is dissolved in dioxane (300 ml) and water (100 ml), thereto is added 6 N hydrochloric acid (50 ml) and the mixture is heated under reflux for 4 hours. To the mixture is added additional 6 N hydrochloric acid (50 ml) and the reaction mixture is heated under reflux for another one hour. The reaction solution is concentrated under reduced pressure, subjected to azeotropic distillation with toluene, and then the resulting residue is suspended in diisopropyl ether. The precipitates are collected by filtration, washed with diisopropyl ether and dried to give the title compound (27.5 g).

APCI-MS M/Z:172[M+H]⁺.

Reference Example 118

Trans-4-(pyrrolidin-1-yl)-cyclohexanecarboxylic acid hydrochloride

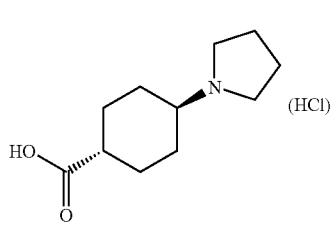

(1) Methyl trans-4-aminocyclohexanecarboxylate hydrochloride (10 g) obtained in Reference Example 113(1), 1,4-diiodobutane (19.2 g), sodium carbonate (16.4 g) are suspended in a mixture of tetrahydrofuran (300 ml) and N,N-dimethyl acetamide (60 ml), and the mixture is stirred at 70° C. for 20 hours. The reaction solution is concentrated under reduced pressure, the residue is dissolved in ethyl acetate-water and the organic layer is separated. The organic layer is washed with water and saturated brine, dried over sodium sulfate and evaporated to remove the solvent under reduced pressure. The resulting residue is purified by NH-silica gel column chromatography (eluent: ethyl acetate/hexane=1/5) to give methyl trans-4-(pyrrolidin-1-yl)cyclohexanecarboxylate (10.9 g).

APCI-MS M/Z:212[M+H]⁺.

(2) To a solution of methyl trans-4-(pyrrolidin-1-yl)cyclohexanecarboxylate (10.9 g) obtained in Reference Example 118(1) in dioxane (150 ml) is added 2 N hydrochloric acid (80 ml), and the mixture is stirred at 110° C. for 3 hours while evaporating to remove methanol. The reaction solution is concentrated under reduced pressure, the resulting residue is suspended in diethyl ether, and then collected by filtration to give the title compound (11.1 g).

APCI-MS M/Z:198[M+H]⁺.

Reference Example 119

Trans-4-(morpholin-4-yl)cyclohexanecarboxylic acid hydrochloride

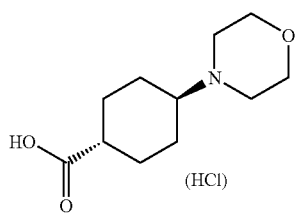

(1) Methyl trans-4-aminocyclohexanecarboxylate hydrochloride (47.5 g) obtained in Reference Example 113(1), bis(2-chloroethyl)ether (34.5 ml), sodium carbonate (77.9 g) and sodium iodide (88 g) are suspended in a mixture of tetrahydrofuran (1400 ml) and N,N-dimethylacetamide (280 ml), and the mixture is heated under reflux for 18 hours. Bis(2-chloroethyl)ether (23 ml) and sodium iodide (22 g) are added to the reaction solution and the mixture is refluxed for additional 6 hours. The reaction solution is concentrated under reduced pressure, and the residue is dissolved in ethyl acetate-water and the organic layer is separated. The organic layer is washed with water and saturated brine, dried over sodium sulfate and evaporated to remove the solvent under reduced pressure. The resulting residue is purified by NH-silica gel column chromatography (eluent: ethyl acetate/hexane=1/30, followed by ethyl acetate/hexane=1/5, and then 1/3) to give methyl trans-4-(morpholin-4-yl)cyclohexanecarboxylate (53.9 g).

APCI-MS M/Z:228[M+H]$^+$.

(2) To a solution of methyl trans-4-(morpholin-4-yl)cyclohexanecarboxylate (53.8 g) obtained in Reference Example 119(1) in dioxane (750 ml) is added 2 N hydrochloric acid (400 ml), and the mixture is stirred at 110° C. for 4 hours while evaporating to remove methanol. The reaction solution is concentrated, and the resulting residue is suspended in diethyl ether, and then the resulting product is collected by filtration to give the title compound (54.8 g).

APCI-MS M/Z:214[M+H]$^+$.

Reference Example 120

Trans-[4-(dimethylamino)cyclohexyl]-acetic acid hydrochloride

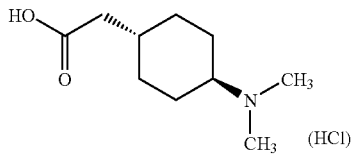

(1) Potassium hydroxide (12.8 g) is dissolved in water (30 ml) and thereto is added diethyl ether (45 ml). Under ice-cooling, to the resulting mixture is added N-nitroso-N-methylurea (5.07 g). The reaction solution is stirred for 10 minutes under cooling, and the organic layer is separated and dried over potassium hydroxide to give a solution of diazomethane in diethyl ether.

(2) Under argon atmosphere, trans-4-(t-butoxycarbonylamino)cyclohexanecarboxylic acid (3.0 g) obtained in Reference Example 116 is suspended in diethyl ether (40 ml), thereto is added triethylamine (1.89 ml) at −10° C., and then isobutyl chloroformate (1.75 ml) is added dropwise to the mixture. The reaction solution is stirred at −10° C. for 30 minutes, and a solution of diazomethane in diethyl ether obtained in Reference Example 120(1) is added dropwise to the reaction solution at −10° C., and the mixture is warmed to room temperature and stirred for 15 hours. Under ice-cooling, 10% aqueous citric acid solution is poured to the solution, and the organic layer is separated. The organic layer is washed with saturated aqueous sodium hydrogen carbonate solution, water and saturated brine, dried over sodium sulfate and evaporated to remove the solvent under reduced pressure. The resulting residue is purified by silica gel column chromatography (eluent: ethyl acetate/hexane=1/3, followed by ethyl acetate/hexane=1/2) to give t-butyl trans-[4-(2-diazoacetyl) cyclohexyl]-carbamate (1.86 g).

APCI-MS M/Z:285[M+NH$_4$]$^+$.

(3) t-Butyl trans-[4-(2-diazoacetyl)cyclohexyl]-carbamate (1.62 g) obtained in Reference Example 120(2) is dissolved in methanol (30 ml) in a light shielding reaction vessel under argon atmosphere, and the mixture is cooled to −25° C. To the reaction solution is added a solution of silver benzoate (153 mg) in triethylamine (2.4 ml), and the mixture is warmed to room temperature and stirred for 3 hours. The reaction solution is concentrated under reduced pressure, the resulting residue is dissolved in ethyl acetate, washed with saturated aqueous sodium hydrogen carbonate solution, saturated aqueous ammonium chloride solution and saturated brine successively, dried over sodium sulfate and evaporated to remove the solvent, which provides methyl trans-4-(t-butoxycarbonylamino)-cyclohexyl]acetate (1.25 g).

APCI-MS M/Z:289[M+NH$_4$]$^+$.

(4) To a solution of methyl trans-[4-(t-butoxycarbonylamino)cyclohexyl]acetate (1.23 g) obtained in Reference Example 120(3) in 1,4-dioxane (8 ml), is added 4 N hydrogen chloride-dioxane solution (8 ml) and the mixture is stirred at room temperature for 5 hours. The reaction solution is concentrated to dryness under reduced pressure to give methyl trans-(4-aminocyclohexyl)acetate hydrochloride (898 mg).

APCI-MS M/Z:172[M+H]$^+$.

(5) Under ice-cooling, to a suspension of methyl trans-(4-aminocyclohexyl)acetate hydrochloride (895 mg) obtained in Reference Example 120(4) in dichloromethane (30 ml), triethylamine (1.2 ml) is added and the mixture is stirred. Aqueous 35% formaldehyde solution (1.71 ml) and sodium triacetoxy borohydride (2.74 g) are added thereto successively under ice-cooling. The reaction solution is warmed to room temperature and stirred for 6 hours. Saturated aqueous sodium hydrogen carbonate solution is poured into the mixture under ice-cooling and the mixture is extracted with chloroform. The organic layer is washed with saturated brine, dried over sodium sulfate, and then the solvent is removed under reduced pressure to give methyl trans-[4-(dimethylamino)cyclohexyl]acetate (771 mg).

APCI-MS M/Z:200[M+H]$^+$.

(6) To a solution of methyl trans-[4-(dimethylamino)cyclohexyl]acetate (760 mg) obtained in Reference Example 120 (5) in dioxane (25 ml), 1 N hydrochloric acid (15 ml) is added and the mixture is heated under reflux for 3 hours. The reaction solution is concentrated under reduced pressure, and the resulting residue is suspended in diethyl ether. The precipitates are collected by filtration and dried to give the title compound (795 mg).

APCI-MS M/Z: 186[M+H]$^+$.

Reference Example 121

Trans-4-(dimethylaminomethyl)-cyclohexanecarboxylic acid hydrochloride

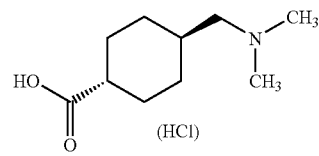

(1) Trans-4-(aminomethyl)cyclohexanecarboxylic acid (6.29 g) is suspended in methanol (32 ml) and to the suspension is added dropwise thionyl chloride (6 ml) under ice-cooling. The reaction solution is warmed to room temperature, stirred overnight and concentrated under reduced pressure to dryness, which provides methyl trans-4-(aminomethyl)cyclohexanecarboxylate hydrochloride (8.69 g).

APCI-MS M/Z:172[M+H]⁺.

(2) Methyl trans-4-(aminomethyl)cyclohexanecarboxylate hydrochloride (8.69 g) obtained in Reference Example 121(1) is suspended in dichloromethane (400 ml), thereto is added triethylamine (11.2 ml), and the mixture is stirred at room temperature for several minutes and thereto are added 35% aqueous formaldehyde solution (15.9 ml) and sodium triacetoxyborohydride (25.43 g) under ice-cooling. The reaction solution is warmed to room temperature, stirred for 2 hours, to the solution is poured a saturated aqueous sodium hydrogen carbonate solution and the solution is extracted with chloroform. The organic layer is washed with water and saturated brine successively, dried over sodium sulfate and evaporated to remove the solvent to give methyl trans-4-(dimethylaminomethyl)cyclohexanecarboxylate (7.42 g).

APCI-MS M/Z:200[M+H]⁺.

(3) Methyl trans-4-(dimethylaminomethyl)-cyclohexanecarboxylate (7.41 g) obtained in Reference Example 121(2) is dissolved in dioxane (140 ml), thereto is added 2 N hydrochloric acid (70 ml), and the mixture is heated under reflux for 3 hours. After allowing to cool, the reaction solution is concentrated under reduced pressure, the resulting residue is subjected to azeotropic distillation with toluene, and then the resulting product is dried to give the title compound (8.45 g).

APCI-MS M/Z:186[M+H]⁺.

Reference Example 122

Trans-4-(t-butoxycarbonylaminomethyl)cyclohexanecarboxylic acid

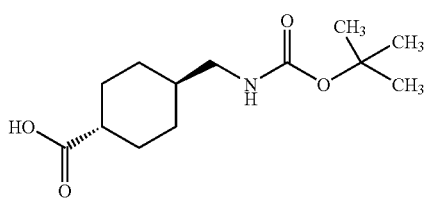

Trans-4-(aminomethyl)cyclohexanecarboxylic acid (8.35 g) is suspended in dioxane (100 ml), thereto are added water (50 ml) and 1 N aqueous sodium hydroxide solution (50 ml), and then di-t-butyl dicarbonate (12.7 g) is added dropwise under ice-cooling. The reaction solution is warmed to room temperature, stirred for 4 hours and the reaction solution is concentrated under reduced pressure. The resulting residue is diluted with ethyl acetate, adjusted to about pH 3-4 by addition of aqueous citric acid solution and extracted with ethyl acetate. The organic layer is washed with water and saturated brine, dried over sodium sulfate and evaporated to remove the solvent under reduced pressure. The resulting residue is suspended in n-hexane, and the resulting product is collected by filtration and dried to give the title compound (13.30 g).

ESI-MS M/Z:256[M−H]⁻.

Reference Example 123

Ethyl 3-(piperidin-4-yl)propionate hydrochloride

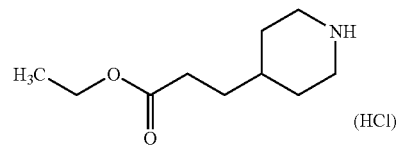

(1) Sixty % sodium hydride in oil (33.6 g) is suspended in tetrahydrofuran (600 ml) and a solution of triethyl phosphonoacetate (188.4 g) in tetrahydrofuran (100 ml) is added dropwise thereto under ice-cooling. The mixture is stirred for 0.5 hours under ice-cooling, and a solution of pyridine-4-carbaldehyde (75.00 g) in tetrahydrofuran (100 ml) is added thereto dropwise and the mixture is stirred for one hour. To the reaction solution is poured ice-water (1000 ml) under ice-cooling and the mixture is extracted with ethyl acetate. The organic layer is washed with water, saturated aqueous sodium hydrogen carbonate solution and saturated brine successively, dried over sodium sulfate and evaporated to remove the solvent under reduced pressure. The resulting residue is suspended in a small amount of diisopropyl ether under ice-cooling and the precipitates are collected by filtration. The precipitates are washed with a small amount of diisopropyl ether and n-hexane successively and dried to give ethyl 3-(pyridin-4-yl)acrylate (77.53 g).

APCI-MS M/Z:178[M+H]⁺.

(2) Ethyl 3-(pyridin-4-yl)acrylate (28.00 g) obtained in Reference Example 123(1) is dissolved in acetic acid (280 ml), thereto is added platinum oxide (1.80 g) and the mixture is shaken under 55 psi hydrogen atmosphere at room temperature for 24 hours. The insoluble materials are removed by filtration and the filtrate is concentrated under reduced pressure. The resulting residue is dissolved in dioxane (200 ml), thereto are added 4 N hydrogen chloride-dioxane (200 ml) and the mixture is evaporated to remove the solvent under reduced pressure. The resulting residue is suspended in diethyl ether-diisopropyl ether, the precipitates are collected by filtration, washed with diisopropyl ether, and dried to give the title compound (33.50 g).

APCI-MS M/Z:186[M+H]⁺.

Reference Example 124

Ethyl(piperidin-4-yl)acetate hydrochloride

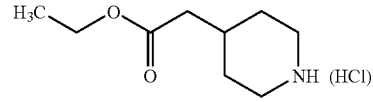

Ethyl(pyridin-4-yl)acetate (50.00 g) is dissolved in acetic acid (500 ml), thereto is added platinum oxide (3.44 g) and the mixture is shaken under 55 psi hydrogen atmosphere at room temperature for 20 hours. The insoluble materials are removed by filtration and the filtrate is concentrated under reduced pressure. The resulting residue is dissolved in dioxane (200 ml), thereto is added 4 N hydrogen chloride-dioxane (400 ml), and then the mixture is evaporated to remove the solvent under reduced pressure. The resulting residue is suspended in diethyl ether-diisopropyl ether, and the precipitates are collected by filtration, washed with diisopropyl ether, and then dried to give the title compound (61.80 g).

APCI-MS M/Z:172[M+H]$^+$.

Reference Example 125

Ethyl 3-(1-isopropylpiperidin-4-yl)propionate

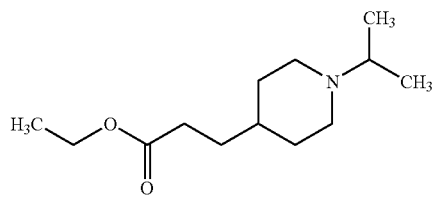

Ethyl 3-(piperidin-4-yl)propionate hydrochloride (70.83 g) obtained in Reference Example 123 is dissolved in ethanol (700 ml), thereto are added 2-iodopropane (38.2 ml) and potassium carbonate (132.3 g) and the mixture is heated under reflux for 6 hours. The insoluble materials are removed by filtration and the filtrate is concentrated under reduced pressure. The resulting residue is diluted with ethyl acetate (800 ml), washed with water and saturated brine successively, dried over sodium sulfate and evaporated to remove the solvent under reduced pressure. The resulting residue is purified by NH-silica gel column chromatography (eluent: n-hexane/ethyl acetate=20/1 followed by 9/1) to give the title compound (57.13 g).

APCI-MS M/Z:228[M+H]$^+$.

Reference Examples 126-127

The corresponding compounds are treated in a similar manner to Reference Example 125 to give the following compounds.

| Ref. Ex. No. | Structure | Physicochemical Properties |
|---|---|---|
| 126 | 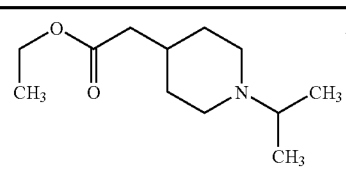 | APCI-MS M/Z: 214 [M + H]$^+$ |
| 127 | 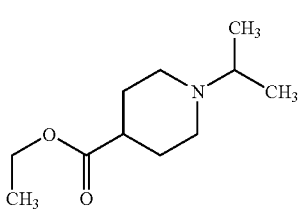 | APCI-MS M/Z: 200 [M + H]$^+$ |

Reference Example 128

3-(1-Isopropylpiperidin-4-yl)propionic acid hydrochloride

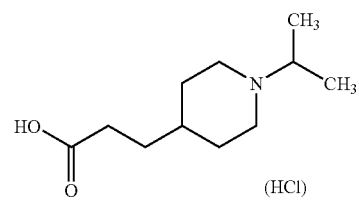

Ethyl 3-(1-isopropylpiperidin-4-yl)propionate (57.12 g) obtained in Reference Example 125 is dissolved in dioxane (1200 ml), thereto is added 2 N hydrochloric acid (600 ml) and the mixture heated under reflux for 3 hours. The reaction solution is concentrated under reduced pressure, subjected to azeotropic distillation with dioxane, and the resulting residue is suspended in diethyl ether-diisopropyl ether (1:1, 500 ml). The precipitates are collected by filtration, washed with diisopropyl ether and dried to give the title compound (55.36 g).

APCI-MS M/Z:200[M+H]$^+$.

Reference Examples 129-130

The corresponding compounds are treated in a similar manner to Reference Example 128 to give the following compounds.

| Ref. Ex. No. | Structure | Physicochemical Properties |
|---|---|---|
| 129 | 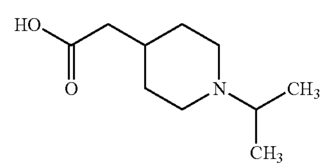 | APCI-MS M/Z: 186 [M + H]$^+$ hydrochloride |
| 130 | 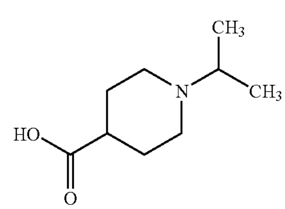 | APCI-MS M/Z: 172 [M + H]$^+$ hydrochloride |

Reference Example 131

1-(Pyridin-4-yl)piperidin-4-carboxylic acid

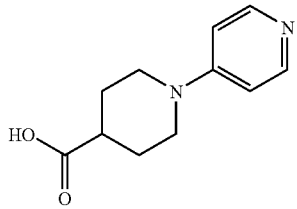

4-Chloropyridine hydrochloride (9.55 g) and triethylamine (26.0 ml) are dissolved in ethanol (10 ml) and water (30 ml), thereto is added ethyl isonicotinate (10.00 g), and then the reaction solution is heated at 150° C. for 96 hours in a sealed tube. After allowing to cool, ethanol is added to the reaction solution and the insoluble materials are removed by filtration. The filtrate is concentrated under reduced pressure, the resulting residue is suspended in chloroform, the precipitates are collected by filtration and recrystallized from water-N,N-dimethylformamide to give the title compound (10.34 g).

APCI-MS M/Z:207[M+H]$^+$.

Reference Example 132

[1-(Pyridin-4-yl)piperidin-4-yl]acetic acid hydrochloride

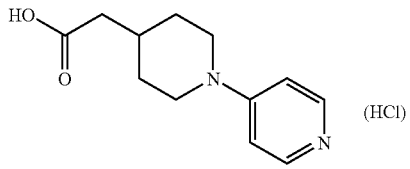

(1) Ethyl(piperidin-4-yl)acetate hydrochloride (5.00 g) obtained in Reference Example 124, 4-chloropyridine hydrochloride (3.62 g) and triethylamine (10.1 ml) are suspended in xylene (130 ml) and heated under reflux for 20 hours. The reaction solution is cooled with water and the insoluble materials are removed by filtration. The filtrate is concentrated under reduced pressure, the resulting residue is diluted with chloroform, washed with water, dried over magnesium sulfate, and then evaporated to remove the solvent under reduced pressure. The resulting residue is purified by NH-silica gel column chromatography (eluent: chloroform/ethyl acetate=4/1) to give ethyl[1-(pyridin-4-yl)piperidin-4-yl]acetate (4.15 g).

APCI-MS M/Z:249[M+H]$^+$.

(2) Ethyl[1-(pyridin-4-yl)piperidin-4-yl]acetate (4.15 g) obtained in Reference Example 132(1) is dissolved in dioxane (200 ml), thereto is added 1 N hydrochloric acid (70 ml) and the mixture is heated under reflux for 4 hours. The reaction solution is concentrated under reduced pressure and the resulting residue is lyophilized to give the title compound (3.90 g).

APCI-MS M/Z:221[M+H]$^+$.

Reference Example 133

3-[1-(Pyrimidin-4-yl)piperidin-4-yl]propionic acid hydrochloride

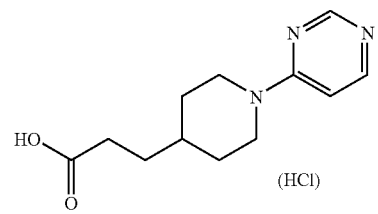

(1) Ethyl 3-(piperidin-4-yl)propionate hydrochloride (5.00 g) obtained in Reference Example 123 is suspended in tetrahydrofuran (50 ml) and thereto are added 4,6-dichloropyrimidine (2.80 g) and diisopropylethylamine (13.1 ml) at room temperature. The reaction solution is stirred for 3 hours at room temperature, thereto is added water, and the mixture is extracted with ethyl acetate. The organic layer is washed with water and saturated brine successively, dried over sodium sulfate and evaporated to remove the solvent under reduced pressure. The resulting residue is purified by silica gel column chromatography (eluent: n-hexane/ethyl acetate=5/1, followed by 3/1) to give ethyl 3-[1-(6-chloropyrimidin-4-yl)piperidin-4-yl]propionate (5.58 g).

APCI-MS M/Z:298/300[M+H]$^+$.

(2) Ethyl 3-[1-(6-chloropyrimidin-4-yl)piperidin-4-yl]propionate (5.54 g) obtained in Reference Example 133(1) is dissolved in ethanol (100 ml), thereto is added 10% palladium-carbon (0.55 g) and the mixture is stirred for 4 hours under hydrogen atmosphere under normal pressure. The insoluble materials are removed by filtration and the filtrate is concentrated under reduced pressure. Ethyl acetate and saturated aqueous sodium hydrogen carbonate solution are poured to the resulting residue, the organic layer is separated, washed with water and saturated brine successively, dried over sodium sulfate and evaporated to remove the solvent under reduced pressure to give ethyl 3-[1-(pyrimidin-4-yl) piperidin-4-yl]propionate (3.57 g).

APCI-MS M/Z:264 [M+H]$^+$.

(3) Ethyl 3-[1-(pyrimidin-4-yl)piperidin-4-yl]-propionate (3.54 g) obtained in Reference Example 133(2) is dissolved in dioxane (140 ml), thereto is added 1 N hydrochloric acid (70 ml) and the mixture is heated under reflux for 3 hours. After allowing to cool, the reaction solution is concentrated under reduced pressure and subjected to diazetropic distillation with dioxane. The resulting residue is suspended in diethyl ether, and the resulting product is collected by filtration, Reference Example 134

3-(1-Isopropylpiperidin-4-yl)acrylic acid hydrochloride

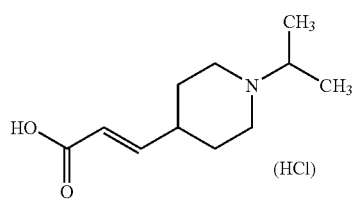

(1) Lithium aluminum hydride (1.10 g) is suspended in tetrahydrofuran (80 ml), and thereto is added a solution of ethyl 1-isopropylpiperidine-4-carboxylate (5.00 g) obtained in Reference Example 127 in tetrahydrofuran (30 ml) dropwise under ice-cooling. The reaction solution is stirred for 2 hours under the ice-cooling, and water (1.1 ml), 15% aqueous sodium hydroxide solution (1.1 ml) and water (3.3 ml) are added dropwise successively and stirred for additional 10 minutes. To the resulting reaction solution is added potassium carbonate, and the mixture is stirred for 20 minutes, and then the insoluble materials are removed by filtration. The filtrate is concentrated under reduced pressure, and then the resulting residue is purified by NH-silica gel column chromatography (eluent: chloroform/ethyl acetate=1/1) to give (1-isopropylpiperidin-4-yl)methanol (4.29 g).

APCI-MS M/Z:158[M+H]$^+$.

(2) Oxalyl chloride (2.0 ml) is dissolved in dichloromethane (120 ml) and thereto is added dropwise a solution of dimethylsulfoxide (3.3 ml) in dichloromethane (15 ml) under dry ice-acetone cooling. After stirring for 10 minutes under ice-cooling, a solution of (1-isopropylpiperidin-4-yl)methanol (3.00 g) obtained in Reference Example 134(1) in dichloromethane (30 ml) is added dropwise over a period of 15 minutes. After addition, the reaction solution is stirred for 2 hours under ice-cooling, and thereto is added dropwise triethylamine (13.3 ml) over a period of 10 minutes. The reaction solution is stirred for one hour while it is warmed to room temperature, and then the solution is poured to saturated aqueous sodium hydrogen carbonate solution. The mixture is extracted with dichloromethane and evaporated to remove the solvent under reduced pressure. The aqueous layer is extracted with ethyl acetate, and the extract is combined with the residue obtained by removing solvent from the above dichloromethane-extract, washed with water and saturated brine and dried over sodium sulfate. The solvent is evaporated under reduced pressure to give the crude material, 1-isopropylpiperidine-4-carbaldehyde (1.96 g).

APCI-MS M/Z:156[M+H]$^+$.

(3) Triethyl phosphonoacetate (7.96 g) is dissolved in tetrahydrofuran (50 ml) and thereto is added gradually 60% sodium hydride in oil (1.45 g) under ice-cooling. After stirring for 20 minutes under ice-cooling, to the mixture is added 1-isopropylpiperidine-4-carbaldehyde (5.03 g) obtained in Reference Example 134(2) in tetrahydrofuran (25 ml). The reaction solution is stirred for 3 hours, diluted with diethyl ether, thereto is added water and the mixture is extracted with ethyl acetate. The organic layer is washed with water and saturated brine, dried over sodium sulfate and evaporated to remove the solvent under reduced pressure. The resulting residue is purified by NH-silica gel column chromatography (eluent: n-hexane/ethyl acetate=9/1) to give ethyl 3-(1-isopropylpiperidin-4-yl)acrylate (6.87 g).

APCI-MS M/Z:226[M+H]$^+$.

(4) Ethyl 3-(1-isopropylpiperidin-4-yl)acrylate (1.01 g) obtained in Reference Example 134(3) is dissolved in ethanol (20 ml), thereto is added 2 N aqueous sodium hydroxide solution (4.5 ml) and the mixture is stirred at room temperature for 24 hours. To the reaction solution is added 2 N hydrochloric acid (9 ml), and the mixture is concentrated under reduced pressure, and then the resulting residue is lyophilized to give the title compound (1.43 g).

APCI-MS M/Z:198[M+H]$^+$.

Reference Example 135

(1-t-Butoxycarbonylpiperidin-4-yl)acetic acid

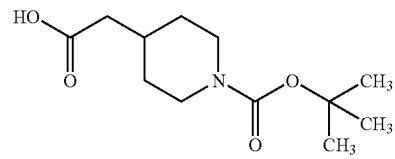

(1) Ethyl(piperidin-4-yl)acetate hydrochloride obtained in Reference Example 124 (10.00 g) is suspended in tetrahydrofuran (95 ml), and thereto are added sodium hydrogen carbonate (12.14 g) and water (150 ml), and then thereto is added a solution of di-t-butyl dicarbonate (11.60 g) in tetrahydrofuran (55 ml) dropwise under ice-cooling. The reaction solution is stirred at room temperature for 20 hours, aqueous potassium carbonate solution is poured to the solution and the mixture is extracted with ethyl acetate. The organic layer is washed with saturated brine, dried over magnesium sulfate and evaporated to remove the solvent under reduced pressure. The resulting residue is purified by silica gel column chromatography (eluent: n-hexane/ethyl acetate=5/1) to give ethyl(1-t-butoxycarbonylpiperidin-4-yl)acetate (13.06 g).

APCI-MS M/Z:272[M+H]$^+$.

(2) Ethyl(1-t-butoxycarbonylpiperidin-4-yl)acetate (13.00 g) obtained in Reference Example 135(1) is dissolved in tetrahydrofuran-ethanol (2:1, 180 ml) and thereto is added a solution of sodium hydroxide (4.80 g) in water (60 ml). The reaction solution is stirred at room temperature overnight, concentrated under reduced pressure and the resulting aqueous layer is washed with diethyl ether. The aqueous layer is acidified with 1 N hydrochloric acid under ice-cooling, and then extracted with ethyl acetate. The organic layer is washed with water and saturated brine, and then dried with magnesium sulfate. The solvent is evaporated under reduced pressure to give the title compound (11.10 g).

ESI-MS M/Z: 242[M−H]$^−$.

Reference Examples 136-137

The corresponding compounds are treated in a similar manner to Reference Example 135 to give the following compounds.

| Ref. Ex. No. | Structure | Physico-chemical Properties |
|---|---|---|
| 136 | 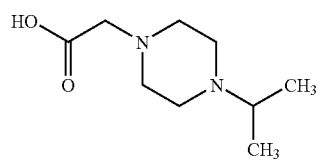 | ESI-MS M/Z: 256 [M − H]⁻ |
| 137 | 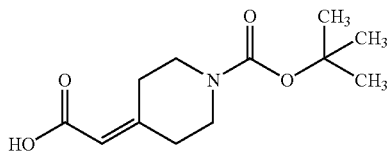 | ESI-MS M/Z: 228 [M − H]⁻ |

Reference Example 138 t-Butyl 4-carboxymethylene-1-piperidinecarboxylate (1) t-Butoxy potassium (4.49 g) is suspended in N,N-dimethylformamide under argon atmosphere, and to the mixture is added dropwise triethyl phosphonoacetate (5.83 g) under ice-cooling. After stirring for 0.5 hours under the ice-cooling, t-butyl 4-oxo-1-piperidinecarboxylate (4.07 g) is added dropwise to the reaction solution, and the mixture is warmed to room temperature and stirred for 1.5 hours. To the reaction solution is added ice-water under ice-cooling, and the precipitates are collected by filtration and dried to give t-butyl 4-ethoxycarbonylmethylene-1-piperidinecarboxylate (3.02 g).

APCI-MS M/Z:287[M+NH₄]⁺.

(2) t-Butyl 4-ethoxycarbonylmethylene-1-piperidinecarboxylate (1.08 g) obtained in Reference Example 138(1) is dissolved in dioxane (12 ml), thereto is added 1 N aqueous sodium hydroxide solution (8 ml) and the mixture is stirred at room temperature overnight. The reaction solution is acidified with 1 N hydrochloric acid, and then extracted with ethyl acetate. The organic layer is washed with water and saturated brine successively, dried over sodium sulfate and evaporated to remove the solvent under reduced pressure. The resulting residue is purified by silica gel column chromatography (eluent: chloroform/methanol=50/1) to give the title compound (0.72 g).

ESI-MS M/Z:240[M−H]⁻.

Reference Example 139

(4-Isopropylpiperazin-1-yl)acetic acid (1) 1-Isopropylpiperazine (1.21 g) is dissolved in acetonitrile (12 ml), thereto is added potassium carbonate (3.15 g), and then a solution of benzyl bromoacetate (2.08 g) in acetonitrile (2 ml) is added dropwise. The reaction solution is heated under reflux for one hour, after allowing to cool, the insoluble materials are removed by filtration and the filtrate is concentrated under reduced pressure. The resulting residue is purified by silica gel column chromatography (eluent: chloroform/methanol=50/1 followed by 9/1) to give benzyl(4-isopropylpiperazin-1-yl)acetate (2.84 g).

APCI-MS M/Z:277[M+H]⁺.

(2) Benzyl(4-isopropylpiperazin-1-yl)acetate (2.83 g) obtained in Reference Example 139(1) is dissolved in methanol (40 ml), thereto is added 10% palladium-carbon (0.31 g), and then the mixture is stirred for 7 hours under hydrogen atmosphere under normal pressure. The insoluble materials are removed by filtration, the filtrate is concentrated under reduced pressure to give the title compound (1.82 g).

APCI-MS M/Z:187[M+H]⁺.

Reference Example 140

3-(4-Isopropylpiperazin-1-yl)propionic acid dihydrochloride

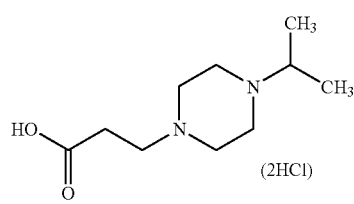

(1) 1-Isopropylpiperazine (650 mg) is dissolved in acetonitrile (7 ml) and thereto is added t-butyl acrylate (743 μl) under ice-cooling. The reaction solution is warmed to room temperature and stirred for 4 hours, and thereto is added additional t-butyl acrylate (148 μl), and then the mixture is stirred at room temperature for another 10 hours. Additional t-butyl acrylate (222 μl) is added to the reaction solution, and the mixture is stirred for 6 hours, thereto is poured water and the solution is extracted with ethyl acetate. The organic layer is washed with saturated brine, dried over sodium sulfate and evaporated to remove the solvent under reduced pressure. The resulting residue is purified by silica gel column chromatography (eluent: chloroform/methanol=20/1 followed by 10/1)

to give t-butyl 3-(4-isopropylpiperazin-1-yl)propionate (1.18 g).

APCI-MS M/Z:257[M+H]⁺.

(2) t-Butyl 3-(4-isopropylpiperazin-1-yl)propionate (1.15 g) obtained in Reference Example 140(1) is dissolved in dioxane (10 ml), and thereto is added 4 N hydrogen chloride-dioxane (25 ml) and the reaction solution is stirred at room temperature for 48 hours. The reaction solution is concentrated under reduced pressure and the resulting residue is suspended in diethyl ether. The precipitates are collected and dried to give the title compound (1.06 g).

APCI-MS M/Z:201[M+H]⁺.

Reference Example 141

Trans-4-(3-oxo-morpholin-4-yl)cyclohexanecarboxylic acid (1)

Sixty % sodium hydride in oil (6.80 g) is suspended in N,N-dimethylacetamide (80 ml) and a solution of 2-benzyloxyethanol (12.9 g) in N,N-dimethylacetamide (50 ml) is added dropwise to the mixture over a period of 10 minutes under ice-cooling. After stirring at room temperature for 15 minutes, the reaction solution is cooled with ice, thereto is added chloroacetic acid (8.13 g) gradually and the mixture is stirred at room temperature for 11 hours. The reaction solution is concentrated under reduced pressure, to the resulting residue is added aqueous sodium hydrogen carbonate solution and the mixture is washed with diethyl ether. The aqueous layer is acidified with conc. hydrochloric acid, and then extracted with ethyl acetate. The organic layer is washed with saturated brine, dried over sodium sulfate and evaporated to remove solvent under reduced pressure to give (2-benzyloxyethoxy)acetic acid (18.24 g).

ESI-MS M/Z:209[M−H]⁻.

(2)

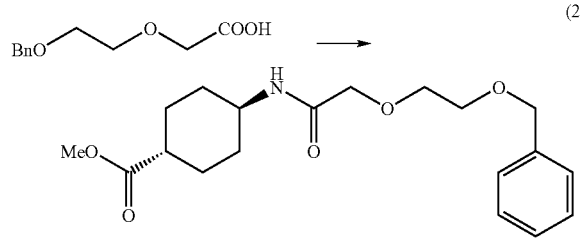

(2-Benzyloxyethoxy)acetic acid (6.51 g) obtained in (1), methyl trans-4-aminocyclohexanecarboxylate hydrochloride (5.27 g) obtained in Reference Example 113(1) and 1-hydroxybenzotriazole (5.06 g) are dissolved in N,N-dimethylformamide (100 ml). To the mixture are added 1-ethyl-3-(3-dimethylaminopropyl)carbodiimide hydrochloride (7.10 g) and triethylamine (4.50 ml) successively under ice-cooling, and the mixture is stirred at room temperature for 3 days. The reaction solution is concentrated under reduced pressure, to the resulting residue is added an aqueous sodium hydrogen carbonate solution and the mixture is extracted with ethyl acetate. The organic layer is washed with a saturated brine, dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-[2-(2-benzyloxyethoxy)acetylamino]cyclohexanecarboxylate (8.24 g).

APCI-MS M/Z:350[M+H]⁺.

(3)

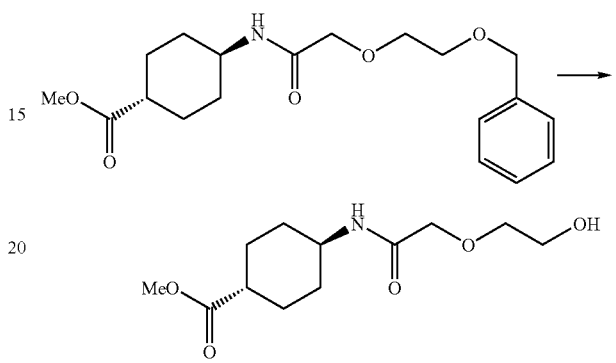

Methyl trans-4-[2-(2-benzyloxyethoxy)acetylamino]-cyclohexanecarboxylate (5.09 g) obtained in (2) is dissolved in acetic acid (150 ml), and thereto is added 5% palladium carbon (1.01 g) and the mixture is stirred for 2.4 hours under hydrogen atmosphere under normal pressure. The reaction solution is filtrated to remove the catalyst, and then the filtrate is concentrated under reduced pressure. The resulting residue is dissolved in chloroform, washed with a saturated sodium hydrogen carbonate solution, dried over sodium sulfate and evaporated to remove the solvent to give methyl trans-4-[2-(2-hydroxyethoxy)acetylamino]cyclohexanecarboxylate (3.32 g).

APCI-MS M/Z:260[M+H]⁺.

(4)

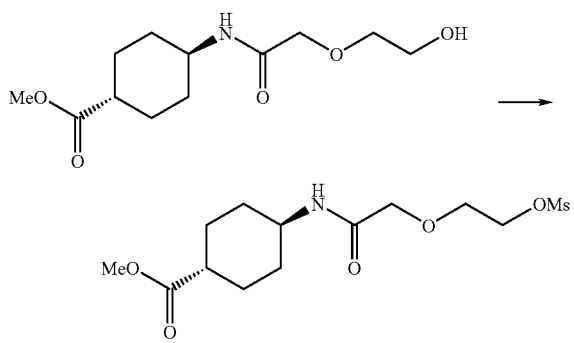

Methyl trans-4-[2-(2-hydroxyethoxy)acetylamino]-cyclohexanecarboxylate (1.37 g) obtained in (3) is dissolved in chloroform (15 ml) and thereto is added triethylamine (890 μl) under ice-cooling. Then, methanesulfonyl chloride (450 μl) is added dropwise at the same temperature. The reaction solution is stirred for 3 hours under ice-cooling, diluted with water and extracted with chloroform. The organic layer is washed with saturated brine, dried over sodium sulfate and removed the solvent by evaporation under reduced pressure to give methyl trans-4-[2-(2-methanesulfonyloxyethoxy)acetylamino]-cyclohexanecarboxylate (1.83 g).

APCI-MS M/Z:338[M+H]$^+$.

(5)

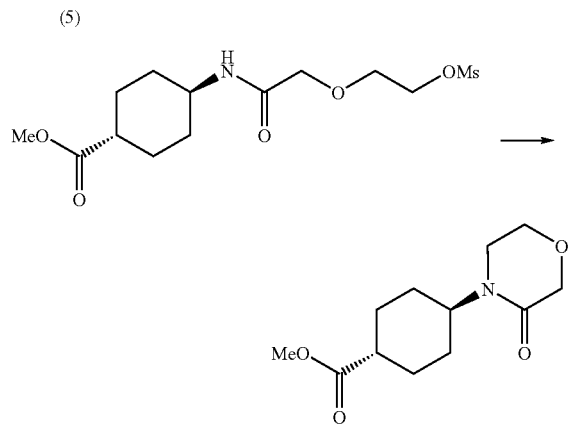

Methyl trans-4-[2-(2-methanesulfonyloxyethoxy)-acetylamino]cyclohexanecarboxylate (1.08 g) obtained in (4) is dissolved in N,N-dimethylacetamide (15 ml), thereto is added 60% sodium hydride in oil (135 mg) under ice-cooling and the mixture is stirred for 16 hours at room temperature. To the residue obtained by concentrating the reaction solution under reduced pressure are added water and excess sodium chloride, and the mixture is extracted with chloroform. The organic layer is dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-(3-oxo-morpholin-4-yl)cyclohexanecarboxylate (715 mg).

APCI-MS M/Z:242[M+H]$^+$.

(6)

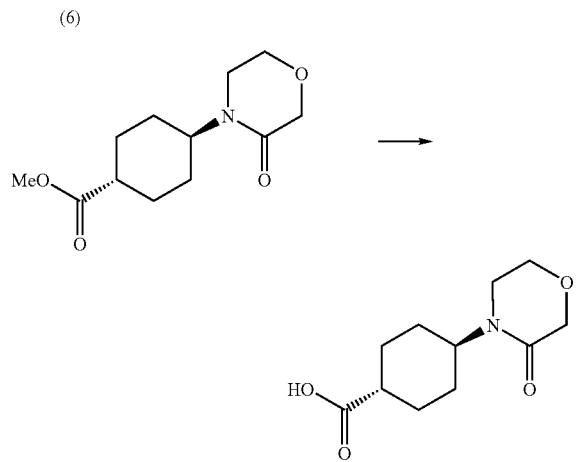

Methyl trans-4-(3-oxo-morpholin-4-yl)cyclohexanecarboxylate (500 mg) obtained in (5) is treated in a similar manner to Reference Example 113(4) to give the title compound (322 mg).

ESI-MS M/Z:226[M−H]$^-$.

Reference Example 142

Trans-4-(2-oxo-oxazolidin-3-yl)cyclohexanecarboxylic acid

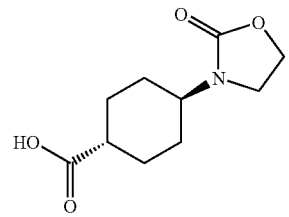

(1) Methyl trans-4-aminocyclohexanecarboxylate hydrochloride (5.00 g) obtained in Reference Example 113(1) is dissolved in chloroform (60 ml), thereto is added triethylamine (11 ml) under ice-cooling, and then a solution of 2-chloroethyl chloroformate (3.3 ml) in chloroform (10 ml) is added dropwise. After stirring at room temperature for 2.5 hours, to the reaction solution is added 5% hydrochloric acid, and then the mixture is extracted with chloroform. The organic layer is washed with saturated brine, dried over sodium sulfate, and then evaporated to remove the solvent under reduced pressure. The resulting residue is suspended in chloroform-diisopropyl ether, the precipitates are collected by filtration and dried to give methyl trans-4-(2-chloroethyloxycarbonylamino)cyclohexanecarboxylate (5.11 g).

APCI-MS M/Z:264/266[M+H]$^+$.

(2) Methyl trans-4-(2-chloroethyloxycarbonylamino)-cyclohexanecarboxylate (3.70 g) obtained in (1) is dissolved in N,N-dimethylacetamide (50 ml), thereto is added 60% sodium hydride in oil (630 mg) under ice-cooling and the mixture is stirred at room temperature for 16.5 hours. To the reaction solution is added water, the mixture is extracted with ethyl acetate, the organic layer is washed with water and saturated brine, and then dried over sodium sulfate. The solvent is removed by evaporation under reduced pressure and the resulting residue is purified by silica gel column chromatography (eluent: hexane/ethyl acetate=1/1 followed by ethyl acetate) to give methyl trans-4-(2-oxo-oxazolidin-3-yl)cyclohexanecarboxylate (1.83 g).

APCI-MS M/Z:228[M+H]$^+$.

(3) Methyl trans-4-(2-oxo-oxazolidin-3-yl)-cyclohexanecarboxylate (1.84 g) obtained in (2) is treated in a similar manner to Reference Example 113(4) to give the title compound (1.75 g).

ESI-MS M/Z:212[M−H]$^-$.

Reference Example 143

Trans-4-(2-oxo-pyrrolidin-1-ylmethyl)cyclohexanecarboxylic acid

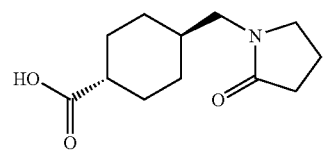

(1) Methyl trans-4-(aminomethyl)cyclohexanecarboxylate hydrochloride (4.57 g) obtained in Reference Example 121(1) is treated in a similar manner to Reference Example 113(2) to give methyl trans-4-(4-chlorobutyrylaminomethyl)cyclohexanecarboxylate (5.35 g).

APCI-MS M/Z:276/278[M+H]$^+$.

(2) Methyl trans-4-(4-chlorobutyrylaminomethyl)-cyclohexanecarboxylate (3.75 g) obtained in (1) is treated in a similar manner to Reference Example 113(3) to give methyl trans-4-(2-oxo-pyrrolidin-1-ylmethyl)cyclohexanecarboxylate (2.07 g).

APCI-MS M/Z:240[M+H]$^+$.

(3) Methyl trans-4-(2-oxo-pyrrolidin-1-ylmethyl)-cyclohexanecarboxylate (2.04 g) obtained in (2) is treated in a similar manner to Reference Example 113(4) to give trans-4-(2-oxo-pyrrolidin-1-ylmethyl)cyclohexanecarboxylic acid (2.41 g).

ESI-MS M/Z:224[M−H]$^-$.

Reference Example 144

Trans-4-[(N-acetyl-N-methylamino)-methyl]cyclohexanecarboxylic acid

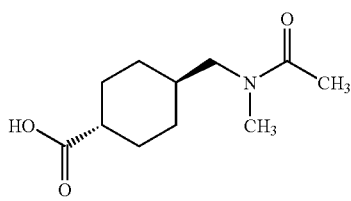

(1) Methyl trans-4-(aminomethyl)cyclohexanecarboxylate hydrochloride (5.86 g) obtained in Reference Example 121(1) is dissolved in chloroform (100 ml), thereto is added triethylamine (12 ml) under ice-cooling, and then acetyl chloride (2.69 g) is added thereto. The mixture is stirred at room temperature for one hour and 40 minutes, and water is added to the reaction solution and the mixture is extracted with chloroform. The organic layer is washed with 10% hydrochloric acid, saturated brine, a saturated aqueous sodium hydrogen carbonate solution and saturated brine successively, dried over magnesium sulfate and evaporated to remove the solvent under reduced pressure. The resulting residue is purified by silica gel column chromatography (eluent: hexane/ethyl acetate=1/1 followed by ethyl acetate) to give methyl trans-4-(acetylaminomethyl)cyclohexanecarboxylate (5.92 g).

APCI-MS M/Z:214[M+H]$^+$.

(2) Methyl trans-4-(acetylaminomethyl)cyclohexanecarboxylate (4.32 g) obtained in (1) is dissolved in N,N-dimethylformamide (50 ml) and thereto are added 60% sodium hydride in oil (1.00 g), methyl iodide (5.91 g) and methanol (5 drops) successively under ice-cooling. After stirring for 8 hours at room temperature, thereto are added additional sodium hydride (430 mg), methyl iodide (1.5 ml) and methanol (2 drops), and the mixture is stirred for 2 hours. To the reaction solution is added water, and the mixture is extracted with ethyl acetate. The organic layer is washed with water and dried over sodium sulfate. The solvent is removed by evaporation and the resulting residue is purified by silica gel column chromatography (eluent: hexane/ethyl acetate=1/2 followed by ethyl acetate) to give methyl trans-4-[(N-acetyl-N-methylamino)methyl]cyclohexanecarboxylate (3.04 g).

APCI-MS M/Z:228[M+H]$^+$.

(3) Methyl trans-4-[(N-acetyl-N-methylamino)-methyl]cyclohexanecarboxylate (3.03 g) obtained in (2) is treated in a similar manner to Reference Example 113(4) to give the title compound (2.67 g).

ESI-MS M/Z:212[M−H]$^-$.

Reference Example 145

5-(2-Oxo-pyrrolidin-1-yl)pentanoic acid

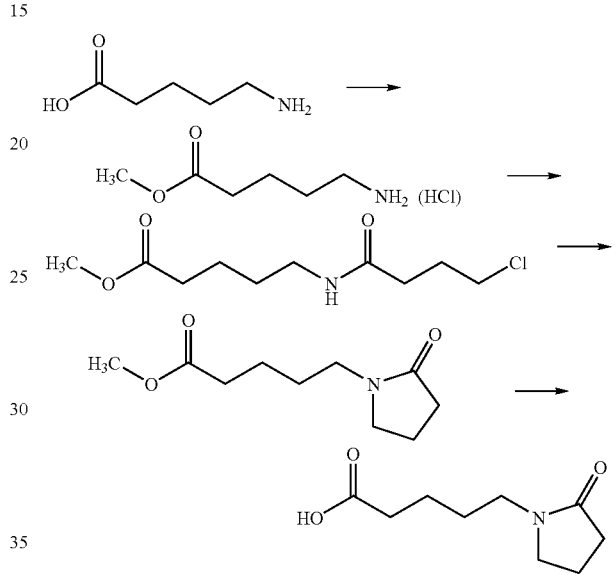

(1) 5-Aminovaleric acid (7.35 g) is dissolved in methanol (50 ml), thereto is added dropwise thionyl chloride (4.9 ml) under ice-cooling, and the reaction solution is warmed to room temperature and stirred for 17 hours. The reaction solution is concentrated under reduced pressure, and the resulting residue is suspended in diethyl ether and the precipitates are collected by filtration to give methyl 5-aminovalerate hydrochloride (9.93 g).

APCI-MS M/Z:132[M+H]$^+$.

(2) Methyl 5-aminovalerate hydrochloride (1.68 g) obtained in (1) is suspended in chloroform (20 ml). To the suspension, triethylamine (2.54 g) is added under ice-cooling, and then 4-chlorobutyryl chloride (1.55 g) is added dropwise. The reaction solution is warmed to room temperature, stirred for 2 hours, ice-water is poured to the reaction solution and the mixture is extracted with chloroform. The organic layer is washed with 10% hydrochloric acid, a saturated aqueous sodium hydrogen carbonate solution and saturated brine, and then dried over sodium sulfate. The resultant is evaporated to remove the solvent under reduced pressure to give methyl 5-(4-chlorobutyrylamino)pentanoate (2.34 g).

APCI-MS M/Z:236/238[M+H]$^+$.

(3) Methyl 5-(4-chlorobutyrylamino)pentanoate (2.33 g) obtained in (2) is dissolved in N,N-dimethylacetamide (20 ml) and 60% sodium hydride in oil (0.47 g) is added thereto gradually under ice-cooling. The reaction solution is warmed to room temperature, stirred for 20 hours and evaporated to remove the solvent under reduced pressure. The resulting residue is purified by silica gel column chromatography (eluent: chloroform followed by chloroform/ethyl acetate=20/1) to give methyl 5-(2-oxopyrrolidin-1-yl)pentanoate (2.15 g).

APCI-MS M/Z:200[M+H]+.

(4) Methyl 5-(2-oxo-pyrrolidin-1-yl)pentanoate (1.00 g) obtained in (3) is dissolved in methanol (20 ml), thereto is added 4 N aqueous sodium hydroxide solution (2.5 ml), the reaction solution is warmed to room temperature and stirred for 18 hours. The reaction solution is washed with diethyl ether, thereto is added 2 N hydrochloric acid (5.0 ml), and then concentrated under reduced pressure. The resulting residue is extracted with chloroform and dried over sodium sulfate. The resultant is evaporated to remove solvent under reduced pressure to give the title compound (0.90 g).

ESI-MS M/Z:184[M−H]−.

Reference Example 146

Methyl 2-formyl-3-hydroxybenzoate and methyl 4-formyl-3-hydroxybenzoate

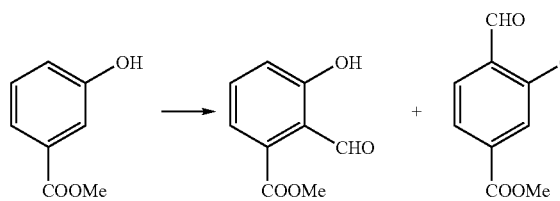

Methyl 3-hydroxybenzoate (75.5 g) is dissolved in trifluoroacetic acid (2 L), thereto is added hexamethylenetetramine (141.4 g) at room temperature and the mixture is heated under reflux for 3 hours. The reaction solution is concentrated under reduced pressure, to the resulting residue is added water, the mixture is adjusted to pH 8 with potassium carbonate and sodium hydrogen carbonate, diluted with water and extracted with ethyl acetate. The organic layer is washed with saturated brine, dried over sodium sulfate and evaporated to remove the solvent under reduced pressure. The resulting residue is purified by silica gel column chromatography (eluent: hexane/ethyl acetate=8/1, 5/1 followed by 2/1) to give methyl 2-formyl-3-hydroxybenzoate (54.6 g) (ESI-MS m/z: 179[M−H]−) and methyl 4-formyl-3-hydroxybenzoate (4.4 g) (ESI-MS m/z: 179[M−H]−).

Reference Example 147

Methyl 4-cyano-3-hydroxybenzoate

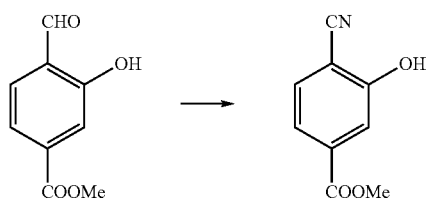

Methyl 4-formyl-3-hydroxybenzoate (1.96 g) obtained in Reference Example 146 is dissolved in formic acid (50 ml), thereto are added hydroxylammonium chloride (0.85 g) and sodium formate (0.85 g) and the mixture is heated under reflux for 14 hours. The reaction solution is concentrated under reduced pressure, diluted with water and extracted with ethyl acetate. The organic layer is washed with saturated brine, dried over sodium sulfate and evaporated to remove the solvent under reduced pressure. The resulting residue is suspended chloroform/diisopropyl ether, and then the precipitates are collected by filtration to give the title compound (0.66 g). Furthermore, the filtrate is concentrated under reduced pressure and the resulting residue is purified by silica gel column chromatography (eluent: hexane/ethyl acetate=3/2) to give the title compound (1.08 g).

ESI-MS M/Z:176[M−H]−.

Reference Example 148

2-(2-Cyano-5-methoxycarbonylphenoxy)-N-(5-chloropyridin-2-yl) acetamide

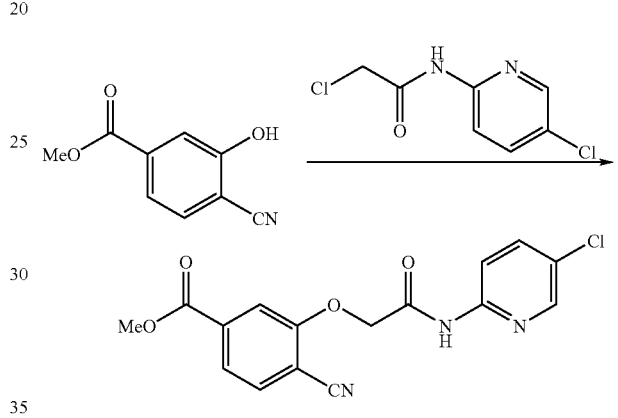

Methyl 4-cyano-3-hydroxybenzoate (655 mg) obtained in Reference Example 147 is dissolved in acetone (20 ml), thereto are added 2-chloro-N-(5-chloropyridin-2-yl) acetamide (897 mg) obtained in Reference Example 20(1), potassium carbonate (773 mg) and sodium iodide (657 mg) and the mixture is heated under reflux for 40 minutes. The reaction solution is concentrated under reduced pressure, thereto is added water and the mixture is extracted with ethyl acetate-tetrahydrofuran. The organic layer is washed with saturated brine, dried over sodium sulfate and evaporated to remove the solvent under reduced pressure. The resulting residue is suspended in chloroform-diisopropyl ether and the precipitates are collected by filtration to give the title compound (1.16 g).

APCI-MS M/Z:346/348[M+H]+.

Reference Example 149

3-Amino-6-methoxycarbonyl-N-(5-chloropyridin-2-yl)benzofuran-2-carboxamide

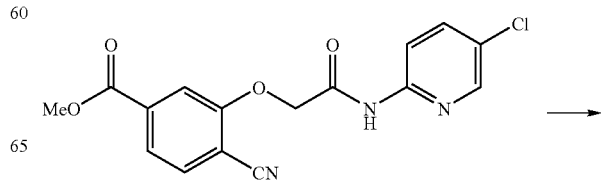

-continued

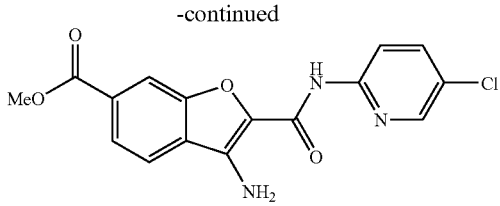

2-(2-Cyano-5-methoxycarbonylphenoxy)-N-(5-chloropyridin-2-yl)acetamide (1.03 g) obtained in Reference Example 148 is dissolved in N,N-dimethylacetamide (10 ml), thereto is added sodium carbonate (97 mg) and the mixture is stirred at 100° C. for 4 hours. The reaction solution is poured to water (50 ml), the precipitates are collected by filtration, washed with water and ethanol and dried to give the title compound (839 mg).

APCI-MS M/Z:346/348[M+H]$^+$.

Reference Example 150

Methyl 2-cyano-3-hydroxybenzoate

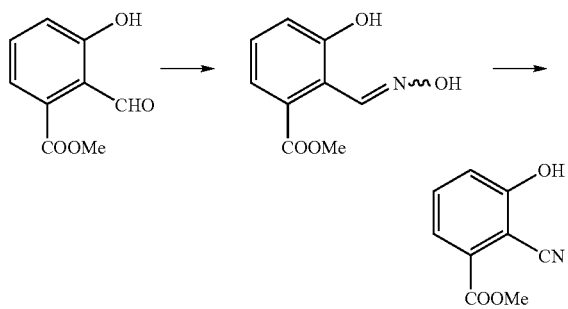

(1) Methyl 2-formyl-3-hydroxybenzoate (9.23 g) obtained in Reference Example 146 is suspended in methanol (150 ml), and an aqueous solution (15 ml) of hydroxylammonium chloride (3.56 g) and an aqueous solution (15 ml) of sodium acetate (4.36 g) are added to the suspension under ice-cooling. The mixture is warmed to room temperature, stirred for 2 hours, and then evaporated to remove methanol. The resulting residue is diluted with water and extracted with chloroform. The organic layer is dried over sodium sulfate and evaporated to remove the solvent under reduced pressure to give methyl 2-hydroxyiminomethyl-3-hydroxybenzoate (9.89 g).

APCI-MS M/Z:196[M+H]$^+$.

(2) Methyl 2-hydroxyiminomethyl-3-hydroxybenzoate (10.57 g) obtained in (1) is suspended in chloroform (100 ml) and thereto is added triethylamine (19.35 g) under ice-cooling. At the same temperature, to the resulting solution is added dropwise trifluoroacetic anhydride (25.40 g) over a period of 30 minutes. The reaction solution is stirred at room temperature for 3 days, thereto is added an aqueous saturated sodium hydrogen carbonate solution and extracted with chloroform. The organic layer is dried over magnesium sulfate and evaporated to remove the solvent under reduced pressure. The resulting residue is dissolved in methanol (150 ml), thereto is added potassium carbonate (15.6 g), and the mixture is stirred at room temperature for 50 minutes. The reaction solution is diluted with water, acidified with conc. hydrochloric acid, and then extracted with chloroform. The organic layer is dried over magnesium sulfate, the solvent thereof is removed by evaporation and the resulting residue is suspended in ethyl acetate-diisopropyl ether. The precipitates are collected by filtration to give the title compound (8.71 g).

ESI-MS M/Z:176[M−H]$^-$.

Reference Example 151

2-(2-Cyano-3-methoxycarbonylphenoxy)-N-(5-chloropyridin-2-yl)acetamide

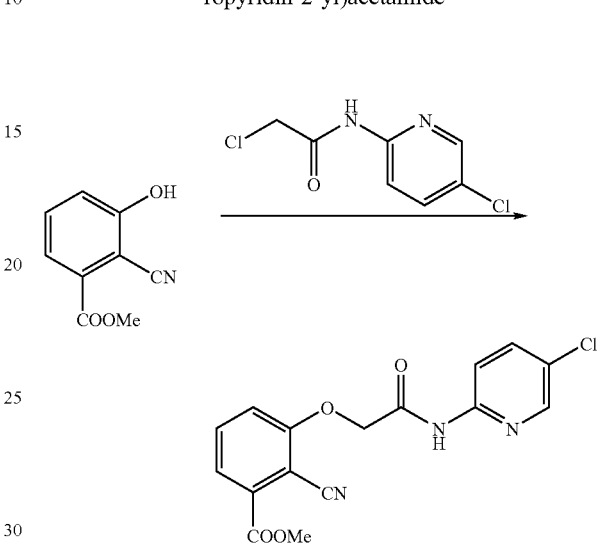

Methyl 2-cyano-3-hydroxybenzoate (1.70 g) obtained in Reference Example 150 is treated in a similar manner to Reference Example 148 to give the title compound (2.69 g).

APCI-MS M/Z:346/348[M+H]$^+$.

Reference Example 152

3-Amino-4-methoxycarbonyl-N-(5-chloropyridin-2-yl)benzofuran-2-carboxamide

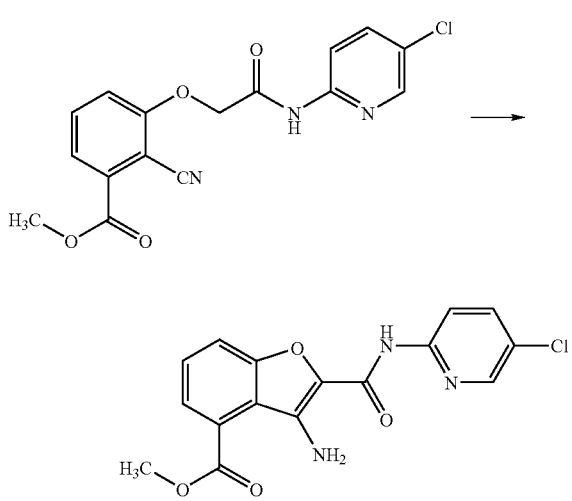

2-(2-Cyano-3-methoxycarbonylphenoxy)-N-(5-chloropyridin-2-yl)acetamide (1.51 g) obtained in Reference Example 151 is treated in a similar manner to Reference Example 149 to give the title compound (335 mg).

APCI-MS M/Z:346/348[M+H]$^+$.

Reference Example 153

3-Amino-5-carboxy-N-(5-chloropyridin-2-yl)benzofuran-2-carboxamide

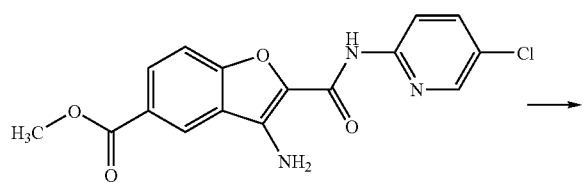

↓

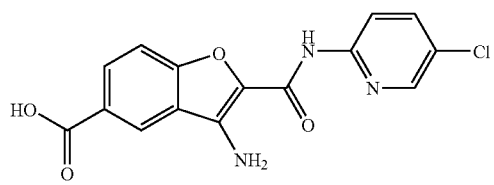

3-Amino-5-methoxycarbonyl-N-(5-chloropyridin-2-yl)benzofuran-2-carboxamide (2.01 g) is suspended in tetrahydrofuran (20 ml)-methanol, thereto is added 4 N aqueous sodium hydroxide solution (5 ml) under ice-cooling and the reaction solution is stirred at room temperature for 13 hours. The reaction solution is concentrated under reduced pressure, the resulting residue is diluted with water, and the mixture is adjusted to around pH 3 by pouring 10% hydrochloric acid. The precipitates are collected by filtration, washed with water and ethanol successively and dried to give the title compound (1.87 g).

ESI-MS M/Z:330[M−H]$^-$.

Reference Examples 154-155

The ester obtained in Reference Example 149 or Reference Example 152 is treated in a similar manner to Reference Example 153 to give the following compounds.

| Ref. Ex. No. | Structure | Physicochemical Properties |
|---|---|---|
| 154 | ![structure] | ESI-MS M/Z: 330/332 [M − H]$^-$ |
| 155 | ![structure] | ESI-MS M/Z: 330/332 [M − H]$^-$ |

Reference Example 156

3-Amino-5-dimethylaminocarbonyl-N-(5-chloropyridin-2-yl)benzofuran-2-carboxamide

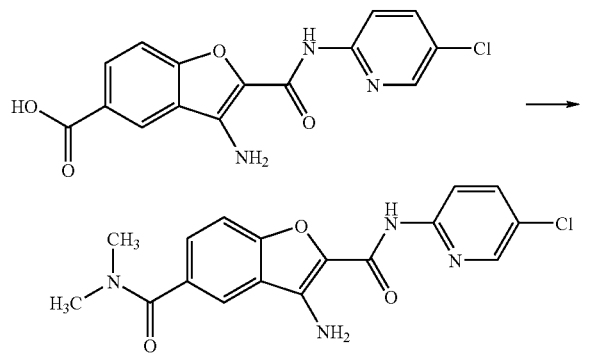

3-Amino-5-carboxy-N-(5-chloropyridin-2-yl)-benzofuran-2-carboxamide (1.51 g) obtained in Reference Example 153 is suspended in pyridine (15 ml), thereto are added dimethylamine hydrochloride (0.77 g), 1-hydroxybenzotriazole (1.37 g) and 1-ethyl-3-(3-dimethylaminopropyl)carbodiimide hydrochloride (1.79 g) successively under ice-cooling and the mixture is stirred at room temperature for 14 hours. The reaction solution is diluted with water (100 ml) and thereto is added saturated aqueous sodium hydrogen carbonate solution to adjust to pH 8-9. The precipitates are collected by filtration, washed with water and ethanol successively, and then dried to give the title compound (1.50 g).

APCI-MS M/Z:359/361[M+H]$^+$.

Reference Examples 157-158

The carboxylic acid obtained in Reference Example 154 or Reference Example 155 is treated in a similar manner to Reference Example 156 to give the following compounds.

INDUSTRIAL APPLICABILITY

The compound of the formula [1] or a pharmaceutically acceptable salt thereof is less toxic and safe, and has an excellent inhibitory effect on activated blood coagulation factor X. Accordingly, the said compound [1] is useful as a medicament for prevention and treatment of diseases caused by thrombus or embolus.

The invention claimed is:
1. A benzofuran derivative of the formula [1]:

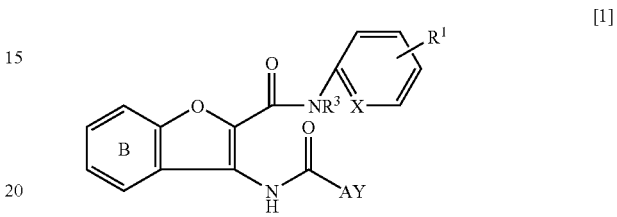

wherein X is a group of the formula: —N—
Y is a cycloalkyl group optionally substituted by a group selected from
  (i) an amino group optionally substituted by a group selected from the following:
    (1) a lower alkyl group;
    (2) a cycloalkyl group,
    (3) a hydroxy-lower alkyl group,
    (4) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
    (5) a lower alkyl group substituted by a cyano group,
    (6) a lower alkyl group substituted by a lower alkoxycarbonyl group,
    (7) a lower alkyl group substituted by a carboxyl group,

| Ref. Ex. No. | Structure | Physicochemical Properties |
|---|---|---|
| 157 | ![structure 157] | APCI-MS M/Z:359/361 [M + H]$^+$ |
| 158 | ![structure 158] | APCI-MS M/Z:359/361[M + H]$^+$ |

309

(8) a lower alkyl group substituted by a carbamoyl group optionally substituted by a lower alkyl group,
(9) a lower alkyl group substituted by an aryl group,
(10) a lower alkoxycarbonyl group,
(11) a lower alkanoyl group substituted by a di-lower alkyl amino group,
(12) a lower alkanoyl group,
(13) a lower alkylsulfonyl group,
(14) a carbamoyl group substituted by a lower alkyl group,
(15) a carbonyl group substituted by an aryl group,
(16) a lower alkanoyl group substituted by a lower alkoxy group,
(17) a lower alkanoyl group substituted by a lower alkanoyloxy group,
(18) an aryl group substituted by a hydroxyl group, and
(19) a hydroxy-lower alkanoyl group,
(ii) a group of a formula:

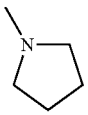

optionally substituted by an oxo group, and
(iii) a lower alkyl group optionally substituted by
an amino group optionally substituted by a group selected from (a) a lower alkyl group, (b) a lower alkoxycarbonyl group, and (c) a lower alkanoyl group; or A is a single bond, a carbon chain optionally having a double bond within or at the end(s) of the chain, or an oxygen atom; $R^1$ is a hydrogen atom, a halogen atom, a lower alkyl group, a lower alkoxy group, a cyano group or an amino group optionally substituted by a lower alkyl group;
Ring B of the formula:

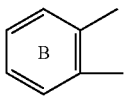

is a benzene ring optionally substituted by a group(s) selected independently from
(i) a halogen atom,
(ii) a lower alkyl group optionally substituted by a group selected from the following:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a hydroxyl group;
(iii) a hydroxy group,
(iv) a lower alkoxy group optionally substituted by a group selected from the following:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group,

310

(7) an amino group optionally substituted by (a) a lower alkyl group, (b) a lower alkoxycarbonyl group, and (c) a lower alkanoyl group,
(8) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(9) a group of the formula: —O—NH—C(=NH)NH$_2$;
(v) a carbonyl group substituted by a group selected from the following:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and
(4) a morpholinyl group,
(vi) an amino group optionally substituted by a group selected from the following:
(1) a lower alkyl group,
(2) a lower alkoxy-lower alkyl group,
(3) a hydroxy-lower alkyl group,
(4) a lower alkanoyl group,
(5) a lower alkoxy-lower alkanoyl group,
(6) a hydroxy-lower alkanoyl group,
(7) a lower alkanoyl group substituted by a lower alkanoyloxy group,
(8) a lower alkanoyl group substituted by an amino group optionally substituted by a group selected from (a) a lower alkyl group and (b) a lower alkanoyl group,
(9) a lower alkoxycarbonyl group,
(10) a lower alkoxycarbonyl group substituted by an aryl group,
(11) a carbamoyl group substituted by a lower alkyl group, and
(12) a lower alkylsulfonyl group,
(vii) a nitro group,
(viii) a cyano group, and
(x) a group of the formula:

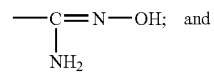

$R^3$ is a hydrogen atom or a lower alkyl group, or a pharmaceutically acceptable salt thereof.

2. The compound according to claim 1, wherein B is an unsubstituted benzene ring; and
Y is a cycloalkyl group optionally substituted by the following:
A) an amino group optionally substituted by the following:
(1) a lower alkyl group,
2) a cycloalkyl group,
(3) a hydroxy-lower alkyl group,
(4) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(5) a lower alkyl group substituted by a cyano group, (6) a lower alkyl group substituted by a lower alkoxycarbonyl group,
(7) a lower alkyl group substituted by a carboxyl group,
(8) a lower alkyl group substituted by a carbamoyl group optionally substituted by a lower alkyl group,
(9) a lower alkyl group substituted by an aryl group,
(10) a lower alkoxycarbonyl group,
(11) a lower alkanoyl group substituted by a di-lower alkyl amino group,
(12) a lower alkanoyl group,
(13) a lower alkylsulfonyl group,
(14) a carbamoyl group substituted by a lower alkyl group,
(15) a carbonyl group substituted by an aryl group,
(16) a lower alkanoyl group substituted by a lower alkoxy group,
(17) a lower alkanoyl group substituted by a lower alkanoyloxy group,
(18) an aryl group substituted by a hydroxy group, or
(19) hydroxy-lower alkanoyl group;
B) a group of a formula:

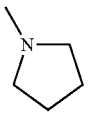

that is optionally substituted by an oxo group; or
C) a lower alkyl group optionally substituted by an amino group optionally substituted by (a) a lower alkyl group, (b) a lower alkoxycarbonyl group, and (c) a lower alkanoyl group.

3. The compound according to claim 1, wherein Ring B is a benzene ring substituted by a lower alkyl group optionally substituted by a group selected from the following:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group, and
(4) a hydroxyl group; and Y is a cycloalkyl group optionally substituted by the following:
A) an amino group optionally substituted by the following:
(1) a lower alkyl group,
(2) a cycloalkyl group,
(3) a hydroxy-lower alkyl group,
(4) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(5) a lower alkyl group substituted by a cyano group,
(6) a lower alkyl group substituted by a lower alkoxycarbonyl group,
(7) a lower alkyl group substituted by a carboxyl group,
(8) a lower alkyl group substituted by a carbamoyl group optionally substituted by a lower alkyl group,
(9) a lower alkyl group substituted by an aryl group,
(10) a lower alkoxycarbonyl group,
(11) a lower alkanoyl group substituted by a di-lower alkyl amino group,
(12) a lower alkanoyl group,
(13) a lower alkylsulfonyl group,
(14) a carbamoyl group substituted by a lower alkyl group,
(15) a carbonyl group substituted by an aryl group,
(16) a lower alkanoyl group substituted by a lower alkoxy group,
(17) a lower alkanoyl group substituted by a lower alkanoyloxy group,
(18) an aryl group substituted by a hydroxy group, or
(19) a hydroxy-lower alkanoyl group;
B) a group of a formula:

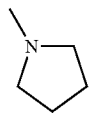

that is optionally substituted by an oxo group; or
C) a lower alkyl group optionally substituted by
an amino group optionally substituted by (a) a lower alkyl group, (b) a lower alkoxycarbonyl group, and (c) a lower alkanoyl group.

4. The compound according to claim 1, wherein Ring B is a benzene ring substituted by a lower alkoxy group optionally substituted by a group selected from the following:
(1) a carboxyl group,
(2) a lower alkoxycarbonyl group,
(3) a lower alkoxy group,
hydroxyl group,
an aminooxy group optionally substituted by a lower alkoxycarbonyl group,
(6) a lower alkoxy group substituted by a lower alkoxy group,
(7) an amino group optionally substituted by (a) a lower alkyl group, (b) a lower alkoxycarbonyl group, and (c) a lower alkanoyl group,
(8) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(9) a group of the formula: —O—NH—C(=NH)NH$_2$; and
Y is a cycloalkyl group optionally substituted by the following:
A) an amino group optionally substituted by the following:
(1) a lower alkyl group,
(2) a cycloalkyl group,
(3) a hydroxy-lower alkyl group,
(4) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(5) a lower alkyl group substituted by a cyano group,
(6) a lower alkyl group substituted by a lower alkoxycarbonyl group,
(7) a lower alkyl group substituted by a carboxyl group,
(8) a lower alkyl group substituted by a carbamoyl group optionally substituted by a lower alkyl group,
(9) a lower alkyl group substituted by an aryl group,
(10) a lower alkoxycarbonyl group,
(11) a lower alkanoyl group substituted by a di-lower alkyl amino group,
(12) a lower alkanoyl group,
(13) a lower alkylsulfonyl group,
(14) a carbamoyl group substituted by a lower alkyl group,
(15) a carbonyl group substituted by an aryl group,

(16) a lower alkanoyl group substituted by a lower alkoxy group,
(17) a lower alkanoyl group substituted by a lower alkanoyloxy group,
(18) an aryl group substituted by a hydroxy group, or
(19) a hydroxy-lower alkanoyl group;
B) a group of a formula:

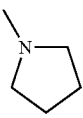

that is optionally substituted by an oxo group; or
C a lower alkyl group optionally substituted by
an amino group optionally substituted by (a) a lower alkyl group, (b) a lower alkoxycarbonyl group, or (c) a lower alkanoyl group.

5. The compound according to claim 1, wherein Ring B is a benzene ring substituted by a carbonyl group substituted by a group selected from the following:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, or (f) a lower alkyl group substituted by an aryl group, and
(4) a morpholinyl group,
Y is a cycloalkyl group optionally substituted by the following:
A) an amino group optionally substituted by the following:
(1) a lower alkyl group,
(2) a cycloalkyl group,
(3) a hydroxy-lower alkyl group,
(4) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(5) a lower alkyl group substituted by a cyano group,
(6) a lower alkyl group substituted by a lower alkoxycarbonyl group,
(7) a lower alkyl group substituted by a carboxyl group,
(8) a lower alkyl group substituted by a carbamoyl group optionally substituted by a lower alkyl group,
(9) a lower alkyl group substituted by an aryl group,
(10) a lower alkoxycarbonyl group,
(11) a lower alkanoyl group substituted by a di-lower alkyl amino group,
(12) a lower alkanoyl group,
(13) a lower alkylsulfonyl group,
(14) a carbamoyl group substituted by a lower alkyl group,
(15) a carbonyl group substituted by an aryl group,
(16) a lower alkanoyl group substituted by a lower alkoxy group,
(17) a lower alkanoyl group substituted by a lower alkanoyloxy group,
(18) an aryl group substituted by a hydroxy group, or
(19) a hydroxy-lower alkanoyl group;
B) a group of a formula:

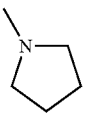

that is optionally substituted by an oxo group; or
C) a lower alkyl group optionally substituted by
an amino group optionally substituted by (a) a lower alkyl group, (b) a lower alkoxycarbonyl group, or (c) a lower alkanoyl group.

6. The compound according to claim 1, wherein the group of the formula:

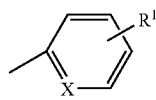

is the group of the formula:

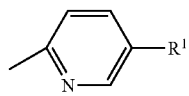

and the group of the formula:

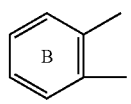

is a group of the formula:

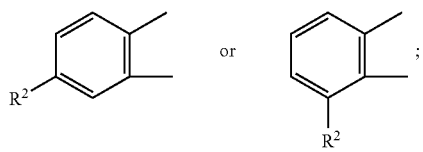

[1] $R^1$ is a halogen atom or a lower alkyl group; $R^2$ is a group selected from the following:
A) a hydrogen atom,
B) a lower alkyl group optionally substituted by a group selected from the following:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a hydroxyl group;
C) a lower alkoxy group optionally substituted by a group selected from the following:
(1) a carboxyl group,
(2) a lower alkoxycarbonyl group,
(3) a lower alkoxy group, (4) a hydroxyl group,
(5) an aminooxy group optionally substituted by a lower alkoxycarbonyl group,
(6) a lower alkoxy group substituted by a lower alkoxy group,
(7) an amino group optionally substituted by a group selected from (a) a lower alkyl group,(b) a lower alkoxycarbonyl group, and(c)a lower alkanoyl group,
(8) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group, and
(9) a group of the formula: —O—NH—C(=NH)NH$_2$; or
D) a carbonyl group substituted by a group selected from the following:
(1) a lower alkoxy group,
(2) a hydroxyl group,
(3) an amino group optionally substituted by a group selected from (a)a lower alkyl group, (b) a lower alkoxy group, (c) a lower alkoxy-lower alkyl group, (d) a hydroxyl lower alkyl group, (e) a lower alkyl group substituted by an amino group optionally substituted by a lower alkyl group, (f) a lower alkyl group substituted by an aryl group, and (g) and
(4) a morpholinyl group,
A is a single bond; and R$^3$ is a hydrogen atom.

7. The compound according to claim 6, wherein Y is a group selected from the following:
(1) a cycloalkyl group substituted by an amino group optionally substituted by a group selected from (a) a lower alkyl group, (b) a lower alkoxycarbonyl group, and (c) a lower alkanoyl group,
(2) a cycloalkyl group substituted by a group of a formula:

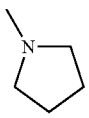

that is optionally substituted by an oxo group,
(3) a cycloalkyl group substituted by an amino group substituted by a lower alkyl group substituted by an amino group optionally substituted by a group selected from (a) a lower alkanoyl group and (b) a lower alkoxycarbonyl group, and
(4) a cyoloalkyl group substituted by a lower alkyl group substituted by an amino group optionally substituted by a lower alkyl group; and
R$^2$ is a group selected from the following:
(1) a hydrogen atom,
(2) a lower alkoxy group,
(3) a lower alkoxy group substituted by a lower alkoxy group,
(4) a lower alkoxy group substituted by a hydroxyl group,
(5) a lower alkoxy group substituted by an amino group optionally substituted by a lower alkyl group,
(6) a lower alkoxycarbonyl group,
(7) a carboxyl group,
(8) an aminocarbonyl group optionally substituted by a group selected from (a) lower alkyl group, and (b) a hydroxy-lower alkyl group,
(9) a morpholinylcarbonyl group,
(10) a lower alkyl group,
(11) a lower alkyl group substituted by a lower alkoxycarbonyl group,
(12) a carboxy-lower alkyl group,
a lower alkyl group substituted by a carbamoyl group optionally substituted by a group selected from (a) a lower alkyl group and (b) a hydroxy-lower alkyl group, and
(13) a hydroxy-lower alkyl group.

8. The compound according to claim 6, wherein Y is a cycloalkyl group substituted by a group of a formula

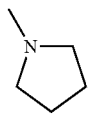

that is optionally substituted by an oxo group, or a cycloalkyl group substituted by an amino group optionally substituted by a. group selected from (a) a lower alkyl group and (b) a lower alkanoyl group; and R$^2$ is a group selected from the following;
(1) a hydrogen atom,
(2) a lower alkoxycarbonyl group,
(3) a morpholinylcarbonyl group,
(4) a lower alkyl group substituted by a lower alkyl group-substituted carbamoyl group,
(5) a carboxy-lower alkyl group, and
(6) a hydroxy-lower alkyl group.

9. The compound according to claim 6, wherein Y is a cycloalkyl group substituted by an oxopyrrolidinyl group, or a cycloalkyl group substituted by an amino group optionally substituted by a group selected from (a) a lower alkyl group and (b) a lower alkanoyl group; and
R$^2$ is a group selected from the following:
(1) a hydrogen atom,
(2) a hydroxy-lower alkyl group,
(3) a carboxy-lower alkyl group,
(4) a lower alkoxy group substituted by a lower alkoxy group, and
(5) a carbonyl group substituted by a group selected from (a) an amino group optionally substituted by a lower alkyl group and (b) a morpholinyl group.

10. The compound according to claim 6, wherein Y is a group selected from the following:
(1) a cycloalkyl group substituted by an amino group substituted by a lower alkyl group having 1 to 3 carbon atoms,
(2) a cycloalkyl group substituted by an amino group substituted by a lower alkanoyl group having 1 to 2 carbon atoms,
(3) a cycloalkyl group substituted by a pyrrolidin-l-yl group optionally substituted by an oxo group,
(4) a cycloalkyl group substituted by a lower alkyl group substituted by an amino group substituted by a lower alkyl group having 1 to 3 carbon atoms, and
(5) a cycloalkyl group substituted by a lower alkyl group substituted by an amino group substituted by a lower alkanoyl group having 1 to 2 carbon atoms.

11. A compound selected from
trans-5-dimethylaminocarbonyl-3-[4-(N-formyl-N-methylamino) cyclohexylcarbonylamino]-N-(5-chloropyridin-2-yl)benzofuran-2-carboxamide;
trans-3-[4-(N-acetyl-N-methylamino)cyclohexylcarbonylamino]-5-(2-hydroxyethyl-N-(5-chloropyridin2yl) benzofuran-2-carboxamide;

trans-5-(morpholine-4-ylcarbonyl)-3-[4-(2-oxo-pyrrolidin-1-yl)cyclohexylcarbonylamino-N-(5-chloropyridin-2-yl)benzofuran-2-carboxamide; and trans-3-(4-dimethylaminocyclohexylcarbonylamino)-N-(5-chloropyridin-2-yl) benzofuran-2-carboxamide
or a pharmaceutically acceptable salt thereof.

12. The compound according to claim 1, which is trans-5-dimethylaminocarbonyl3[4(N-formyl-N-methylamino)cyclohexylcarbonylamino]-N-(5-chloropyridin-2-yl)benzofuran-2-carboxamide; or a pharmaceutically acceptable salt thereof.

13. The compound according to claim 1, which is trans-3-[4-(N-acetyl-N-methylamino)cyclohexylcarbonylamino]-5-(2-hydroxyethyl-N-(5-chloropyridin-2-yl)benzofuran-2-carboxamide; or a pharmaceutically acceptable salt thereof.

14. The compound according to claim 1, which is trans-5-(morpholine-4-ylcarbonyl)-3-[4-(2-oxo-pyrrolidin-1-yl)cyclohexylcarbonylamino-N-(5-chloropyridin-2-yl)benzofuran-2-carboxamide; or a pharmaceutically acceptable salt thereof.

15. The compound according to claim 1, which is trans-3-(4-dimethylaminocyclohexylcarbonylamino)-N-(5-chloropyridin-2-yl) benzofuran-2-carboxamide;
or a pharmaceutically acceptable salt thereof.

16. A pharmaceutical composition, which comprises as an active ingredient a compound according to any one of claims 1, 2, 3, 4, 5, 6, 11 and 12-15 or a pharmaceutically acceptable salt thereof; and a pharmaceutically acceptable carrier.

17. A method for treatment of thrombosis, which comprises administering an effective amount of a compound according to any one of claims 1, 2, 3, 4, 5, 6, 11 and 12-15 or a pharmaceutically acceptable salt thereof, to a patient in need thereof.

\* \* \* \* \*